(12) United States Patent
Darios et al.

(10) Patent No.: US 11,065,238 B2
(45) Date of Patent: Jul. 20, 2021

(54) INHIBITORS OF GANGLIOSIDES METABOLISM FOR THE TREATMENT OF MOTOR NEURON DISEASES

(71) Applicants: ICM (INSTITUT DU CERVEAU ET DE LA MOELLE ÉPINIÈRE), Paris (FR); SORBONNE UNIVERSITE, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR); APHP (ASSISTANCE PUBLIQUE—HÔPITAUX DE PARIS), Paris (FR); ÉCOLE PRATIQUE DES HAUTES ÉTUDES, Paris (FR)

(72) Inventors: Frédéric Darios, Antony (FR); Giovanni Stevanin, Sevran (FR); Fanny Mochel, Paris (FR); Julien Branchu, Paris (FR); Maxime Boutry, Paris (FR)

(73) Assignees: ICM (INSTITUT DU CERVEAU ET DE LA MOELLE ÉPINIÈRE), Paris (FR); SORBONNE UNIVERSITE, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE, Paris (FR); APHP (ASSISTANCE PUBLIQUE—HÔPITAUX DE PARIS), Paris; ÉCOLE PRATIQUE DES HAUTES ÉTUDES, Paris (FR)

( * ) Notice: Subject to any disclaimer, the term of this patent is extended or adjusted under 35 U.S.C. 154(b) by 0 days.

(21) Appl. No.: 16/345,695

(22) PCT Filed: Nov. 3, 2017

(86) PCT No.: PCT/EP2017/078156
§ 371 (c)(1),
(2) Date: Apr. 26, 2019

(87) PCT Pub. No.: WO2018/083223
PCT Pub. Date: May 11, 2018

(65) Prior Publication Data
US 2019/0350913 A1    Nov. 21, 2019

(30) Foreign Application Priority Data
Nov. 4, 2016 (EP) .................... 16197362

(51) Int. Cl.
*A61K 31/45* (2006.01)
*A61K 31/137* (2006.01)
*A61K 31/4025* (2006.01)
*A61K 31/5375* (2006.01)
*A61K 31/7068* (2006.01)
*A61K 31/7105* (2006.01)
*A61K 45/06* (2006.01)

(52) U.S. Cl.
CPC ............ *A61K 31/45* (2013.01); *A61K 31/137* (2013.01); *A61K 31/4025* (2013.01); *A61K 31/5375* (2013.01); *A61K 31/7068* (2013.01); *A61K 31/7105* (2013.01); *A61K 45/06* (2013.01)

(58) Field of Classification Search
None
See application file for complete search history.

(56) References Cited

U.S. PATENT DOCUMENTS

| | | |
|---|---|---|
| 4,246,345 A | 1/1981 | Kinast et al. |
| 4,266,025 A | 5/1981 | Kinast et al. |
| 4,405,714 A | 9/1983 | Kinast et al. |
| 4,806,650 A | 2/1989 | Schroder et al. |
| 4,816,397 A | 3/1989 | Boss et al. |
| 4,946,778 A | 8/1990 | Ladner et al. |
| 4,994,572 A | 2/1991 | Fleet |
| 5,043,273 A | 8/1991 | Scudder et al. |
| 5,200,523 A | 4/1993 | Fleet |
| 5,225,539 A | 7/1993 | Winter |
| 5,236,838 A | 8/1993 | Rasmussen et al. |
| 5,302,609 A | 4/1994 | Shayman et al. |
| 5,472,969 A | 12/1995 | Platt et al. |
| 5,525,616 A | 6/1996 | Platt et al. |
| 5,549,892 A | 8/1996 | Friedman et al. |
| 5,622,972 A | 4/1997 | Bryant et al. |
| 5,916,911 A | 6/1999 | Shayman et al. |
| 5,952,370 A | 9/1999 | Shayman et al. |
| 5,981,732 A | 11/1999 | Cowsert |

(Continued)

FOREIGN PATENT DOCUMENTS

| | | |
|---|---|---|
| EP | 0240907 | 10/1987 |
| EP | 0566556 | 10/1993 |

(Continued)

OTHER PUBLICATIONS

Henriques et al. Human Molecular Genetics vol. 24, 7390-7405 (Year: 2015).*

(Continued)

*Primary Examiner* — Brian Whiteman
(74) *Attorney, Agent, or Firm* — Lathrop GPM LLP; James H. Velema, Esq.; Judith L. Stone-Hulslander

(57) ABSTRACT

The present invention relates to inhibitors of gangliosides metabolism for treating motor neuron diseases, in particular hereditary spastic paraplegias.

14 Claims, 45 Drawing Sheets
Specification includes a Sequence Listing.

(56) References Cited

U.S. PATENT DOCUMENTS

| | | | |
|---|---|---|---|
| 6,030,995 | A | 2/2000 | Shayman et al. |
| 6,046,321 | A | 4/2000 | Cowsert |
| 6,051,598 | A | 4/2000 | Shayman et al. |
| 6,107,091 | A | 8/2000 | Cowsert |
| 6,255,336 | B1 | 6/2001 | Shayman et al. |
| 6,280,989 | B1 | 8/2001 | Kapitonov et al. |
| 6,365,354 | B1 | 4/2002 | Bennett et al. |
| 6,410,323 | B1 | 6/2002 | Roberts et al. |
| 6,451,600 | B1 | 9/2002 | Rasmussen et al. |
| 6,465,488 | B1 | 10/2002 | Butters et al. |
| 6,506,559 | B1 | 1/2003 | Fire et al. |
| 6,566,131 | B1 | 5/2003 | Cowsert |
| 6,566,135 | B1 | 5/2003 | Watt |
| 6,569,889 | B2 | 5/2003 | Shayman et al. |
| 6,573,099 | B2 | 6/2003 | Graham |
| 6,610,703 | B1 | 8/2003 | Jacob et al. |
| 6,660,749 | B2 | 12/2003 | Butters et al. |
| 6,916,802 | B2 | 7/2005 | Shayman et al. |
| 7,501,439 | B2 | 3/2009 | Mugrage et al. |
| 2007/0275998 | A1 | 11/2007 | Butters et al. |
| 2009/0082303 | A1 | 3/2009 | Fuse et al. |
| 2014/0161896 | A1* | 6/2014 | Peer ............... A61K 9/127 424/499 |
| 2014/0288093 | A1* | 9/2014 | Krainc ............. A61P 25/18 514/259.3 |
| 2019/0142782 | A1* | 5/2019 | Spedding ......... A61K 31/137 |

FOREIGN PATENT DOCUMENTS

| | | |
|---|---|---|
| WO | WO 1998/030219 A1 | 7/1998 |
| WO | WO 1999/032619 | 7/1999 |
| WO | WO 2001/036646 | 5/2001 |
| WO | WO 2001/068836 | 9/2001 |
| WO | WO 2005/040118 | 5/2005 |
| WO | WO 2005/108600 | 11/2005 |
| WO | WO 2007/140184 | 12/2007 |
| WO | 2010091104 A1 | 8/2010 |
| WO | 2010091164 A1 | 8/2010 |
| WO | WO 2011/066352 | 6/2011 |
| WO | WO 2011/086347 | 7/2011 |
| WO | WO 2011/095772 | 8/2011 |
| WO | WO 2011/133918 | 10/2011 |
| WO | WO 2012/117219 | 9/2012 |
| WO | WO 2012/129084 | 9/2012 |
| WO | WO 2013/059119 | 4/2013 |
| WO | WO 2014/043068 | 3/2014 |
| WO | WO 2015/147639 | 10/2015 |

OTHER PUBLICATIONS

Dodge et al. PNAS 112 pp. 8100-8105 (Year: 2015).*
Fakhr et al. Cancer Gene Therapy 23: 73-82 (Year: 2016).*
Hagedorn et al. Nucleic Acid Research 45, pp. 2262-2282 (Year: 2017).*
Yamanaka et al. Biochemistry 59, 1242-1251 (Year: 2020).*
Köhler et al. (1975) "Continuous cultures of fused cells secreting antibody of predefined specificity." Nature, 256 (5517), pp. 495-497.
Cote et al. (1983) "Generation of human monoclonal antibodies reactive with cellular antigens." Proc Natl Acad Sci USA, 80(7), pp. 2026-2030.
Cole et al. (1985) "The EBV-Hybridoma Technique" Human Hybridomas and Monoclonal Antibodies, Plenum Press, 16 pp.
Tuerk et al. (1990) "Systematic Evolution of Ligands by Exponential Enrichment: RNA Ligands to Bacteriophage T4 DNA Polymerase." Science, 249(4968), 7 pp.
Jayasena (1999) "Aptamers: an emerging class of molecules that rival antibodies in diagnostics." Clin Chem., 45(9), pp. 1628-1650.
Colas et al. (1996) "Genetic selection of peptide aptamers that recognize and inhibit cyclin-dependent kinase 2." Nature, 380(6574), pp. 548-550.
Tuschl et al. (1999) "Targeted mRNA degradation by double-stranded RNA in vitro." Genes Dev., 13(24), pp. 3191-3197.
Elbashir et al. (2001) "Duplexes of 21-nucleotide RNAs mediate RNA interference in cultured mammalian cells." Nature, 411(6836), pp. 494-498.
Hannon (2002) "RNA interference." Nature, 418(6894), pp. 244-251.
Brummelkamp et al. (2002) "A system for stable expression of short interfering RNAs in mammalian cells." Science, 296(5567), pp. 550-553.
Richards et al. (2012) "Discovery and Characterization of an Inhibitor of Glucosylceramide Synthase," J Med Chem., 55(9), pp. 4322-4335.
Frohlich et al. (2011) "1-Deoxy-o-galactonojirimycins with dansyl capped N-substituents as p-galactosidase inhibitors and potential probes for GM1 gangliosidosis affected cell lines" Carbohydr Res., 346(12), pp. 1592-1598.
Jenkinson et al. (2013) "C-Branched Iminosugars: alpha-Glucosidase Inhibition by Enantiomers of isoDMDP, isoDGDP and isoDAB—L-isoDMDP Compared to Miglitol and Miglustat" J. Org. Chem., 78 (15), pp. 7380-7397.
Takayama et al. (1999) "Selective Inhibition of (3-1,4- and a-1,3-Galactosyltransferases: Donor Sugar-Nucleotide Based Approach," Bioorg Med Chem, 7(2), pp. 401-409.
Saotome et al. (2001) "Combinatorial library of ¢ve-membered iminocyclitol and the inhibitory activities against glyco-enzymes," Chem Biol., 8(11), pp. 1061-1070.
Carson et al. (1994) "Studies on Morpholinosphingolipids: Potent Inhibitors of Glucosylceramide Synthase," Tetrahedron Lett., 35, pp. 2659-2662.
Miura et al. (1998) "Synthesis and Evaluation of Morpholino- and Pyrrolidinosphingolipids as Inhibitors of Glucosylceramide Synthase," Bioorg Med Chem, 6(9), pp. 1481-1489.
Lee et al. (1999) "Improved Inhibitors of Glucosylceramide Synthase," J. Bio. Chem., vol. 274, No. 21, pp. 14662-14669.
Shayman et al. (2014) "The development and use of small molecule inhibitors of glycosphingolipid metabolism for lysosomal storage diseases," Lipid Res., 55(7), pp. 1215-1225.
Koltun et al. (2011) "Discovery of a new class of glucosylceramide synthase inhibitors," Bioorg Med Chem Lett., 21(22), pp. 6773-6777.
Carillo et al. (1988) "The Multiple Sequence Alignment Problem in Biology," SIAM J. Appl. Math., 48(5), pp. 1073-1082.
Devereux et al. (1984) "A comprehensive set of sequence analysis programs for the VAX," Nucl. Acid.Res., 12(Pt 1), pp. 387-395.
Altschul et al. (1990) "Basic Local Alignment Search Tool," J. Mol. Biol., 215(3), pp. 403-410.
Denora et al. (2016) "Motor neuron degeneration in spastic paraplegia 11 mimics amyotrophic lateral sclerosis lesions." Brain, 139(Pt 6), pp. 1723-1734.
Murmu et al. (2011) "Cellular distribution and subcellular localization of spatacsin and spastizin, two proteins involved in hereditary spastic paraplegia" Mol Cell Neurosci., 47(3), pp. 191-202.
Dobrenis et al. (1992) "Neuronal lysosomal enzyme replacement using fragment C of tetanus toxin." Proc Natl Acad Sci USA, 89(6), pp. 2297-2301.
Natoli et al. (1986) "Neuronal lysosomal enzyme replacement using fragment C of tetanus toxin." Proc Natl Acad Sci USA, 89(6), pp. 2297-2301.
Seyer et al. (2016) "A murine monoclonal antibody detecting N-acetyl- and N-glycolyl-GM2: characterization of cell surface reactivity." Cancer Res., 46(8), pp. 4116-4120.
Graham (2001) "Isolation of Lysosomes from Tissues and Cells by Differential and Density Gradient Centrifugation," Curr Protoc Cell Biol., 3.6.1-3.6.21, 21 pp.
Esteves et al. (2014) "Loss of Association of REEP2 with Membranes Leads to Hereditary Spastic Paraplegia," The American J of Human Genetics, 94, 10 pp.
Folch et al. (1957) "A Simple Method for the Isolation and Purification of Total Lipides From Animal Tissues," J Biol Chem., 226, 14 pp.

(56) References Cited

OTHER PUBLICATIONS

Martin et al. (2012) "Spatacsin and spastizin act in the same pathway required for proper spinal motor neuron axon outgrowth in zebrafish." Neurobiol Dis., 48(3), pp. 299-308.
Boomkamp et al. (2010) "Lysosomal storage of oligosaccharide and glycosphingolipid in imino sugar treated cells," Glycoconj J. 27(3):297-308.
Daniotti et al. (2011) "Metabolic pathways and intracellular trafficking of gangliosides," Life. 63(7):513-520.
International Search Report and Written Opinion from PCT/EP2017/078156 dated Apr. 25, 2018.
Karimzadeh et al. (2014) "GM2-Gangliosidosis (Sandhoff and Tay Sachs disease): Diagnosis and Neuroimaging Findings (An Iranian Pediatric Case Series)," Iran J Child Neurol. 8(3): 55-60.
Renvoisé et al. (2014) "Lysosomal abnormalities in hereditary spastic paraplegia types SPG15 and SPG11," Ann Clin Transl Neurol.1(6):379-389.
Sultana et al. (2015) "Lack of enzyme activity in GBA2 mutants associated with hereditary spastic paraplegia/cerebellar ataxia (SPG46)," Biochem Biophys Res Commun. 465(1):35-40.
Tesson et al. (2015) "Delving into the complexity of hereditary spastic paraplegias: how unexpected phenotypes and inheritance modes are revolutionizing their nosology," Hum Genet. 134(6):511-38.
McManus et al., "Gene silencing in mammals by small interfering RNAs", Nature Reviews Genetics, Oct. 2002, vol. 3, No. 10, pp. 737-747.
Hatanaka et al., "Synthesis of a Carbon-linked CMP-NANA Analog and Its Inhibitory Effects on GM3 and GD3 Synthases", Heterocycles, 1996, vol. 43, No. 3, pp. 531-534.
Platt et al., "Prevention of Lysosomal Storage in Tay-Sachs Mice Treated with N-Butyldeoxynojirimycin", Science, Apr. 1997, vol. 276, No. 5311, pp. 428-431.
Park et al., "Increased Expression of GM1 Detected by Electrospray Mass Spectrometry in Rat Primary Embryonic Cortical Neurons Exposed to Glutamate Toxicity", Analytical Chemistry, Aug. 2016, vol. 88, No. 15, pp. 7844-7852.
Stevanin et al., "Mutations in SPG11, encoding spatacsin, are a major cause of spastic paraplegia with thin corpus callosum", Nature Genetics, Mar. 2007, vol. 39, No. 3, pp. 366-372.
Pasca et al., "Functional cortical neurons and astrocytes from human pluripotent stem cells in 3D culture", Nature Methods, Jul. 2015, vol. 12, No. 7, pp. 671-678.
Hughes et al., "The value of spontaneous alternation behavior (SAB) as a test of retention in pharmacological investigations of memory", Neuroscience and Biobehavioral Reviews, Sep. 2004, vol. 28, No. 5, pp. 497-505.
Schnutgen et al., "A directional strategy for monitoring Cre-mediated recombination at the cellular level in the mouse", Nature Biotechnology, May 2003, vol. 21, No. 5, pp. 562-565.
Seyer et al., "Annotation of the human cerebrospinal fluid lipidome using high resolution mass spectrometry and a dedicated data processing workflow", Metabolomics, 2016, vol. 12, pp. 91.
Martin et al., "Loss of function of glucocerebrosidase GBA2 is responsible for motor neuron defects in hereditary spastic paraplegia", American Journal of Human Genetics, Feb. 2013, vol. 92, No. 2, pp. 238-244.
Chang et al., "Spastic paraplegia proteins spastizin and spatacsin mediate autophagic lysosome reformation", Journal of Clinical Investigation, Dec. 2014, vol. 124, No. 12, pp. 5249-5262.
Harlalka et al., "Mutations in B4GALNT1 (GM2 synthase) underlie a new disorder of ganglioside biosynthesis", Brain, Dec. 2013, vol. 136, No. 12, pp. 3618-3624.
Boukhris et al., "Alteration of Ganglioside Biosynthesis Responsible for Complex Hereditary Spastic Paraplegia", American Journal of Human Genetics, Jul. 2013, vol. 93, No. 1, pp. 118-123.
European search report of the patent application EP16197362.3 dated Apr. 12, 2017 (4 pages).

\* cited by examiner

FIG. 1B
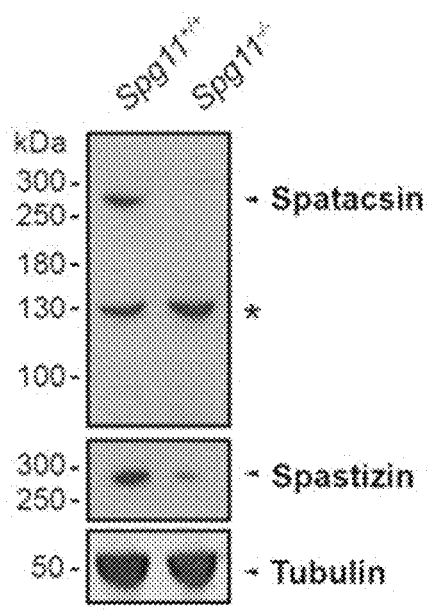
Spg11+/+ 16 months
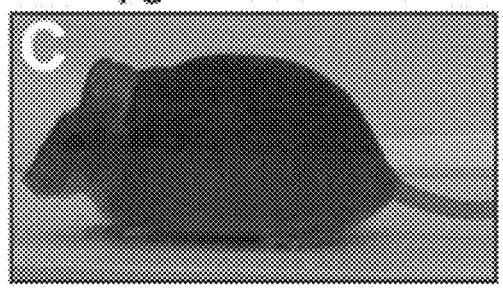
FIG. 1C
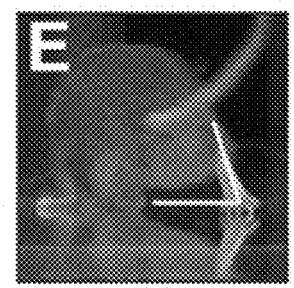
FIG. 1E
Spg11-/- 16 months
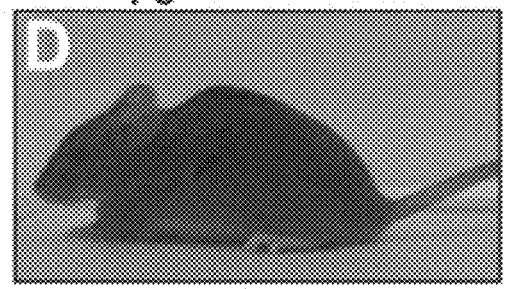
FIG. 1D
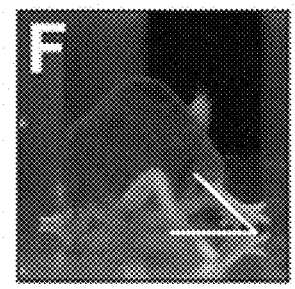
FIG. 1F FIG. 1G
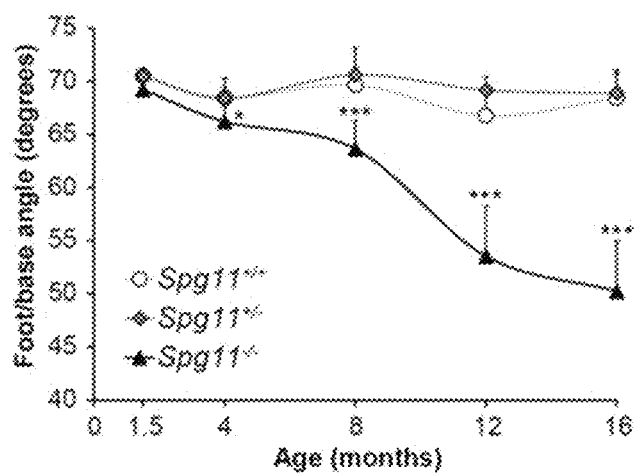
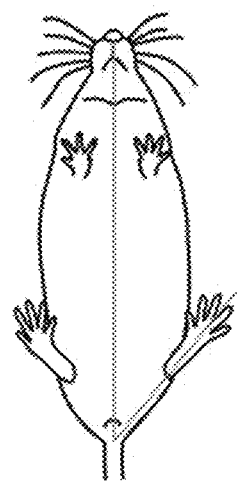
FIG. 1H
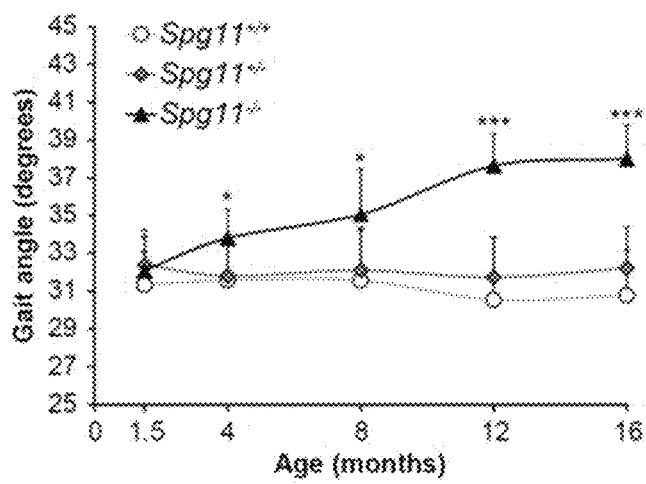
FIG. 1I FIG. 1J
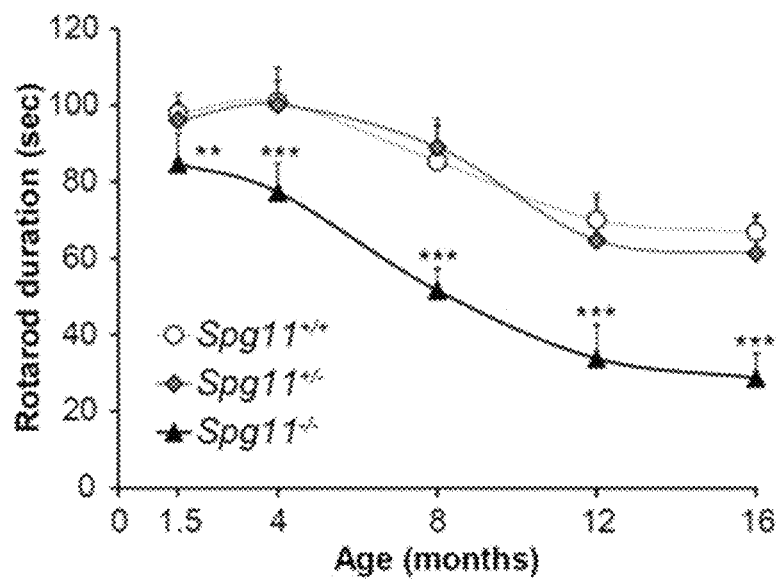
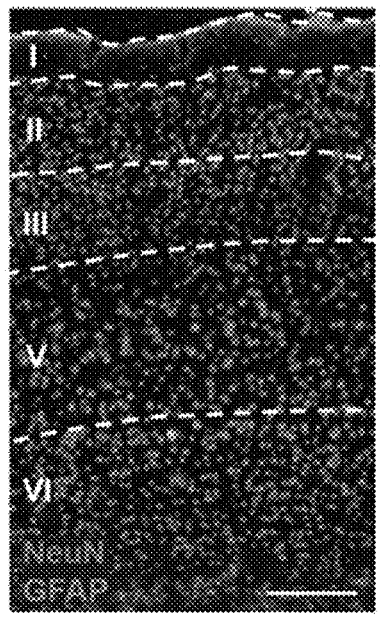
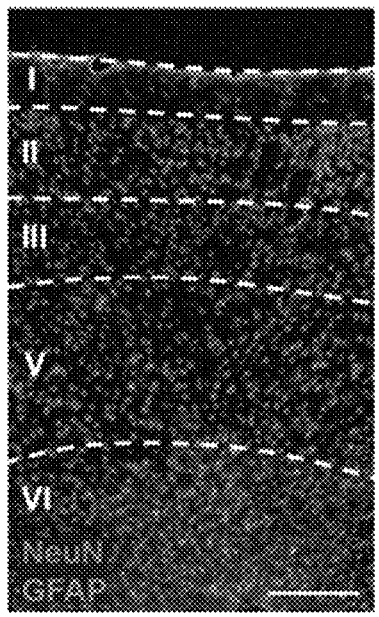
FIG. 1K  FIG. 1L

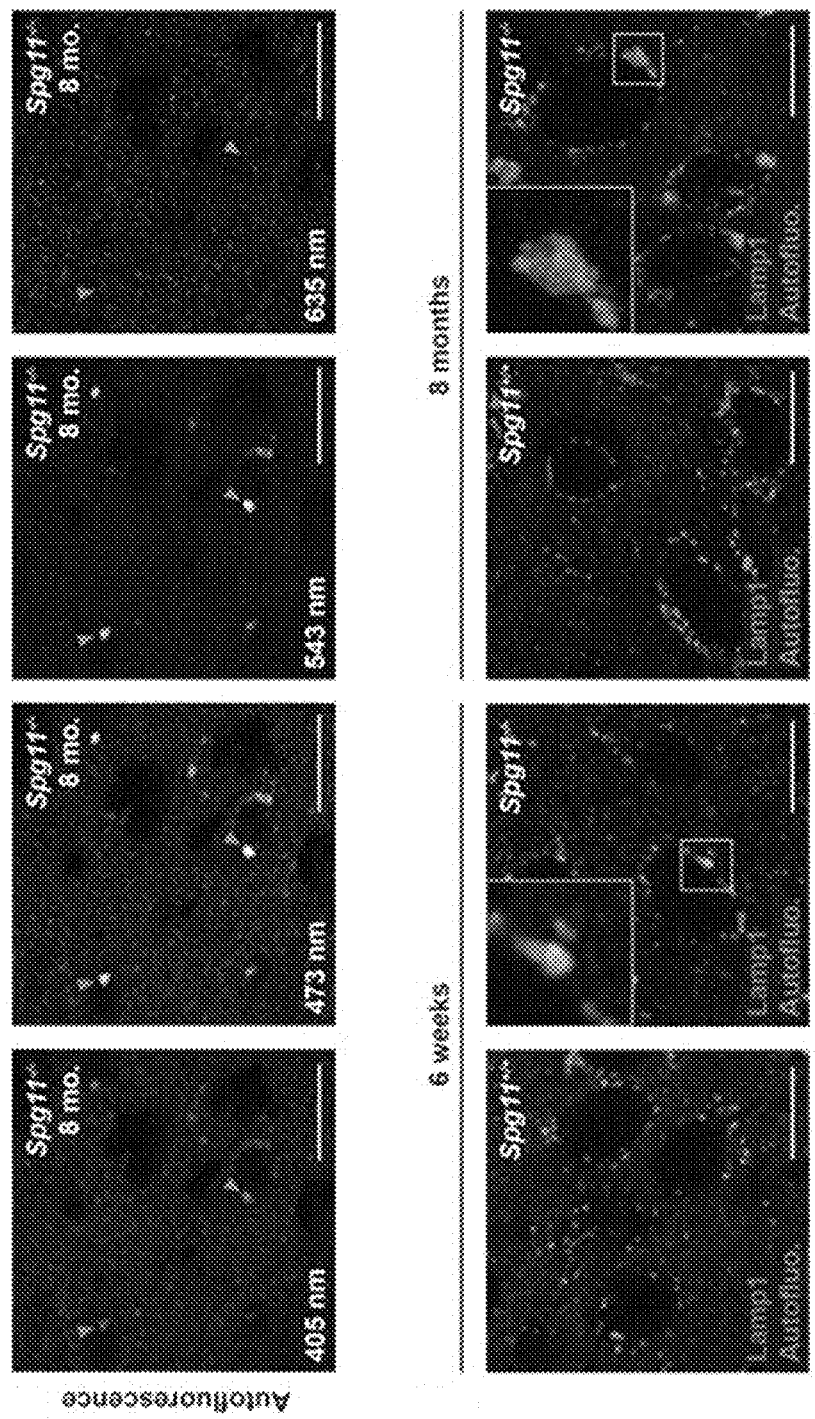

FIG. 3B
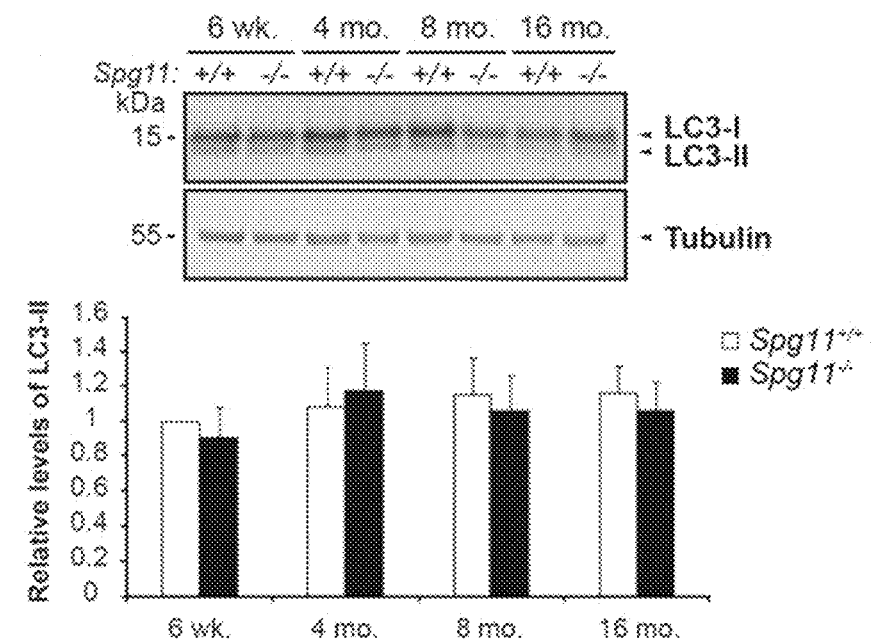
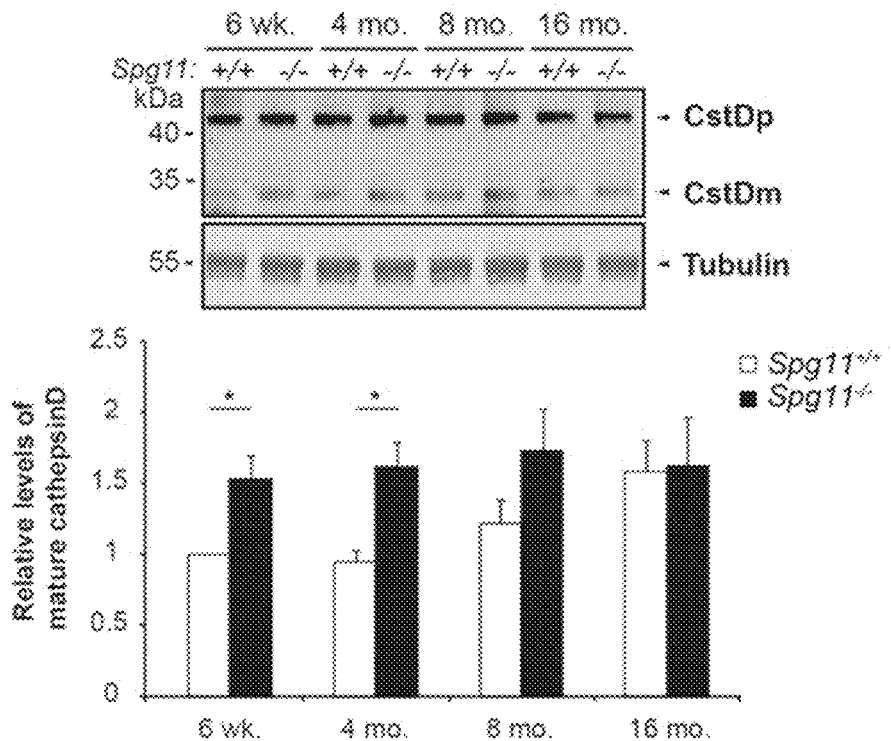
FIG. 3C

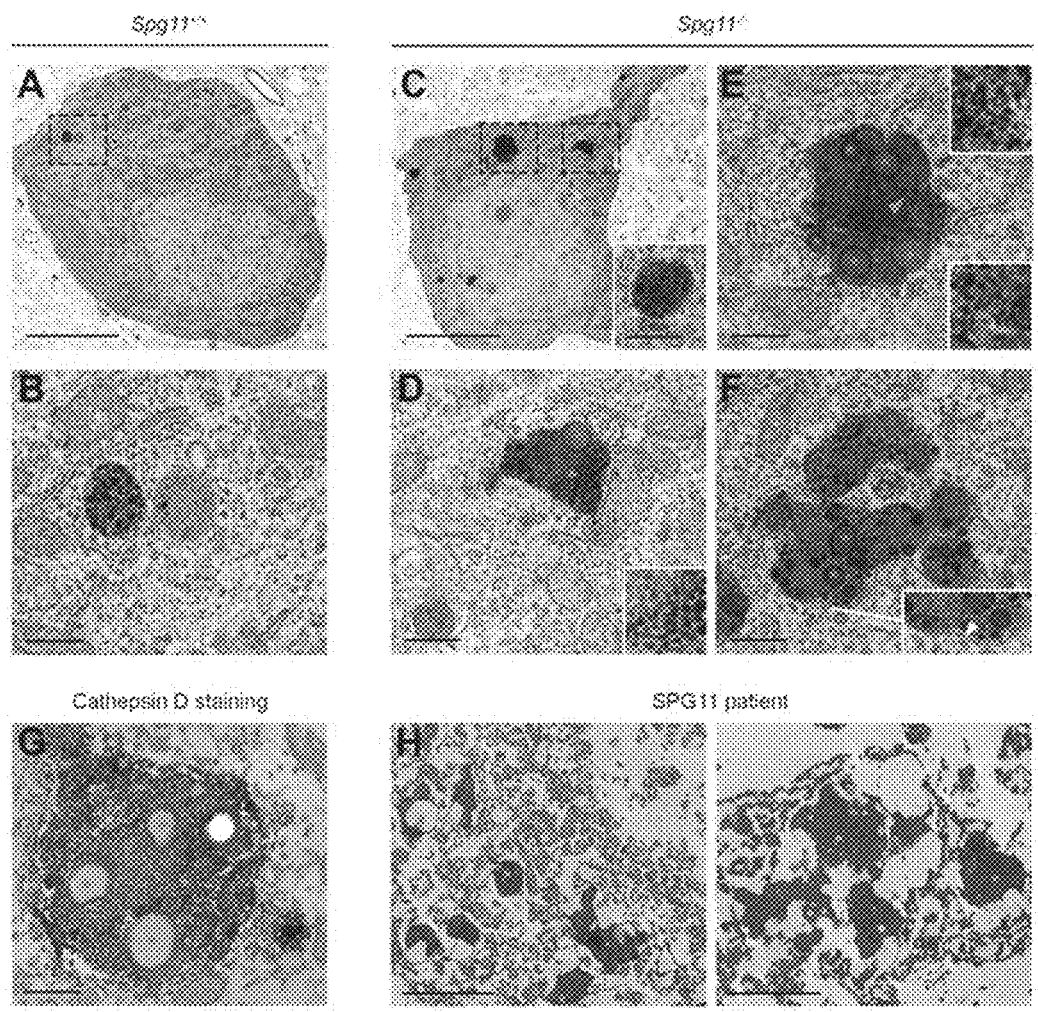
FIGS. 4A-H

FIG. 5A
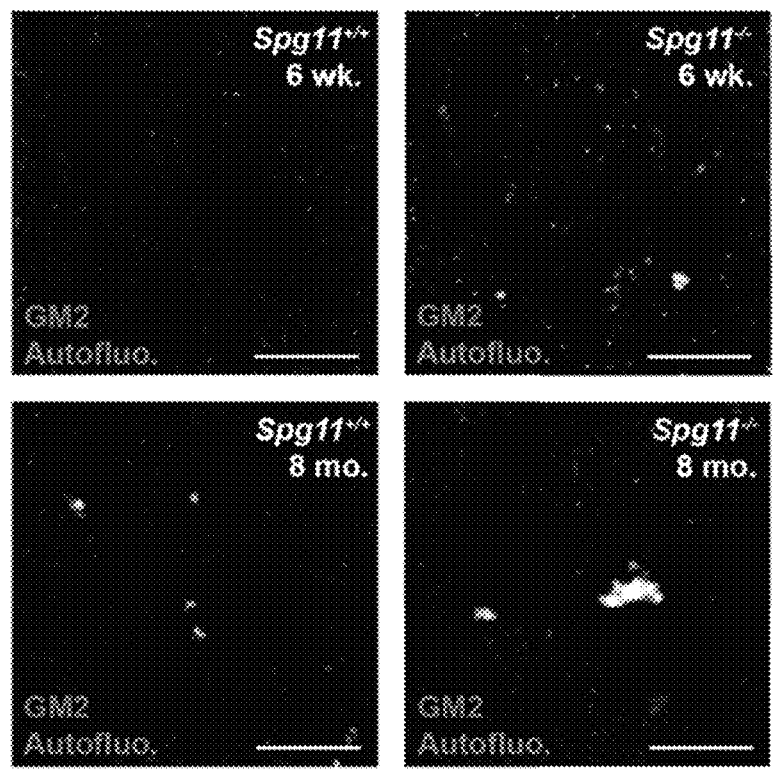
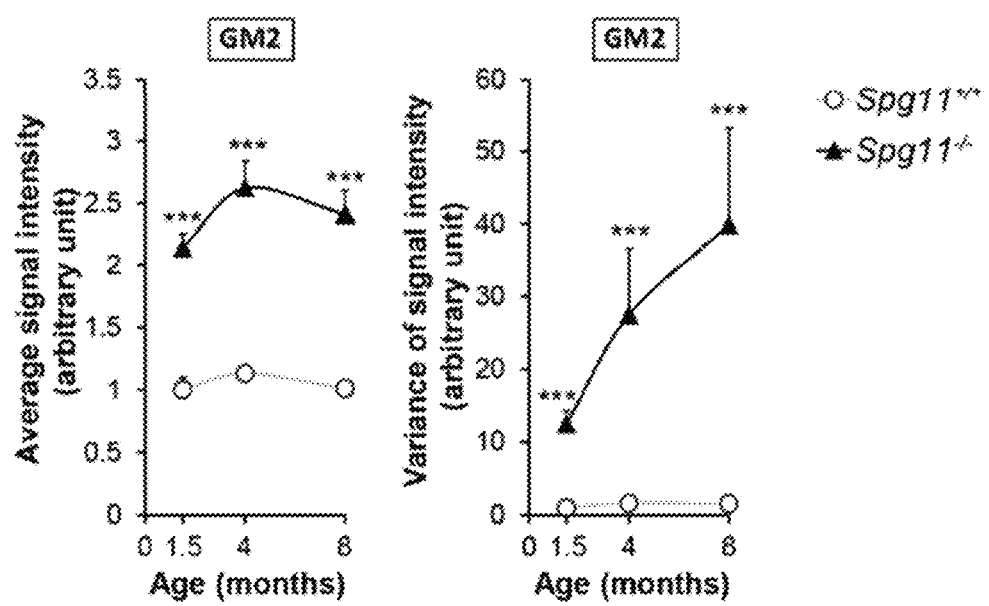
FIG. 5B

FIG. 5C
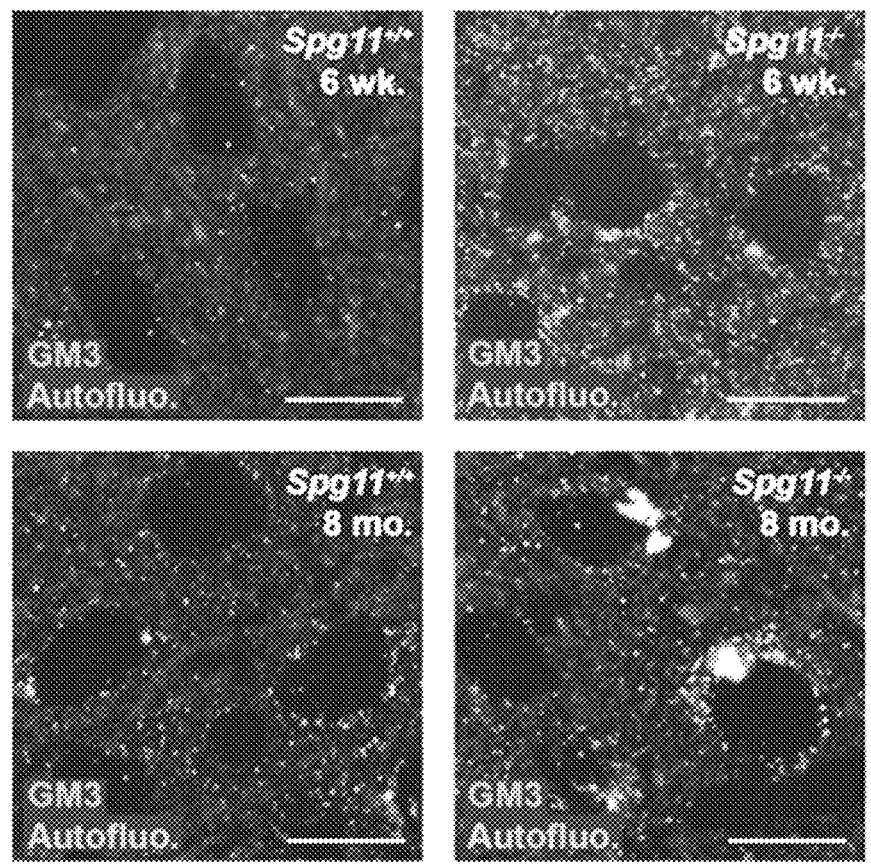
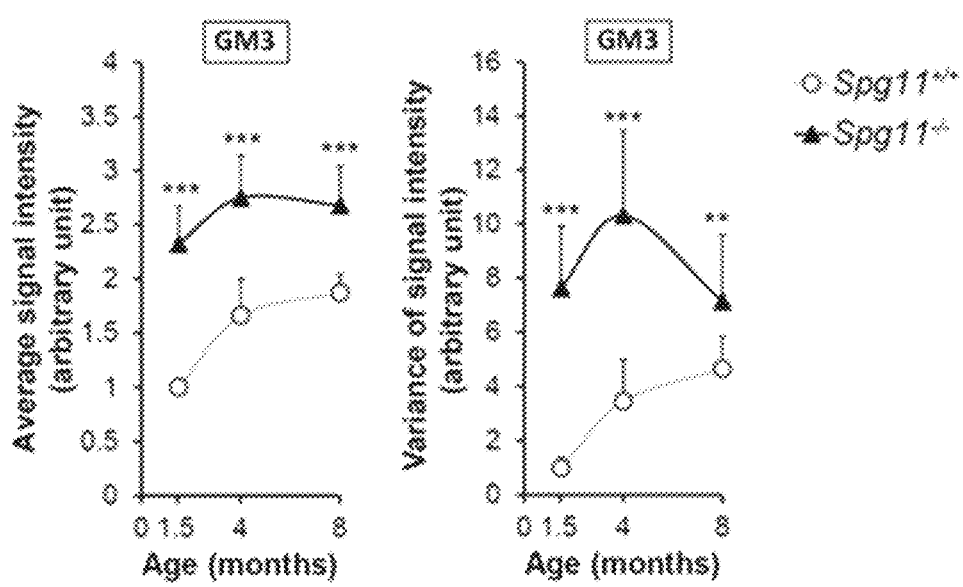
FIG. 5D

FIG. 5E
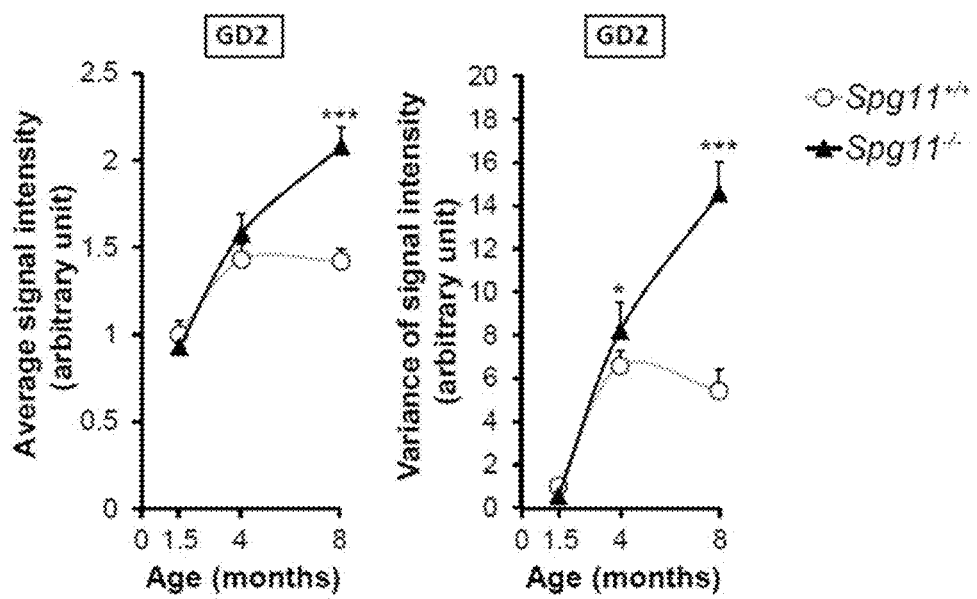
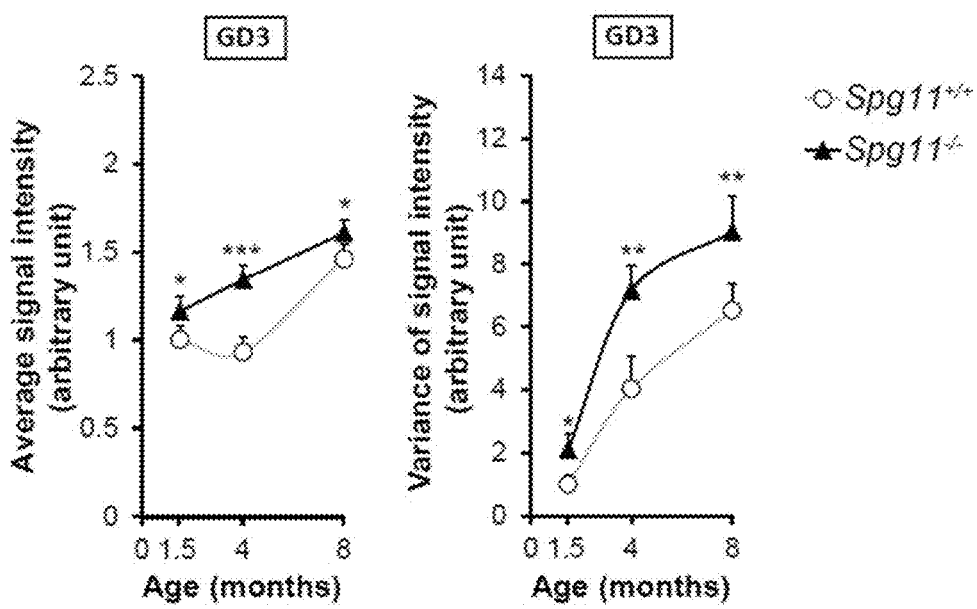
FIG. 5F

FIG. 6A
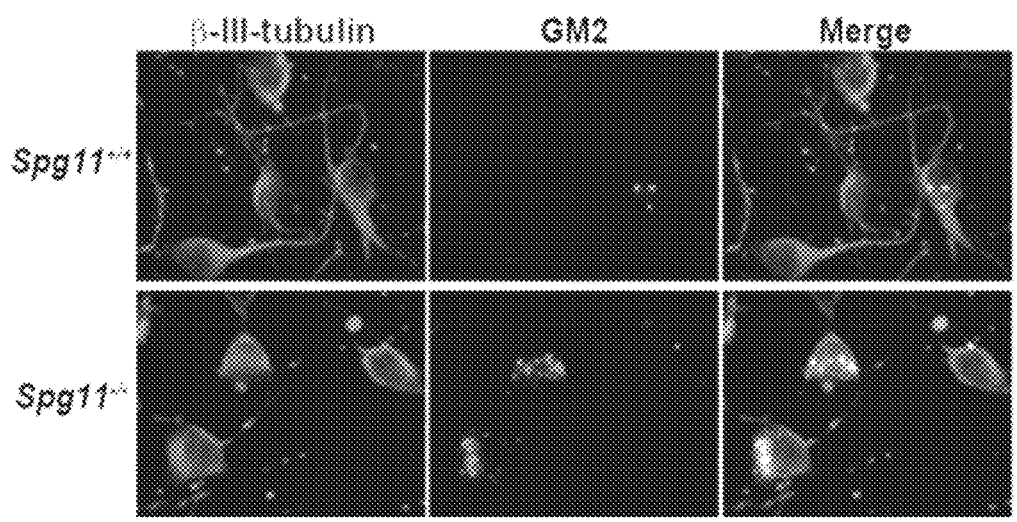
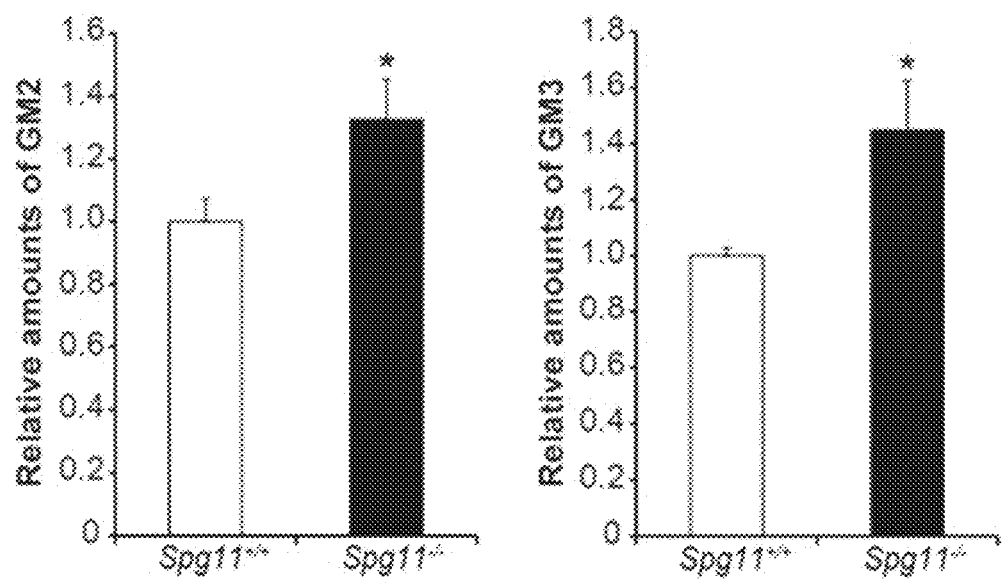
FIG. 6B

FIG. 6C
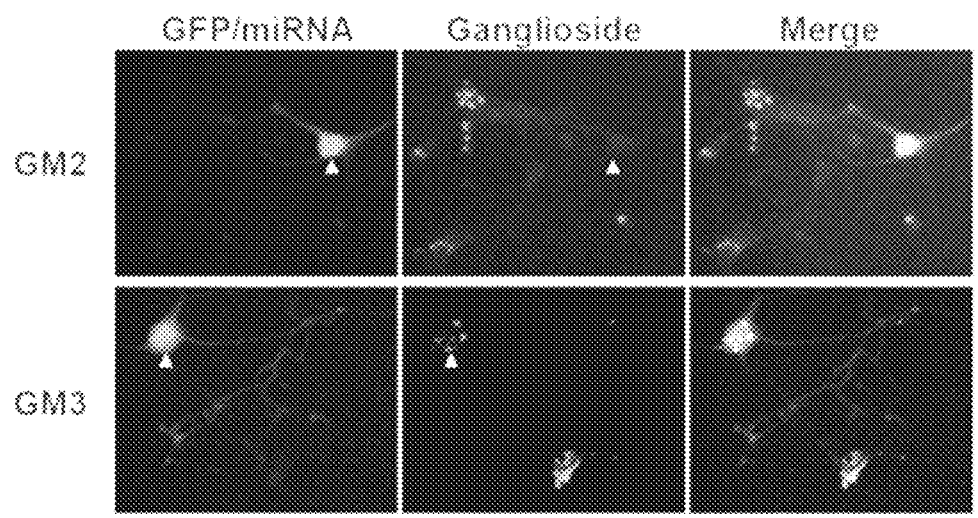
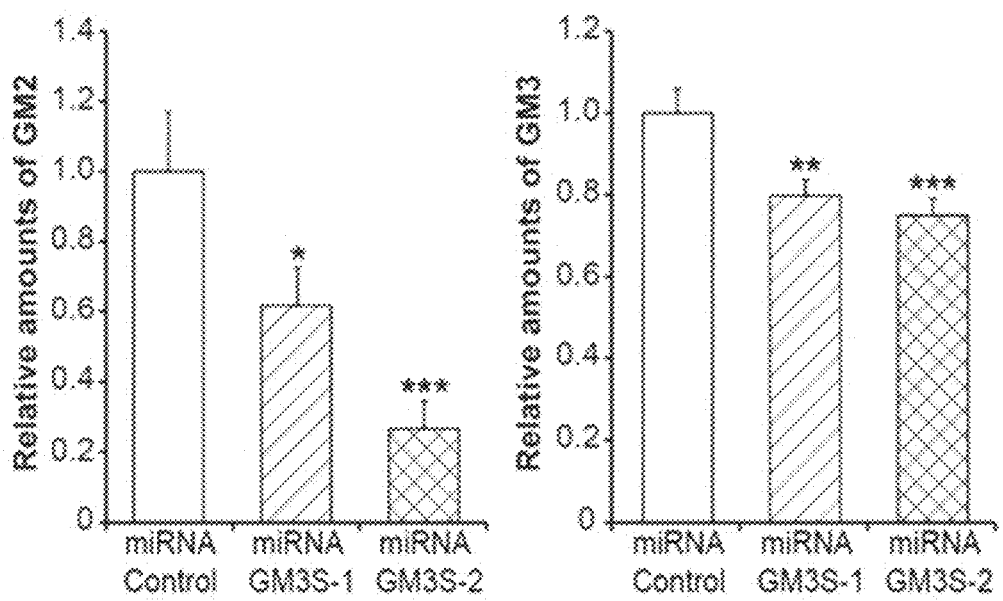
FIG. 6D

FIG. 6E
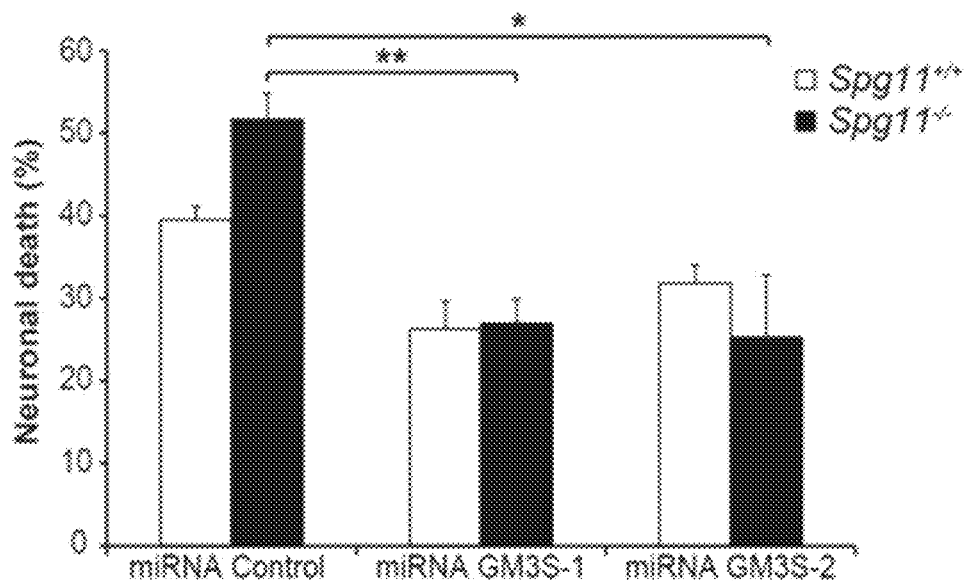
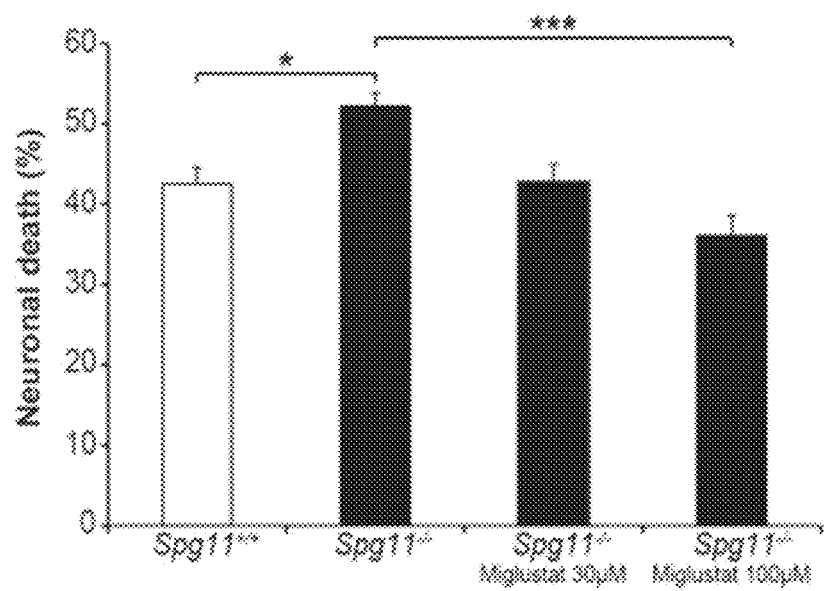
FIG. 6F

FIG. 8A                    FIG. 8B

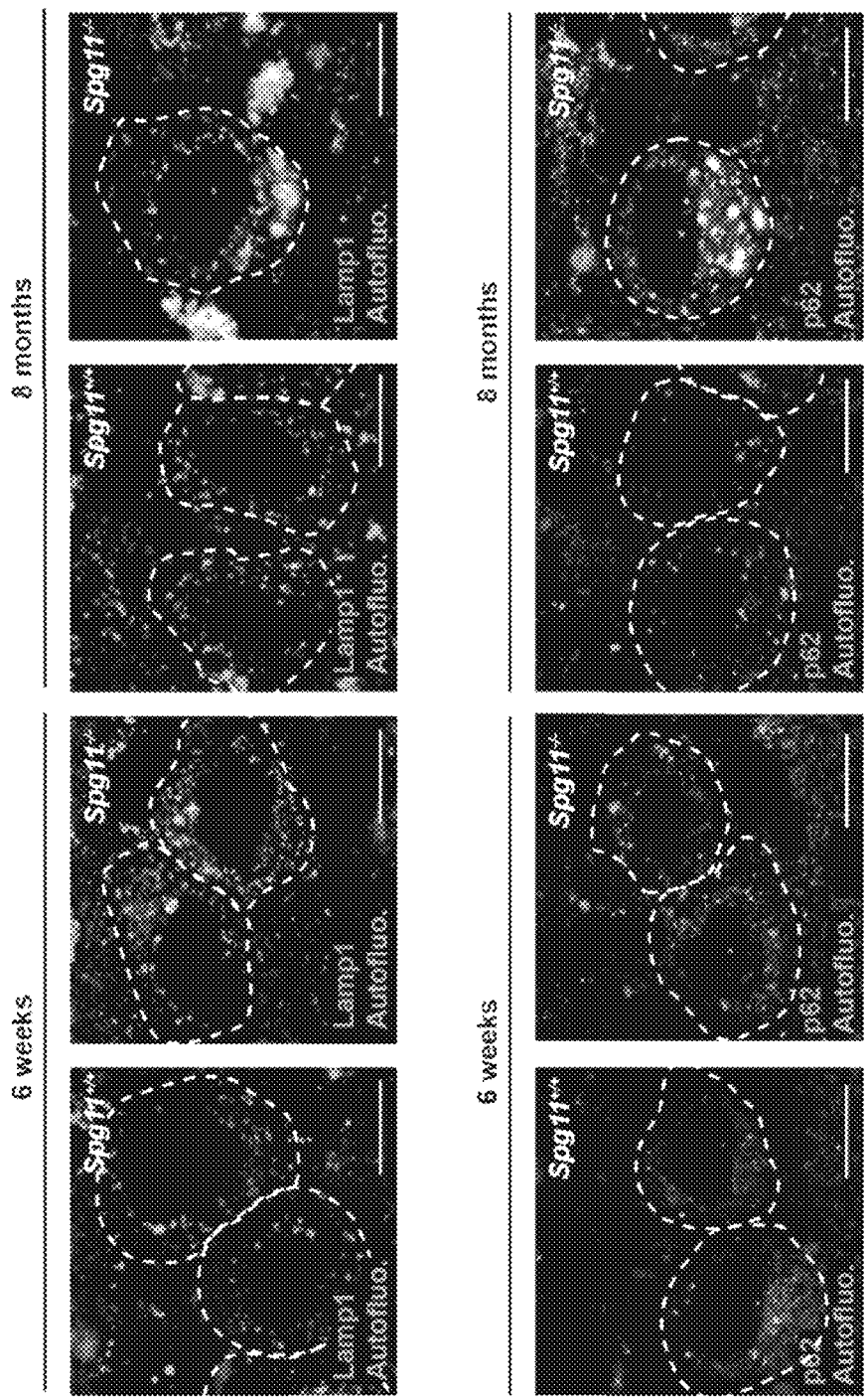

FIG. 10A
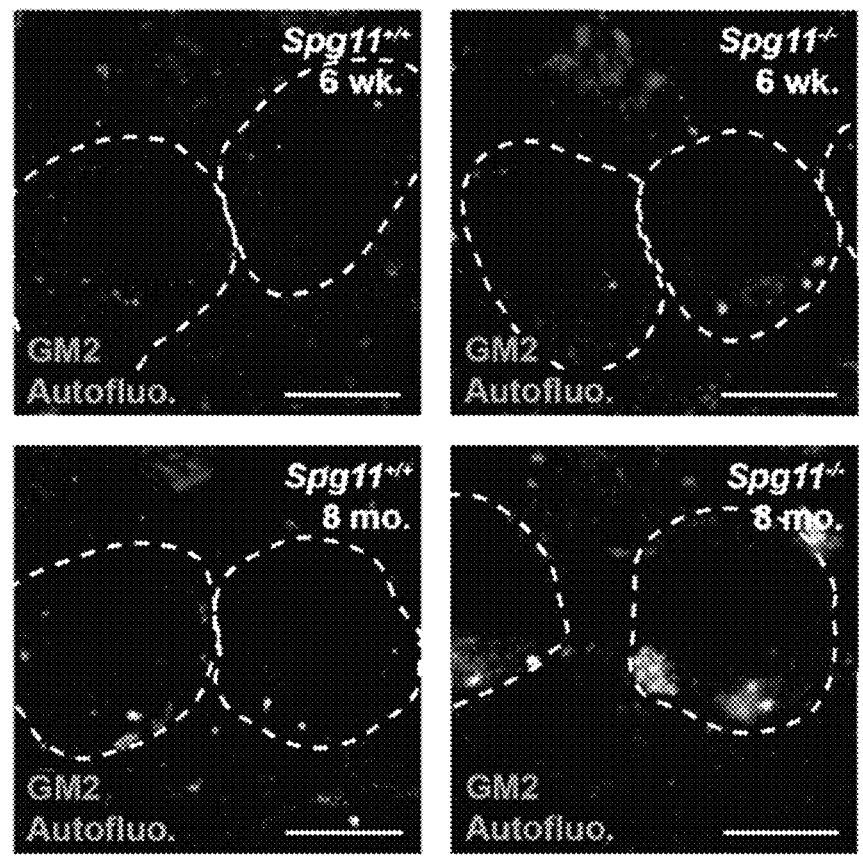
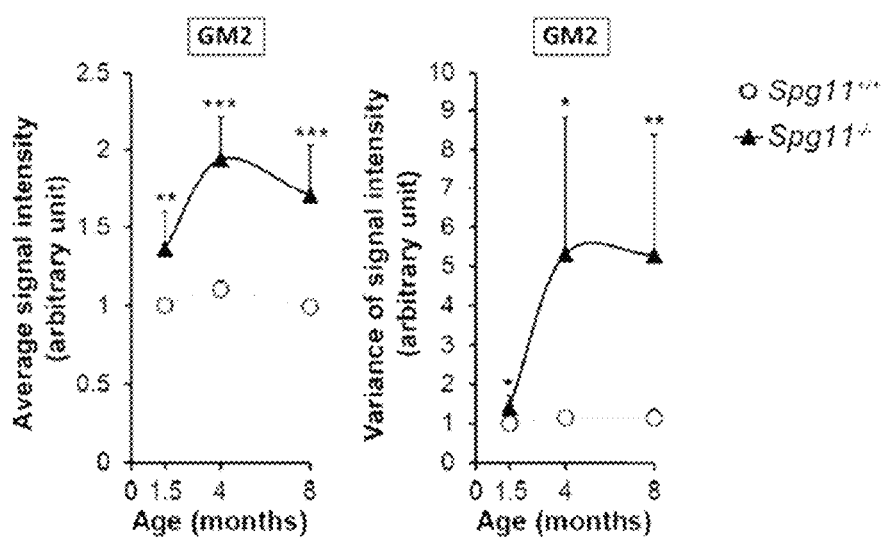
FIG. 10B

FIG. 10C
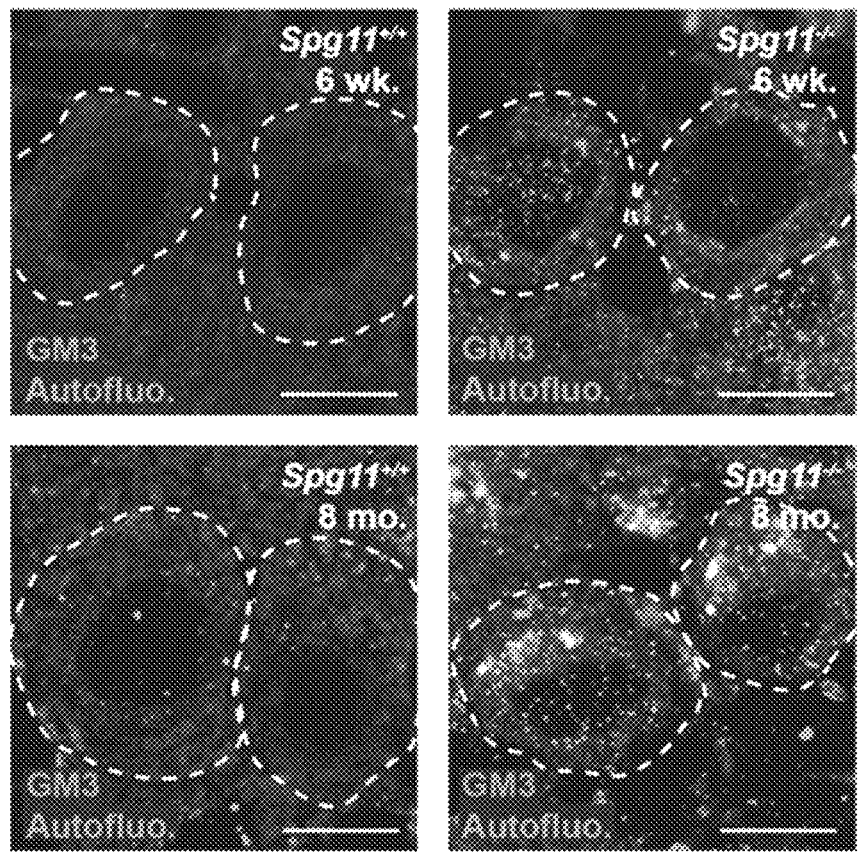
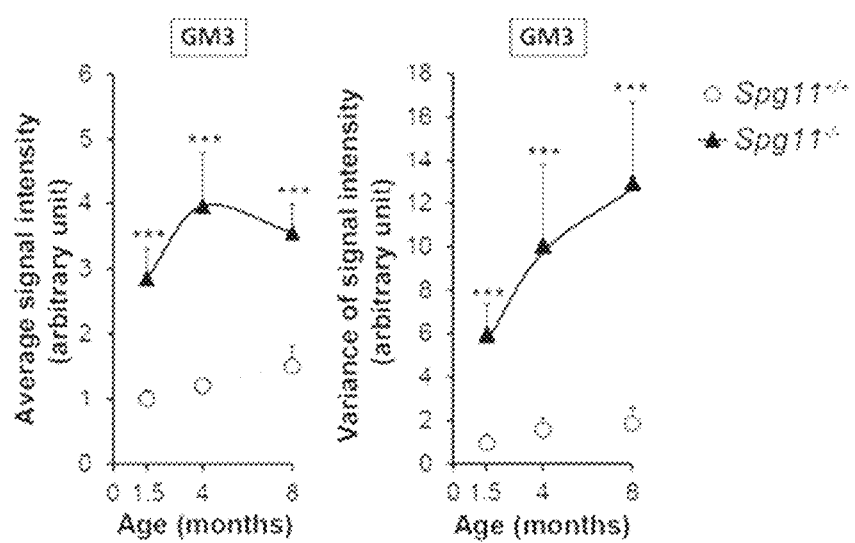
FIG. 10D

FIG. 11A
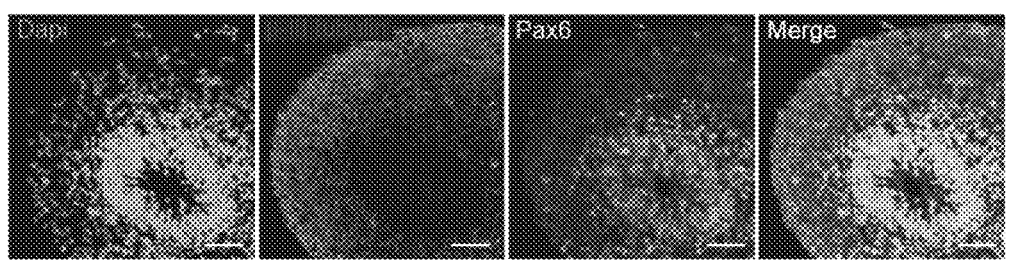
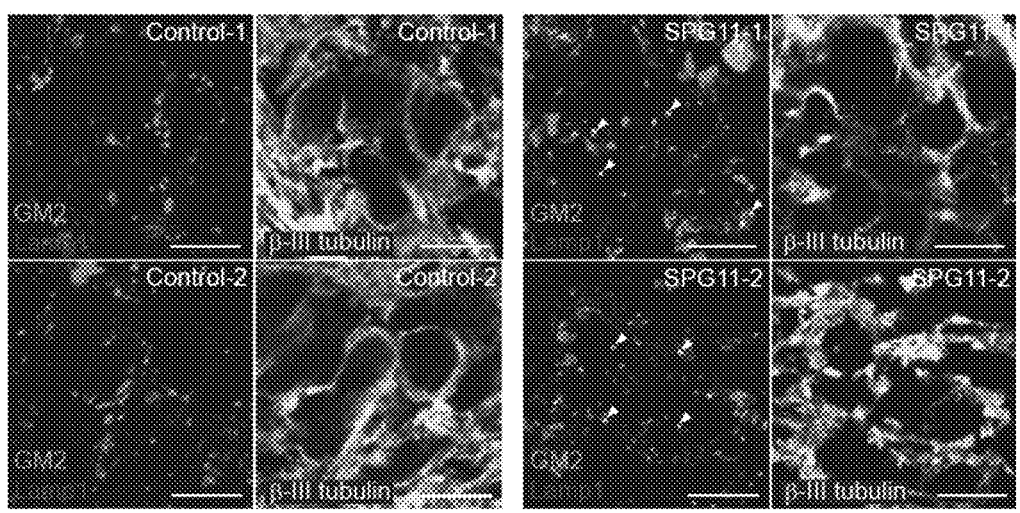
FIG. 11B

FIG. 11C
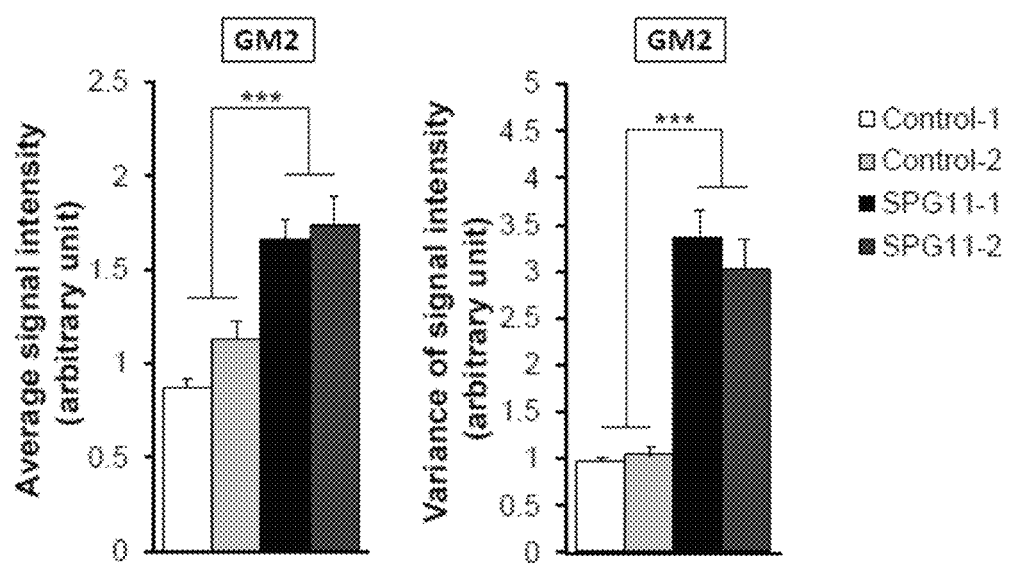
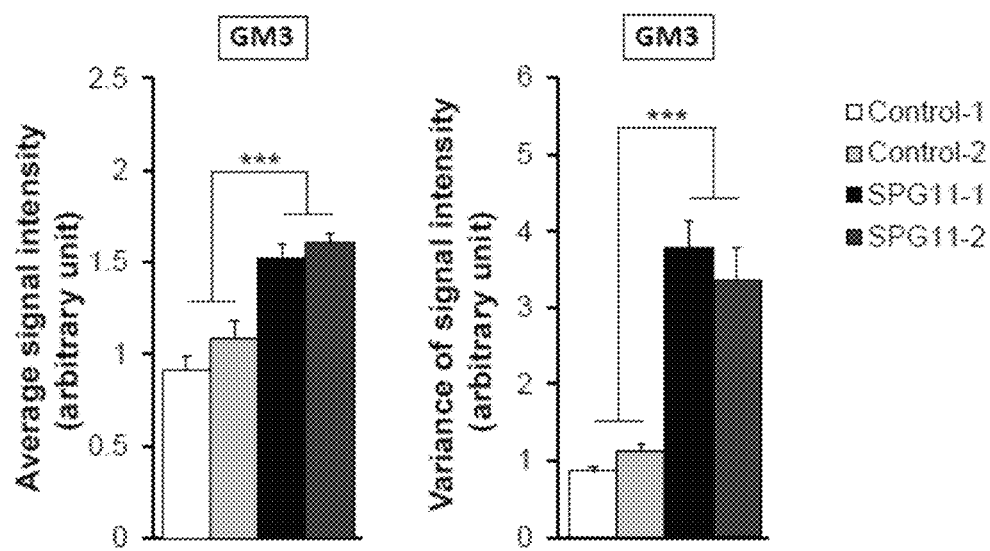
FIG. 11D

FIG. 11E
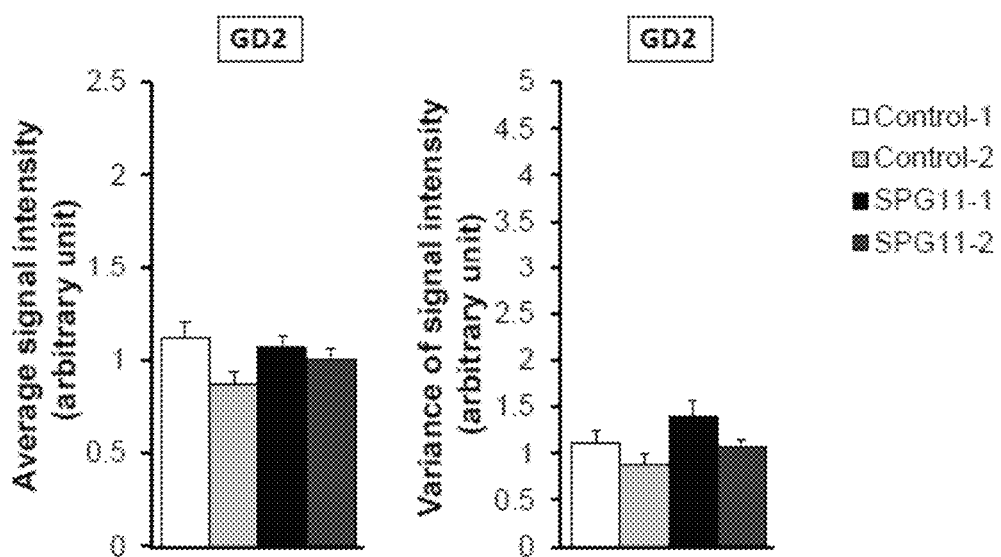
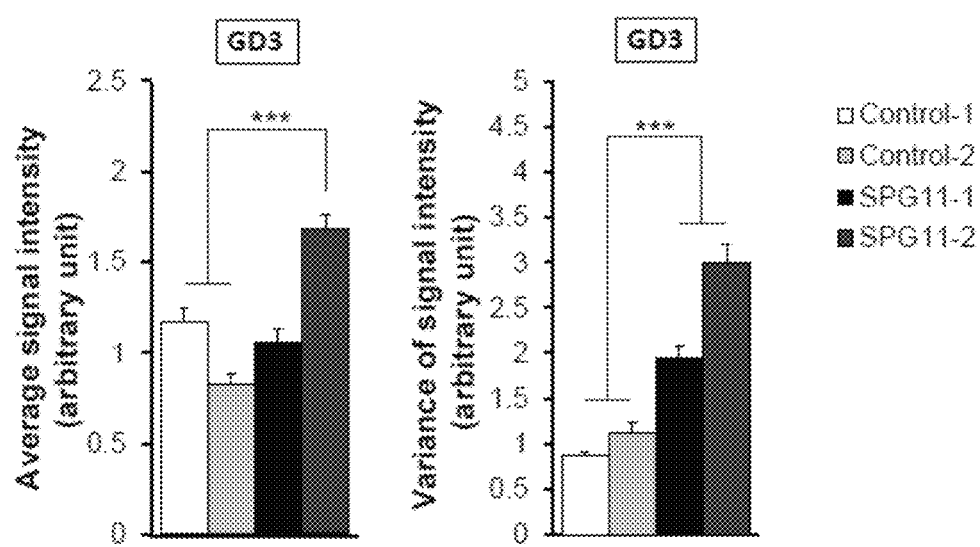
FIG. 11F

FIG. 12A
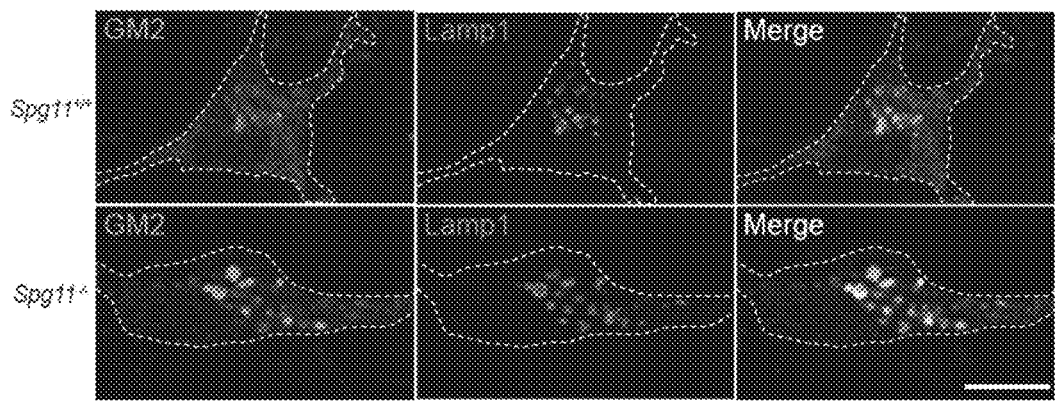
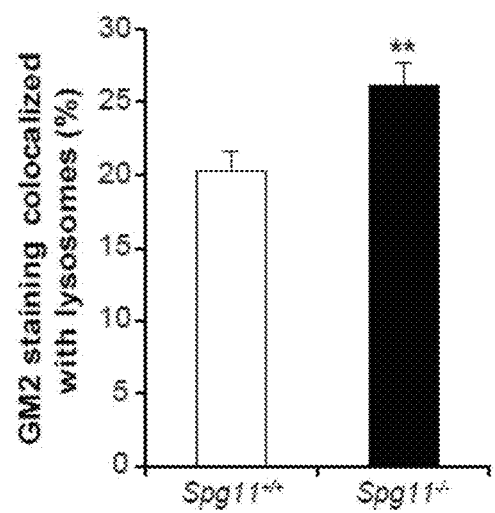
FIG. 12B

FIG. 13A
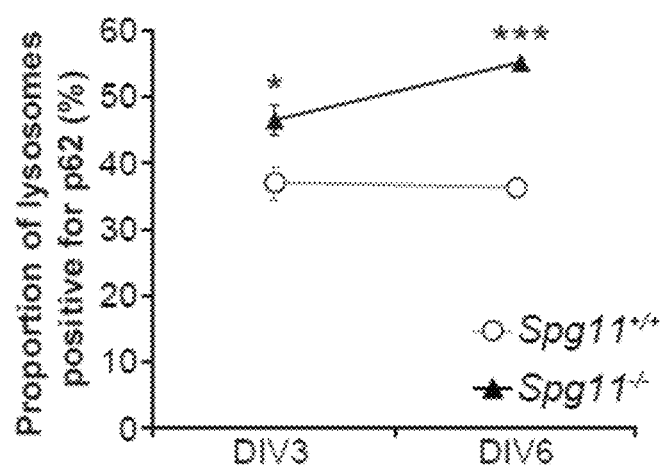
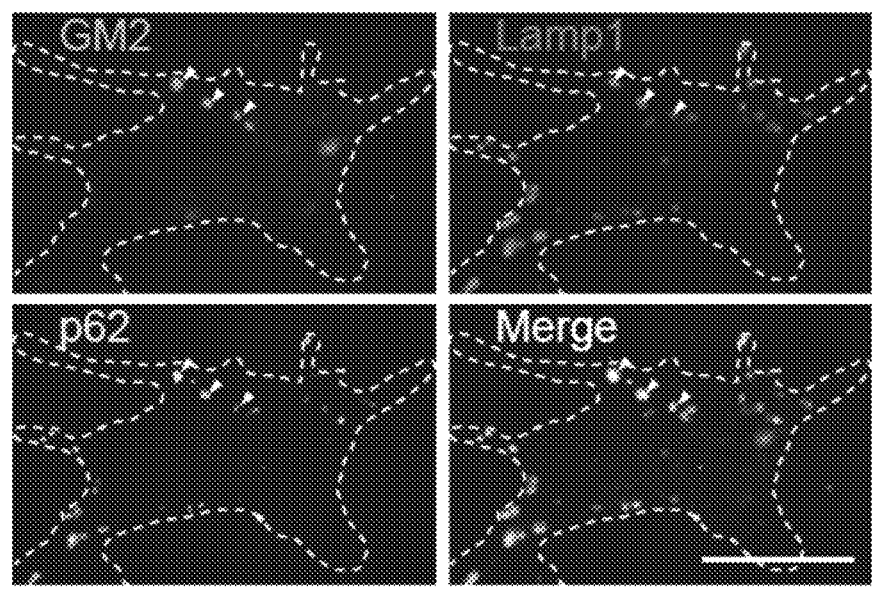
FIG. 13B

FIG. 13C
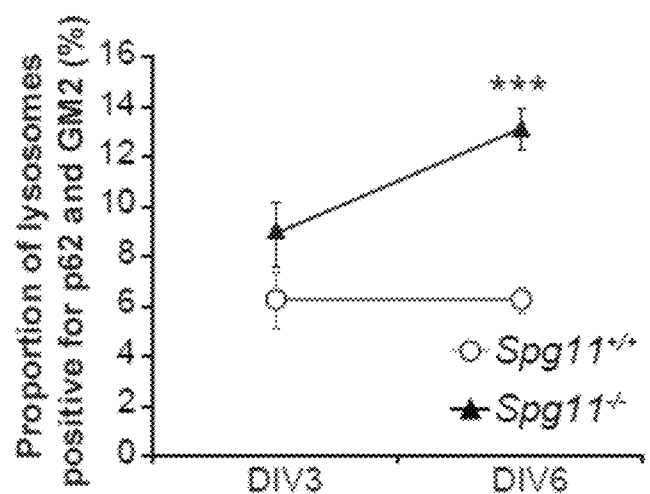
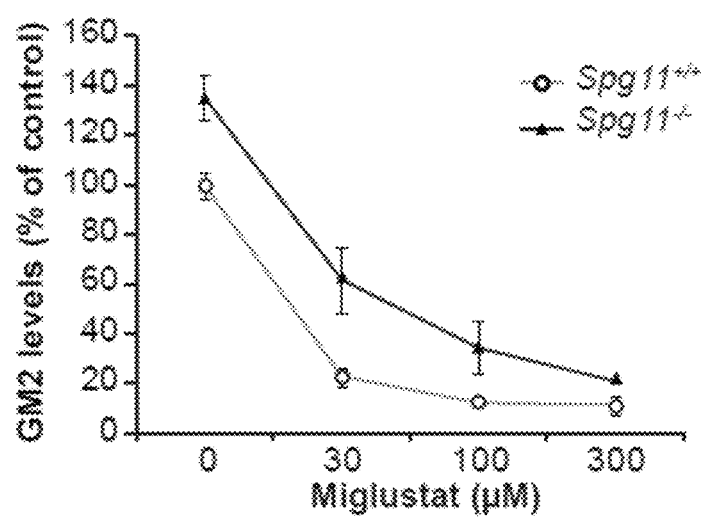
FIG. 13D

FIG. 13E
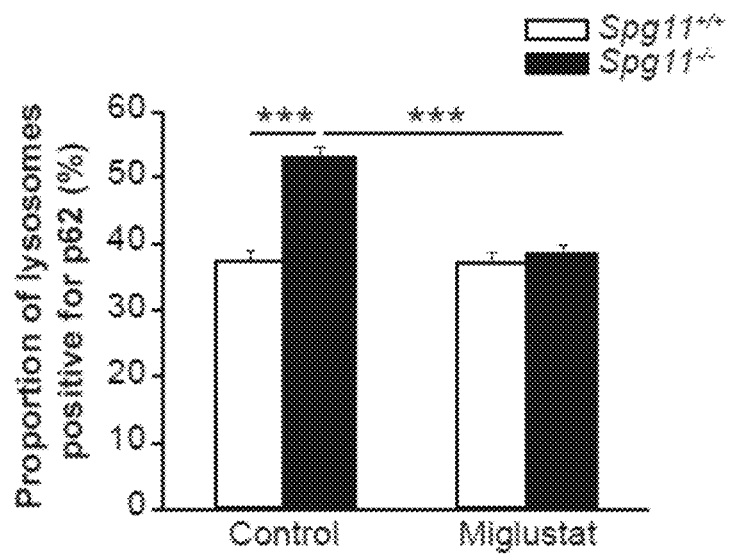
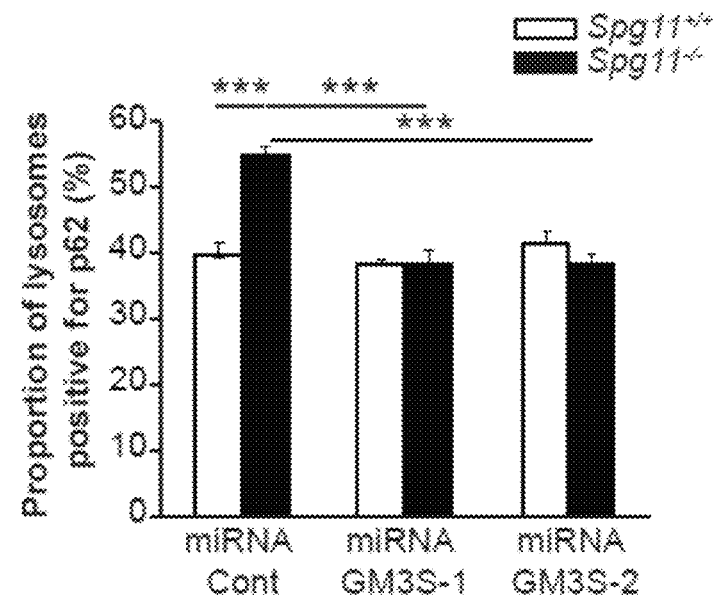
FIG. 13F

FIG. 13H
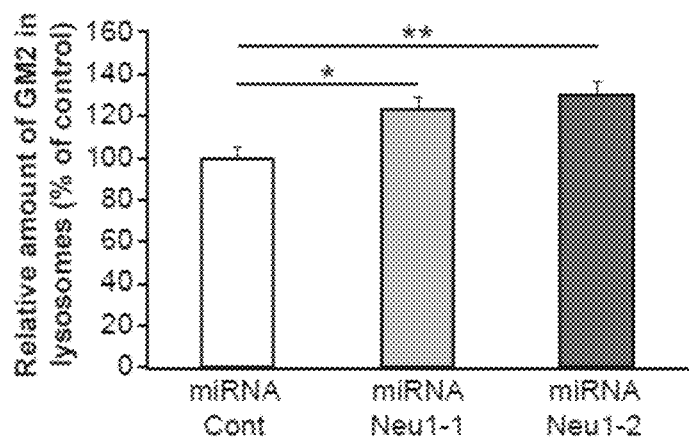
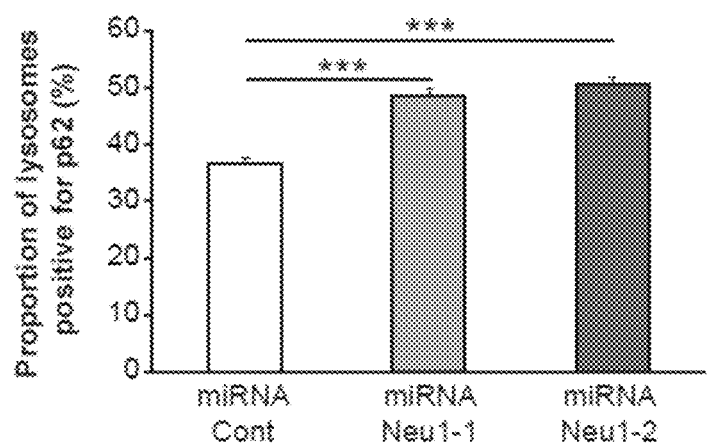
FIG. 13I

FIG. 14A
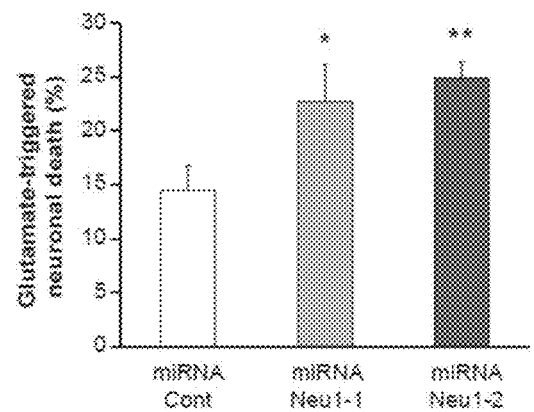
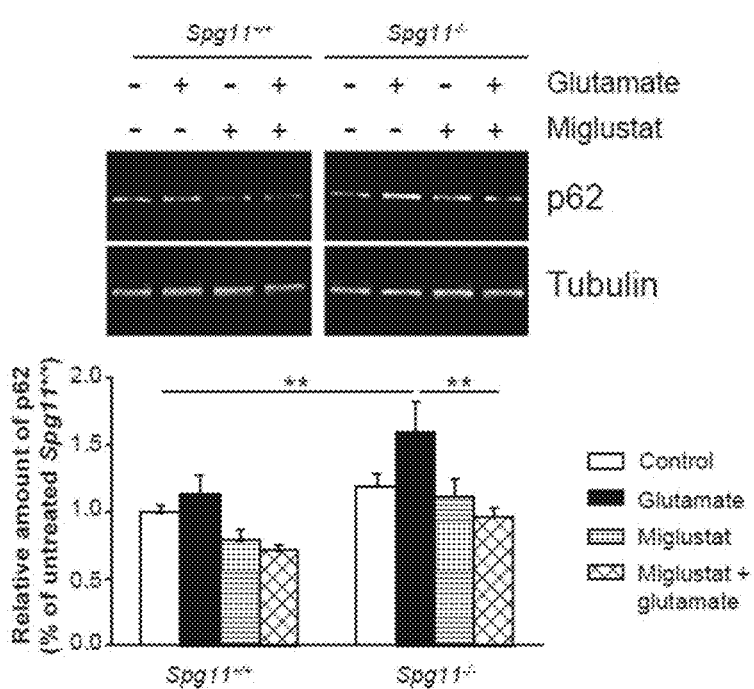
FIG. 14B

FIG. 15A
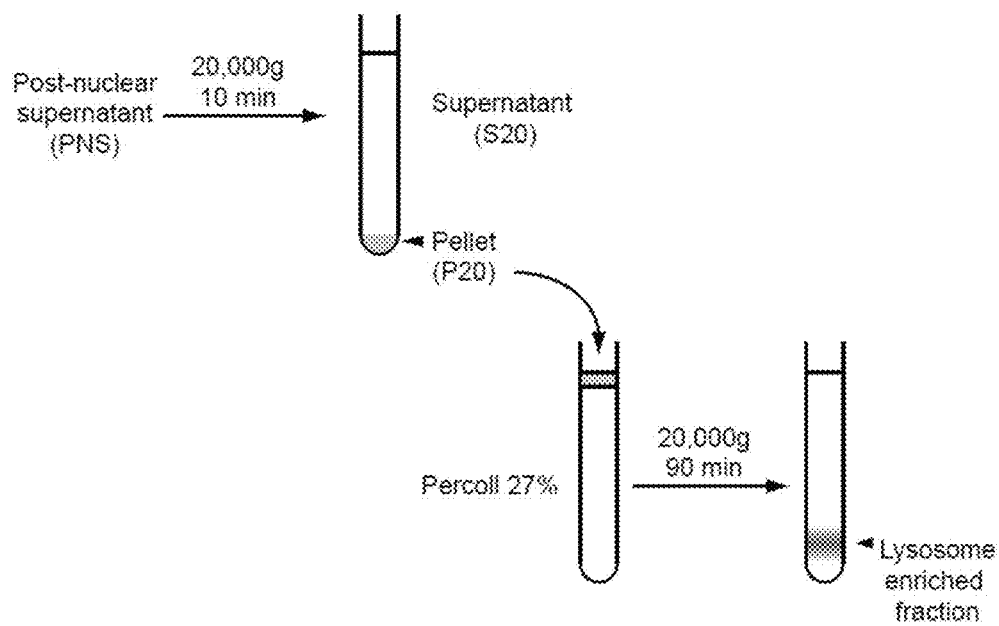
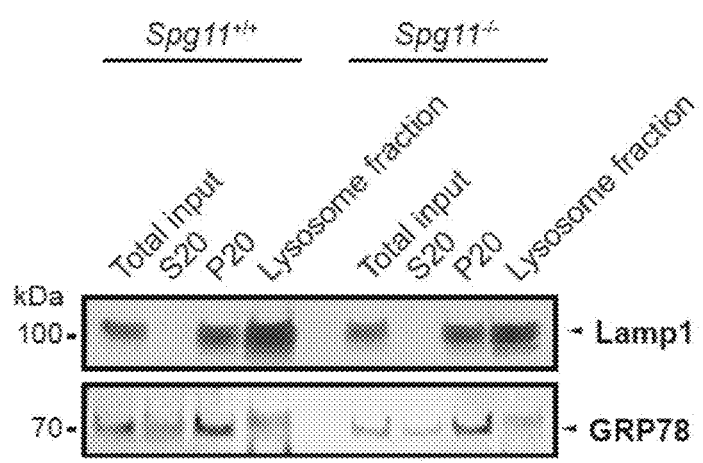
FIG. 15B

FIG. 17A
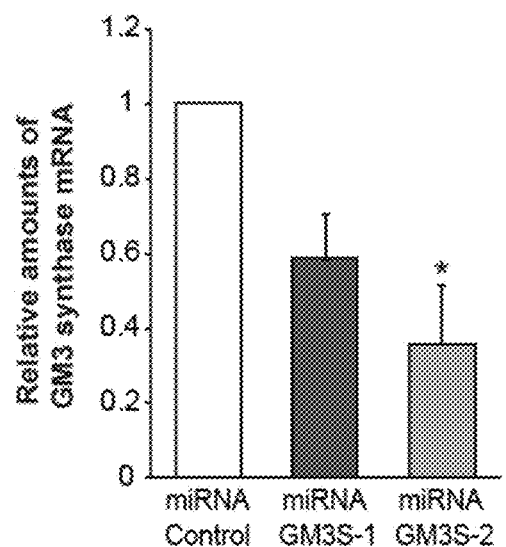
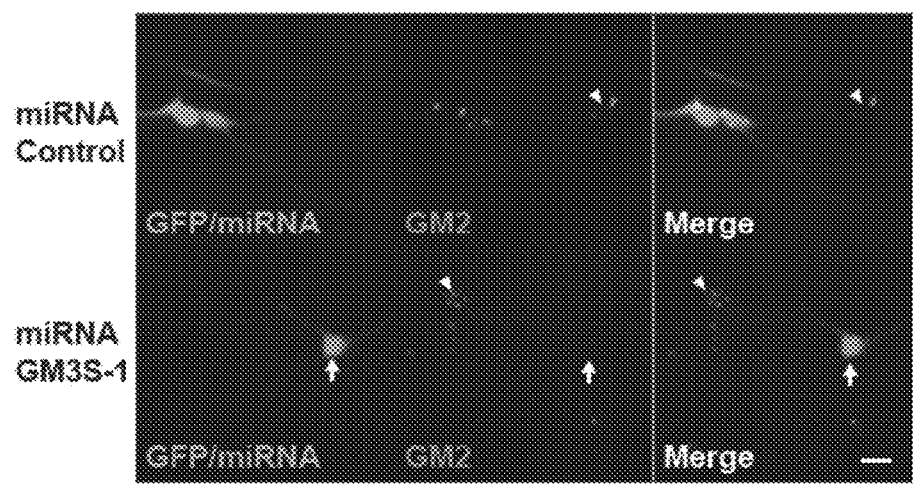
FIG. 17B

FIG. 19A
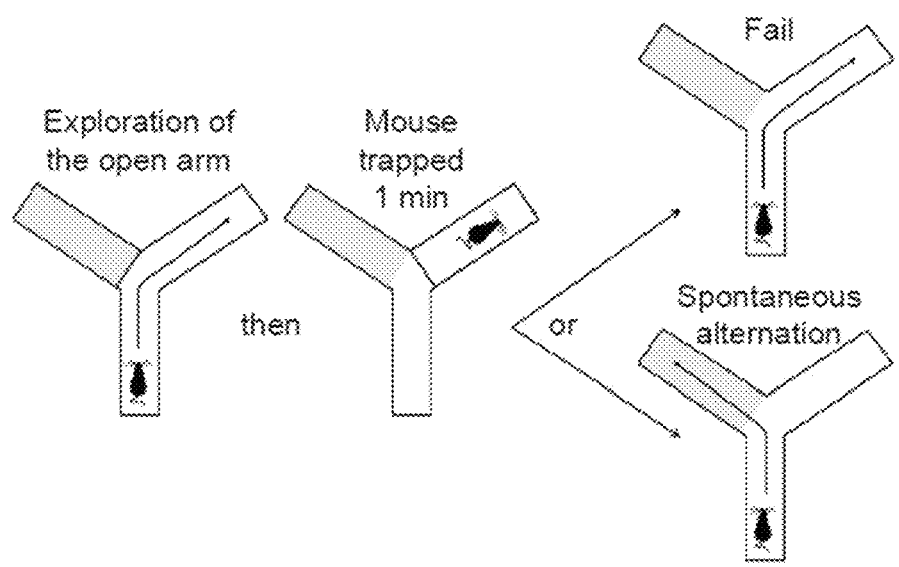
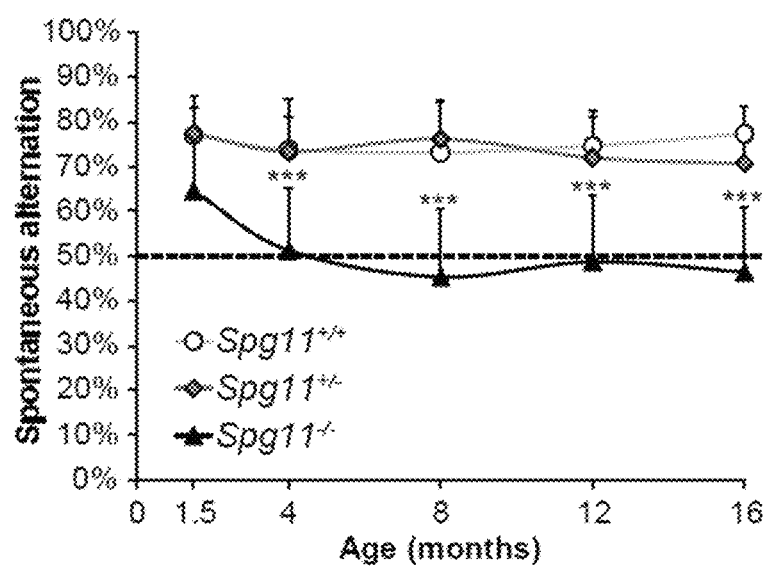
FIG. 19B

FIG. 19C
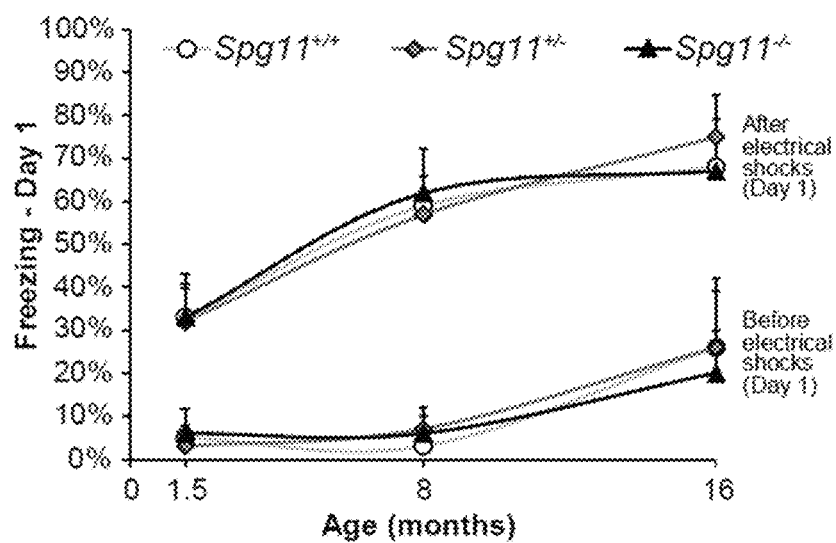
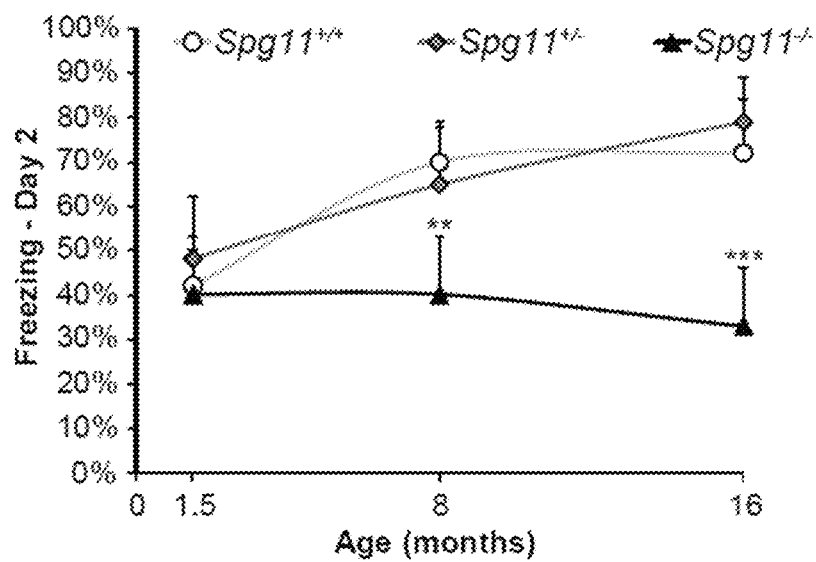
FIG. 19D

FIG. 20A
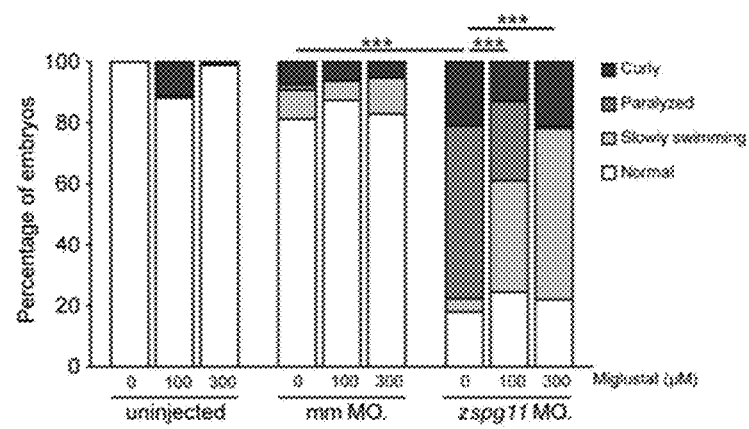
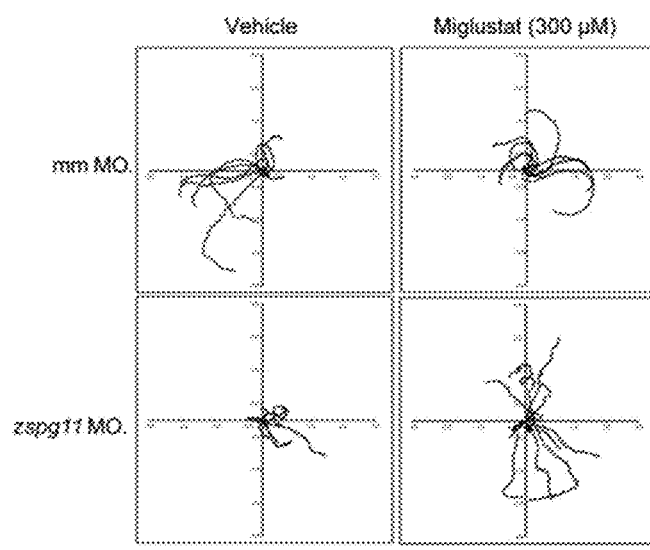
FIG. 20B

FIG. 20C
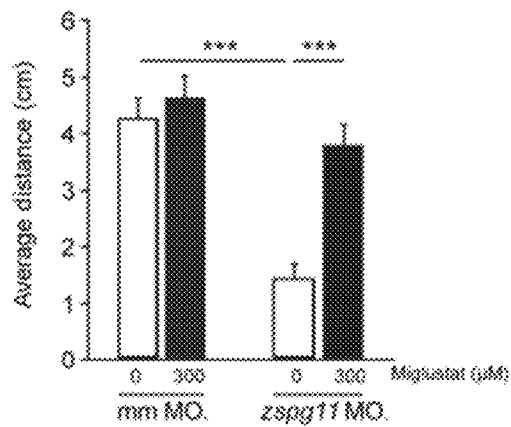
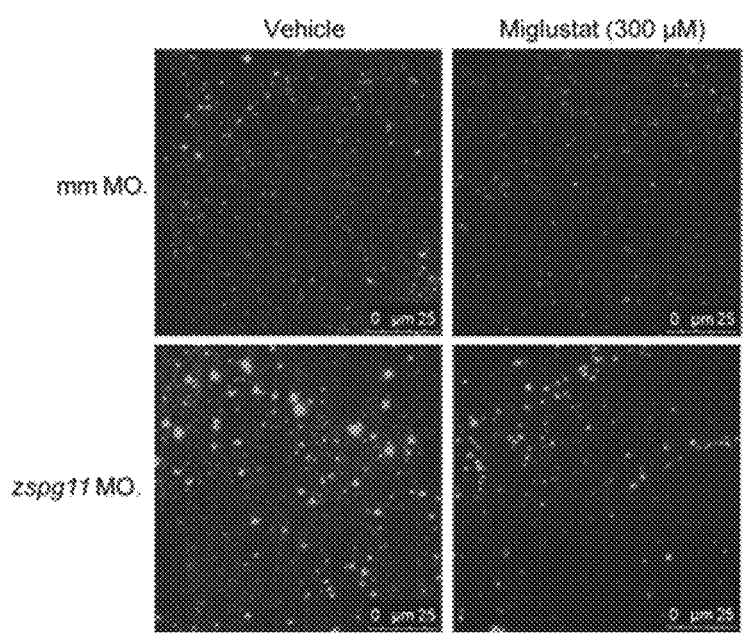
FIG. 20D

INHIBITORS OF GANGLIOSIDES METABOLISM FOR THE TREATMENT OF MOTOR NEURON DISEASES

RELATED APPLICATIONS

This application is a 35 U.S.C. § 371 filing of International Patent Application No. PCT/EP2017/078156, filed Nov. 3, 2017, which claims priority to European Patent Application No. 16197362.3, filed Nov. 4, 2016, the entire disclosures of which are hereby incorporated herein by reference in their entirety.

FIELD OF INVENTION

The present invention relates to the field of motor neuron diseases, in particular to methods for treating motor neuron diseases. The present invention relates to inhibitors of gangliosides metabolism for treating motor neuron diseases.

BACKGROUND OF INVENTION

Hereditary spastic paraplegias (HSP) constitute the second most frequent group of motor neuron diseases and are characterized by corticospinal tract neurodegeneration variably associated with other brain alterations in complex forms. They are characterized by progressive bilateral weakness, spasticity and a loss of vibration sense in the lower limbs. These symptoms are mostly due to the degeneration of upper motor neuron axons in the corticospinal tracts.

SPG11 (spastic paraplegia type 11) is the most common form of autosomal recessive HSP, accounting for 14 to 25% of cases and up to 70% of complex recessive forms. The main symptoms generally appear during the first decade of life and include spastic gait disorder, cognitive impairment, peripheral neuropathy, cerebellar ataxia, Parkinsonism and retinal degeneration. It is caused by a mutation in the SPG11 gene. The SPG11 gene (also referred to as SPATACSIN or KIAA1840) encodes a 2,443-amino acid protein called spatacsin. The vast majority of the mutations in SPG11 patients are nonsense or frameshift mutations as well as intragenic rearrangements predicted to result in a loss of spatacsin function.

The full-blown manifestations in SPG11 patients are indistinguishable from those observed in SPG15 patients, who have mutations of the ZFYVE26/SPG15 gene encoding spastizin. Spatacsin and spastizin interact with the adaptor protein complex AP5, one of the subunits of which, AP5-Z1 is encoded by the gene mutated in SPG48 patients.

No cure for this disease is currently available and a molecular characterization of the pathological mechanisms upstream from neuronal death is therefore required to identify putative therapeutic targets. Putative treatments in SPG11 might therefore be of interest to other forms of HSP as well, including SPG48 and SPG15, but also allelic disorders such as progressive amyotrophic lateral sclerosis and Charcot Marie Tooth diseases carrying mutations in genes in the same pathways.

The Applicant generated a Spg11-knockout mouse model to explore the consequences of a loss of spatacsin function at an early stage of the disease and to investigate the mechanisms preceding neuronal death. The Applicant observed early motor deficits consistent with the symptoms observed in humans.

Surprisingly, the Applicant discovered that inhibiting gangliosides metabolism (in particular inhibiting the glucosylceramide synthase or downregulating GM3 synthase) protected Spg11-knockout neurons from death. Inhibitors of glucosylceramide synthase are usually used for the treatment of lysosomal storage diseases (LSDs) which are severe multisystemic human genetic disorders, including a neuronal alteration as part of their phenotype, and are caused by the deficiency of a single enzyme. So far, despite the considerable genetic heterogeneity of motor neuron diseases such as HSP, the functions of the proteins encoded by the mutated genes converge on a small number of cellular functions, including impaired cellular membrane trafficking, more particularly, axonal transport of macromolecules and organelles. Surprisingly, the Applicant discovered that SPG11 loss of function leads to progressive lysosome dysfunction, mimicking a milder LSD-like phenotype as no compound accumulate specifically in lysosomes through a complete blockage of an enzymatic function.

Even more surprisingly, the Applicant observed that motor deficit symptoms were preceded by lysosomal accumulation of lipids, including ganglioside monosialic (GM)2 and GM3 gangliosides which also preceded neuronal death.

SUMMARY

One object of the invention is a composition for use in treating a motor neuron disease comprising, consisting of or consisting essentially of at least one inhibitor of gangliosides metabolism.

In one embodiment, said inhibitor of ganglioside metabolism is selected from the group comprising small organic molecules, antibodies, antagonists, inhibitor scaffold, aptamers, ribozymes, peptides, chemical chaperones, ribonucleic acid interference (RNAi), oligonucleotide antisense, small interfering RNA (siRNA), antisense RNA (asRNA), morpholinos, and engineered nucleases.

In another embodiment, said inhibitor of gangliosides metabolism is an inhibitor of glucosylceramide synthase and is preferably selected from the group comprising: imino sugars, analogs of D-threo-1-phenyl-2-decanoylamino-3-morpholino-propanol (PDMP), ceramide analogs, carboxamides, carbamates, glycoside hydrolase chaperones.

In another embodiment, said inhibitor of glucosylceramide synthase is selected from the group comprising: quinuclidin-3-yl (2-(4'-fluoro-[1, -biphenyl]-3-yl)propan-2-yl)carbamate (GZ161), N-butyldeoxynojirimycin (NB-DNJ), N-[(1R,2R)-1-(2,3-dihydro-1,4-benzodioxin-6-yl)-1-hydroxy-3-(1-pyrrolidinyl)-2-propanyl]octanamide, N-(5-adamantane-1-yl-methoxypentyl) deoxynojirimycin (AMP-DNJ); N-butyl-1-deoxy-nojirimycin (KTB-DNJ); N-ethyl-1-dexynojirimycin (NE-DNJ); N-butyldeoxymannojixamycin; N-5-carboxyl-1-deoxynojiramycin; N-docecyl-1-deoxynojirimycin; nojirimycin bisulfate; nojiximycin-1-sulfonic acid; N-(n-nonyl)-1-deoxynojirimycin; N-(7-oxadecyl)-1-deoxynojirimycin; N-(7-oxa-9,9,9,-trifluorononyl)-1-deoxynojirimycin; (2R,3S,4R,5S)-2-(Hydroxymethyl)-3,4,5-piperidinetriol; N-butyldeoxygalactonojirimycin (NB-DGJ); N-(n-nonyl) deoxynojirimycin; (3S,4S)-3-(hydroxymethyl)pyrrolidine-3,4-diol (isoLAB); 1,4-dideoxy-1,4-imino-D-arabinitol, (2S,3R,4S,5R)-3,4,5-trihydroxy-6-oxopiperidine-2-carboxylic acid, D-glucaro-delta-lactam, 1,4-dideoxy-2-hydroxymethyl-1,4-imino-D-threitol; (2S,3S,4R)-2,4-bis(hydroxymethyl)pyrrolidine-3,4-diol, isoDGDP, D-threo-1-phenyl-2-decanoylamino-3-morpholino-propanol (PDMP); enantiomers of PDMP, L-threo- and DL-erythro-1-phenyl-2-amino-1,3-propanediol, the D-threo (R,R) enantiomer; 1-phenyl-2-palmitoylamino-3-morpholino-1-propanol; 1-phenyl-2-palmitoylamino-3-pyrrolidino-1-propanol (P4), D-threo-1-ethylenedioxyphenyl-2-palmitoyl-3-pyrrolidino-propanol (EtDO-P4); DL-threo-1-phenyl-2-palmitoylamino-3-pyrrolidino-1-propanol (DL-threo-P4); 2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide; N-((1R,2R)-1-(2,3-dihydrobenzo[b][1,4]dioxin-6-yl)-1-hydroxy-3-(pyrrolidin-1-yl)propan-2-yl)nonanamide; BML-119; IV-231B, (S)-quinuclidin-3-yl (2-(2-(4-fluorophenyl)thiazol-4-yl)propan-2-yl)carbamate (S)-2-hydroxysuccinate (GZ 452), quinuclidin-3-yl (2-(4'-fluoro-[1, -biphenyl]-3-yl)propan-2-yl)carbamate, (1R,2R)-octanoic acid[2-(2',3'-dihydro-benzo[1,4]dioxin-6'-yl)-2-hydroxy-1-pyrrolidin-1-ylmethyl-ethyl]-amide-L-tartaric acid, EXEL-0346, isofagomine, trans-4-(2-amino-3,5-dibrombenzylamino)-cyclohexanol, 5-(4-chlorophenyl)-6-ethyl-2,4-pyrimidinediamine, (3R,4R,5R)-5-(hydroxymethyl)-3,4-piperidinediol, ambroxol, imiglucerase,), α-homogalactonojirimycin, α-homoallonojirimycin, β-1-C-butyl-DGJ, N-nonyl-DNJ.

In another embodiment, said inhibitor of gangliosides metabolism is an inhibitor of GM3 synthase. In one embodiment, the inhibitor of GM3 synthase is a miRNA, preferably selected from the group comprising: SEQ ID NO: 3, SEQ ID NO: 4 and function conservative variants thereof. In one embodiment, the inhibitor of GM3 synthase is the carbon-linked analog of cytidine monophospho-N-acetylneuraminic acid.

In another embodiment, the composition is to be administered by oral, topical, transdermal, intramuscular, subcutaneous, intravenous, parenteral, intranasal administration.

In another embodiment, the motor neuron disease is selected from the group comprising hereditary spastic paraplegia (HSP) (such as, for example, HSP presenting peripheral neuropathies), hereditary spastic paraparesis, familial spastic paraplegias, French settlement disease, or Strumpell-Lorrain disease, infantile-onset ascending hereditary spastic paralysis, MASA syndrome, also called CRASH syndrome and Gareis-Mason syndrome, cataracts with motor neuronopathy, short stature and skeletal abnormalities, MAST syndrome, Allan-Hemdon-Dudley syndrome, Troyer syndrome, Lison syndrome, spastic ataxias (in particular hereditary spastic ataxia, such as, for example, spastic ataxia 2), SPOAN syndrome, peripheral neuropathies, Kjellin syndrome, hereditary and sensory motor neuropathies (HMSN). In one embodiment, the motor neuron disease is HSP, preferably selected from SPG11, SPG15, SPG48, SPG4 and SPG7.

Another object of the invention is a pharmaceutical composition for use in treating a motor neuron disease comprising, consisting of or consisting essentially of at least one inhibitor of gangliosides metabolism as described here above and a pharmaceutically acceptable excipient.

Another object of the invention is a medicament for use in treating a motor neuron disease comprising, consisting of or consisting essentially of at least one inhibitor of gangliosides metabolism as described here above.

Definitions

In the present invention, the following terms have the following meanings:
"About": preceding a figure means plus or less 10% of the value of said figure.
"Inhibitor of gene expression" refers to a natural or synthetic compound that has a biological effect to inhibit or significantly reduce the expression of a gene. Consequently, in one embodiment, an "inhibitor of the expression of enzymes or of a cofactor of an enzyme of the gangliosides metabolism pathway" refers to a natural or synthetic compound that has a biological effect to inhibit or significantly reduce the expression of the gene(s) encoding for the enzymes or their cofactors involved in the pathways of gangliosides metabolism.
"Antagonist" is used indifferently to denote a "true" antagonist or an inverse agonist of a receptor. A "true" receptor antagonist is a compound which binds to a receptor and blocks the biological activation of that receptor. In one embodiment, a true receptor antagonist prevents the action of the receptor agonist, for example, by competing with the agonist for said receptor. An inverse agonist is a compound which binds to the same receptor as the agonist but exerts the opposite effect. Inverse agonists have the ability to decrease the constitutive level of receptor activation in the absence of an agonist.
"Inhibitor or Antagonist of at least one enzyme or of at least one cofactor of an enzyme of the gangliosides metabolism pathways" includes any chemical entity that, upon administration to a patient or to a cell expressing a functional ganglioside metabolism pathway (in particular functional enzymes, ligands thereof, etc.), results in inhibition or down-regulation of a biological activity associated with activation of at least one enzyme of the gangliosides metabolism pathways in the patient or cell, including any of the downstream biological effects otherwise resulting from the binding of the enzyme of the gangliosides metabolism pathways to its natural ligand. Such inhibitor or antagonist includes any agent that can block activation of the enzyme of the gangliosides metabolism pathways or any of the downstream biological effects of the enzyme of the gangliosides metabolism pathways. For example, such inhibitors or antagonists can be a competitive inhibitor and act by occupying the ligand binding site or a portion thereof of the enzymes of the gangliosides metabolism pathways, thereby making the enzyme inaccessible to its natural ligand so that its normal biological activity is prevented or reduced. Other examples of such inhibitors or antagonists include without limitation non-competitive inhibitors, uncompetitive inhibitors and mixed inhibitors. Non-competitive inhibitors refer to inhibitors reducing the activity of the target enzyme and binding equally well to the enzyme whether or not it has already bound the substrate. Non-competitive inhibitors may bind to the target enzyme whether or not the substrate has already been bound, but if it has a higher affinity for binding the target enzyme in one state or the other, it is called a mixed inhibitor. Uncompetitive inhibitors refer to inhibitors binding only to the complex formed between the enzyme and the substrate, acting typically in reactions with two or more substrates or products.
"Peptide" refers to a linear polymer of amino acids of at least 2 amino acids and less than 50 amino acids linked together by peptide bonds. Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. Stereoisomers (e.g., D-amino acids) of the twenty conventional amino acids, unnatural amino acids such as alpha,alpha-disubstituted amino acids, N-alkyl amino acids, lactic acid, and other unconventional amino acids may also be suitable components for compounds of the technology provided herein. Examples of unconventional amino acids include: beta-alanine, 1-naphthylalanine, 2-naphthylalanine, 3-pyridylalanine, 4-hydroxyproline, O-phosphoserine, N-acetylserine, N-formylmethionine, 3-methylhistidine, 5-hydroxylysine, nor-leucine, and other similar amino acids and imino acids (e.g., 4-hydroxyproline).

"Pharmaceutically acceptable excipient" refers to an excipient that does not produce any adverse, allergic or other unwanted reactions when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

"Small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

"Subject" refers to a mammal, preferably a human. In one embodiment, a subject may be a "patient", i.e. a female or a male, an adult or a child, who/which is awaiting the receipt of, or is receiving medical care or was/is/will be the object of a medical procedure, or is monitored for the development of a disease.

"Therapeutically effective amount" refers to means level or amount of agent that is aimed at, without causing significant negative or adverse side effects to the target, (1) delaying or preventing the onset of a motor neuron disease; (2) slowing down or stopping the progression, aggravation, or deterioration of one or more symptoms of the motor neuron disease; (3) bringing about ameliorations of the symptoms of the motor neuron disease; (4) reducing the severity or incidence of the motor neuron disease; or (5) curing the motor neuron disease. A therapeutically effective amount may be administered prior to the onset of the motor neuron disease, for a prophylactic or preventive action. Alternatively or additionally, the therapeutically effective amount may be administered after the onset of the motor neuron disease, for a therapeutic action. In one embodiment, a therapeutically effective amount of the composition is an amount that is effective in reducing at least one symptom of a motor neuron disease.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for the targeted pathologic disorder if, after receiving a therapeutic amount of the composition of the present invention, the patient shows observable effects on one or more of the followings; (i) decrease in neuronal cell death; (iii) alleviation or decrease of cognitive impairment or of pyramidal signs; (iv) relief to some extent, of one or more of the symptoms associated with the specific disorder or condition; (v) reduced morbidity and mortality, and (vi) improvement in quality of life issues. The above parameters for assessing successful treatment and improvement in the disorder are readily measurable by routine procedures familiar to a physician.

DETAILED DESCRIPTION

The Applicants herein demonstrated, using a SPG11$^{-/-}$ mouse model recapitulating the main features of human SPG11 pathology, that SPG11 is associated with lipid (in particular GM2, GM3, GD2 and GD3) accumulation within lysosomes. This accumulation of lipid was further confirmed in SPG11 human patients and in a zebrafish model of the SPG11 disorder. These experimental results thus strongly support the use of an inhibitor of ganglioside metabolism, and in particular of an inhibitor of gangliosides synthesis, for treating this disease.

One object of the invention is a composition for treating or for use in treating a motor neuron disease, wherein said composition comprises, consists of or consists essentially of at least one inhibitor of gangliosides metabolism.

Gangliosides metabolism relates to the biosynthesis of the O-, a-, b- and c-series of gangliosides from ceramide. Such metabolism involves different pathways and in particular sequential activities of enzymes such as sialyltransferase and glycosyltransferase.

In one embodiment, the inhibitor of gangliosides metabolism (that may also be referred to herein as an inhibitor of the ganglioside metabolism pathways) is thus an inhibitor of ganglioside biosynthesis.

In one embodiment, said inhibitor inhibits (i) the activity of at least one enzyme (or of at least one cofactor thereof) of the ganglioside metabolism pathways, and/or (ii) the protein expression of at least one enzyme (or of at least one cofactor thereof) of the ganglioside metabolism pathways. In one embodiment, said inhibitor is an inhibitor of the gene expression of at least one enzyme (or of at least one cofactor thereof) of the gangliosides metabolism pathways described herein and/or an inhibitor of downstream pathways.

Examples of inhibitors of the activity or of the protein expression of at least one enzyme (or of at least one cofactor thereof) of the gangliosides metabolism pathways include without limitation, small organic molecules, peptides, inhibitor scaffolds, antagonists, antibodies, aptamers, and chemical chaperones.

In one embodiment, the inhibitor of gangliosides metabolism is a competitive inhibitor of at least one enzyme of the gangliosides metabolism pathway (or of at least one cofactor thereof).

In another embodiment, the inhibitor of gangliosides metabolism is an uncompetitive inhibitor of at least one enzyme of the gangliosides metabolism pathway (or of at least one cofactor thereof).

In another embodiment, the inhibitor of gangliosides metabolism is a non-competitive inhibitor of at least one enzyme of the gangliosides metabolism pathway (or of at least one cofactor thereof).

In another embodiment, the inhibitor of gangliosides metabolism is a mixed inhibitor of at least one enzyme of the gangliosides metabolism pathway (or of at least one cofactor thereof).

In one embodiment, the inhibitor of the invention is a selective inhibitor of at least one enzyme of the gangliosides metabolism pathways (or of at least one cofactor thereof).

As used herein, the term "selective inhibitor" refers to a compound having an half maximal inhibitory concentration ($IC_{50}$) inferior or equal to about 5, 10, 20, 30, 40, 50, 60, 70, 80, 90, 100, 200, 300, 400, 500, 600, 700, 800, 900, nM, 1, 5, 10, 20, 30, 40, 50, 60, 70, 80, 90, 100, 150, 200 µM.

In one embodiment, compounds of the invention are considered active if their $IC_{50}$ values are inferior or equal to 200 µM. For instance, compounds with a smaller $IC_{50}$ value, for example an $IC_{50}$ of 10 nM, are considered more potent than a compound with a larger $IC_{50}$ value, for example, an $IC_{50}$ value of 1 µM.

Techniques to determine the $IC_{50}$ of a compound are well known to the skilled artisan and include without limitation, functional antagonist assay, competition binding assays, cell-based cAMP assay, western blot, and qRT-PCR.

For instance, $IC_{50}$ can be determined in the presence of a range of concentrations of the inhibitor of the invention in order to establish a dose-response curve. From that dose response curve, an $IC_{50}$ value may be deduced which represents the concentration of antagonist necessary to inhibit 50% of the response to an agonist in defined concentration. The $IC_{50}$ value may be readily determined by the one skilled in the art by fitting the dose-response plots with a dose-response equation. $IC_{50}$ values can be converted into affinity constant (Ki) using the assumptions of Cheng and Prusoff.

Techniques to determine the activity of an enzyme (or of a cofactor thereof) of the gangliosides metabolism pathways such as for example: glucosylceramide synthase, GM3 synthase, glucosylceramidase beta (GBA)2 and GBA1 or any enzyme from the gangliosides metabolism pathways are well known to the skilled artisan. For instance, the activity of the glucosylceramide synthase may be measured as the amount of UDP-glucose consumed during the reaction catalyzed by this enzyme. In particular, another enzyme, e.g. UDP-glucose dehydrogenase, is generally used to create NADH from UDP-glucose, which then quantitatively converts low fluorescence resazurin, an oxidation-reduction indicator, to high fluorescence resorufm by means of diaphorase (i.e. NADH dehydrogenase) and the NADH molecule that is formed by the UDP-glucose dehydrogenase. The reaction catalyzed by the glucosylceramide synthase transfers glucose from UDP-glucose to C6-ceramide to give UDP and glucosylceramide as products; the assay thus measures the disappearance of the UDP-glucose substrate.

In one embodiment, the ganglioside metabolism inhibitor is a small organic molecule.

In one embodiment, the ganglioside metabolism inhibitor is a peptide.

In one embodiment, the ganglioside metabolism inhibitor is an inhibitor scaffold.

Inhibitor scaffolds are selected on a structure-based design of a central molecular scaffold that is useful for the selective and potent inhibition of the enzyme or cofactor thereof. Techniques to design inhibitor scaffolds are well known to the skilled artisan and include without limitation, the use of shape and electrostatic similarity search combined with docking method and MM-GBSA approach.

In one embodiment, the ganglioside metabolism inhibitor is a chemical chaperone. "Chemical chaperones" as used herein are a class of small molecules that function to enhance the folding and/or stability of proteins. Chemical Chaperones are a broad and diverse group of molecules, and they can influence protein stability and polypeptide organization through a variety of mechanisms. Different classes of chemical chaperones exist, and include, in particular, osmolytes, hydrophobic compounds, and pharmacological chaperones. Osmolytes are polar small molecules that are synthesized or taken up by cells to maintain the integrity of cellular components during periods of osmotic or other forms of stress. Non limiting examples of these include glycerol, trehalose, trimethylamine n-oxide (TMAO), and glycine. Hydrophobic compounds that have varying degrees of hydrophobicity that still are soluble in aqueous environments can act as chemical chaperones as well. These compounds are thought to act by binding to solvent-exposed hydrophobic segments of unfolded or improperly folded proteins, thereby "protecting" them from aggregation. 4-phenylbutyrate (PBA) is a prominent example of this group of compounds, along with lysophosphatidic acids and other lipids and detergents. Pharmacological chaperones composed of protein ligands, cofactors, competitive inhibitors, and other small molecules that bind specifically to certain proteins. Because these molecules are active only on a specific protein, they are referred to as pharmacological chaperones.

In one embodiment, the gangliosides metabolism inhibitor is an antagonist.

In one embodiment, the antagonist may consist in an antibody directed against at least one enzyme of the gangliosides metabolism pathways (or against at least one cofactor thereof) such as for example the glucosylceramide synthase, the GM synthases (GM1, GM2, GM3 synthases), the GD synthases (GD1a, GD1b, GD2, GD3 synthases), GT synthases (GT1a, GT1b, GT2, GT3 synthases), Gb synthases (Gb1, Gb2, Gb3 synthases) or directed against a ligand of at least one enzyme of the gangliosides metabolism pathways, in such a way that said antibody impairs the binding of a ligand to said enzyme.

Antibodies directed against at least one enzyme of the gangliosides metabolism pathways (or against at least one cofactor thereof) can be obtained according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies directed to enzymes of the gangliosides metabolism pathways or to ligands or cofactors of enzymes of the gangliosides metabolism pathways can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce single chain antibodies directed to an enzyme of the gangliosides metabolism pathways, or directed to ligands of an enzyme of the gangliosides metabolism pathways.

Other antagonists of at least one enzyme of the gangliosides metabolism pathways (or of at least one cofactor thereof) useful in practicing the present invention also include fragments of an antibody directed to an enzyme of the gangliosides metabolism pathway (e.g. glucosylceramide synthase), or fragments of an antibody directed to a ligand or cofactor of an enzyme of the gangliosides metabolism pathway (e.g. glucosylceramide synthase ligands).

Examples of antibody fragments include, but are not limited to, F(ab')2 fragments, which can be generated by pepsin digestion of an intact antibody molecule, and Fab fragments, which can be generated by reducing the disulfide bridges of the F(ab')2 fragments. Other examples of antibody fragments include, without limitation, Fv and in particular scFv. Alternatively, Fab and/or scFv expression libraries can be constructed to allow rapid identification of fragments having the desired specificity to glucosylceramide synthase.

Humanized antibodies (or fragment thereof) directed to at least one enzyme of the gangliosides metabolism pathways or ligands or cofactor thereof can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816, 397).

Then after raising antibodies directed against the enzyme of the ganglioside metabolism pathway (e.g. against glucosylceramide synthase) or against a ligand or cofactor thereof as above described, the skilled man in the art can easily select those blocking the activation of enzymes of the gangliosides metabolism pathways.

In another embodiment the antagonist of the invention is an aptamer. Aptamers are a class of molecules that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformational constrained antibody variable region displayed by a platform protein, such as E. coli Thioredoxin A that are selected from combinatorial libraries by two hybrid methods (Colas et al., 1996).

Then after raising aptamers directed against at least one enzyme of the gangliosides metabolism pathways or against a ligand or cofactor thereof as above described, the skilled man in the art can easily select those blocking enzymes of the gangliosides metabolism pathways activation.

In one embodiment, the inhibitor for use of the present invention is an inhibitor of the gene expression of at least one enzyme of the gangliosides metabolism pathways (or of at least one cofactor thereof). In one embodiment, the term "inhibit" refers to a decreased expression level as compared to a reference expression level, such as, for example, a level inferior or equal to 90%, 80%, 70%, 60%, 50%, 40%, 30%, 20%, 10%, or less of the reference expression level. In one embodiment, the inhibition of gene expression is measured after contacting a cell with a compound tested for its impact on gene expression, and the reference expression level correspond to an expression level measured in a cell not contacted with said compound.

Methods to determine the level of gene expression are well-known to the skilled artisan, and include, without limitation, determining the transcriptome (in an embodiment relating to the transcription level of a gene), and/or the proteome (in an embodiment relating to the translation level of a gene).

Methods to determine the level of gene expression include without limitation, the determination of the level of the gene product at the transcription level or at the translation level or at the secretion/release level of said gene product.

In one embodiment of the invention, the level of gene expression is assessed at the transcription level (i.e., at the mRNA level).

In vitro methods for assessing the transcription level of a gene are well known in the prior art. Examples of such methods include, but are not limited to, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like.

In one embodiment of the invention, the level of gene expression is assessed at the translation level (i.e., at the protein level).

In vitro methods for assessing the translation level of a gene are well-known in the art. Examples of such methods include, but are not limited to, immunohistochemistry, Multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA), flow cytometry (FACS) and the like.

Examples of inhibitors of the gene expression of at least one enzyme of the gangliosides metabolism pathways (or of a cofactor thereof) include without limitation, RNAi, oligonucleotide antisense (including, without limitation, antisense RNA or DNA molecules), small inhibitory RNAs (siRNA), ribozymes, aptamers, morpholinos, and engineered nucleases.

Other examples of inhibitors of gene expression of at least one enzyme of the gangliosides metabolism pathways (or of a cofactor thereof) include without limitation, an antisense RNA or DNA molecules, small inhibitory RNAs (siRNAs), short hairpin RNA (shRNA), micro RNA (miRNA), DNAzymes, modified or synthetic DNA or RNA degradation-resistant polynucleoside amides, peptide nucleic acids (PNAs), locked nucleic acids (LNAs) and other nucleobase-containing polymers.

In one embodiment, the inhibitor of the gene expression of at least one enzyme of the gangliosides metabolism pathways (or of a cofactor thereof) is a miRNA. miRNA are gene-regulatory RNAs that are loaded onto the RNA-induced silencing complex (RISC) and interact with partially-complementary targets on mRNA to suppress protein expression. The miRNA is generally single-stranded, and on loading onto RISC, the miRNA "guide" sequence (also referred as the seed region) is held on the surface of RISC where it can interact with the target mRNA. The targets recognized by the miRNA guide sequence are most commonly on the 3'-untranslated region (UTR) of an RNA. Binding can suppress assembly of an initiation complex on the 5' cap of an mRNA because the mRNA is bound into a circular shape at the initiation of translation, bringing the 3'-UTR and 5'-UTR close together.

In one embodiment, the inhibitors of the gene expression of at least one enzyme of the gangliosides metabolism pathways (or of a cofactor thereof) for use in the present invention are based on anti-sense oligonucleotide constructs. Anti-sense oligonucleotides, including anti-sense RNA molecules and anti-sense DNA molecules, would act to directly block the translation of the enzyme of the ganglioside metabolism pathway (e.g. ganglioside synthase) mRNA (or of a cofactor thereof) by binding thereto and thus preventing protein translation or increasing mRNA degradation, thus decreasing the level of gangliosides metabolism, and thus activity, in a cell. For example, antisense oligonucleotides of at least about 15 bases and complementary to unique regions of the mRNA transcript sequence encoding ganglioside synthase can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732, which are incorporated herein by reference).

Small inhibitory RNAs (siRNAs) can also function as inhibitors of gene expression of at least one enzyme of the gangliosides metabolism pathways (or of a cofactor thereof) for use in the present invention.

Gene expression of at least one enzyme of the gangliosides metabolism (or of a cofactor thereof) can be reduced by contacting a subject or cell with a small double stranded RNA (dsRNA), or a vector or construct causing the production of a small double stranded RNA, such that gene expression of the enzyme of the ganglioside metabolism pathway (e.g., glucosylceramide synthase) or of a cofactor thereof is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO01/36646, WO 99/32619, and WO01/68836, which are incorporated herein by reference).

Ribozymes can also function as inhibitors of gene expression of at least one enzyme of the gangliosides metabolism pathways (or of a cofactor thereof) for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of ganglioside synthase mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of at least one enzyme or of a cofactor of an enzyme of the gangliosides metabolism pathways gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of an antisense oligonucleotide siRNA or ribozyme nucleic acid to the cells and preferably cells expressing at least one enzyme of the gangliosides metabolism pathways. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, Oxford University Press, USA 1993 and in Murry, vol 7 Humana Press 1991.

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, for example, heat and lipid solvent stability; high transduction frequencies in cells of diverse lineages, and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Inhibitors of the gangliosides metabolism for use in the present invention can also be morpholinos also known as a morpholino oligomer and as a phosphorodiamidate morpholino oligomer (PMO). Morpholinos are a type of oligomer molecule (colloquially, an oligo) used in molecular biology to modify gene expression. The molecular structure has a backbone of methylenemorpholine rings and phosphorodiamidate linkages. Morpholinos block access of other molecules to small (~25 base) specific sequences of the base-pairing surfaces of ribonucleic acid (RNA).

Inhibitors of the gangliosides metabolism for use in the present invention can also be engineered nucleases or "molecular scissors" used for genome editing. Genome editing, or genome editing with engineered nucleases (GEEN) is a type of genetic engineering in which DNA is inserted, deleted or replaced in the genome of an organism using engineered nucleases, or "molecular scissors" as well known to the skilled artisan. These nucleases create site-specific double-strand breaks (DSBs) at desired locations in the genome. The induced double-strand breaks are repaired through non-homologous end-joining (NHEJ) or homologous recombination (HR), resulting in targeted mutations. There are currently four families of engineered nucleases being used: meganucleases, zinc finger nucleases (ZFNs), transcription activator-like effector-based nucleases (TALEN), and the CRISPR-Cas system.

In one embodiment, the inhibitor of the invention inhibits accumulation of mono-sialoganglioside (GM) 1a, GM1b, GM2, GM3 and/or GM4; di-sialogangliosides (GD)1a, GD1b, GD1c, GD1α, GD2, GD3; tri-sialogangliosides (GT) 1a, GT1b, GT2, GT3; quadri-sialogangliosides (GQ)1b, GQ1c, GQ2, GQ3; penta-sialogangliosides (GP)1c. In one embodiment, the inhibitor of the invention inhibits the accumulation of GM2, GM3, GD2 and/or GD3.

In another embodiment, the inhibitor of the invention inhibits aggregation of mono-sialoganglioside (GM) 1a, GM1b, GM2, GM3 and/or GM4; di-sialogangliosides (GD) 1a, GD1b, GD1c, GD1α, GD2, GD3; tri-sialogangliosides (GT)1a, GT1b, GT2, GT3; quadri-sialogangliosides (GQ) 1b, GQ1c, GQ2, GQ3; penta-sialogangliosides (GP)1c. In one embodiment, the inhibitor of the invention inhibits the aggregation of GM2, GM3, GD2 and/or GD3.

In one embodiment, the inhibitor of the invention inhibits the synthesis, accumulation and/or aggregation of GM2.

In one embodiment, the inhibitor of the invention inhibits the synthesis, accumulation and/or aggregation of GM3.

In one embodiment, the inhibitor of the invention inhibits the synthesis, accumulation and/or aggregation of GD2.

In one embodiment, the inhibitor of the invention inhibits the synthesis, accumulation and/or aggregation of GD3.

In one embodiment, the inhibitor of gangliosides metabolism inhibits glucosylceramide synthase or a cofactor thereof.

In another embodiment, the inhibitor of gangliosides metabolism inhibits GM3 synthase or a cofactor thereof.

In another embodiment, the inhibitor of gangliosides metabolism inhibits GM2 synthase or a cofactor thereof.

In another embodiment, the inhibitor of gangliosides metabolism inhibits GD3 synthase or a cofactor thereof.

In another embodiment, the inhibitor of gangliosides metabolism inhibits GD2 synthase or a cofactor thereof.

In another embodiment, the inhibitor of gangliosides metabolism inhibits lactosylceramide synthase or a cofactor thereof.

In another embodiment, the inhibitor of gangliosides metabolism inhibits β1,4-GalNAc transferase or a cofactor thereof.

In another embodiment, the inhibitor of gangliosides metabolism inhibits β-1,4-N-acetyl-galactosaminyltransferase or a cofactor thereof.

In another embodiment, the inhibitor of gangliosides metabolism inhibits UDP-Gal:βGalNAc β-1,3-galactisyltransferase or a cofactor thereof.

In another embodiment, the inhibitor of gangliosides metabolism inhibits sialyltransferase IV or a cofactor thereof.

In another embodiment, the inhibitor of gangliosides metabolism inhibits sialyltransferase VII or a cofactor thereof.

In another embodiment, the inhibitor of gangliosides metabolism inhibits Gb3 synthase or a cofactor thereof.

In another embodiment, the inhibitor of gangliosides metabolism inhibits iGb3 synthase or a cofactor thereof.

In another embodiment, the inhibitor of gangliosides metabolism inhibits Lc3 synthase or a cofactor thereof.

In another embodiment, the inhibitor of gangliosides metabolism inhibits GT1c synthase or a cofactor thereof.

In another embodiment, the inhibitor of gangliosides metabolism inhibits GT2 synthase or a cofactor thereof.

In another embodiment, the inhibitor of gangliosides metabolism inhibits GT3 synthase or a cofactor thereof.

In another embodiment, the inhibitor of gangliosides metabolism inhibits GA1 synthase or a cofactor thereof.

In another embodiment, the inhibitor of gangliosides metabolism inhibits GA2 synthase or a cofactor thereof.

In another embodiment, the inhibitor of gangliosides metabolism inhibits GD1b synthase or a cofactor thereof.

In another embodiment, the inhibitor of gangliosides metabolism inhibits GM1a synthase or a cofactor thereof.

Examples of glucosylceramide synthase inhibitors include, without limitation, compounds of the following groups: imino sugars, analogs of D-threo-1-phenyl-2-decanoylamino-3-morpholino-propanol (PDMP) or ceramide analogs, carboxamides, carbamates, peptides, glycoside hydrolases, and enzyme therapy.

In one embodiment of the invention, the inhibitor of gangliosides metabolism is an imino sugar compound.

Examples of imino sugar compounds include, without limitation, the following sub-groups: alkyl-substituted imino sugar compound, adamantyl-substituted imino sugar compound, and pyrrolidine derivative imino sugar compound.

In one embodiment of the invention, the inhibitor of gangliosides metabolism is an alkyl-substituted imino sugar compound.

Examples of alkyl-substituted imino sugar compounds are described in patent applications WO2007140184, WO2011086347, EP0566556, WO2011095772, WO2015147639, Richards S et al. (J Med Chem. 2012 May 10; 55(9):4322-35), Fröhlich R F et al. Carbohydr Res. 2011 Sep. 6; 346(12): 1592-1598, which are all incorporated herein by reference.

In one embodiment of the invention, the inhibitor of gangliosides metabolism is an adamantyl-substituted imino sugar compound.

Examples of adamantyl-substituted imino sugar compounds are described in patent applications WO2007140184, WO2005040118, WO2015147639, which are all incorporated herein by reference.

In one embodiment of the invention, the inhibitor of gangliosides metabolism is a pyrrolidine derivative imino sugar compound.

Examples of pyrrolidines derivatives imino sugar compound are described in patent applications WO2007140184, WO2011086347, WO2011095772, WO2012117219, WO2013059119, Jenkinson et al. J. Org. Chem., 2013, 78 (15), pp 7380-7397; which are all incorporated herein by reference.

In one embodiment of the invention, the inhibitor of gangliosides metabolism is a compound as described in the patent application U.S. Pat. No. 6,610,703 incorporated herein by reference and is selected from N-nonyl-DNJ or N-decyl-DNJ.

In one embodiment of the invention, the inhibitor of gangliosides metabolism is a compound as described in the patent application WO2007140184 incorporated herein by reference and is preferably selected from the group comprising N—(N'-{4'-azido-2'-nitrophenyl)-6-aminohexyl)-deoxynojirimycin, N—(N'-{2',4'-dinitrophenyl)-6-aminohexyl)-deoxynojirimycin (NAP-DNJ), N—(N'-{2,4-dinitrophenyl)-6-aminohexyl)-DNJ (NDP-DNJ), N-(alkylphenyl)-DNJ derivatives, and N-butyl-DNJ (NB-DNJ).

In one embodiment, the inhibitor of gangliosides metabolism is a compound as described in the patent application WO2007140184 incorporated herein by reference and is selected from the group comprising the following formulas:

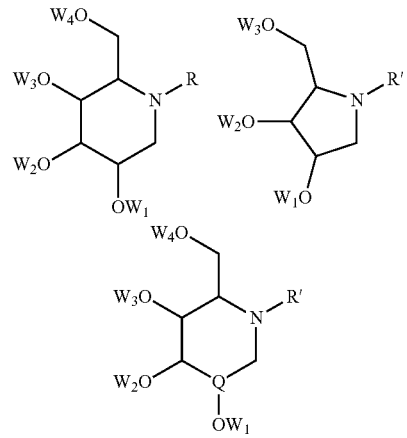

wherein R' is:

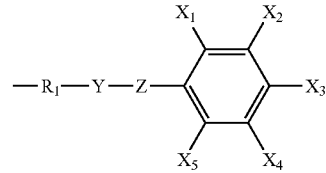

wherein R' is:

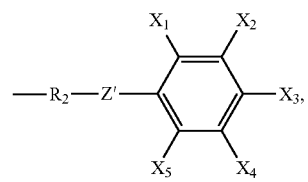

wherein $R_1$ is a substituted or unsubstituted alkyl group;
wherein $R_2$ is a substituted or unsubstituted alkyl group;
wherein Q is absent or is CH, provided that if Q is absent OW1 is also absent;
wherein $W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;

wherein $X_{1-5}$ are independently selected from H, NO$_2$, N$_3$, or NH$_2$;
wherein Y is absent or is a substituted or unsubstituted Q-alkyl group, other than carbonyl;
wherein Z is selected from a bond or NH;
provided that when Z is a bond, Y is absent, and
provided that when Z is NH, Y is a substituted or unsubstituted Q-alkyl group, other than carbonyl;
and wherein Z' is a bond or NH.

Additional examples of pyrrolidines derivatives are also described in WO2012117219 incorporated herein by reference and comprise, without limitation, isoDAB (1,4-dideoxy-2-hydroxymethyl-1,4-imino-D-threitol); isoDMDP, isoDGDP, and L-isoDMDP [(2S,3S,4R)-2,4-bis(hydroxymethyl)pyrrolidine-3,4-diol].

In one embodiment of the invention, the inhibitor of gangliosides metabolism is a compound as described in the patent application WO2011086347 and comprises (3S,4S)-3-(hydroxymethyl)pyrrolidine-3,4-diol (1,4-dideoxy-2-hydroxymethyl-1,4-imino-L-threitol (isoLAB) and a compound having the following formula:

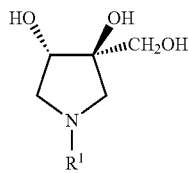

wherein R$^1$ is selected from H; linear or branched, substituted or unsubstituted alkyl, alkenyl, alkynyl and aralkyl and wherein the optional substitution may be with one or more groups independently selected from: —OH; —F; —Cl; —Br; —I; —NH$_2$; alkylamino; dialkylamino; linear or branched alkyl, alkenyl, alkynyl and aralkyl; aryl; heteroaryl; linear or branched alkoxy; aryloxy; aralkoxy; -(alkylene)oxy(alkyl); —CN; —NO$_2$; —COOH; —COO(alkyl); —COO(aryl); —C(O)NH(alkyl); —C(O)NH(aryl); sulfonyl; alkylsulfonyl; arylsulfonyl; sulfamoyl; alkylsulfamoyl; alkylthio; alkylsulfonamide; arylsulfonamide; —NHNH$_2$; and —NHOH;
or an isostere, pharmaceutically acceptable salt or derivative (i.e., a compound which is obtained (or obtainable) by chemical derivatization of the compound disclosed hereinabove) thereof.

In one embodiment, the inhibitor of gangliosides metabolism is a compound inhibiting the glucosylceramide synthase as described in the patent application WO2013059119 incorporated herein by reference and is selected from the group comprising: N-((1R,2R)-1-(2,3-dihydrobenzo[b][1,4]dioxin-6-yl)-1-hydroxy-3-(pyrrolidin-1-yl)propan-2-yl)cinnamamide, N-((1R,2R)-1-(2,3-dihydrobenzo[b][1,4]dioxin-6-yl)-1-hydroxy-3-(pyrrolidin-1-yl)propan-2-yl)-2-phenylcyclopropanecarboxamide, 2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide, N-((1R,2R-1-(2,3-dihydrobenzo[b][1,4]dioxin-6-yl)-1-hydroxy-3-(pyrrolidin-1-yl)propan-2-yl)-2,3-dihydro-1H-indene-2-carboxamide, N-((1R,2R)-1-(2,3-dihydrobenzo[b][1,4]dioxin-6-yl)-1-hydroxy-3-(pyrrolidin-1-yl)propan-2-yl)-N-methyl-3-phenylpropanamide, N-((1R,2R)-1-hydroxy-1-(2-methoxyphenyl)-3-(pyrrolidin-1-yl)propan-2-yl)octanamide, N-((1R,2R)-1-(3-(dimethylamino)phenyl)-1-hydroxy-3-(pyrrolidin-1-yl)propan-2-yl)octanamide, N-((1R,2R)-1-(2,3-dihydrobenzo[b][1,4]dioxin-6-yl)-1-hydroxy-3-(pyrrolidin-1-yl)propan-2-yl)-3-(3-fluorophenyl)propanamide, N-((1R,2R)-1-(2,3-dihydrobenzo[b][1,4]dioxin-6-yl)-1-hydroxy-3-(pyrrolidin-1-yl)propan-2-yl)-3-(4-fluorophenyl)propanamide, N-((1R,2R)-1-(2,3-dihydrobenzo[b][1,4]dioxin-6-yl)-1-hydroxy-3-(pyrrolidin-1-yl)propan-2-yl)-3-phenylbutanamide, N-((1R,2R)-1-(2,3-dihydrobenzo[b][1,4]dioxin-6-yl)-1-hydroxy-3-(pyrrolidin-1-yl)propan-2-yl)-3-(2-methoxyphenyl)propanamide, N-((1R,2R)-1-(2,3-dihydrobenzo[b][1,4]dioxin-6-yl)-1-hydroxy-3-(pyrrolidin-1-yl)propan-2-yl)-2-(phenylamino)acetamide, 2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide oxylate monohydrate, and N-((1R,2R)-1-(2,3-dihydrobenzo[b][1,4]dioxin-6-yl)-1-hydroxy-3-(pyrrolidin-1-yl)propan-2-yl)-2-phenylacetamido.

In one embodiment, the inhibitor of gangliosides metabolism is described in the patent application WO2013059119 and is a compound having the following formula:

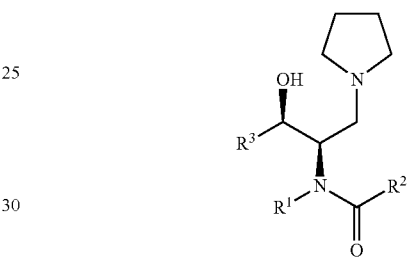

wherein:
R$^1$ is H or C$_{1-3}$alkyl;
R$^2$ is (i) —(CH2)$_{1-3}$C$_6$H$_5$, with the proviso that R$^1$ is —C$_{1-3}$alkyl;
(ii) —CH2-C(R$^a$$_2$)$_{1,2}$—C$_6$H$_5$, wherein R$^a$ independently is H or C$_{1-3}$ alkyl; with the proviso that at least one R$^a$ is C$_{1-3}$alkyl;
(iii) —(CH2)$_{1,2}$NHC$_6$H$_5$;
(iv) —CH=CHC$_6$H$_5$;

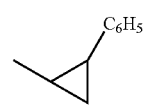

wherein for (i) through (v) the C$_6$H$_5$ group optionally is substituted with one or two of -halo or —OR$^a$; or

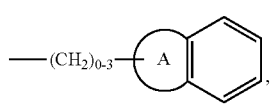

wherein the fused ring A is a 4- to 8-membered ring, saturated or partially unsaturated, and comprising carbon atoms and optionally one or two heteroatoms selected from O, S and NR$^a$, and wherein the fused phenyl ring is optionally substituted with one or two substituents; and R³ is

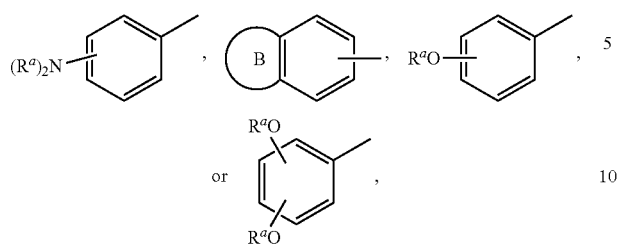

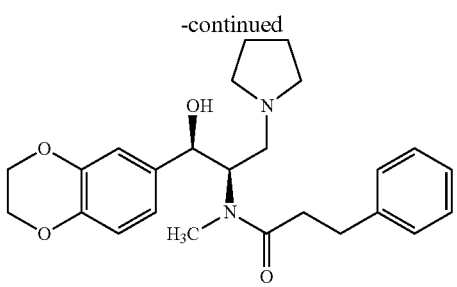

wherein the fused ring B is a five- or six-membered ring, saturated or partially or fully unsaturated, comprising carbon atoms and one or two heteroatoms selected from O, S and NR$^a$, and wherein the phenyl ring is optionally substituted with one or two substituents;

or a pharmaceutically acceptable salt, solvate, hydrate, or prodrug thereof.

In particular, the inhibitor of gangliosides metabolism is described in the patent application WO2013059119 incorporated herein by reference and is selected from the group comprising compounds having the following formulas:

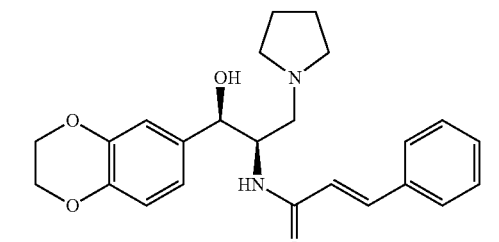

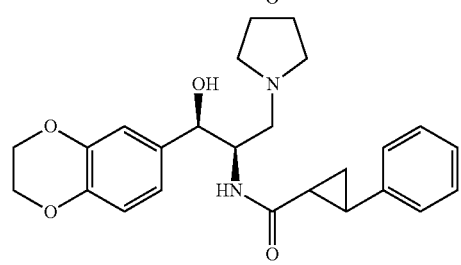

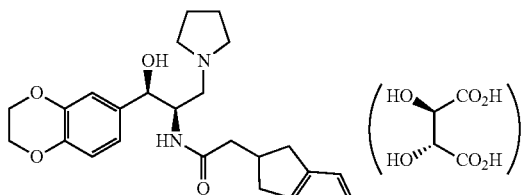

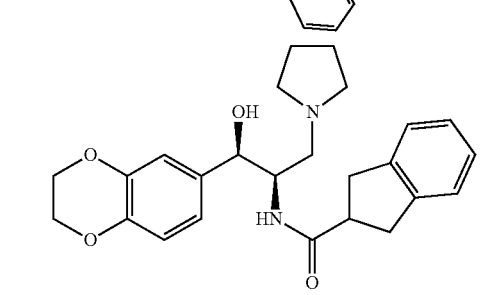

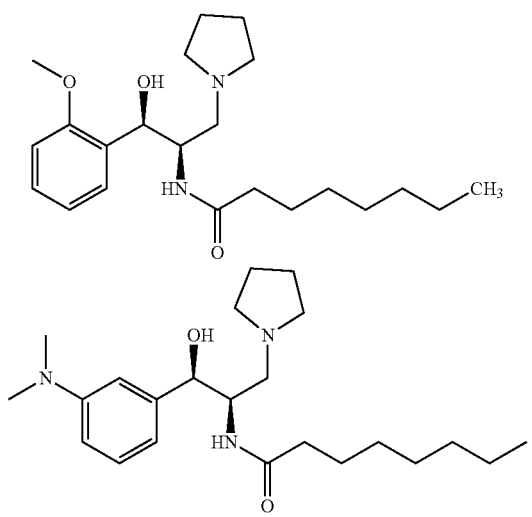

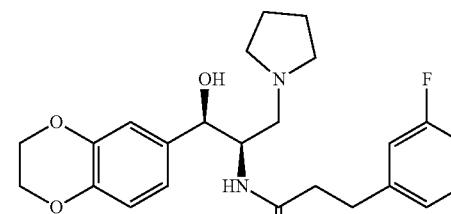

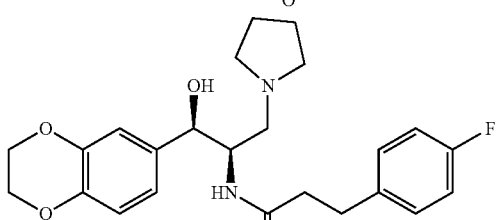

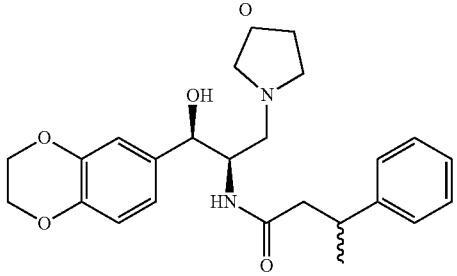

-continued

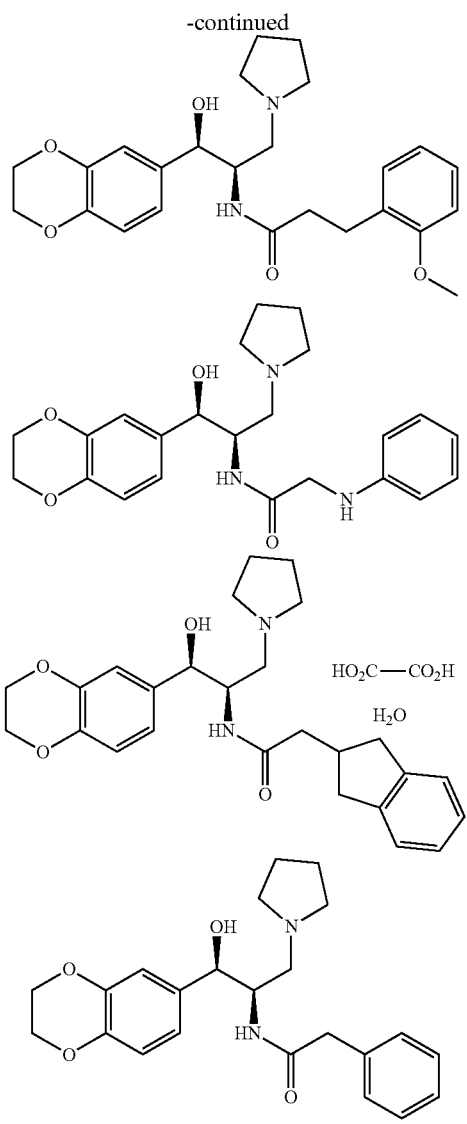

Examples of pyrrolidines derivative imino sugar compound include without limitation, hydroxylated pyrrolidines derivatives and substituted pyrrolidines derivatives.

Examples of pyrrolidine derivative imino sugar are described in Jenkinson et al. J. Org. Chem., 2013, 78 (15), pp 7380-7397 incorporated herein by reference and include without limitation, 1,4-dideoxy-2-hydroxymethyl-1,4-imino-D-threitol (isoDAB); (2S,3S,4R)-2,4-bis(hydroxymethyl)pyrrolidine-3,4-diol (isoDMDP), enantiomeric pairs of isoDMDP, and isoDGDP.

Examples of hydroxylated pyrrolidine derivatives are described in Takayama S et al. (Bioorg Med Chem. 1999 February; 7(2):401-9) incorporated herein by reference and include without limitation compounds having the following formulas:

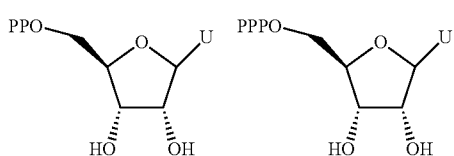

-continued

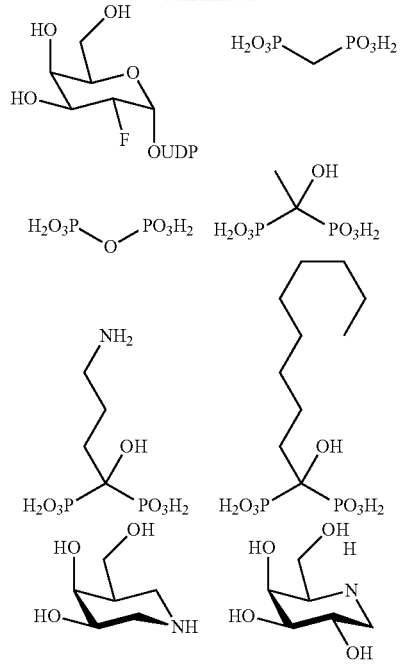

Examples of substituted pyrrolidines derivatives are described in Saotome C et al. (Chem Biol. 2001 November; 8(11):1061-70) incorporated herein by reference and include without limitation compounds having the following formulas:

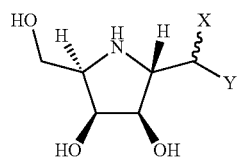

wherein X is BuNH, $(CH_3)_2NCH_2CH_2NH$, $CH_3(CH_2)_9NH$, $HOCH_2CH_2NH$, $CH_3O(CH_2)_3NH$, $PhCH_2CH_2NH$ or a compound having the following formula:

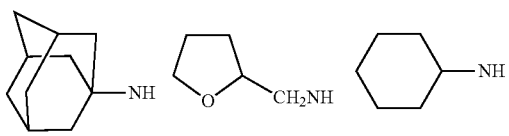

and wherein Y is H, $CH_2NH_2$ or $CONH_2$.

In one embodiment, the inhibitor of gangliosides metabolism from the imino sugars group include without limitation, 1,5-dideoxy-1,5-imino-D-glucitol also known as deoxynojirimycin (DNJ); N-butyldeoxynojirimycin (NB-DNJ) also known as miglustat, Zavesca™; N-hydroxyethyl-DNJ (miglitol); the adamantyl analog of miglustat also known as N-(5-adamantane-1-yl-methoxypentyl) deoxynojirimycin (AMP-DNJ); N-butyl-1-deoxy-nojirimycin (KTB-DNJ); N-ethyl-1-dexynojirimycin (NE-DNJ); N-butyldeoxymannojixamycin; N-5-carboxyl-1-deoxynojiramycin; N-docecyl-1-deoxynojirimycin; nojirimycin bisulfate; nojiximycin-1-sulfonic acid; N-(n-nonyl)-1-deoxynojirimycin; N-(7-oxadecyl)-1-deoxynojirimycin; N-(7-oxa-9,9,9,- trifluorononyl)-1-deoxynojirimycin; (2R,3S,4R,5S)-2-(Hydroxymethyl)-3,4,5-piperidinetriol also named 1-deoxy galactonojirimycin (DGJ) or migalastat; N-butyldeoxygalactonojirimycin (NB-DGJ); N-(n-nonyl)deoxynojirimycin; (3S,4S)-3-(hydroxymethyl)pyrrolidine-3,4-diol (isoLAB); 1,4-dideoxy-1,4-imino-D-arabinitol, (2S,3R,4S,5R)-3,4,5-trihydroxy-6-oxopiperidine-2-carboxylic acid or D-glucaro-delta-lactam.

In one embodiment, the inhibitor of gangliosides metabolism is miglustat.

Methods of synthesizing deoxynojirimycin derivatives are disclosed, for example, in U.S. Pat. Nos. 5,622,972; 5,200,523; 5,043,273; 4,994,572; 4,246,345; 4,266,025; 4,405,714; and 4,806,650 and U.S. Patent application publication no. 2007/0275998, which are all incorporated herein by reference.

Methods of synthesizing derivatives of 1,5-dideoxy-1,5-imino-D-glucitol are described in U.S. Pat. Nos. 5,525,616; 5,472,969; 6,660,749 and 6,465,488 all incorporated herein by reference.

In one embodiment of the invention, the inhibitor of gangliosides metabolism is a ceramide analog.

In one embodiment of the invention, the inhibitor of gangliosides metabolism is a 1-phenyl-2-decanoylamino-3-morpholino-propanol (PDMP) analog.

Examples of ceramide analogs or analogs of 1-phenyl-2-decanoylamino-3-morpholino-propanol (PDMP) include without limitation, D-threo-1-phenyl-2-decanoylamino-3-morpholino-propanol (PDMP); enantiomers of PDMP, L-threo- and DL-erythro-1-phenyl-2-amino-1,3-propane-diol, the D-threo (R,R) enantiomer; 1-phenyl-2-palmitoyl-amino-3-morpholino-1-propanol (PPMP); 1-phenyl-2-palmitoylamino-3-pyrrolidino-1-propanol (P4), D-threo-1-ethylenedioxyphenyl-2-palmitoyl-3-pyrrolidino-propanol (EtDO-P4); DL-threo-1-phenyl-2-palmitoylamino-3-pyrrolidino-1-propanol (DL-threo-P4); 2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide; N-((1R,2R)-1-(2,3-dihydrobenzo[b][1,4]dioxin-6-yl)-1-hydroxy-3-(pyrrolidin-1-yl)propan-2-yl)octanamide, also known as Genz-112638 and homologue of eliglustat; N-((1R,2R)-1-(2,3-dihydrobenzo[b][1,4]dioxin-6-yl)-1-hydroxy-3-(pyrrolidin-1-yl)propan-2-yl)nonanamide also named Genz-123346; BML-119; and IV-231B.

In one embodiment, the inhibitor of ganglioside metabolism is a compound inhibiting the glucosylceramide synthase as described in the patent application WO2011066352 and comprises in particular the amorphous and a crystalline form of GENZ 112638 hemitartrate having the following formula:

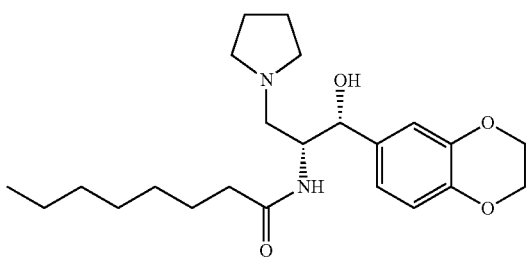 [SMILES: CCCCCCCC(=O)N[C@H](CN1CCCC1)[C@H](O)c1ccc2c(c1)OCCO2]

Other examples of analogs of ceramide also comprise morpholino derivatives; pyrrolidino derivatives described in Carson et al. Tetrahedron Lett., 1994, 35, 2659-2662; Miura T et al. Bioorg Med Chem. 1998 September; 6(9):1481-9 which are all incorporated herein by reference and having the following formula:

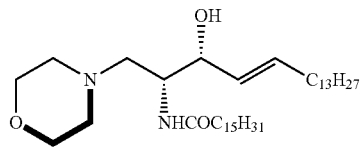

Examples of ceramide analogs or analogs of PDMP that are contemplated by the invention include but are not limited to those described in U.S. Pat. No. 6,916,802 incorporated herein by reference and include without limitation compounds having the following formulas:

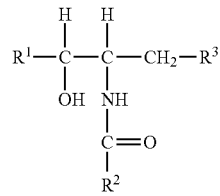

wherein:

$R^1$ is a phenyl group, preferably a substituted phenyl group such as p-methoxy, hydroxy, dioxane substitutions such as methylenedioxy, ethylenedioxy, and trimethylenedioxy, cyclohexyl or other acyclic group, t-butyl or other branched aliphatic group, or a long alkyl or alkenyl chain, preferably 7 to 15 carbons long with a double bond next to the kernel of the structure. The aliphatic chain can have a hydroxyl group near the two asymmetric centers, corresponding to phytosphingosine.

$R^2$ is an alkyl residue of a fatty acid, 2 to 18 carbons long. The fatty acid can be saturated or unsaturated, or possess a small substitution at the C-2 position (e.g., a hydroxyl group). It is contemplated that the $R^2$ group fatty acid may be 2, 3, 4, 5, 6, 7, 8, 9, 10, 11, 12, 13, 14, 15, 16, 17, or 18 carbons long. Longer fatty acids also may be useful. Preferably $R^2$ in the above structure is either 5 carbons or 7 carbons in length.

$R^3$ is a tertiary amine, preferably a cyclic amine such as pyrrolidine, azetidine, morpholine or piperidine, in which the nitrogen atom is attached to the kernel (i.e., a tertiary amine).

Examples of ceramide analogs or analogs of PDMP that are contemplated by the invention include but are not limited to those described in Lee et al. JBC 1999 Vol. 274, No. 21:14662-14669; Shayman and Larsen J Lipid Res. 2014 July; 55(7):1215-25 which are incorporated herein by reference and include without limitation, N-(5-adamantane-1-yl-methoxypentyl) deoxynojirimycin, D-threo-1-ethylenedioxyphenyl-2-palmitoyl-3-pyrrolidino-propanol (EtDO-P4), eliglustat tartrate (Cerdelga™), -(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide, Isofagomine, 1-deoxygalactonojirimycin (migalastat), Ambroxol, pyrimethamine [2,4-diamino 5-(4-chlorophenyl)-6-ethylpyrimidine] as well as compounds having the following formulas:

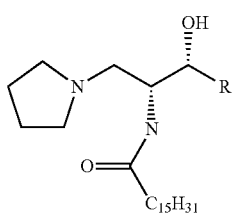

wherein R is selected from:

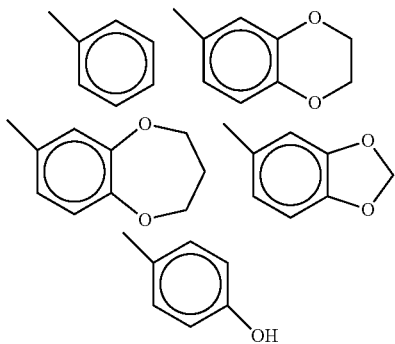

In one embodiment of the invention, the inhibitor of ganglioside metabolism is described in U.S. Pat. No. 6,051,598 incorporated herein by reference and is selected from the group comprising 1-phenyl-2-palmitoylamino-3-pyrrolidino-1-propanol; D-threo-1-pyrrolidino-1-deoxyceramide; (1R,2R)-1-phenyl-2-acylamino-3-cyclic amino-1-propanol; (2R,3R)-2-palmitoyl-sphingosyl amine; 1-cyclic amino-1-deoxyceramide; and 1-cyclic amino-2-hexadecanoylamino-3-hydroxy-octadec-4,5-ene.

In one embodiment of the invention, the inhibitor of ganglioside metabolism is described in U.S. Pat. Nos. 5,302,609, 5,952,370; 5,916,911; 6,030,995 incorporated herein by reference and is selected from the compounds having the following formula:

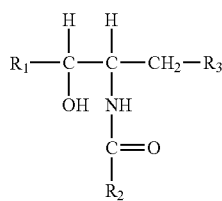

where $R_1$ is an aromatic structure, an alicyclic structure, a branched aliphatic structure or a linear aliphatic group having 5 to 15 carbons;
$R^2$ is an aliphatic chain having 9 to 18 carbons; and
$R^3$ is pyrrolidino;
and functional homologues, isomers and pharmaceutically acceptable salts thereof.

In one embodiment of the invention, the inhibitor of ganglioside metabolism is described in U.S. Pat. Nos. 6,569,889, 6,255,336 incorporated herein by reference and is selected from the group comprising 4'-hydroxy-1-phenyl-2-palmitoylamino-3-pyrrolidino-1-propanol; 3',4'-ethylenedioxy-1-phenyl-2-palmitoylamino-3-pyrrolidino-1-propanol; D-t-3',4'-ethylenedioxy-1-phenyl-2-palmitoylamino-3-pyrrolidino-1-propanol; D-t-4-hydroxy-1-phenyl-2-palmitoylamino-3-pyrrolidino-1-propanol, pharmaceutically acceptable salts thereof and mixtures thereof. As used herein, the term "pharmaceutically acceptable salts" is intended to mean salts of the compounds of the present invention with pharmaceutically acceptable acids, e.g., inorganic acids such as sulfuric, hydrochloric, phosphoric, etc. or organic acids such as acetic.

In one embodiment of the invention, the inhibitor of ganglioside metabolism is a carboxamide derivative.

In one embodiment, the inhibitor of ganglioside metabolism is an inhibitor of the glucosylceramide synthase described in the patent application WO2010091104 incorporated herein by reference and is selected from the group comprising the following compounds: 2-[(4-chlorophenyl)oxy]-N-[(1R)-2-(4-methylpiperazin-1-yl)-2-oxo-1-{[(phenylmethyl)oxy]methyl}ethyl]pyridine-3-carboxamide; N-[(1R)-2-(4-methylpiperazin-1-yl)-2-oxo-1-{[(phenylmethyl)oxy]methyl}ethyl]-2-{[3-(trifluoromethyl)phenyl]oxy}pyridine-3-carboxamide; N-[(1R)-2-(4-methylpiperazin-1-yl)-2-oxo-1-{[(phenylmethyl)oxy]methyl}ethyl]-2-{[3-(trifluoromethyl)-phenyl]oxy}pyridine-3-carboxamide; 2-[(4-chloro-2-methylphenyl)oxy]-N-[(1R)-2-(4-methylpiperazin-1-yl)-2-oxo-1-{[(phenylmethyl)oxy]methyl}ethyl]pyridine-3-carboxamide; 2-[(4-chloro-2-methylphenyl)oxy]-N-[(1R)-2-(4-methylpiperazin-1-yl)-2-oxo-1-{[(phenylmethyl)oxy]-methyl}ethyl]pyridine-3-carboxamide; 2-[(4-chlorophenyl)oxy]-N-[(1R)-2-(4-methyl-1,4-diazepan-1-yl)-2-oxo-1-{[(phenylmethyl)oxy]methyl}ethyl]pyridine-3-carboxamide; 2-[(4-chlorophenyl)oxy]-N-[(1R)-2-(4-methyl-1,4-diazepan-1-yl)-2-oxo-1-{[(phenylmethyl)oxy]-methyl}ethyl]pyridine-3-carboxamide; 2-[(4-methylphenyl)oxy]-N-[(1R)-2-(4-methylpiperazin-1-yl)-2-oxo-1-{[(phenylmethyl)oxy]methyl}ethyl]benzamide; 2-[(4-methylphenyl)oxy]-N-[(1R)-2-(4-methylpiperazin-1-yl)-2-oxo-1-{[(phenylmethyl)oxy]methyl}ethyl]benzamide; 2-[(4-chlorophenyl)oxy]-N-[(1S)-2-(4-methylpiperazin-1-yl)-2-oxo-1-{[(phenylmethyl)oxy]methyl}ethyl]pyridine-3-carboxamide; 2-[(2-chloro-4-methylphenyl)oxy]-N-[(1R)-2-(4-methylpiperazin-1-yl)-2-oxo-1-{[(phenylmethyl)oxy]methyl}ethyl]pyridine-3-carboxamide; 2-[(2-chloro-4-methylphenyl)oxy]-N-[(1R)-2-(4-methylpiperazin-1-yl)-2-oxo-1-{[(phenylmethyl)oxy]methyl}-ethyl]pyridine-3-carboxamide; 2-[(4-methylphenyl)oxy]-N-[(1S)-2-(4-methylpiperazin-1-yl)-2-oxo-1-{[(phenylmethyl)oxy]methyl}ethyl]pyridine-3-carboxamide; 2-[(4-methylphenyl)oxy]-N-[(1S)-2-(4-methylpiperazin-1-yl)-2-oxo-1-{[(phenylmethyl)oxy]-methyl}ethyl]pyridine-3-carboxamide; N-[(1S)-2-(4-methylpiperazin-1-yl)-2-oxo-1-{[(phenylmethyl)oxy]methyl}ethyl]-2-{[3-(trifluoromethyl)phenyl]oxy}pyridine-3-carboxamide; N-[(1S)-2-(4-methylpiperazin-1-yl)-2-oxo-1-{[(phenylmethyl)oxy]methyl}ethyl]-2-{[3-(trifluoromethyl)-phenyl]oxy}pyridine-3-carboxamide; 2-[(4-chlorophenyl)oxy]-N-{(1R)-1-[(4-methylpiperazin-1-yl)carbonyl]-3-[(phenylmethyl)oxy]propyl}pyridine-3-carboxamide; 2-[(4-chlorophenyl)oxy]-N-{(1R)-1-[(4-methylpiperazin-1-yl)carbonyl]-3-[(phenylmethyl)oxy]-propyl}pyridine-3-carboxamide; 2-[(4-chlorophenyl)oxy]-N-[(1R)-2-[(1-methylpiperidin-4-yl)amino]-2-oxo-1-{[(phenylmethyl)oxy]methyl}ethyl]pyridine-3-carboxamide; 2-[(4-chlorophenyl)oxy]-N-[(1R)-2-[(1-methylpiperidin-4-yl)amino]-2-oxo-1-{[(phenylmethyl)oxy]-methyl}ethyl]pyridine-3-carboxamide; 2-[(4-chlorophenyl)oxy]-N-[(1R)-2-{4-[3-(dimethylamino)propyl]piperazin-1-yl}-2-oxo-1-{[(phenylmethyl)oxy]methyl}ethyl]pyridine-3-carboxamide;

2-[(4-chlorophenyl)oxy]-N-[(1R)-2-{4-[3-(dimethylamino)propyl]piperazin-1-yl}-2-oxo-1-{[(phenylmethyl)oxy]methyl}ethyl]pyridine-3-carboxamide; 2-[(4-chlorophenyl)oxy]-N-{(1R)-1-[(4-methylpiperazin-1-yl)carbonyl]-4-phenylbutyl}pyridine-3-carboxamide; 2-[(4-chlorophenyl)oxy]-N-{(1R)-1-[(4-methylpiperazin-1-yl)carbonyl]-4-phenylbutyl}pyridine-3-carboxamide; 2-[(2,4-dichlorophenyl)oxy]-N-[(1R)-2-(3-methylhexahydropyrrolo[1,2-a]-pyrazin-2(1H)-yl)-2-oxo-1-{[(phenylmethyl)oxy]methyl}ethyl]pyridine-3-carboxamide; 2-[(2,4-dichlorophenyl)oxy]-N-[(1R)-2-(3-methylhexahydropyrrolo[1,2-a]pyrazin-2(1H)-yl)-2-oxo-1-{[(phenylmethyl)oxy]methyl}ethyl]pyridine-3-carboxamide; 2-[(4-chlorophenyl)oxy]-N-[(1R)-2-(4-cyclopropylpiperazin-1-yl)-2-oxo-1-{[(phenylmethyl)oxy]methyl}ethyl]pyridine-3-carboxamide; 2-[(4-chlorophenyl)oxy]-N-[(1R)-2-(4-cyclopropylpiperazin-1-yl)-2-oxo-1-{[(phenylmethyl)oxy]methyl}ethyl]pyridine-3-carboxamide; 2-[(4-chlorophenyl)oxy]-N-[(1S)-2-(4-methyl-1,4-diazepan-1-yl)-2-oxo-1-{[(phenylmethyl)oxy]methyl}ethyl]pyridine-3-carboxamide; 2-[(4-chlorophenyl)oxy]-N-[(1S)-2-(4-methyl-1,4-diazepan-1-yl)-2-oxo-1-{[(phenylmethyl)oxy]methyl}ethyl]pyridine-3-carboxamide; 2-{[2-chloro-4-(trifluoromethyl)phenyl]oxy}-N-[(1R)-2-[3-(dimethylamino)-azetidin-1-yl]-2-oxo-1-{[(phenylmethyl)oxy]methyl}ethyl]pyridine-3-carboxamide; 2-{[2-chloro-4-(trifluoromethyl)phenyl]oxy}-N-[(1R)-2-[3-(dimethylamino)azetidin-1-yl]-2-oxo-1-{[(phenylmethyl)oxy]methyl}ethyl]pyridine-3-carboxamide; 2-[(2,4-dichlorophenyl)oxy]-N-[(1R)-2-(5,6-dihydro[1,2,4]triazolo[4,3-a]pyrazin-7(8H)-yl)-2-oxo-1-{[(phenylmethyl)oxy]methyl}ethyl]pyridine-3-carboxamide; 2-[(2,4-dichlorophenyl)oxy]-N-[(1R)-2-(5,6-dihydro[1,2,4]triazolo[4,3-a]pyrazin-7(8H)-yl)-2-oxo-1-{[(phenylmethyl)oxy]methyl}ethyl]pyridine-3-carboxamide; 2-[(2,4-dichlorophenyl)oxy]-N-[(1R)-2-[3-(hydroxymethyl)hexahydropyrrolo[1,2-a]pyrazin-2(1H)-yl]-2-oxo-1-{[(phenylmethyl)oxy]methyl}ethyl]pyridine-3-carboxamide; 2-[(2,4-dichlorophenyl)oxy]-N-[(1R)-2-[3-(hydroxymethyl)hexahydropyrrolo[1,2-a]pyrazin-2(1H)-yl]-2-oxo-1-{[(phenylmethyl)oxy]methyl}ethyl]pyridine-3-carboxamide; 2-[(2,4-dichlorophenyl)oxy]-N-[(1R)-2-(1,3-dihydro-2H-pyrrolo[3,4-c]pyridin-2-yl)-2-oxo-1-{[(phenylmethyl)oxy]methyl}ethyl]pyridine-3-carboxamide; 2-[(2,4-dichlorophenyl)oxy]-N-[(1R)-2-(1,3-dihydro-2H-pyrrolo[3,4-c]pyridin-2-yl)-2-oxo-1-{[(phenylmethyl)oxy]methyl}ethyl]pyridine-3-carboxamide; 2-[(4-chlorophenyl)oxy]-N-[(1R)-2-(4-methylpiperidin-1-yl)-2-oxo-1-{[(phenylmethyl)oxy]methyl}ethyl]pyridine-3-carboxamide; 2-[(4-chlorophenyl)oxy]-N-[(1R)-2-(4-methylpiperidin-1-yl)-2-oxo-1-{[(phenylmethyl)oxy]methyl}ethyl]pyridine-3-carboxamide; 2-[(2,4-dichlorophenyl)oxy]-N-[(1R)-2-oxo-1-{[(phenylmethyl)oxy]methyl}-2-(1,5,6,7-tetrahydro-4H-imidazo[4,5-b]pyridin-4-yl)ethyl]pyridine-3-carboxamide; 2-[(2,4-dichlorophenyl)oxy]-N-[(1R)-2-oxo-1-{[(phenylmethyl)oxy]methyl}-2-(1,5,6,7-tetrahydro-4H-imidazo[4,5-b]pyridin-4-yl)ethyl]pyridine-3-carboxamide; 2-[(4-chlorophenyl)oxy]-N-[(1R)-2-[4-(2-fluoroethyl)piperazin-1-yl]-2-oxo-1-{[(phenylmethyl)oxy]methyl}ethyl]pyridine-3-carboxamide; 2-[(4-chlorophenyl)oxy]-N-[(1R)-2-[4-(2-fluoroethyl)piperazin-1-yl]-2-oxo-1-{[(phenylmethyl)oxy]methyl}ethyl]pyridine-3-carboxamide; 2-[(4-chlorophenyl)oxy]-N-[(1R)-2-(4-ethylpiperazin-1-yl)-2-oxo-1-{[(phenylmethyl)oxy]methyl}ethyl]pyridine-3-carboxamide; 2-[(4-chlorophenyl)oxy]-N-[(1R)-2-(4-ethylpiperazin-1-yl)-2-oxo-1-{[(phenylmethyl)oxy]methyl}ethyl]pyridine-3-carboxamide; 2-[(4-chlorophenyl)oxy]-N-[(1R)-2-[4-(2-hydroxyethyl)piperazin-1-yl]-2-oxo-1-{[(phenylmethyl)oxy]methyl}ethyl]pyridine-3-carboxamide; 2-[(4-chlorophenyl)oxy]-N-[(1R)-2-[4-(2-hydroxyethyl)piperazin-1-yl]-2-oxo-1-[(phenylmethyl)oxy]methyl}ethyl]pyridine-3-carboxamide; N-[(1R)-2-(1-azabicyclo[2.2.2]oct-3-ylamino)-2-oxo-1-{[(phenylmethyl)oxy]methyl}ethyl]-2-{[2-chloro-4-(trifluoromethyl)phenyl]oxy}-pyridine-3-carboxamide; N-[(1R)-2-[(3S)-1-azabicyclo[2.2.2]oct-3-ylamino]-2-oxo-1-{[(phenylmethyl)oxy]methyl}ethyl]-2-{[2-chloro-4-(trifluoromethyl)phenyl]oxy}pyridine-3-carboxamide; N-[(1R)-2-[(3R)-1-azabicyclo[2.2.2]oct-3-ylamino]-2-oxo-1-{[(phenylmethyl)oxy]methyl}ethyl]-2-{[2-chloro-4-(trifluoromethyl)phenyl]oxy}pyridine-3-carboxamide; N-[(1R)-2-[(3S)-1-azabicyclo[2.2.2]oct-3-ylamino]-1-({[(3-methylphenyl)methyl]oxy}methyl)-2-oxoethyl]-2-{[2-chloro-4-(trifluoromethyl)phenyl]oxy}-pyridine-3-carboxamide; 2-[(4-chlorophenyl)oxy]-N-[(1R)-1-({[(3-methylphenyl)methyl]oxy}methyl)-2-(4-methylpiperazin-1-yl)-2-oxoethyl]pyridine-3-carboxamide; 2-[(2-chloro-4-fluorophenyl)oxy]-N-[(1l)-1-({[(4-methylphenyl)methyl]oxy}-methyl)-2-(4-methylpiperazin-1-yl)-2-oxoethyl]pyridine-3-carboxamide; 2-[(2-chloro-4-fluorophenyl)oxy]-N-[(1R)-1-({[(4-methylphenyl)methyl]oxy}methyl)-2-(4-methylpiperazin-1-yl)-2-oxoethyl]pyridine-3-carboxamide; 2-[(4-fluoro-2-methylphenyl)oxy]-N-[(1R)-1-({[(4-methylphenyl)methyl]-oxy}methyl)-2-(4-methylpiperazin-1-yl)-2-oxoethyl]pyridine-3-carboxamide; 2-[(4-fluoro-2-methylphenyl)oxy]-N-[(1R)-1-({[(4-methylphenyl)methyl]oxy}methyl)-2-(4-methylpiperazin-1-yl)-2-oxoethyl]pyridine-3-carboxamide; 2-[(4-chloro-2-methylphenyl)oxy]-N-[(1R)-1-({[(4-fluorophenyl)methyl]-oxy}methyl)-2-(4-methylpiperazin-1-yl)-2-oxoethyl]pyridine-3-carboxamide; 2-[(4-chloro-2-methylphenyl)oxy]-N-[(1R)-1-({[(4-fluorophenyl)methyl]oxy}methyl)-2-(4-methylpiperazin-1-yl)-2-oxoethyl]pyridine-3-carboxamide; 2-[(2-chloro-4-fluorophenyl)oxy]-N-[(1R)-1-({[(4-fluorophenyl)methyl]-oxy}methyl)-2-(4-methylpiperazin-1-yl)-2-oxoethyl]pyridine-3-carboxamide; 2-[(2-chloro-4-fluorophenyl)oxy]-N-[(1R)-1-({[(4-fluorophenyl)methyl]oxy}methyl)-2-(4-methylpiperazin-1-yl)-2-oxoethyl]pyridine-3-carboxamide; 2-[(4-fluoro-2-methylphenyl)oxy]-N-[(1R)-1-({[(4-fluorophenyl)methyl]-oxy}methyl)-2-(4-methylpiperazin-1-yl)-2-oxoethyl]pyridine-3-carboxamide; 2-[(4-fluoro-2-methylphenyl)oxy]-N-[(1R)-1-({[(4-fluorophenyl)methyl]-oxy}methyl)-2-(4-methylpiperazin-1-yl)-2-oxoethyl]pyridine-3-carboxamide; N-[(1R)-1-({[(2-chlorophenyl)methyl]oxy}methyl)-2-(4-methylpiperazin-1-yl)-2-oxoethyl]-2-[(4-chlorophenyl)oxy]pyridine-3-carboxamide; N-[(1R)-1-({[(2-chlorophenyl)methyl]oxy}methyl)-2-(4-methylpiperazin-1-yl)-2-oxoethyl]-2-[(4-chlorophenyl)oxy]pyridine-3-carboxamide; 2-[(4-chlorophenyl)oxy]-N-[(1R)-2-(4-methylpiperazin-1-yl)-1-{[(naphthalen-2-ylmethyl)oxy]methyl}-2-oxoethyl]pyridine-3-carboxamide; 2-[(4-chlorophenyl)oxy]-N-[(1R)-2-(4-methylpiperazin-1-yl)-1-{[(naphthalen-2-ylmethyl)oxy]methyl}-2-oxoethyl]pyridine-3-carboxamide; 2-[(4-chlorophenyl)oxy]-N-[(1R)-1-[({[3-(methyloxy)phenyl]methyl}oxy)methyl]-2-(4-methylpiperazin-1-yl)-2-oxoethyl]pyridine-3-carboxamide; 2-[(4-chlorophenyl)oxy]-N-[(1R)-1-[({[3-(methyloxy)phenyl]methyl}oxy)methyl]-2-(4-methylpiperazin-1-yl)-2-oxoethyl]pyridine-3-carboxamide; 2-[(4-chlorophenyl)oxy]-N-[(1R)-1-({[(4-methylphenyl)methyl]oxy}methyl)-2-(4-methylpiperazin-1-yl)-2-oxoethyl]pyridine-3-carboxamide; 2-[(4-chlorophenyl)oxy]-N-[(1R)-1-({[(4-methylphenyl)methyl]oxy}methyl)-2-(4-methylpiperazin-1-yl)-2-oxoethyl]pyridine-3-carboxamide; N-[(1R)-1-({[(3-chlorophenyl)methyl]oxy}methyl)-2-(4-methylpiperazin-1-yl)-2-oxoethyl]-2-[(4-chlorophenyl)oxy]pyridine-3-carboxamide; N-[(1R)-1-({[(3-chlorophenyl)methyl]oxy}methyl)-2-(4-methylpiperazin-1-yl)-2-oxoethyl]-2-[(4-chlorophenyl)oxy] pyridine-3-carboxamide; N-[(1R)-1-({[(4-chlorophenyl) methyl]oxy}methyl)-2-(4-methylpiperazin-1-yl)-2-oxoethyl]-2-[(4-chlorophenyl)oxy]pyridine-3-carboxamide; N-[(1R)-1-({[(4-chlorophenyl)methyl]oxy}methyl)-2-(4-methylpiperazin-1-yl)-2-oxoethyl]-2-[(4-chlorophenyl)oxy] pyridine-3-carboxamide; 2-[(4-chlorophenyl)oxy]-N-[(1R)-1-({[(2,4-dimethylphenyl)methyl]oxy}methyl)-2-(4-methylpiperazin-1-yl)-2-oxoethyl]pyridine-3-carboxamide; 2-[(4-chlorophenyl)oxy]-N-[(1R)-1-({[(2,4-dimethylphenyl)methyl]oxy}methyl)-2-(4-methylpiperazin-1-yl)-2-oxoethyl]pyridine-3-carboxamide; 2-[(4-chlorophenyl)oxy]-N-[(1R)-2-(4-methylpiperazin-1-yl)-2-oxo-1-{[(pyridin-3-ylmethyl)oxy]methyl}ethyl]pyridine-3-carboxamide; 2-[(4-chlorophenyl)oxy]-N-[(1R)-2-(4-methylpiperazin-1-yl)-2-oxo-1-{[(pyridin-3-yl methyl)oxy]methyl}ethyl]pyridine-3-carboxamide; 2-[(4-chlorophenyl)oxy]-N-[(1R)-1-[({[4-(1-methylethyl)phenyl]methyl}oxy)-methyl]-2-(4-methylpiperazin-1-yl)-2-oxoethyl]pyridine-3-carboxamide; 2-[(4-chlorophenyl)oxy]-N-[(1R)-1-[({[4-(1-methylethyl) phenyl]methyl}oxy)methyl]-2-(4-methylpiperazin-1-yl)-2-oxoethyl]pyridine-3-carboxamide; 2-[(4-chlorophenyl) oxy]-N-[(1R)-1-({[(2-methylphenyl)methyl]oxy}methyl)-2-(4-methylpiperazin-1-yl)-2-oxoethyl]pyridine-3-carboxamide; 2-[(4-chlorophenyl)oxy]-N-[(1R)-1-({[(2-methylphenyl)methyl]oxy}methyl)-2-(4-methylpiperazin-1-yl)-2-oxoethyl]pyridine-3-carboxamide; N-[(1R)-1-({[(2-chloropyridin-4-yl)methyl]oxy}methyl)-2-(4-methylpiperazin-1-yl)-2-oxoethyl]-2-{[2-chloro-4-(trifluoromethyl)phenyl]oxy}pyridine-3-carboxamide; N-[(1R)-1-({[(2-chloropyridin-4-yl)methyl]oxy}methyl)-2-(4-methylpiperazin-1-yl)-2-oxoethyl]-2-{[2-chloro-4-(trifluoromethyl)phenyl]oxy}pyridine-3-carboxamide; 2-{[2-chloro-4-(trifluoromethyl)phenyl]oxy}-N-[(1R)-1-{[(2,3-dihydro-1,4-benzodioxin-6-ylmethyl)oxy]methyl}-2-(4-methylpiperazin-1-yl)-2-oxoethyl]pyridine-3-carboxamide; 2-{[2-chloro-4-(trifluoromethyl)phenyl]oxy}-N-[(1R)-1-({[(2-methyl-1,3-oxazol-5-yl)methyl]oxy}methyl)-2-(4-methylpiperazin-1-yl)-2-oxoethyl]pyridine-3-carboxamide; 2-{[2-chloro-4-(trifluoromethyl)phenyl]oxy}-N-[(1R)-1-({[(2-methyl-1,3-oxazol-5-yl)methyl]-oxy}methyl)-2-(4-methylpiperazin-1-yl)-2-oxoethyl]pyridine-3-carboxamide; 2-{[2-chloro-4-(trifluoromethyl)phenyl]oxy}-N-{(1R)-1-{[(2,3-dihydro-1,4-benzodioxin-6-ylmethyl)oxy]methyl}-2-[3-(dimethylamino)azetidin-1-yl]-2-oxoethyl}pyridine-3-carboxamide; 2-{[2-chloro-4-(trifluoromethyl)phenyl]oxy}-N-{(1R)-1-{[(2,3-dihydro-1,4-benzodioxin-6-ylmethyl)oxy]methyl}-2-[3-(dimethylamino)azetidin-1-yl]-2-oxoethyl}pyridine-3-carboxamide; 2-{[2-chloro-4-(trifluoromethyl)phenyl]oxy}-N-[(1R)-2-[(3R)-3-(dimethylamino)-pyrrolidin-1-yl]-1-({[(3-methylphenyl)methyl]oxy}methyl)-2-oxoethyl]pyridine-3-carboxamide; 2-{[2-chloro-4-(trifluoromethyl)phenyl]oxy}-N-[(1R)-2-[(3R)-3-(dimethylamino)pyrrolidin-1-yl]-1-({[(3-methylphenyl)methyl]oxy}methyl)-2-oxoethyl]pyridine-3-carboxamide; 2-[(2,4-dichlorophenyl)oxy]-N-[(1R)-2-(4-methylpiperazin-1-yl)-2-oxo-1-{[(pyridin-4-ylmethyl)oxy]methyl}ethyl]pyridine-3-carboxamide; 2-[(2,4-dichlorophenyl)oxy]-N-[(1R)-2-(4-methylpiperazin-1-yl)-2-oxo-1-{[(pyridin-4-ylmethyl)oxy]methyl}ethyl]pyridine-3-carboxamide; 2-[(2,4-dichlorophenyl)oxy]-N-[(1R)-1-({[(2,6-dichloropyridin-4-yl)methyl]oxy}methyl)-2-(4-methylpiperazin-1-yl)-2-oxoethyl]pyridine-3-carboxamide; 2-[(2,4-dichlorophenyl)oxy]-N-[(1R)-1-({[(2,6-dichloropyridin-4-yl)methyl]oxy}methyl)-2-(4-methylpiperazin-1-yl)-2-oxoethyl]pyridine-3-carboxamide; 2-{[2-chloro-4-(trifluoromethyl)phenyl]oxy}-N-[(1R)-2-(4-methylpiperazin-1-yl)-2-oxo-1-{[(pyridin-4-ylmethyl)oxy]methyl}ethyl]pyridine-3-carboxamide; 2-{[2-chloro-4-(trifluoromethyl)phenyl]oxy}-N-[(1R)-2-(4-methylpiperazin-1-yl)-2-oxo-1-{[(pyridin-4-ylmethyl)oxy]methyl}ethyl]pyridine-3-carboxamide; N-[(1R)-1-({[(2-bromopyridin-4-yl)methyl]oxy}methyl)-2-(4-methylpiperazin-1-yl)-2-oxoethyl]-2-{[2-chloro-4-(trifluoromethyl)phenyl]oxy}pyridine-3-carboxamide; 2-{[2-chloro-4-(trifluoromethyl)phenyl]oxy}-N-{(1R)-1-{[(2,3-dihydro-1,4-benzodioxin-6-ylmethyl)oxy]methyl}-2-[3-(methylamino)azetidin-1-yl]-2-oxoethyl}pyridine-3-carboxamide; N-[(1R)-2-(3-aminoazetidin-1-yl)-1-{[(2,3-dihydro-1,4-benzodioxin-6-ylmethyl)oxy]methyl}-2-oxoethyl]-2-{[2-chloro-4-(trifluoromethyl)phenyl]oxy}pyridine-3-carboxamide; 2,4-dichloro-N-alpha-{[1-(2,4-dichlorophenyl)cyclopropyl]carbonyl}-N-[2-(dimethylamino)ethyl]-L-phenylalaninamide; 2-{[2-chloro-4-(trifluoromethyl)phenyl]oxy}-N-[(1R)-2-(4-methylpiperazin-1-yl)-2-oxo-1-{[(phenylmethyl)oxy]methyl}ethyl]pyridine-3-carboxamide; 2-[(4-bromo-2-chlorophenyl)oxy]-N-[(1R)-2-(4-methylpiperazin-1-yl)-2-oxo-1-{[(phenylmethyl)oxy]methyl}ethyl]pyridine-3-carboxamide; 2-[(4-chloro-2-methoxyphenyl)oxy]-N-[(1R)-2-(4-methylpiperazin-1-yl)-2-oxo-1-{[(phenylmethyl)oxy]methyl}ethyl]pyridine-3-carboxamide; 2-{[2-bromo-4-(trifluoromethyl)phenyl]oxy}-N-[(1R)-2-(4-methylpiperazin-1-yl)-2-oxo-1-{[(phenylmethyl)oxy]methyl}ethyl]pyridine-3-carboxamide; 2-[(2,4-dichloro-6-methylphenyl)oxy]-N-[(1R)-2-(4-methylpiperazin-1-yl)-2-oxo-1-{[(phenylmethyl)oxy]methyl}ethyl]pyridine-3-carboxamide; N-[(1R)-2-(4-methylpiperazin-1-yl)-2-oxo-1-{[(phenylmethyl)oxy]methyl}ethyl]-2-{[4-(trifluoromethyl)phenyl]oxy}pyridine-3-carboxamide; 2-[(2,4-difluorophenyl)oxy]-N-[(1R)-2-(4-methylpiperazin-1-yl)-2-oxo-1-{[(phenylmethyl)oxy]methyl}ethyl]pyridine-3-carboxamide; 2-[(2,6-dichlorophenyl)oxy]-N-[(1R)-2-(4-methylpiperazin-1-yl)-2-oxo-1-{[(phenylmethyl)oxy]methyl}ethyl]pyridine-3-carboxamide; 2-[(2-chloro-6-methylphenyl)oxy]-N-[(1R)-2-(4-methylpiperazin-1-yl)-2-oxo-1-{[(phenylmethyl)oxy]methyl}ethyl]pyridine-3-carboxamide; 2-[(2,4-dichlorophenyl)oxy]-N-[(1R)-2-(4-methylpiperazin-1-yl)-2-oxo-1-{[(phenylmethyl)oxy]methyl}ethyl]pyridine-3-carboxamide; 2-{[2-chloro-5-(trifluoromethyl)phenyl]oxy}-N-[(1R)-2-(4-methylpiperazin-1-yl)-2-oxo-1-{[(phenylmethyl)oxy]methyl}ethyl]pyridine-3-carboxamide; N-[(1R)-2-(4-methylpiperazin-1-yl)-2-oxo-1-{[(phenylmethyl)oxy]methyl}ethyl]-2-(phenyloxy)pyridine-3-carboxamide; 2-[(3,4-dimethylphenyl)oxy]-N-[(1R)-2-(4-methylpiperazin-1-yl)-2-oxo-1-{[(phenylmethyl)oxy]methyl}ethyl]pyridine-3-carboxamide; 2-[(2,6-difluorophenyl)oxy]-N-[(1R)-2-(4-methylpiperazin-1-yl)-2-oxo-1-{[(phenylmethyl)oxy]methyl}ethyl]pyridine-3-carboxamide; N-[(1R)-2-(4-methylpiperazin-1-yl)-2-oxo-1-{[(phenylmethyl)oxy]methyl}ethyl]-2-(naphthalen-1-yloxy)pyridine-3-carboxamide; 2-[(4-fluorophenyl)oxy]-N-[(1R)-2-(4-methylpiperazin-1-yl)-2-oxo-1-{[(phenylmethyl)oxy]methyl}ethyl]pyridine-3-carboxamide; 2-[(4-methylphenyl)oxy]-N-[(1R)-2-(4-methylpiperazin-1-yl)-2-oxo-1-{[(phenylmethyl)oxy]methyl}ethyl]pyridine-3-carboxamide; 2-[(4-bromophenyl)oxy]-N-[(1R)-2-(4-methylpiperazin-1-yl)-2-oxo-1-{[(phenylmethyl)oxy]methyl}ethyl]pyridine-3-carboxamide; 2-{[2-chloro-4-(methyloxy)phenyl]oxy}-N-[(1R)-2-(4-methylpiperazin-1-yl)-2-oxo-1-{[(phenylmethyl)oxy]methyl}ethyl]pyridine-3- carboxamide; 2-[(2-bromo-4-chlorophenyl)oxy]-N-[(1R)-2-(4-methylpiperazin-1-yl)-2-oxo-1-{[(phenylmethyl)oxy]methyl}ethyl]pyridine-3-carboxamide; N-[(1R)-2-(4-methylpiperazin-1-yl)-2-oxo-1-{[(phenylmethyl)oxy]methyl}ethyl]-2-[(2,4,6-trichlorophenyl)oxy]pyridine-3-carboxamide; 2-{[3-(dimethylamino)phenyl]oxy}-N-[(1R)-2-(4-methylpiperazin-1-yl)-2-oxo-1-{[(phenylmethyl)oxy]methyl}ethyl]pyridine-3-carboxamide; 2-[(4-chloro-2-methylphenyl)oxy]-N-[(1R)-1-({[(3-methylphenyl)methyl]oxy}methyl)-2-(4-methylpiperazin-1-yl)-2-oxoethyl]pyridine-3-carboxamide; 2-[(4-chlorophenyl)oxy]-N-[(1R)-1-[(4-methylpiperazin-1-yl)carbonyl]-3-(phenyloxy)propyl]pyridine-3-carboxamide; 2-{[2-chloro-4-(trifluoromethyl)phenyl]oxy}-N-[(1R)-1-({[(4-fluorophenyl)methyl]oxy}methyl)-2-(4-methylpiperazin-1-yl)-2-oxoethyl]pyridine-3-carboxamide; 2-[(2,4-dichlorophenyl)oxy]-N-[(1R)-1-[(4-methylpiperazin-1-yl)carbonyl]-3-(phenyloxy)propyl]pyridine-3-carboxamide; N-[(1S)-1-({[(4-chlorophenyl)methyl]oxy}methyl)-2-(4-methylpiperazin-1-yl)-2-oxoethyl]-1-(2,4-dichlorophenyl)cyclopropane carboxamide; 2-[(2,4-dichlorophenyl)oxy]-5-fluoro-N-[(1R)-2-(4-methylpiperazin-1-yl)-2-oxo-1-{[(phenylmethyl)oxy]methyl}ethyl]pyridine-3-carboxamide; 2-[(4-fluoro-2-methylphenyl)oxy]-N-[(1R)-2-(4-methylpiperazin-1-yl)-2-oxo-1-{[(phenylmethyl)oxy]methyl}ethyl]pyridine-3-carboxamide; 2-[(2-chloro-4-fluorophenyl)oxy]-N-[(1R)-2-(4-methylpiperazin-1-yl)-2-oxo-1-{[(phenylmethyl)oxy]methyl}ethyl]pyridine-3-carboxamide; 2-[(4-chlorophenyl)oxy]-6-methyl-N-[(1R)-2-(4-methylpiperazin-1-yl)-2-oxo-1-{[(phenylmethyl)oxy]methyl}ethyl]pyridine-3-carboxamide; 2-[(4-chlorophenyl)oxy]-5-fluoro-N-[(1R)-2-(4-methylpiperazin-1-yl)-2-oxo-1-{[(phenylmethyl)oxy]methyl}ethyl]pyridine-3-carboxamide; 2-[(2,4-dichlorophenyl)oxy]-N-[(1R)-2-[methyl(1-methylpiperidin-4-yl)amino]-2-oxo-1-{[(phenylmethyl)oxy]methyl}ethyl]pyridine-3-carboxamide; 2-{[2-chloro-4-(trifluoromethyl)phenyl]oxy}-N-[(1R)-2-[methyl(1-methylpiperidin-4-yl)amino]-2-oxo-1-{[(phenylmethyl)oxy]methyl}ethyl]pyridine-3-carboxamide; 2-[(2,4-dichlor ophenyl)oxy]-N-[(1R)-2-[(1-methylpiperidin-4-yl)amino]-2-oxo-1-{[(phenylmethyl)oxy]methyl}ethyl]pyridine-3-carboxamide; 5-bromo-2-[(4-chlorophenyl)oxy]-N-[(1R)-2-(4-methylpiperazin-1-yl)-2-oxo-1-{[(phenylmethyl)oxy]methyl}ethyl]pyridine-3-carboxamide; 2-{[4-chloro-2-(phenylmethyl)phenyl]oxy}-N-[(1R)-2-(4-methylpiperazin-1-yl)-2-oxo-1-{[(phenylmethyl)oxy]methyl}ethyl]pyridine-3-carboxamide; N-[(3S)-1-azabicyclo[2.2.2]oct-3-yl]-N'2'-{[1-(2,4-dichlorophenyl)-cyclopropyl]-carbonyl}-3-(2,3-dihydro-1,4-benzodioxin-6-yl)-L-alaninamide; 2-{[2-chloro-4-(trifluoromethyl)phenyl]oxy}-N-[(1R)-1-{[(2,2-dimethylpropyl)oxy]methyl}-2-(4-methylpiperazin-1-yl)-2-oxoethyl]pyridine-3-carboxamide; 2-[(4-chloro-2-methylphenyl)oxy]-N-[(1R)-1-{[(cyclohexylmethyl)oxy]methyl}-2-(4-methylpiperazin-1-yl)-2-oxoethyl]pyridine-3-carboxamide; N-[(1R)-1-{[(cyclohexylmethyl)oxy]methyl}-2-(4-methylpiperazin-1-yl)-2-oxoethyl]-2-[(2,4-dichlorophenyl)oxy]pyridine-3-carboxamide; 2-[(2-chloro-4-fluorophenyl)oxy]-N-[(1R)-1-{[(cyclohexylmethyl)oxy]methyl}-2-(4-methylpiperazin-1-yl)-2-oxoethyl]pyridine-3-carboxamide; 2-{[2-chloro-4-(trifluoromethyl)phenyl]oxy}-N-[(1R)-1-({[(1-methylcyclopropyl)methyl]oxy}methyl)-2-(4-methylpiperazin-1-yl)-2-oxoethyl]pyridine-3-carboxamide; 2-[(2,4-dichlorophenyl)oxy]-N-[(1R)-1-({[(1-methylcyclopropyl)methyl]oxy}methyl)-2-(4-methylpiperazin-1-yl)-2-oxoethyl]pyridine-3-carboxamide; 2-{[2-chloro-4-(trifluoromethyl)phenyl]oxy}-N-{(1R)-1-({[(1-methylcyclopropyl)methyl]oxy}methyl)-2-[(1-methylpiperidin-4-yl)amino]-2-oxoethyl}-pyridine-3-carboxamide; 2-[(4-chlorophenyl)oxy]-N-[(1R)-1-({[(1-methylcyclopropyl)methyl]oxy}methyl)-2-(4-methylpiperazin-1-yl)-2-oxoethyl]pyridine-3-carboxamide; N-[(1R)-1-[(bicyclo[2.2.1]hept-2-yloxy)methyl]-2-(4-methylpiperazin-1-yl)-2-oxoethyl]-2-[(4-chlorophenyl)oxy]pyridine-3-carboxamide; 2-[(4-chlorophenyl)oxy]-N-[(1R)-1-[(cyclohexyloxy)methyl]-2-(4-methylpiperazin-1-yl)-2-oxoethyl]pyridine-3-carboxamide; 2-[(4-chlorophenyl)oxy]-N-[(1R)-1-{[(cyclohexylmethyl)oxy]methyl}-2-(4-methylpiperazin-1-yl)-2-oxoethyl]pyridine-3-carboxamide; 2-[(4-chlorophenyl)oxy]-N-[(1R)-2-(4-methylpiperazin-1-yl)-2-oxo-1-{[(1-phenylethyl)oxy]methyl}ethyl]pyridine-3-carboxamide; 2-[(4-chlorophenyl)oxy]-N-[(1R)-2-(4-methylpiperazin-1-yl)-2-oxo-1-{[(phenylmethyl)oxy]methyl}ethyl]benzamide; 2-[(4-chlorophenyl)oxy]-N-[(1R)-2-(4-methylpiperazin-1-yl)-2-oxo-1-{[(phenylmethyl)amino]methyl}ethyl]pyridine-3-carboxamide; 2-{[2-chloro-4-(trifluoromethyl)phenyl]oxy}-N-[(1R)-2-oxo-2-{(3R)-3-[(phenylmethyl)amino]pyrrolidin-1-yl}-1-{[(phenylmethyl)oxy]methyl}ethyl]pyridine-3-carboxamide; 2-[(4-chlorophenyl)oxy]-N-[(1R)-2-[(3R)-3-(dimethylamino)pyrrolidin-1-yl]-2-oxo-1-{[(phenylmethyl)oxy]methyl}ethyl]pyridine-3-carboxamide; 2-{[2-chloro-4-(trifluoromethyl)phenyl]oxy}-N-[(1R)-2-[(3R)-3-(dimethylamino)pyrrolidin-1-yl]-2-oxo-1-{[(phenylmethyl)oxy]methyl}ethyl]pyridine-3-carboxamide; 2-{[2-chloro-4-(trifluoromethyl)phenyl]oxy}-N-[(1R)-2-[3-(methylamino)pyrrolidin-1-yl]-2-oxo-1-{[(phenylmethyl)oxy]methyl}ethyl]pyridine-3-carboxamide; 2-{[2-chloro-4-(trifluoromethyl)phenyl]oxy}-N-[(1R)-2-{3-[methyl(phenylmethyl)amino]pyrrolidin-1-yl}-2-oxo-1-{[(phenylmethyl)oxy]methyl}ethyl]pyridine-3-carboxamide; 2-{[2-chloro-4-(trifluoromethyl)phenyl]oxy}-N-[(1R)-2-oxo-2-{(3R)-3-[(2-phenylethyl)amino]pyrrolidin-1-yl}-1-{[(phenylmethyl)oxy]methyl}ethyl]pyridine-3-carboxamide; 2-{[2-chloro-4-(trifluoromethyl)phenyl]oxy}-N-[(1R)-2-{(3R)-3-[(2-methylpropyl)amino]pyrrolidin-1-yl}-2-oxo-1-{[(phenylmethyl)oxy]methyl}ethyl]-pyridine-3-carboxamide; 2-{[2-chloro-4-(trifluoromethyl)phenyl]oxy}-N-[(1R)-2-[(3R)-3-(methylamino)pyrrolidin-1-yl]-2-oxo-1-{[(phenylmethyl)oxy]methyl}ethyl]pyridine-3-carboxamide; 2-{[2-chloro-4-(trifluoromethyl)phenyl]oxy}-N-[(1R)-2-[(3S)-3-(methylamino)pyrrolidin-1-yl]-2-oxo-1-{[(phenylmethyl)oxy]methyl}ethyl]pyridine-3-carboxamide; 2-{[2-chloro-4-(trifluoromethyl)phenyl]oxy}-N-[(1S)-2-[(3S)-3-(dimethylamino)pyrrolidin-1-yl]-1-{[(phenylmethyl)oxy]methyl}ethyl]pyridine-3-carboxamide; 2-{[2-chloro-4-(trifluoromethyl)phenyl]oxy}-N-[(1S)-2-[(phenylmethyl)oxy]-1-(pyrrolidin-1-ylmethyl)ethyl]pyridine-3-carboxamide; 2-{[2-chloro-4-(trifluoromethyl)phenyl]oxy}-N-[(1S)-2-(4-methylpiperazin-1-yl)-1-{[(phenylmethyl)oxy]methyl}ethyl]pyridine-3-carboxamide; 2-[(2,4-dichlorophenyl)oxy]-N-[(1S)-2-morpholin-4-yl-1-{[(phenylmethyl)oxy]methyl}ethyl]pyridine-3-carboxamide; 2-[(2,4-dichlorophenyl)oxy]-N-[(1S)-2-[3-(dimethylamino)pyrrolidin-1-yl]-1-{[(phenylmethyl)oxy]methyl}ethyl]pyridine-3-carboxamide; 2-[(2,4-dichlorophenyl)oxy]-N-[(1S)-2-(4-methylpiperazin-1-yl)-1-{[(phenylmethyl)oxy]methyl}ethyl]pyridine-3-carboxamide; 2-[(2,4-dichlorophenyl)oxy]-N-[(1S)-2-[(3R)-3-(dimethylamino)pyrrolidin-1-yl]-1-{[(phenylmethyl)oxy]methyl}ethyl]pyridine-3-carboxamide; 2-[(2,4-dichlorophenyl)oxy]-N-[(1S)-2-[(3S)-3-(dimethylamino)pyrrolidin-1-yl]-1-{[(phenylmethyl)oxy]methyl}ethyl]pyridine-3-carboxamide; (R)-2-(tert-butoxycarbonylamino)-3-((1-methylcyclopropyl)methoxy)propanoic acid.

In one embodiment, the inhibitor of ganglioside metabolism is an inhibitor of the glucosylceramide synthase described in the patent application WO2010091164 incorporated herein by reference and is selected from the group comprising: 1-(2,4-dichlorophenyl)-N-[(2S)-3-(1H-indol-3-yl)-1-(4-methylpiperazin-1-yl)-1-oxopropan-2-yl]cyclopropanecarboxamide; 1-(2,4-dichlorophenyl)-N-[(1S)-2-[3-(dimethylamino)azetidin-1-yl]-1-(1H-indol-3-ylmethyl)-2-oxoethyl]cyclopropanecarboxamide; Nalpha-{[1-(2,4-dichlorophenyl)cyclopropyl]carbonyl}-N-[2-(dimethylamino)-ethyl]-L-tryptophanamide; 1-(2,4-dichlorophenyl)-N-[(1S)-1-(1H-indol-3-ylmethyl)-2-(4-methyl-1,4-diazepan-1-yl)-2-oxoethyl] cyclopropanecarboxamide; 1-(2,4-dichlorophenyl)-N-[(1S)-1-(1H-indol-3-ylmethyl)-2-oxo-2-piperazin-1-ylethyl] cyclopropanecarboxamide; 1-(2,4-dichlorophenyl)-N-[(1S)-1-(1H-indol-3-ylmethyl)-2-morpholin-4-yl-2-oxoethyl] cyclopropanecarboxamide; 1-(2,4-dichlorophenyl)-N-[(1S)-2-{4-[3-(dimethylamino)propyl]piperazin-1-yl}-1-(1H-indol-S-ylmethyl]-1-oxoethyllcyclopropanecarboxamide; Nalpha-{[1-(2,4-dichlorophenyl)cyclopropyl]carbonyl}-N-(1-methylpiperidin-4-yl)-L-tryptophanamide; Nalpha-{[1-(2,4-dichlorophenyl)cyclopropyl]carbonyl}-N-[3-(dimethylamino)-propyl]-L-tryptophanamide; N-[(3S)-1-azabicyclo[2.2.2]oct-3-yl]-Nalpha-{[1-(2,4-dichlorophenyl)-cyclopropyl]carbonyl}-L-tryptophanamide; 1-(4-chlorophenyl)-N-[(1S)-1-(1H-indol-3-ylmethyl)-2-(4-methylpiperazin-1-yl)-2-oxoethyl] cyclopropanecarboxamide; N-[(1S)-1-(1H-indol-3-ylmethyl)-2-(4-methylpiperazin-1-yl)-2-oxoethyl]-1-[4-(methyloxy)phenyl]cyclopropanecarboxamide; N-[(1S)-1-[(2,4-dichlorophenyl)methyl]-2-(4-methylpiperazin-1-yl)-2-oxoethyl]-1-[4-(trifluoromethyl)phenyl] cyclopropanecarboxamide; N-[(1S)-1-[(2-chlorophenyl) methyl]-2-(4-methylpiperazin-1-yl)-2-oxoethyl]-1-(2,4-dichlorophenyl)cyclopropanecarboxamide; 1-(2,4-dichlorophenyl)-N-[(1S)-1-{[4-(methyloxy)phenyl] methyl}-2-(4-methylpiperazin-1-yl)-2-oxoethyl] cyclopropanecarboxamide; N-[(2S)-3-(3-chlorophenyl)-1-(4-methylpiperazin-1-yl)-1-oxopropan-2-yl]-1-(2,4-dichlorophenyl)cyclopropanecarboxamide; 2-(2,4-dichlorophenyl)-N-[(1S)-1-[(2,4-dichlorophenyl)methyl]-2-(4-methylpiperazin-1-yl)-2-oxoethyl]-2-methylpropanamide; 1-(2,4-dichlorophenyl)-N-[(1S)-1-[(3,4-dichlorophenyl)methyl]-2-(4-methylpiperazin-1-yl)-2-oxoethyl]cyclopropanecarboxamide; 1-(2,4-dichlorophenyl)-N-[(1S)-1-[(4-fluorophenyl)methyl]-2-(4-methylpiperazin-1-yl)-2-oxoethyl] cyclopropanecarboxamide; 1-(2,4-dichlorophenyl)-N-[(1S)-1-[(2,4-dichlorophenyl)methyl]-2-(4-methylpiperazin-1-yl)-2-oxoethyl]cyclopropanecarboxamide; 4-bromo-Nalpha-{[1-(2,4-dichlorophenyl)cyclopropyl]carbonyl}-N-[2-(dimethyl-amino)ethyl]-L-phenylalaninamide; 1-(2,4-dichlorophenyl)-N-[(1S)-1-{[4-(ethyloxy)phenyl]methyl}-2-(4-methyl-piperazin-1-yl)-2-oxoethyl] cyclopropanecarboxamide; 1-(2,4-dichlorophenyl)-N-[(1S)-1-[(2,4-dimethylphenyl)methyl]-2-(4-methyl-piperazin-1-yl)-2-oxoethyl]cyclopropanecarboxamide; 1-(2,4-dichlorophenyl)-N-[(1S)-2-(4-methylpiperazin-1-yl)-1-(naphthalen-2-ylmethyl)-2-oxoethyl] cyclopropanecarboxamide; 1-(2,4-dichlorophenyl)-N-[(1S)-1-[(4-methylphenyl)methyl]-2-(4-methyl-piperazin-1-yl)-2-oxoethyl]cyclopropanecarboxamide; N-[(1S)-1-[(4-bromophenyl)methyl]-2-(4-methylpiperazin-1-yl)-2-oxoethyl]-1-(2,4-dichlorophenyl) cyclopropanecarboxamide; 1-(3,4-dichlorophenyl)-N-[(1S)-1-[(2,4-dichlorophenyl)methyl]-2-(4-methylpiperazin-1-yl)-2-oxoethyl]cyclopropanecarboxamide; N-[(1S)-1-[(4-chlorophenyl)methyl]-2-(4-methylpiperazin-1-yl)-2-oxoethyl]-1-(2,4-dichlorophenyl) cyclopropanecarboxamide; 1-(2,4-dichlorophenyl)-N-[(1S)-1-[(2-fluorophenyl)methyl]-2-(4-methylpiperazin-1-yl)-2-oxoethyl]cyclopropanecarboxamide; 1-(2,4-dichlorophenyl)-N-[(1S)-2-(4-methylpiperazin-1-yl)-2-oxo-1-{[4-(trifluoromethyl)phenyl]methyl}ethyl] cyclopropanecarboxamide; 1-(2,4-dichlorophenyl)-N-[2-(4-methylpiperazin-1-yl)-2-oxo-1-(phenylmethyl)-ethyl] cyclopropane-carboxamide; 1-(2,6-dichlorophenyl)-N-[(1S)-1-[(2,4-dichlorophenyl)methyl]-2-(4-methylpiperazin-1-yl)-2-oxoethyl] cyclopropanecarboxamide; 1-(2,4-dichlorophenyl)-N-{(1S)-2-(4-methylpiperazin-1-yl)-2-oxo-1-[(3,4,5-trifluorophenyl)methyl] ethyl}cyclopropanecarboxamide; 1-(2,4-dichlorophenyl)-N-[(1S)-1-[(3,4-difluorophenyl) methyl]-2-(4-methylpiperazin-1-yl)-2-oxoethyl]cyclopropanecarboxamide; 1-(2,4-dichlorophenyl)-N-[(1S)-1-[(4-hydroxyphenyl)methyl]-2-(4-methylpiperazin-1-yl)-2-oxoethyl]cyclopropanecarboxamide; N-[(1S)-1-[(2,4-dichlorophenyl)methyl]-2-(4-methylpiperazin-1-yl)-2-oxoethyl]-1-[3-(trifluoromethyl)phenyl] cyclopropanecarboxamide; 1-(2-chlorophenyl)-N-[(1S)-1-[(2,4-dichlorophenyl)methyl]-2-(4-methyl-piperazin-1-yl)-2-oxoethyl]cyclopropanecarboxamide; N-[(1S)-1-[(2,4-dichlorophenyl)methyl]-2-(4-methylpiperazin-1-yl)-2-oxoethyl]-1-(4-fluorophenyl)cyclopropanecarboxamide; N-[(1S)-1-[(2,4-dichlorophenyl)methyl]-2-(4-methylpiperazin-1-yl)-2-oxoethyl]-1-[2-(trifluoromethyl)phenyl]cyclopropanecarboxamide; N-[(1S)-1-[(2,4-dichlorophenyl) methyl]-2-(4-methylpiperazin-1-yl)-2-oxoethyl]-1-(2,4-difluorophenyl)cyclopropanecarboxamide; N-[(3S)-1-azabicyclo[2.2.2]oct-3-yl]-N-2-{[1-(2,4-dichlorophenyl) cyclopropyl]-carbonyl}-5-phenyl-L-norvalinamide; 4-bromo-N-{[1-(2,4-dichlorophenyl)cyclopropyl]carbonyl}-L-phenylalanyl-N-[2-(dimethylamino)ethyl]-L-prolinamide; 2,4-dichloro-N-alpha-{[1-(2,4-dichlorophenyl)cyclopropyl]carbonyl}-N-[2-(dimethylamino)ethyl]-L-phenylalaninamide; 2,4-dichloro-Nalpha-{[1-(2,4-dichlorophenyl)cyclopropyl]carbonyl}-N-methyl-N-(1-methylpyrrolidin-3-yl)-L-phenylalaninamide; 2,4-dichloro-Nalpha-{[1-(2,4-dichlorophenyl)cyclopropyl]carbonyl}-N-methyl-N-(1-methylpiperidin-4-yl)-L-phenylalaninamide; 1-(2,4-dichlorophenyl)-N-{(1S)-1-[(2,4-dichlorophenyl) methyl]-2-[(3R)-3-(dimethylamino)-pyrrolidin-1-yl]-2-oxoethyl}cyclopropanecarboxamide; 1-(2,4-dichlorophenyl)-N-{(1S)-1-[(2,4-dichlorophenyl)methyl]-2-[(3S)-3-(dimethylamino)-pyrrolidin-1-yl]-2-oxoethyl}cyclopropanecarboxamide; 2,4-dichloro-Nalpha-{[1-(2,4-dichlorophenyl)cyclopropyl]carbonyl}-N-[2-(dimethylamino)-1-methylethyl]-L-phenylalaninamide; 2,4-dichloro-Nalpha-{[1-(2,4-dichlorophenyl)cyclopropyl] carbonyl}-N-[1-(phenylmethyl)-piperidin-4-yl]-L-phenylalaninamide; 1-(2,4-dichlorophenyl)-N-[(1S)-1-[(2,4-dichlorophenyl)methyl]-2-(4-methylpiperazin-1-yl)-2-oxoethyl]cyclopropanecarboxamide; 1-(2,4-dichlorophenyl)-N-[(1R)-1-[(2,4-dichlorophenyl)methyl]-2-(4-methylpiperazin-1-yl)-2-oxoethyl] cyclopropanecarboxamide; 1-(2,4-dichlorophenyl)-N-[(1S)-2-(4-methylpiperazin-1-yl)-2-oxo-1-(phenylmethyl)ethyl]-cyclo propanecarboxamide; 1-(2,4-dichlorophenyl)-N-[(1S)-2-(4-methylpiperazin-1-yl)-1-(naphthalen-1-ylmethyl)-2-oxoethyl]cyclopropanecarboxamide; 1-(2,4-dichlorophenyl)-N-{(1S)-1-[(2,4-dichlorophenyl)methyl]-2-[(8aR)-hexahydropyrrolo-[1,2-a]pyrazin-2(1H)-yl]-2-oxoethyl}cyclopropanecarboxamide; N-1-azabicyclo[2.2.2]

oct-3-yl-2,4-dichloro-Nalpha-{[1-(2,4-dichlorophenyl)cyclopropyl]-carbonyl}-L-phenylalaninamide; 2,4-dichloro-Nalpha-{[1-(2,4-dichlorophenyl)cyclopropyl]carbonyl}-N-[2-(diethylamino)-ethyl]-L-phenylalaninamide; 2,4-dichloro-Nalpha-{[1-(2,4-dichlorophenyl)cyclopropyl]carbonyl}-N-[2-(1-methylpyrrolidin-2-yl)ethyl]-L-phenylalaninamide; 2,4-dichloro-Nalpha-{[1-(2,4-dichlorophenyl)cyclopropyl]carbonyl}-N-(2-piperidin-1-ylethyl)-L-phenylalaninamide; 2,4-dichloro-Nalpha-{[1-(2,4-dichlorophenyl)cyclopropyl]carbonyl}-N-[3-(dimethylamino)-propyl]-L-phenylalaninamide; 2,4-dichloro-Nalpha-{[1-(2,4-dichlorophenyl)cyclopropyl]carbonyl}-N-(1-ethylpiperidin-3-yl)-L-phenylalaninamide; 2,4-dichloro-Nalpha-{[1-(2,4-dichlorophenyl)cyclopropyl]carbonyl}-N-[1-(phenylmethyl)pyrrolidin-3-yl]-L-phenylalaninamide; N-[(1S)-1-[(4-acetylphenyl)methyl]-2-(4-methylpiperazin-1-yl)-2-oxoethyl]-1-(2,4-dichlorophenyl)cyclopropanecarboxamide; 1-(2,4-dichlorophenyl)-N-[(1S)-2-(4-methylpiperazin-1-yl)-2-oxo-1-{[1-(phenyl-methyl)-1H-imidazol-5-yl]methyl}ethyl]cyclopropanecarboxamide; 1-(2,4-dichlorophenyl)-N-[(1S)-1-[(2-methylphenyl)methyl]-2-(4-methylpiperazin-1-yl)-2-oxoethyl]cyclopropanecarboxamide; 1-(2,4-dichlorophenyl)-N-[(1S)-1-[(3-methylphenyl)methyl]-2-(4-methylpiperazin-1-yl)-2-oxoethyl]cyclopropanecarboxamide; 1-(2,4-dichlorophenyl)-N-[(1S)-1-[(3-fluorophenyl)methyl]-2-(4-methylpiperazin-1-yl)-2-oxoethyl]cyclopropanecarboxamide; N-[(1S)-1-[(4-cyanophenyl)methyl]-2-(4-methylpiperazin-1-yl)-2-oxoethyl]-1-(2,4-dichlorophenyl)cyclopropanecarboxamide; 1-(2,4-dichlorophenyl)-N-{(1S)-1-[(2,4-dichlorophenyl)methyl]-2-[4-(1-methylethyl)-piperazin-1-yl]-2-oxoethyl}cyclopropanecarboxamide; 1-(2,4-dichlorophenyl)-N-[(1S)-2-(4-methylpiperazin-1-yl)-2-oxo-1-{[3-(trifluoromethyl)phenyl]methyl}ethyl]cyclopropanecarboxamide; 1-(2,4-dichlorophenyl)-N-[(1S)-2-(4-methylpiperazin-1-yl)-2-oxo-1-{[2-(trifluoromethyl)-phenyl]methyl}ethyl]cyclopropanecarboxamide; 1-(2,4-dichlorophenyl)-N-[(1S)-2-(4-methylpiperazin-1-yl)-2-oxo-1-(pyridin-2-ylmethyl)ethyl]cyclopropanecarboxamide; N-[(1S)-1-(cyclohexylmethyl)-2-(4-methylpiperazin-1-yl)-2-oxoethyl]-1-(2,4-dichloro-phenyl)cyclopropanecarboxamide; 3,4-dichloro-Nalpha-{[1-(2,4-dichlorophenyl)cyclopropyl]carbonyl}-N-[2-(dimethylamino)ethyl]-L-phenylalaninamide; Nalpha-{[1-(2,4-dichlorophenyl)cyclopropyl]carbonyl}-N-[2-(dimethylamino)-ethyl]-4-(trifluoromethyl)-L-phenylalaninamide; 2,4-dichloro-Nalpha-{[1-(2,4-dichlorophenyl)cyclopropyl]carbonyl}-N-[3-(dimethylamino)-propyl]-N-methyl-L-phenylalaninamide; 2,4-dichloro-Nalpha-{[1-(2,4-dichlorophenyl)cyclopropyl]carbonyl-N-[3-(dimethylamino)-2,2-dimethylpropyl]-L-phenylalaninamide; 2,4-dichloro-Nalpha-{[1-(2,4-dichlorophenyl)cyclopropyl]carbonyl}-N-[(1-methylpiperidin-2-yl)methyl]-L-phenylalaninamide; 2,4-dichloro-Nalpha-{[1-(2,4-dichlorophenyl)cyclopropyl]carbonyl}-N-(2-pyrrolidin-1-ylpropyl)-L-phenylalaninamide; 1-(2,4-dichlorophenyl)-N-[(1S)-1-[(3,5-dichlorophenyl)methyl]-2-(4-ethylpiperazin-1-yl)-2-oxoethyl]cyclopropanecarboxamide; 1-(2,4-dichlorophenyl)-N-{(1S)-1-[(3,5-dichlorophenyl)methyl]-2-[4-(2-hydroxyethyl)-piperazin-1-yl]-2-oxoethyl}cyclopropanecarboxamide; 1-(2,4-dichlorophenyl)-N-{(1S)-1-[(3,5-dichlorophenyl)methyl]-2-[4-(2-fluoroethyl)piperazin-1-yl]-1-oxoethyl}cyclopropanecarboxamide; 4-bromo-Nalpha-{[1-(2,4-dichlorophenyl)cyclopropyl]carbonyl}-N-[2-(dimethylamino)-ethyl]-N-methyl-L-phenylalaninamide; Nalpha-{[1-(2,4-dichlorophenyl)cyclopropyl]carbonyl}-N-[2-(dimethylamino)-ethyl]-N-methyl-4-(trifluoromethyl)-L-phenylalaninamide; N'2'-{[1-(2,4-dichlorophenyl)cyclopropyl]carbonyl}-N-[2-(dimethylamino)ethyl]-N-methyl-L-leucinamide; 2,4-dichloro-Nalpha-{[1-(2,4-dichlorophenyl)cyclopropyl]carbonyl}-N-methyl-N-[(3R)-1-methylpyrrolidin-3-yl]-L-phenylalaninamide; 2,4-dichloro-Nalpha-{[1-(2,4-dichlorophenyl)cyclopropyl]carbonyl}-N-methyl-N-[1-(phenylmethyl)piperidin-4-yl]-L-phenylalaninamide; Nalpha-{[1-(2,4-dichlorophenyl)cyclopropyl]carbonyl}-N-methyl-N-[1-(phenylmethyl)-piperidin-4-yl]-4-(trifluoromethyl)-L-phenylalaninamide; 1-(2,4-dichlorophenyl)-N-[(1S)-2-[3-(dimethylamino)azetidin-1-yl]-2-oxo-1-{[4-(trifluoromethyl)phenyl]methyl}ethyl]cyclopropanecarboxamide; Nalpha-{[1-(2,4-dichlorophenyl)cyclopropyl]carbonyl}-N-[2-(dimethylamino)ethyl]-N-ethyl-4-(trifluoromethyl)-L-phenylalaninamide; Nalpha-{[1-(2,4-dichlorophenyl)cyclopropyl]carbonyl}-N-methyl-N-[(3R)-1-methyl-pyrrolidin-3-yl]-4-(trifluoromethyl)-L-phenylalaninamide; Nalpha-{[1-(2,4-dichlorophenyl)cyclopropyl]carbonyl}-N-(2-pyrrolidin-1-ylethyl)-4-(trifluoromethyl)-L-phenylalaninamide; N-[(1S)-1-({[(4-chlorophenyl)methyl]oxy}methyl)-2-(4-methylpiperazin-1-yl)-2-oxoethyl]-1-(2,4-dichlorophenyl)cyclopropanecarboxamide; N-[(1S)-1-({[(3-chlorophenyl)methyl]oxy}methyl)-2-(4-methylpiperazin-1-yl)-2-oxoethyl]-1-(2,4-dichlorophenyl)cyclopropanecarboxamide; N-[(1S)-1-({[(2-chlorophenyl)methyl]oxy}methyl)-2-(4-methylpiperazin-1-yl)-2-oxoethyl]-1-(3,5-dichlorophenyl)cyclopropanecarboxamide; 1-(3,5-dichlorophenyl)-N-[(1S)-1-({[(4-fluorophenyl)methyl]oxy}methyl)-2-(4-methylpiperazin-1-yl)-2-oxoethyl]cyclopropanecarboxamide; 1-(3,5-dichlorophenyl)-N-[(1S)-1-[({[2-(methyloxy)phenyl]methyl}oxy)methyl]-2-(4-methylpiperazin-1-yl)-2-oxoethyl]cyclopropanecarboxamide; 1-(2,4-dichlorophenyl)-N-[(1R)-2-(4-methylpiperazin-1-yl)-2-oxo-1-{[(phenylmethyl)oxy]-methyl}ethyl]cyclopropanecarboxamide; 1-(2,4-dichlorophenyl)-N-[(1S)-2-(4-methylpiperazin-1-yl)-2-oxo-1-{[(phenylmethyl)oxy]-methyl}ethyl]cyclopropanecarboxamide; N-[(3S)-1-azabicyclo[2.2.2]oct-3-yl]-N'2'-{[1-(2,4-dichlorophenyl)-cyclopropyl]-carbonyl}-3-(2,3-dihydro-1,4-benzodioxin-6-yl)-L-alaninamide; N-[(3R)-1-azabicyclo[2.2.2]oct-3-yl]-N'2'-{[1-(2,4-dichlorophenyl)cyclopropyl]-carbonyl}-3-(2,3-dihydro-1,4-benzodioxin-6-yl)-L-alaninamide; N'2'-{[1-(2,4-dichlorophenyl)cyclopropyl]carbonyl}-3-(2,3-dihydro-1,4-benzodioxin-6-yl)-N-[2-(dimethylamino)ethyl]-N-methyl-L-alaninamide; N-[(3S)-1-azabicyclo[2.2.2]oct-3-yl]-4-chloro-Nalpha-{[1-(2,4-dichlorophenyl)-cyclopropyl]-carbonyl}-3-(trifluoromethyl)-L-phenylalaninamide; N-[(3S)-1-azabicyclo[2.2.2]oct-3-yl]-Nalpha-{[1-(2,4-dichlorophenyl)-cyclopropyl]carbonyl}-O-methyl-3-(methyloxy)-L-tyrosinamide; N-[(3S)-1-azabicyclo[2.2.2]oct-3-yl]-4-chloro-Nalpha-{[1-(2,4-dichlorophenyl)-ycolopropyl]carbonyl}-2-fluoro-L-phenylalaninamide; N-[(3S)-1-azabicyclo[2.2.2]oct-3-yl]-4-chloro-Nalpha-{[1-(2,4-dichlorophenyl)-ycolopropyl]carbonyl}-2-fluoro-L-phenylalaninamide; N-[(1S)-2-(3-amino-8-azabicyclo[3.2.1]oct-8-yl)-1-(2,3-dihydro-1,4-benzodioxin-6-ylmethyl)-2-oxoethyl]-1-{4-[(trifluoromethyl)oxy]phenyl}cyclopropanecarboxamide; 3-(2,3-dihydro-1,4-benzodioxin-6-yl)-N-[2-(dimethylamino)ethyl]-N-methyl-N-2-[(1-{4-[(trifluoromethyl)oxy]phenyl}cyclopropyl)carbonyl]-L-alaninamide; N-[(1S)-2-(3-amino-8-azabicyclo[3.2.1]oct-8-yl)-1-(2,3-dihydro-1,4-benzodioxin-6-ylmethyl)-2-oxoethyl]-1-[2-fluoro-4-(trifluoromethyl)phenyl]cyclopropanecarboxamide; N-(azetidin-3-ylmethyl)-4-bromo-Nalpha-[(1-{4-[(trifluoromethyl)oxy]phenyl}cyclopropyl)-carbonyl]-L-phenylalaninamide; N-[(1S)-2-(3-amino-8-azabicyclo[3.2.1]oct-8-yl)-1-[(4-bromophenyl)methyl]-2-oxoethyl]-1-[4-[(trifluoromethyl)oxy]phenyl]cyclopropanecarboxamide; N-[(1S)-2-(2,6-diazaspiro [3.3] hept-2-yl)-2-oxo-1-{[4-(trifluoromethyl)phenyl]-methyl}ethyl]-1-(2,4-dichlorophenyl)cyclopropanecarboxamide; 4-bromo-Nalpha-{[1-(2,4-dichlorophenyl)cyclopropyl]carbonyl}-N-[2-(methylamino)ethyl]-L-phenylalaninamide; 1-(2,4-dichlorophenyl)-N-{(1S)-1-[(2,4-dichlorophenyl)methyl]-2-oxo-2-piperazin-1-ylethyl}cyclopropanecarboxamide; 2,4-dichloro-Nalpha-{[1-(2,4-dichlorophenyl)cyclopropyl]carbonyl}-N-methyl-N-[2-(methylamino)ethyl]-L-phenylalaninamide; 2-(2,4-dichlorophenyl)-N-[(1S)-1-[(2,4-dichlorophenyl)methyl]-2-(4-methyl-piperazin-1-yl)-2-oxoethyl]propanamide; Nalpha-{[1-(2,4-dichlorophenyl)cyclopropyl]carbonyl}-N-(pyrrolidin-2-ylmethyl)-4-(trifluoromethyl)-L-phenylalaninamide; N-[(1S)-2-(3-aminoazetidin-1-yl)-2-oxo-1-{[4-(trifluoromethyl)phenyl]methyl}-ethyl]-1-(2,4-dichlorophenyl)cyclopropanecarboxamide; 4-bromo-Nalpha-{[1-(2,4-dichlorophenyl)cyclopropyl]carbonyl}-N-(1-methylpiperidin-3-yl)-L-phenylalaninamide; N-1-azabicyclo[2.2.2]oct-3-yl-4-bromo-Nalpha-{[1-(2,4-dichlorophenyl)-cyclopropyl]-carbonyl}-L-phenylalaninamide; N-[(3R)-1-azabicyclo[2.2.2]oct-3-yl]-4-bromo-Nalpha-{[1-(2,4-dichlorophenyl)-cyclopropyl]carbonyl}-L-phenylalaninamide; 1-(2,4-dichlorophenyl)-N-{(1S)-1-[(2,4-dichlorophenyl)methyl]-2-[(8aS)-hexahydropyrrolo[1,2-a]pyrazin-2(1H)-yl]-2-oxoethyl}cyclopropanecarboxamide; N-[(1S)-2-[(3R)-3-aminopyrrolidin-1-yl]-2-oxo-1-{[4-(trifluoromethyl)phenyl]-methyl}ethyl]-1-(2,4-dichlorophenyl)cyclopropanecarboxamide; N-1-azabicyclo[2.2.2]oct-3-yl-Nalpha-{[1-(2,4-dichlorophenyl)cyclopropyl]-carbonyl}-4-(trifluoromethyl)-L-phenylalaninamide; Nalpha-{[1-(2,4-dichlorophenyl)cyclopropyl]carbonyl}-N-(pyrrolidin-3-ylmethyl)-4-(trifluoromethyl)-L-phenylalaninamide; N-[(3R)-1-azabicyclo[2.2.2]oct-3-yl]-Nalpha-{[1-(2,4-dichlorophenyl)-cyclopropyl]carbonyl}-4-(trifluoromethyl)-L-phenylalaninamide; N-[(3R)-1-azabicyclo[2.2.2]oct-3-yl]-2,4-dichloro-Nalpha-{[1-(2,4-dichlorophenyl)cyclopropyl]carbonyl}-L-phenylalaninamide; Nalpha-{[1-(2,4-dichlorophenyl)cyclopropyl]carbonyl}-N-[2-(dimethylamino)-ethyl]-L-phenylalaninamide; Nalpha-{[1-(2,4-dichlorophenyl)cyclopropyl]carbonyl}-N-[2-(dimethylamino)-ethyl]-N-methyl-L-phenylalaninamide; Nalpha-{[1-(2,4-dichlorophenyl)cyclopropyl]carbonyl}-N-[2-(methylamino)-ethyl]-4-(trifluoromethyl)-L-phenylalaninamide; Nalpha-{[1-(2,4-dichlorophenyl)cyclopropyl]carbonyl}-N-[2-(methylamino)-ethyl]-4-(trifluoromethyl)-L-phenylalaninamide; N-(2-aminoethyl)-2,4-dichloro-Nalpha-{[1-(2,4-dichlorophenyl)cyclopropyl]-carbonyl}-L-phenylalaninamide; N-{(1S)-2-(3-amino-8-azabicyclo[3.2.1]oct-8-yl)-1-[(2,4-dichlorophenyl)methyl]-2-oxoethyl}-1-(2,4-dichlorophenyl)cyclopropanecarboxamide; 4-bromo-Nalpha-{[1-(2,4-dichlorophenyl)cyclopropyl]carbonyl}-N-(2-methyl-1-azabicyclo[2.2.2]oct-3-yl)-L-phenylalaninamide; 2,4-dichloro-Nalpha-{[1-(2,4-dichlorophenyl)cyclopropyl]carbonyl}-N-(8-methyl-8-azabicyclo[3.2.1]oct-3-yl)-L-phenylalaninamide; N-1-azabicyclo[2.2.2]oct-3-yl-2,4-dichloro-Nalpha-{[1-(2,4-dichlorophenyl)-cyclopropyl]carbonyl}-N-methyl-L-phenylalaninamide; Nalpha-{[1-(2,4-dichlorophenyl)cyclopropyl]carbonyl}-N-[2-(dimethylamino)-ethyl]-beta-methylphenylalaninamide; N-1-azabicyclo[2.2.2]oct-3-yl-Nalpha-{[1-(2,4-dichlorophenyl)-cyclopropyl]-carbonyl}-2,4-bis(trifluoromethyl)-L-phenylalaninamide; N-[(3R)-1-azabicyclo[2.2.2]oct-3-yl]-Nalpha-{[1-(2,4-dichlorophenyl)-cyclopropyl]carbonyl}-L-phenylalaninamide; (betaS)—N-[(3R)-1-azabicyclo[2.2.2]oct-3-yl]-Nalpha-{[1-(2,4-dichlorophenyl)-cyclopropyl]carbonylJ-beta-methyl-L-phenylalaninamide; N-[(3S)-1-azabicyclo[2.2.2]oct-3-yl]-Nalpha-{[1-(2,4-dichlorophenyl)-cyclopropyl]carbonyl}-L-phenylalaninamide; N-1-azabicyclo[2.2.2]oct-3-yl-Nalpha-{[1-(2,4-dichlorophenyl)-cyclopropyl]carbonyl}-N-methyl-L-phenylalaninamide; N-1-azabicyclo[2.2.2]oct-3-yl-Nalpha-({1-[4-(methyloxy)phenyl]cyclopropyl}-carbonyl)-4-(trifluoromethyl)-L-phenylalaninamide; N-{(1S)-2-(3-amino-8-azabicyclo[3.2.1]oct-8-yl)-1-[(4-bromophenyl)methyl]-2-oxoethyl}-1-(2,4-dichlorophenyl)cyclopropanecarboxamide; N-[(3S)-1-azabicyclo[2.2.2]oct-3-yl]-Nalpha-{[1-(2,4-dichlorophenyl)-cyclopropyl]carbonyl}-2,4-bis(trifluoromethyl)-L-phenylalaninamide; N-[(3S)-1-azabicyclo[2.2.2]oct-3-yl]-4-chloro-Nalpha-{[1-(2,4-dichlorophenyl)-cyclopropyl]carbonyl}-L-phenylalaninamide; N-[(1S)-1-{[[(3S)-1-azabicyclo[2.2.2]oct-3-ylamino]carbonyl}-3-phenylpropyl]-1-(2,4-dichlorophenyl)cyclopropanecarboxamide; N-[(3S)-1-azabicyclo[2.2.2]oct-3-yl]-4-chloro-Nalpha-{[1-(2,4-dichlorophenyl)-cyclopropyl]carbonyl}4-(trifluoromethyl)-L-phenylalaninamide; N-[(3S)-1-azabicyclo[2.2.2]oct-3-yl]-Nalpha-{[1-(2,4-dichlorophenyl)-cyclopropyl]carbonyl}-1-(phenylmethyl)-L-histidinamide; N-[(3S)-1-azabicyclo[2.2.2]oct-3-yl]-N~2~-{[1-(2,4-dichlorophenyl)cyclopropyl]-carbonyl}-3-(2,2-difluoro-1,3-benzodioxol-5-yl)-L-alaninamide; 4-bromo-Nalpha-{[1-(2,4-dichlorophenyl)cyclopropyl]carbonyl}-N-[3-(1H-imidazol-1-yl)propyl]-L-phenylalaninamide; N-[(3S)-1-azabicyclo[2.2.2]oct-3-yl]-Nalpha-{[1-(2,4-dichlorophenyl)-cyclopropyl]carbonyl}-2-fluoro-4-(trifluoromethyl)-L-phenylalaninamide; 4-bromo-Nalpha-{[1-(2,4-dichlorophenyl)cyclopropyl]carbonyl}-N-[(1S,3S,4S)-1-oxido-1-azabicyclo[2.2.2]oct-3-yl]-L-phenylalaninamide; N-[(3S)-1-azabicyclo[2.2.2]oct-3-yl]-4-chloro-Nalpha-{[1-(2,4-dichlorophenyl)-cyclopropyl]carbonyl}-2-fluorophenylalaninamide; 1-(2,4-dichlorophenyl)-N-[(1S)-2-(6-methyl-2,6-diazaspiro[3.3]hept-2-yl)-2-oxo-1-{[4-(trifluoromethyl)phenyl]methyl}ethyl]cyclopropanecarboxamide; N-[(3S)-1-azabicyclo [2.2.2]oct-3-yl]-Nalpha-({1-[4-(methyloxy)phenyl]-cyclopropyl}carbonyl)-4-(trifluoromethyl)-L-phenylalaninamide; N-[(3R)-1-azabicyclo[2.2.2]oct-3-yl]-Nalpha-({1-[4-(methyloxy)phenyl]-cyclopropyl}carbonyl)-4-(trifluoromethyl)-L-phenylalaninamide; N-[(3R)-1-azabicyclo[2.2.2]oct-3-yl]-4-bromo-Nalpha-({1-[4-(methyloxy)phenyl]-cyclopropyl}carbonyl)-L-phenylalaninamide; N-[(3S)-1-azabicyclo [2.2.2]oct-3-yl]-4-bromo-Nalpha-({1-[4-(methyloxy)phenyl]-cyclopropyljcarbonyO-L-phenylalaninamide; 4-bromo-Nalpha-{[1-(2,4-dichlorophenyl)cyclopropyl]carbonyl}-N-pyridin-4-yl-L-phenylalaninamide; N-[(3S)-1-azabicyclo[2.2.2]oct-3-yl]-4-phenyl-Nalpha-({1-(2,4-dichlorophenyl)-cyclopropyl]carbonyl}-L-phenylalaninamide; N-1-azabicyclo[2.2.2]oct-4-yl-4-bromo-Nalpha-{[1-(2,4-dichlorophenyl)-cyclopropyl)carbonyl]-L-phenylalaninamide; N-[(3S)-1-azabicyclo[2.2.2]oct-3-yl]-3-cyclohexyl-N-2-{[1-(2,4-dichlorophenyl)-cyclopropyl]

carbonyl}-L-alaninamide; N-[(3S)-1-azabicyclo[2.2.2]oct-3-yl]-Nalpha-({1-[2-fluoro-4-(trifluoromethyl)-phenyl]cyclopropyl}carbonyl)-4-(trifluoromethyl)-L-phenylalaninamide; 1-(2,4-dichlorophenyl)-N-{(1S)-1-[(2,4-dichlorophenyl)methyl]-2-[3-(dimethyl-amino)-8-azabicyclo[3.2.1]oct-8-yl]-2-oxoethyl}cyclopropanecarboxamide; N-{(1S)-2-(4-amino-4-methylpiperidin-1-yl)-1-[(2,4-dichlorophenyl)methyl]-2-oxoethyl}-1-(2,4-dichlorophenyl)cyclopropanecarboxamide; N-[(3S)-1-azabicyclo[2.2.2]oct-3-yl]-N'2'-{[1-(2,4-dichlorophenyl)cyclopropyl]-carbonyl}-N'2'-methyl-5-phenyl-L-norvalinamide; N'2'-{[1-(2,4-dichlorophenyl)cyclopropyl]carbonyl}-N-[2-(dimethylamino)ethyl]-N-methyl-5-phenyl-L-norvalinamide; 1-(2,4-dichlorophenyl)-N-{(1S)-1-[(2,4-dichlorophenyl)methyl]-2-[(3R)-3-methylpiperazin-1-yl]-2-oxoethyl}cyclopropanecarboxamide; N-[(3S)-1-azabicyclo[2.2.2]oct-3-yl]-4-bromo-Nalpha-[(1-{4-[(trifluoromethyl)oxy]phenyl}cyclopropyl)carbonyl]-L-phenylalaninamide; N-[(3S)-1-azabicyclo[2.2.2]oct-3-yl]-4-bromo-Nalpha-({1-[2-fluoro-4-(trifluoromethyl)phenyl]cyclopropyl}carbonyl)-L-phenylalaninamide; (betaS)—N-[(3S)-1-azabicyclo[2.2.2]oct-3-yl]-4-bromo-Nalpha-{[1-(2,4-dichlorophenyl)-cyclopropyl]carbonyl}-beta-methylphenylalaninamide; (betaS)—N-[(3S)-1-azabicyclo[2.2.2]oct-3-yl]-4-bromo-Nalpha-{[1-(2,4-dichlorophenyl)-cyclopropyl]carbonyl}-beta-methylphenylalaninamide; Nalpha-{[1-(2,4-dichlorophenyl)cyclopropyl]carbonyl}-N-[trans-4-phenylpyrrolidin-3-yl]-4-(trifluoromethyl)-L-phenylalaninamide; N-1-azabicyclo[2.2.2]oct-3-yl-4-bromo-Nalpha-{[1-(2,4-dichlorophenyl)-cyclopropyl]carbonyl}-D-phenylalaninamide; N-{(1S)-2-(3-amino-8-azabicyclo[3.2.1]oct-8-yl)-1-[(4-bromophenyl)methyl]-2-oxoethyl}-1-{4-[(trifluoromethyl)oxy]phenyl}cyclopropanecarboxamide; N-[(3S)-1-azabicyclo[2.2.2]oct-3-yl]-5-(4-chlorophenyl)-N~2~-{[1-(2,4-dichlorophenyl)-cyclopropyl]carbonyl}-L-norvalinamide; N-{(1S)-2-[(3R)-3-aminopiperidin-1-yl]-1-[(2,4-dichlorophenyl)methyl]-2-oxoethyl}-1-(2,4-dichlorophenyl)cyclopropanecarboxamide; N-{(1S)-2-(4-amino-4-methylpiperidin-1-yl)-1-[(4-bromophenyl)methyl]-2-oxoethyl}-1-(2,4-dichlorophenyl)cyclopropanecarboxamide; N-{(1S)-2-(4-aminopiperidin-1-yl)-1-[(2,4-dichlorophenyl)methyl]-2-oxoethyl}-1-(2,4-dichlorophenyl)cyclopropanecarboxamide; 1-(2,4-dichlorophenyl)-N-{(1S)-1-[(2,4-dichlorophenyl)methyl]-2-[(3S)-3-methylpiperazin-1-yl]-2-oxoethyl}cyclopropanecarboxamide; 2,4-dichloro-Nalpha-{[1-(2,4-dichlorophenyl)cyclopropyl]carbonyl}-N-[(2S)-pyrrolidin-2-ylmethyl]-L-phenylalaninamide; 2,4-dichloro-Nalpha-{[1-(2,4-dichlorophenyl)cyclopropyl]carbonyl}-N-[(2R)-pyrrolidin-2-ylmethyl]-L-phenylalaninamide; 2,4-dichloro-Nalpha-{[1-(2,4-dichlorophenyl)cyclopropyl]carbonyl}-N-[(3R)-pyrrolidin-3-ylmethyl]-L-phenylalaninamide; 2,4-dichloro-Nalpha-{[1-(2,4-dichlorophenyl)cyclopropyl]carbonyl}-N-[(3S)-pyrrolidin-3-ylmethyl]-L-phenylalaninamide; N-{(1S)-2-[(3S)-3-aminopyrrolidin-1-yl]-1-[(2,4-dichlorophenyl)methyl]-2-oxoethyl}-1-(2,4-dichlorophenyl)cyclopropanecarboxamide; N-{(1S)-2-[(3R)-3-aminopyrrolidin-1-yl]-1-[(2,4-dichlorophenyl)methyl]-2-oxoethyl}-1-(2,4-dichlorophenyl)cyclopropanecarboxamide; 2,4-dichloro-Nalpha-{[1-(2,4-dichlorophenyl)cyclopropyl]carbonyl}-N-[(3R)-piperidin-3-yl]-L-phenylalaninamide; N-{(1S)-2-[(3S)-3-aminopiperidin-1-yl]-1-[(2,4-dichlorophenyl)methyl]-2-oxoethyl}-1-(2,4-dichlorophenyl)cyclopropanecarboxamide; 4-bromo-Nalpha-{[1-(2,4-dichlorophenyl)cyclopropyl]carbonyl}-N-[(3S)-pyrrolidin-3-yl]-L-phenylalaninamide; 4-bromo-Nalpha-{[1-(2,4-dichlorophenyl)cyclopropyl]carbonyl}-N-[(3R)-pyrrolidin-3-yl]-L-phenylalaninamide; N-(3-aminocyclohexyl)-2,4-dichloro-Nalpha-{[1-(2,4-dichlorophenyl)-cyclopropyl]carbonyl}-L-phenylalaninamide; N-[(1S)-1-(biphenyl-4-ylmethyl)-2-(4-methylpiperazin-1-yl)-2-oxoethyl]-1-(2,4-dichlorophenyl)cyclopropanecarboxamide; N-[(1S)-2-(4-amino-4-methylpiperidin-1-yl)-1-(biphenyl-4-ylmethyl)-2-oxoethyl]-1-(2,4-dichlorophenyl)cyclopropanecarboxamide; N-[(1S)-1-(biphenyl-4-ylmethyl)-N-[2-(dimethylamino)ethyl]-2-oxoethyl]-1-(2,4-dichloro phenyl)cyclo propanecarboxamide; N-(2-aminocyclohexyl)-2,4-dichloro-Nalpha-{[1-(2,4-dichlorophenyl)-cyclopropyl]carbonyl}-L-phenylalaninamide; N-[(1R,2R)-2-aminocyclohexyl]-2,4-dichloro-Nalpha-{[1-(2,4-dichlorophenyl)-cyclopropyl]carbonyl}-L-phenylalaninamide; N-[(1S,2S)-2-aminocyclohexyl]-2,4-dichloro-Nalpha-{[1-(2,4-dichlorophenyl)-cyclopropyl]carbonyl}-L-phenylalaninamide; 2,4-dichloro-Nalpha-{[1-(2,4-dichlorophenyl)cyclopropyl]carbonyl}-N-[(3S)-piperidin-3-yl]-L-phenylalaninamide; N-{(1S)-2-(4-aminopiperidin-1-yl)-1-[(4-bromophenyl)methyl]-2-oxoethyl}-1-(2,4-dichlorophenyl)cyclopropanecarboxamide; 4-bromo-Nalpha-{[1-(2,4-dichlorophenyl)cyclopropyl]carbonyl}-N-[(3R)-piperidin-3-yl]-L-phenylalaninamide; N-{(1S)-1-[(4-bromophenyl)methyl]-2-[4-(methylamino)piperidin-1-yl]-2-oxoethyl}-1-(2,4-dichlorophenyl)cyclopropanecarboxamide; N-(2-amino-2-methylpropyl)-Nalpha-{[1-(2,4-dichlorophenyl)cyclopropyl]-carbonyl}-4-(trifluoromethyl)-L-phenylalaninamide; N-[(1S)-2-[(3R)-3-(methylamino)pyrrolidin-1-yl]-2-oxo-1-{[4-(trifluoromethyl)-phenyl]-methyl}ethyl]-1-{4-[(trifluoromethyl)oxy]phenyl}-cyclopropanecarboxamide; N-{(1S)-1-[(4-bromophenyl)methyl]-2-[(3R)-3-(methylamino)pyrrolidin-1-yl]-2-oxoethyl}-1-{4-[(trifluoromethyl)oxy]phenyl}cyclopropanecarboxamide; N-(2-amino-2-methylpropyl)-4-bromo-Nalpha-{[1-(2,4-dichlorophenyl)-cyclopropyl]carbonyl}-L-phenylalaninamide; N-[(1S)-2-[(3S)-3-(methylamino)pyrrolidin-1-yl]-2-oxo-1-{[4-(trifluoromethyl)-phenyl]methyl}ethyl]-1-{4-[(trifluoromethyl)oxy]phenyl}cyclopropanecarboxamide; N-{(1S)-1-[(4-bromophenyl)methyl]-2-[(3S)-3-(methylamino)pyrrolidin-1-yl]-2-oxoethyl}-1-{4-[(trifluoromethyl)oxy]phenyl}cyclopropanecarboxamide; N-[(1S)-2-(2,7-diazaspiro [4.4] non-2-yl)-2-oxo-1-{[4-(trifluoromethyl)phenyl]-methyl}ethyl]-1-(2,4-dichlorophenyl)cyclopropanecarboxamide; N-[(1S)-2-(2,8-diazaspiro [4.5] dec-8-yl)-2-oxo-1-{[4-(trifluoromethyl)phenyl]-methyl}ethyl]-1-(2,4-dichlorophenyl)cyclopropanecarboxamide; N-[(1S)-2-(1,7-diazaspiro [4.4] non-7-yl)-2-oxo-1-{[4-(trifluoromethyl)phenyl]-methyl}ethyl]-1-(2,4-dichlorophenyl)cyclopropanecarboxamide; N-[(3S)-1-azabicyclo[2.2.2]oct-3-yl]-4-bromo-Nalpha-{[1-(2-fluorophenyl)-cyclopropyl]carbonyl}-L-phenylalaninamide; 4-bromo-Nalpha-{[1-(2,4-dichlorophenyl)cyclopropyl]carbonyl}-N-[(3S)-piperidin-3-yl]-L-phenylalaninamide; 4-bromo-Nalpha-{[1-(2,4-dichlorophenyl)cyclopropyl]carbonyl}-N-piperidin-3-yl-L-phenylalaninamide; 4-bromo-Nalpha-{[1-(2,4-dichlorophenyl)cyclopropyl]carbonyl}-N-piperidin-3-yl-L-phenylalaninamide; N-{(1S)-1-[(4-bromophenyl)methyl]-2-[(3S)-3-(methylamino)pyrrolidin-1-yl]-2-oxoethyl}-1-[2-fluoro-4-(trifluoromethyl)phenyl]cyclopropanecarboxamide; N-{(1S)-1-[(4-bromophenyl)

methyl]-2-[(3R)-3-(methylamino)pyrrolidin-1-yl]-2-oxoethyl}-1-[2-fluoro-4-(trifluoromethyl)phenyl]cyclopropanecarboxamide; N-[(3S)-1-azabicyclo[2.2.2]oct-3-yl]-4-bromo-Nalpha-[(1-{4-[(difluoromethyl)-oxy]phenyl}cyclopropyl)carbonyl]-L-phenylalaninamide; 1-[2-fluoro-4-(trifluoromethyl)phenyl]-N-[(1S)-2-[(3R)-3-(methylamino)-pyrrolidin-1-yl]-2-oxo-1-{[4-(trifluoromethyl)phenyl]methyl}ethyl]cyclopropanecarboxamide; N-[(3S)-1-azabicyclo[2.2.2]oct-3-yl]-Nalpha-[(1-{4-[(difluoromethyl)oxy]-phenyl}cyclopropyl)carbonyl]-4-(trifluoromethyl)-L-phenylalaninamide; 4-bromo-Nalpha-{[1-(2,4-dichlorophenyl)cyclopropyl]carbonyl}-N-piperidin-4-yl-L-phenylalaninamide; 4-bromo-N-[(3R)-piperidin-3-yl]-Nalpha-[(1-{4-[(trifluoromethyl)oxy]phenyl}cyclopropyl)carbonyl]-L-phenylalaninamide; N-(2-aminoethyl)-4-bromo-Nalpha-{[1-(2,4-dichlorophenyl)cyclopropyl]-carbonyl}-L-phenylalaninamide; 4-bromo-Nalpha-{[1-(2,4-dichlorophenyl)cyclopropyl]carbonyl}-N-methyl-N-[2-(methylamino)ethyl]-L-phenylalaninamide; N-(2-aminoethyl)-4-bromo-Nalpha-{[1-(2,4-dichlorophenyl)cyclopropyl]-carbonyl}-N-methyl-L-phenylalaninamide; 4-bromo-Nalpha-({1-[2-fluoro-4-(trifluoromethyl)phenyl]cyclopropyl}-carbonyl)-N-methyl-N-[2-(methylamino)ethyl]-L-phenylalaninamide; 4-bromo-N-[2-(dimethylamino)ethyl]-Nalpha-{[1-(2-fluorophenyl)cyclopropyl]-carbonyl}-N-methyl-L-phenylalaninamide; 4-bromo-N-methyl-N-[2-(methylamino)ethyl]-Nalpha-[(1-{4-[(trifluoromethyl)oxy]phenyl}-cyclopropyl)carbonyl]-L-phenylalaninamide; 4-bromo-N-[2-(dimethylamino)ethyl]-N-methyl-Nalpha-[(1-{4-[(trifluoromethyl)oxy]-phenyl}cyclopropyl)carbonyl]-L-phenylalaninamide; N-{(1S)-2-(4-amino-4-methylpiperidin-1-yl)-1-[(4-bromophenyl)methyl]-2-oxoethyl}-1-{4-[(trifluoromethyl)oxy]phenyl}cyclopropanecarboxamide; N'2'-{[1-(2,4-dichlorophenyl)cyclopropyl]carbonyl}-5-phenyl-N-[(3R)-piperidin-3-yl]-L-norvalinamide; 1-(2,4-dichlorophenyl)-N-[(1S)-2-oxo-2-{3-[(phenylmethyl)amino]-8-azabicyclo[3.2.1]oct-8-yl}-1-{[4-(trifluoromethyl)phenyl]methyl}ethyl]cyclopropane-carboxamide; N-[(1S)-2-(3-amino-8-azabicyclo[3.2.1]oct-8-yl)-2-oxo-1-{[4-(trifluoromethyl)-phenyl]methyl}ethyl]-1-(2,4-dichlorophenyl)cyclopropanecarboxamide; 1-(2,4-dichlorophenyl)-N-[(1S)-2-{3-[(2-methylpropyl)amino]-8-azabicyclo-[3.2.1]oct-8-yl}-2-oxo-1-{[4-(trifluoromethyl)phenyl]methyl}-ethyl]-cyclopropane-carboxamide; 1-(2,4-dichlorophenyl)-N-[(1S)-2-oxo-2-(3-pyrrolidin-1-yl-8-azabicyclo[3.2.1]oct-8-yl)-1-{[4-(trifluoromethyl)phenyl]methyl}ethyl]cyclopropanecarboxamide; N-[(1S)-2-(3-amino-8-azabicyclo[3.2.1]oct-8-yl)-2-oxo-1-{[4-(trifluoromethyl)-phenyl]methyl}ethyl]-1-(2,4-dichlorophenyl)cyclopropanecarboxamide; 4-bromo-N-[2-(dimethylamino)ethyl]-Nalpha-({1-[2-fluoro-4-(trifluoromethyl)-phenyl]cyclopropyl}carbonyl)-N-methyl-L-phenylalaninamide; N-8-azabicyclo[3.2.1]oct-3-yl-Nalpha-{[1-(2,4-dichlorophenyl)cyclopropyl-carbonyl}-4-(trifluoromethyl)-L-phenylalaninamide; 4-bromo-Nalpha-{[1-(3-fluorophenyl)cyclopropyl]carbonyl}-N-piperidin-4-yl-L-phenylalaninamide; 4-bromo-N-piperidin-4-yl-Nalpha-{[1-(2,4,5-trifluorophenyl)cyclopropyl]-carbonyl}-L-phenylalaninamide; N-[(3S)-1-azabicyclo[2.2.2]oct-3-yl]-2-chloro-Nalpha-{[1-(2,4-dichlorophenyl)-cyclopropyl]-carbonyl}-4-fluoro-L-phenylalaninamide; N-[(1S)-2-(3-amino-8-azabicyclo[3.2.1]oct-8-yl)-2-oxo-1-{[4-(trifluoromethyl)-phenyl]methyl}ethyl]-1-{4-[(trifluoromethyl)oxy]phenyl}cyclopropane-carboxamide; N-[(1S)-2-(3-amino-8-azabicyclo[3.2.1]oct-8-yl)-2-oxo-1-{[4-(trifluoromethyl)-phenyl]methyl}ethyl]-1-[2-fluoro-4-(trifluoromethyl)phenyl]cyclopropane-carboxamide; N-[(1S)-2-(3-amino-8-azabicyclo[3.2.1]oct-8-yl)-2-oxo-1-{[4-(trifluoromethyl)-phenyl]methyl}ethyl]-1-(2,4-dichlorophenyl)cyclopropanecarboxamide; 4-bromo-Nalpha-{[1-(2,4-dichlorophenyl)cyclopropyl]carbonyl}-N-methyl-N-[(3R)-piperidin-3-yl]-L-phenylalaninamide; N-{(1S)-2-(3-amino-8-azabicyclo[3.2.1]oct-8-yl)-1-[(4-bromophenyl)methyl]-2-oxoethyl}-1-(2,4-dichlorophenyl)cyclopropanecarboxamide; 4-bromo-Nalpha-{[1-(2,4-dichlorophenyl)cyclopropyl]carbonyl}-N-methyl-N-piperidin-4-yl-L-phenylalaninamide; N-[(3R)-piperidin-3-yl]-1-(biphenyl-4-ylmethyl)-2-oxoethyl]-1-(2,4-dichlorophenyl)-cyclopropanecarboxamide; N-piperidin-4-yl-1-(biphenyl-4-ylmethyl)-2-oxoethyl]-1-(2,4-dichlorophenyl)-cyclopropane carboxamide; 2,4-dichloro-Nalpha-{[1-(2,4-dichlorophenyl)cyclopropyl]carbonyl}-N-piperidin-4-yl-L-phenylalaninamide; 2,4-dichloro-Nalpha-{[1-(2,4-dichlorophenyl)cyclopropyl]carbonyl}-N-piperidin-4-yl-L-phenylalaninamide; N-(cis-4-aminocyclohexyl)-4-bromo-Nalpha-{[1-(2,4-dichlorophenyl)-cyclopropyl]carbonyl}-L-phenylalaninamide; N-(trans-4-aminocyclohexyl)-4-bromo-Nalpha-{[1-(2,4-dichlorophenyl)-cyclopropyl]carbonyl}-L-phenylalaninamide; 4-bromo-Nalpha-{[1-(2,4-dichlorophenyl)cyclopropyl]carbonyl}-N-(2-methylpiperidin-4-yl)-L-phenylalaninamide; N-[(3S)-1-azabicyclo[2.2.2]oct-3-yl]-4-bromo-N-alpha-{[1-(2,3-difluorophenyl)-cyclopropyl]carbonyl}-L-phenylalaninamide; N-[(3S)-1-azabicyclo[2.2.2]oct-3-yl]-4-bromo-N-alpha-{[1-(2,6-difluorophenyl)-cyclopropyl]carbonyl}-L-phenylalaninamide; 2,4-dichloro-N-[(3R)-piperidin-3-yl]-Nalpha-[(1-{4-[(trifluoromethyl)oxy]-phenyl}cyclopropyl)carbonyl]-L-phenylalaninamide; N-{(1S)-2-(3-amino-8-azabicyclo[3.2.1]oct-8-yl)-1-[(2,4-dichlorophenyl)methyl]-2-oxoethyl}-1-{4-[(trifluoromethyl)oxy]phenyl}cyclopropanecarboxamide; 2,4-dichloro-N-[(3S)-pyrrolidin-3-yl]-Nalpha-[(1-{4-[(trifluoromethyl)oxy]-phenyl}cyclopropyl)carbonyl]-L-phenylalaninamide; N-[(3R)-piperidin-3-yl]-4-(trifluoromethyl)-Nalpha-[(1-{4-[(trifluoromethyl)-oxy]phenyl}cyclopropyl)carbonyl]-L-phenylalaninamide; N-[(1S)-2-[(3R)-3-aminopiperidin-1-yl]-2-oxo-1-{[4-(trifluoromethyl)phenyl]-methyl}ethyl]-1-{4-[(trifluoromethyl)oxy]phenyl}cyclopropanecarboxamide; N-[(3S)-piperidin-3-yl]-4-(trifluoromethyl)-Nalpha-[(1-{4-[(trifluoromethyl)oxy]-phenyl}cyclopropyl)carbonyl]-L-phenylalaninamide; N-[(1S)-2-(4-amino-4-methylpiperidin-1-yl)-2-oxo-1-{[4-(trifluoromethyl)-phenyl]methyl}ethyl]-1-{4-[(trifluoromethyl)oxy]phenyl}cyclopropanecarboxamide; N-[(3S)-pyrrolidin-3-yl]-4-(trifluoromethyl)-Nalpha-[(1-{4-[(trifluoromethyl)-oxy]phenyl}cyclopropyl)carbonyl]-L-phenylalaninamide; 4-bromo-N-[(3S)-pyrrolidin-3-yl]-Nalpha-[(1-{4-[(trifluoromethyl)oxy]phenyl}-cyclopropyl)carbonyl]-L-phenylalaninamide; N-[(3R)-piperidin-3-yl]-Nalpha-[(1-{4-[(trifluoromethyl)oxy]phenyl}-cyclopropyl)carbonyl]-L-phenylalaninamide; N-[(1S)-2-(3-amino-8-azabicyclo[3.2.1]oct-8-yl)-2-oxo-1-(phenylmethyl)ethyl]-1-{4-[(trifluoromethyl)oxy]phenyl}cyclopropanecarboxamide; N-[(3S)-pyrrolidin-3-yl]-Nalpha-[(1-{4-[(trifluoromethyl)oxy]phenyl}-cyclopropyl)carbonyl]-L-phenylalaninamide; 3-cyclohexyl-N-[(3R)-piperidin-3-yl]-N~2~-[(1-{4-[(trifluoromethyl)oxy]phenyl}-cyclopropyl)carbonyl]-L-alaninamide; N-[(1S)-2-(3-amino-8-azabicyclo[3.2.1]oct-8-yl)-1-(cyclohexylmethyl)-2-oxoethyl]-1-{4-[(trifluoromethyl)oxy]phenyl}cyclopropanecarboxamide; 3-cyclohexyl-N-[(3S)-pyrrolidin-3-yl]-N~2~-[(1-{4-[(trifluoromethyl)oxy]

phenyl}-cyclopropyl)carbonyl]-L-alaninamide; N-piperidin-4-yl-Nalpha-[(1-{4-[(trifluoromethyl)oxy] phenyl}cyclopropyl)-carbonyl]-L-phenylalaninamide; N-piperidin-4-yl-4-(trifluoromethyl)-Nalpha-[(1-{4-[(trifluoromethyl)oxy]-phenyl}cyclopropyl) carbonyl]-L-phenylalaninamide; 3-cyclohexyl-N-piperidin-4-yl-N'2'-[(1-{4-[(trifluoromethyl)oxy]phenyl}-cyclopropyl)carbonyl]-L-alaninamide; 2,4-dichloro-N-piperidin-4-yl-Nalpha-[(1-{4-[(trifluoromethyl)oxy]phenyl}-cyclopropyl)carbonyl]-L-phenylalaninamide; N-{(1S)-2-[(2,4-dichlorophenyl)methyl]-2-[4-(methylamino)piperidin-1-yl]-2-oxoethyl}-1-{4-[(trifluoromethyl)oxy] phenyl}cyclopropanecarboxamide; N-{(1S)-2-(4-aminopiperidin-1-yl)-1-[(2,4-dichlorophenyl)methyl]-2-oxoethyl}-1-{4-[(trifluoromethyl)oxy] phenyl}cyclopropanecarboxamide; N-[(1S)-2-[4-(methylamino)piperidin-1-yl]-2-oxo-1-{[4-(trifluoromethyl)phenyl]-methyl}ethyl]-1-{4-[(trifluoromethyl)oxy]phenyl}cyclopropanecarboxamide; N-[(1S)-2-(4-aminopiperidin-1-yl)-2-oxo-1-{[4-(trifluoromethyl)phenyl]methyl}-ethyl]-1-{4-[(trifluoromethyl)oxy]phenyl}cyclopropanecarboxamide; N-{(1S)-1-[(4-bromophenyl)methyl]-2-[4-(methylamino)piperidin-1-yl]-2-oxoethyl}-1-{4-[(trifluoromethyl)oxy] phenyl}cyclopropanecarboxamide; N-{(1S)-2-(4-aminopiperidin-1-yl)-1-[(4-bromophenyl)methyl]-2-oxoethyl}-1-{4-[(trifluoromethyl)oxy] phenyl}cyclopropanecarboxamide; N-[(1S)-2-[4-(methylamino)piperidin-1-yl]-2-oxo-1-(phenylmethyl) ethyl]-1-{4-[(trifluoromethyl)oxy] phenyl}cyclopropanecarboxamide; N-[(1S)-2-(4-aminopiperidin-1-yl)-2-oxo-1-(phenylmethyl)ethyl]-1-{4-[(trifluoromethyl)oxy]phenyl}cyclopropanecarboxamide; N-{(1S)-1-(cyclohexylmethyl)-2-[4-(methylamino)piperidin-1-yl]-2-oxoethyl}-1-{4-[(trifluoromethyl)oxy] phenyl}cyclopropanecarboxamide; N-[(1S)-2-(4-aminopiperidin-1-yl)-1-(cyclohexylmethyl)-2-oxoethyl]-1-{4-[(trifluoromethyl)oxy]phenyl}cyclopropanecarboxamide; 4-bromo-N-piperidin-4-yl-Nalpha-[(1-{4-[(trifluoromethyl)oxy]phenyl}-cyclopropyl)-carbonyl]-L-phenylalaninamide; N-{(1S)-2-(4-amino-4-methylpiperidin-1-yl)-1-[(4-bromophenyl)methyl]-2-oxoethyl}-1-(2,3,4-trifluorophenyl)cyclopropanecarboxamide; 4-bromo-N-[(3R)-piperidin-3-yl]-Nalpha-{[1-(2,3,4-trifluorophenyl)-cyclopropyl]carbonyl}-L-phenylalaninamide; N-{(1S)-2-(3-amino-8-azabicyclo [3.2.1]oct-8-yl)-1-[(4-bromophenyl)methyl]-2-oxoethyl}-1-(2,3,4-trifluorophenyl)cyclopropanecarboxamide; N-{(1S)-2-(4-amino-4-methylpiperidin-1-yl)-1-[(4-bromophenyl)methyl]-2-oxoethyl}-1-(2,3-difluorophenyl) cyclopropanecarboxamide; 4-bromo-Nalpha-{[1-(2,3-difluorophenyl)cyclopropyl]carbonyl}-N-[(3R)-piperidin-3-yl]-L-phenylalaninamide; N-{(1S)-2-(3-amino-8-azabicyclo [3.2.1]oct-8-yl)-1-[(4-bromophenyl)methyl]-2-oxoethyl}-1-(2,3-difluorophenyl)cyclopropanecarboxamide; N-{(1S)-2-(4-amino-4-methylpiperidin-1-yl)-1-[(4-bromophenyl)methyl]-2-oxoethyl}-1-(4-fluorophenyl)cyclopropanecarboxamide; 4-bromo-Nalpha-{[1-(4-fluorophenyl)cyclopropyl]carbonyl}-N-[(3R)-piperidin-3-yl]-L-phenylalaninamide; N-{(1S)-2-(3-amino-8-azabicyclo [3.2.1]oct-8-yl)-1-[(4-bromophenyl)methyl]-2-oxoethyl}-1-(4-fluorophenyl)cyclopropanecarboxamide; 2,4-dichloro-Nalpha-({1-[2-fluoro-4-(trifluoromethyl)phenyl] cyclopropyl}-carbonyl)-N-[(3R)-piperidin-3-yl]-L-phenylalaninamide; N-{(1S)-2-(3-amino-8-azabicyclo [3.2.1]oct-8-yl)-1-[(2,4-dichlorophenyl)methyl]-2-oxoethyl}-1-[2-fluoro-4-(trifluoromethyl)phenyl] cyclopropanecarboxamide; 2,4-dichloro-Nalpha-({1-[2-fluoro-4-(trifluoromethyl)phenyl]cyclopropyl}-carbonyl)-N-[(3S)-pyrrolidin-3-yl]-L-phenylalaninamide; N-[(1S)-2-(4-amino-4-methylpiperidin-1-yl)-2-oxo-1-{[4-(trifluoromethyl)-phenyl]methyl}ethyl]-1-[2-fluoro-4-(trifluoromethyl)phenyl]cyclopropanecarboxamide; Nalpha-({1-[2-fluoro-4-(trifluoromethyl)phenyl] cyclopropyl}carbonyl)-N-[(3R)-piperidin-3-yl]-4-(trifluoromethyl)-L-phenylalaninamide; Nalpha-({1-[2-fluoro-4-(trifluoromethyl)phenyl]cyclopropyl}carbonyl)-N-[(3S)-pyrrolidin-3-yl]-4-(trifluoromethyl)-L-phenylalaninamide; 4-bromo-Nalpha-({1-[2-fluoro-4-(trifluoromethyl)phenyl] cyclopropyl}-carbonyl)-N-[(3R)-piperidin-3-yl]-L-phenylalaninamide; N-{(1S)-2-(3-amino-8-azabicyclo[3.2.1]oct-8-yl)-1-[(4-bromophenyl)methyl]-2-oxoethyl}-1-[2-fluoro-4-(trifluoromethyl)phenyl]cyclopropanecarboxamide; 4-bromo-Nalpha-({1-[2-fluoro-4-(trifluoromethyl)phenyl] cyclopropyl}carbonyl)-N-[(3S)-pyrrolidin-3-yl]-L-phenylalaninamide; Nalpha-({1-[2-fluoro-4-(trifluoromethyl)phenyl]cyclopropyl}carbonyl)-N-[(3R)-piperidin-3-yl]-L-phenylalaninamide; N-[(1S)-2-(3-amino-8-azabicyclo [3.2.1]oct-8-yl)-2-oxo-1-(phenylmethyl)ethyl]-1-[2-fluoro-4-(trifluoromethyl)phenyl]cyclopropanecarboxamide; Nalpha-({1-[2-fluoro-4-(trifluoromethyl)phenyl] cyclopropyl}carbonyl)-N-[(3S)-pyrrolidin-3-yl]-L-phenylalaninamide; 3-cyclohexyl-N'2'-({1-[2-fluoro-4-(trifluoromethyl)phenyl]cyclopropyl}-carbonyl)-N-[(3R)-piperidin-3-yl]-L-alaninamide; N-[(1S)-2-(3-amino-8-azabicyclo[3.2.1]oct-8-yl)-1-(cyclohexylmethyl)-2-oxoethyl]-1-[2-fluoro-4-(trifluoromethyl)phenyl] cyclopropanecarboxamide; 3-cyclohexyl-N'2'-({1-[2-fluoro-4-(trifluoromethyl)phenyl]cyclopropyl}-carbonyl)-N-[(3S)-pyrrolidin-3-yl]-L-alaninamide; 2,4-dichloro-Nalpha-({1-[2-fluoro-4-(trifluoromethyl)phenyl] cyclopropyl}-carbonyl)-N-piperidin-4-yl-L-phenylalaninamide; Nalpha-({1-[2-fluoro-4-(trifluoromethyl)phenyl]cyclopropyl}carbonyl)-N-piperidin-4-yl-4-(trifluoromethyl)-L-phenylalaninamide; 4-bromo-Nalpha-({1-[2-fluoro-4-(trifluoromethyl)phenyl] cyclopropyl}-carbonyl)-N-piperidin-4-yl-L-phenylalaninamide; Nalpha-({1-[2-fluoro-4-(trifluoromethyl)phenyl]cyclopropyl}carbonyl)-N-piperidin-4-yl-L-phenylalaninamide; 3-cyclohexyl-N'2'-({1-[2-fluoro-4-(trifluoromethyl)phenyl]cyclopropyl}-carbonyl)-N-piperidin-4-yl-L-alaninamide; 1-[2-fluoro-4-(trifluoromethyl)phenyl]-N-[(1S)-2-[4-(methylamino) piperidin-1-yl]-2-oxo-1-{[4-(trifluoromethyl)phenyl] methyl}ethyl]cyclopropanecarboxamide; N-[(1S)-2-(4-aminopiperidin-1-yl)-2-oxo-1-{[4-(trifluoromethyl)phenyl] methyl}-ethyl]-1-[2-fluoro-4-(trifluoromethyl)phenyl] cyclopropanecarboxamide; N—{(S)-1-[(2,4-dichlorophenyl)methyl]-2-[4-(methylamino)piperidin-1-yl]-2-oxoethyl}-1-[2-fluoro-4-(trifluoromethyl)phenyl] cyclopropanecarboxamide; N-{(1S)-2-(4-aminopiperidin-1-yl)-1-[(2,4-dichlorophenyl)methyl]-2-oxoethyl}-1-[2-fluoro-4-(trifluoromethyl)phenyl] cyclopropanecarboxamide; N-{(1S)-1-[(4-bromophenyl) methyl]-2-[4-(methylamino)piperidin-1-yl]-2-oxoethyl}-1-[2-fluoro-4-(trifluoromethyl)phenyl] cyclopropanecarboxamide; N-{(1S)-2-(4-aminopiperidin-1-yl)-1-[(4-bromophenyl)methyl]-2-oxoethyl}-1-[2-fluoro-4-(trifluoromethyl)phenyl]cyclopropanecarboxamide; 1-[2-fluoro-4-(trifluoromethyl)phenyl]-N-[(1S)-2-[4-(methylamino)piperidin-1-yl]-2-oxo-1-(phenylmethyl) ethyl]cyclopropanecarboxamide; N-[(1S)-2-(4-aminopiperidin-1-yl)-2-oxo-1-(phenylmethyl)ethyl]-1-[2-fluoro-4-(trifluoromethyl)phenyl]

cyclopropanecarboxamide; N-{(1S)-1-(cyclohexylmethyl)-2-[4-(methylamino)piperidin-1-yl]-2-oxoethyl}-1-[2-fluoro-4-(trifluoromethyl)phenyl]cyclopropanecarboxamide; N-[(1S)-2-(4-aminopiperidin-1-yl)-1-(cyclohexylmethyl)-2-oxoethyl]-1-[2-fluoro-4-(trifluoromethyl)phenyl]cyclopropanecarboxamide; N-{(1S)-2-(4-amino-4-methylpiperidin-1-yl)-1-[(4-bromophenyl)methyl]-2-oxoethyl}-1-[2-fluoro-4-trifluoromethyl)phenyl]cyclopropanecarboxamide; N—{(S)-2-(4-amino-4-methylpiperidin-1-yl)-1-[(4-bromophenyl)methyl]-2-oxoethyl}-1-(2,4-difluorophenyl)cyclopropanecarboxamide; 4-bromo-Nalpha-{[1-(2,4-difluorophenyl)cyclopropyl]carbonyl}-N-[(3R)-piperidin-3-yl]-L-phenylalaninamide; N-{(1S)-2-(3-amino-8-azabicyclo[3.2.1]oct-8-yl)-1-[(4-bromophenyl)methyl]-2-oxoethyl}-1-(2,4-difluorophenyl)cyclopropanecarboxamide; 4-bromo-Nalpha-({1-[4-fluoro-3-(trifluoromethyl)phenyl]cyclopropyl}carbonyl)-N-[(3R)-piperidin-3-yl]-L-phenylalaninamide; N-{(1S)-2-(3-amino-8-azabicyclo[3.2.1]oct-8-yl)-1-[(4-bromophenyl)methyl]-2-oxoethyl}-1-[4-fluoro-3-(trifluoromethyl)phenyl]cyclopropanecarboxamide; N-{(1S)-2-(4-amino-4-methylpiperidin-1-yl)-1-[(4-bromophenyl)methyl]-2-oxoethyl}-1-[4-fluoro-3-(trifluoromethyl)phenyl]cyclopropanecarboxamide; N-{(1S)-2-(4-amino-4-methylpiperidin-1-yl)-1-[(4-bromophenyl)methyl]-2-oxoethyl}-1-(2-fluorophenyl)cyclopropanecarboxamide; 4-bromo-Nalpha-{[1-(2-fluorophenyl)cyclopropyl]carbonyl}-N-[(3R)-piperidin-3-yl]-L-phenylalaninamide; N-{(1S)-2-(3-amino-8-azabicyclo[3.2.1]oct-8-yl)-1-[(4-bromophenyl)methyl]-2-oxoethyl}-1-(2-fluorophenyl)cyclopropanecarboxamide; N-[(3S)-1-azabicyclo[2.2.2]oct-3-yl]-4-bromo-Nalpha-{[1-(2,4,5-trifluorophenyl)-cyclopropyl]carbonyl}-L-phenylalaninamide; N-{(1S)-2-(3-amino-8-azabicyclo[3.2.1]oct-8-yl)-1-[(4-bromophenyl)methyl]-2-oxoethyl}-1-(2,4,5-trifluorophenyl)cyclopropanecarboxamide; 4-bromo-N-[(3R)-piperidin-3-yl]-Nalpha-{[1-(2,4,5-trifluorophenyl)-cyclopropyl]carbonyl}-L-phenylalaninamide; N-{(1R)-2-(3-amino-8-azabicyclo[3.2.1]oct-8-yl)-1-[(4-bromophenyl)methyl]-2-oxoethyl}-1-{4-[(trifluoromethyl)oxy]phenyl}cyclopropanecarboxamide; N-(azetidin-3-ylmethyl)-4-bromo-N-methyl-Nalpha-[(1-{4-[(trifluoromethyl)-oxy]phenyl}cyclopropyl)carbonyl]-L-phenylalaninamide; N-[(1S)—l-[(4-bromophenyl)methyl]-2-(2,5-diazabicyclo[2.2.1]hept-2-yl)-2-oxoethyl]-1-{4-[(trifluoromethyl)oxy]phenyl}cyclopropanecarboxamide; N-[(1S)-1-[(4-bromophenyl)methyl]-2-(2,5-diazabicyclo[2.2.1] hept-2-yl)-2-oxoethyl]-1-(2,4-dichlorophenyl)cyclopropanecarboxamide; N-[(3S)-1-azabicyclo[2.2.2]oct-3-yl]-4-bromo-Nalpha-{[1-(4-fluorophenyl)-cyclopropyl]carbonyl}-L-phenylalaninamide; N-[(1S)-1-[(4-bromophenyl)methyl]-2-{4-[(1-methylethyl)amino]piperidin-1-yl}-2-oxoethyl]-1-(2,4-dichlorophenyl)cyclopropanecarboxamide; N-(azetidin-3-ylmethyl)-4-bromo-Nalpha-{[1-(2,4-dichlorophenyl)cyclopropyl]-carbonyl}-N-methyl-L-phenylalaninamide; N-[(3S)-1-azabicyclo[2.2.2]oct-3-yl]-4-bromo-Nalpha-{[1-(2,3,4-trifluorophenyl)-cyclopropyl]carbonyl}-L-phenylalaninamide; N-[(3S)-1-azabicyclo[2.2.2]oct-3-yl]-4-bromo-Nalpha-({1-4-fluoro-3-(trifluoromethyl)-phenyl]cyclopropyl}carbonyl)-L-phenylalaninamide; N-(cis-4-aminocyclohexyl)-4-bromo-Nalpha-({1-[2-fluoro-4-(trifluoromethyl)-phenyl]cyclopropyl]carbonyl}-L-phenylalaninamide; N-(cis-4-aminocyclohexyl)-4-bromo-Nalpha-[(1-{4-[(trifluoromethyl)oxy]-phenyl}cyclopropyl)carbonyl)-L-phenylalaninamide; N-[(3S)-1-azabicyclo[2.2.2]oct-3-yl]-4-bromo-Nalpha-({1-[4-fluoro-2-(trifluoromethyl)phenyl]ycyclopropyl}carbonyl)-L-phenylalaninamide; N-[(3S)-1-azabicyclo[2.2.2]oct-3-yl]-4-bromo-Nalpha-{[1-(2,4-difluorophenyl)-cyclopropyl] carbonyl}-L-phenylalaninamide; N-{(1S)-2-(3-amino-8-azabicyclo[3.2.1]oct-8-yl)-1-[(4-fluorophenyl)methyl]-2-oxoethyl}-1-{4-[(trifluoromethyl)oxy]phenyl}cyclopropanecarboxamide; N-[(3S)-1-azabicyclo[2.2.2]oct-3-yl]-4-bromo-Nalpha-({1-[2-(trifluoromethyl)-phenyl]cyclopropyl}carbonyl)-L-phenylalaninamide; 4-fluoro-N-[(3R)-piperidin-3-yl]-Nalpha-[(1-{4-[(trifluoromethyl)oxy]phenyl}-cyclopropyl)carbonyl]-L-phenylalaninamide; N-{(1S)-2-(4-aminopiperidin-1-yl)-1-[(4-fluorophenyl)methyl]-2-oxoethyl}-1-{4-[(trifluoromethyl)oxy]phenyl}cyclopropanecarboxamide; N-[(1S)-1-[(4-bromophenyl)methyl]-2-(4-hydroxypiperidin-1-yl)-2-oxoethyl]-1-(2,4-dichlorophenyl)cyclopropanecarboxamide; N-[(3S)-1-azabicyclo[2.2.2]oct-3-yl]-4-(trifluoromethyl)-Nalpha-[(1-{4-[(trifluoromethyl)-oxy]phenyl}cyclopropyl)carbonyl]-L-phenylalaninamide; N-[(3S)-1-azabicyclo[2.2.2]oct-3-yl]-2,4-dichloro-N-alpha-{[1-(2,4-dichlorophenyl)-cyclopropyl]carbonyl}-L-phenylalaninamide; N-[(3S)-1-azabicyclo[2.2.2]oct-3-yl]-4-bromo-N-alpha-{[1-(2,4-dichlorophenyl)-cyclopropyl]carbonyl}-L-phenylalaninamide; N-[(3S)-1-azabicyclo[2.2.2]oct-3-yl]-N-alpha-{[1-(2,4-dichlorophenyl)-cyclopropyl]-carbonyl}-4-(trifluoromethyl)-L-phenylalaninamide; 4-bromo-Nalpha-[2-(2,4-dichlorophenyl)-2-methylpropanoyl]-N-[(3R)-piperidin-3-yl]-L-phenylalaninamide; 4-bromo-Nalpha-(2-methyl-2-{4-[(trifluoromethyl)oxy]phenyl}propanoyl)-N-[(3R)-piperidin-3-yl]-L-phenylalaninamide; N-{(1S)-2-(3-amino-8-azabicyclo[3.2.1]oct-8-yl)-1-[(4-bromophenyl)methyl]-2-oxoethyl}-2-methyl-2-{4-[(trifluoromethyl)oxy]phenyl}propanamide; N-{(1S)-2-(4-amino-4-methylpiperidin-1-yl)-1-[(4-bromophenyl)methyl]-2-oxoethyl}-2-(2,4-dichlorophenyl)-2-methylpropanamide; 1-(2,4-dichlorophenyl)-N-[(1S)-1-({[(1-methylcyclopropyl)methyl]oxy}methyl)-2-(4-methylpiperazin-1-yl)-2-oxoethyl]cyclopropanecarboxamide; N-1-azabicyclo[2.2.2]oct-3-yl-N'2'-{[1-(2,4-dichlorophenyl)cyclopropyl]carbonyl}-3-(1-methylcyclopropyl)-L-alaninamide.

Examples of carbamates are described in patent applications WO2012129084, WO2014043068 which are all incorporated by reference.

In one embodiment, the inhibitor of ganglioside metabolism is described in the patent application WO2012129084 incorporated herein by reference and is selected from the group comprising 1-azabicyclo[2.2.2]oct-3-yl [2-(2,4'-difluorobiphenyl-4-yl)propan-2-yl]carbamate; 1-azabicyclo[2.2.2]oct-3-yl {2-[4-(1,3-benzothiazol-6-yl)phenyl]propan-2-yl}carbamate; 1-azabicyclo[3.2.2]non-4-yl {1-[5-(4-fluorophenyl)pyridin-2-yl]cyclopropyl}carbamate; 1-azabicyclo[2.2.2]oct-3-yl {1-[3-(4-fluorophenoxy)phenyl]cyclopropyl}carbamate; 1-azabicyclo[2.2.2]oct-3-yl {1-[4-(1,3-benzothiazol-5-yl)phenyl]cyclopropyl}carbamate; 1-azabicyclo[2.2.2]oct-3-yl [1-(4'-fluoro-3'-methoxybiphenyl-4yl)cyclopropyl]carbamate; 1-azabicyclo[2.2.2]oct-3-yl [3-(4'-fluorobiphenyl-4-yl)oxetan-3-yl]carbamate; 1-azabicyclo[2.2.2]oct-3-yl {1-[6-(4-fluorophenoxy)pyridin-2-yl]cyclopropyl}carbamate; 1-azabicyclo[2.2.2]oct-3-yl [3-(4'-fluorobiphenyl-4-yl)pentan-3-yl]carbamate; 1-azabicyclo[2.2.2]oct-3-yl {2-[2-(4-fluorophenyl)-2H-indazol-6-yl]propan-2-yl}carbamate; 1-azabicyclo[2.2.2]oct-3-yl {2-[2-(1H-pyrrol-1-yl)pyridin-4-yl]propan-2-yl}carbamate; 1-(3-ethyl-1-azabicyclo[2.2.2]oct-3-yl)-3-[1-(4'-fluorobiphenyl-4-yl)cyclopropyl]urea; N-(1-azabicyclo[2.2.2]oct-3-yl)-N'-

[1-(4'-fluorobiphenyl-4yl)cyclopropyl]ethanediamide; 1-azabicyclo[2.2.2]oct-3-yl (1-{4[(4,4difluorocyclohexyl)oxy]phenyl}cyclopropyl) carbamate; 1-(4-methyl-1-azabicyclo[3.2.2]non-4-yl)-3-[1-(5-phenylpyridin-2-yl)cyclopropyl]urea; 1-[1-(4'-fluorobiphenyl-4-yl)cyclopropyl]-1-methyl-3-(3-methyl-1-azabicyclo[2.2.2]oct-3-yl)urea; 1-[1-(4'-fluorobiphenyl-4-yl)cyclopropyl]-1-methyl-3-(3-methyl-1-azabicyclo[2.2.2]oct-3-yl)urea; 1-{2-[4'-(2-methoxyethoxy)biphenyl-4-yl]propan-2-yl}-3-(3-methyl-1-azabicyclo[2.2.2]oct-3-yl)urea; 2-(1-azabicyclo[3.2.2]non-4-yl)-N-[1-(5-phenylpyridin-2-yl)cyclopropyl]acetamide; 3-(4'-fluorobiphenyl-4-yl)-3-methyl-N-(4-methyl-1-azabicyclo[3.2.2]non-4-yl)butanamide; N-[2-(biphenyl-4-yl)propan-2-yl]-N'-(3-methyl-1-azabicyclo[2.2.2]oct-3-yl)sulfuric diamide; N-[2-(4'-fluorobiphenyl-4-yl)propan-2-yl]-N'-(3-methyl-1-azabicyclo[2.2.2]oct-3-yl)sulfuric diamide; 1-(3-butyl-1-azabicyclo[2.2.2]oct-3-yl)-3-{2-[1-(4-fluorophenyl)-1H-pyrazol-4-yl]propan-2-yl}urea; 1-azabicyclo[2.2.2]oct-3-yl [4-(4-fluorophenyl)-2-methylbut-3-yn-2-yl] carbamate; 1-(3-butyl-1-azabicyclo[2.2.2]oct-3-yl)-3-[4-(4-fluorophenyl)-2-methylbut-3-yn-2-yl]urea; N-[1-(4'-fluorobiphenyl-4-yl)cyclopropyl]-1,4-diazabicyclo[3.2.2]nonane-4-carboxamide; 1-(2-(4'-fluoro-[1,1'-biphenyl]-4-yl)propan-2-yl)-3-(3-methyl-1-azabicyclo[3.2.2]nonan-3-yl)urea; 1-(2-(4'-fluoro-[1,1'-biphenyl]-4-yl)propan-2-yl)-3-(4-methyl-1-azabicyclo[4.2.2]decan-4-yl)urea; 1-(2-(4'-fluoro-[1,1'-biphenyl]-4-yl)propan-2-yl)-3-(3-methyl-1-azabicyclo[4.2.2]decan-3-yl)urea; and 1-(2-(4'-fluoro-[1,1'-biphenyl]-4-yl)propan-2-yl)-3-(5-methyl-1-azabicyclo[4.2.2]decan-5-yl)urea.

In one embodiment, the inhibitor of ganglioside metabolism is described in the patent application WO2012129084 incorporated herein by reference and is a compound having the following formula:

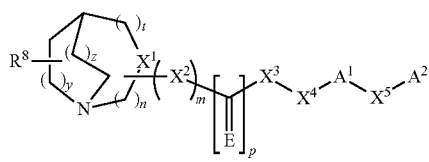

I or a pharmaceutically acceptable salt or prodrug thereof, wherein:
n is 1, 2 or 3;
m is 0 or 1;
p is 0 or 1;
t is 0, 1 or 2;
y is 1 or 2;
z is 0, 1 or 2;
E is S, O, NH, NOH, NNO$_2$, NCN, NR, NOR or NSO$_2$R;
$X^1$ is $CR^1$ when m is 1 or N when m is 0;
$X^2$ is O, —NH, —CH$_2$—, SO$_2$, NH—SO$_2$; CH(C$_1$-C$_6$)alkyl or —NR$^2$;
$X^3$ is O, —NH, —CH$_2$—, CO, —CH(C$_1$-C$_6$) alkyl, SO$_2$NH, —CO—NH— or —NR$^3$;
$X^4$ is $CR^4R^5$, CH$_2$CR$^4$R$^5$ or CH$_2$—(C$_1$-C$_6$)alkyl-CR$^4$R$^5$;
$X^5$ is a direct bond, O, S, SO$_2$, CR$^4$R$^5$; (C$_1$-C$_6$)alkyl, (C$_1$-C$_6$)alkyloxy, (C$_1$-C$_6$)alkenyl, (C$_1$-C$_6$)alkenyloxy;
R is (C$_6$-C$_{12}$)aryl, (C$_2$-C$_9$)heteroaryl, (C$_1$-C$_6$)alkyl, (C$_2$-C$_9$)heteroaryl(C$_1$-C$_6$)alkyl;
$R^1$ is H, CN, (C$_1$-C$_6$)alkylcarbonyl, or (C$_1$-C$_6$)alkyl;
$R^2$ and $R^3$ are each independently —H, (C$_1$-C$_6$)alkyl optionally substituted by one or more substituents selected from the group consisting of halogen, (C$_1$-C$_6$)alkyl, (C$_6$-C$_{12}$)aryl, (C$_2$-C$_9$)heteroaryl, (C$_1$-C$_6$)alkyl(C$_6$-C$_{12}$)aryl, halo(C$_6$-C$_{12}$)aryl, and halo(C$_2$-C$_9$)heteroaryl, or optionally when $X^2$ is —NR$^2$ and $X^3$ is —NR$^3$, $R^2$ and $R^3$ may be taken together with the nitrogen atoms to which they are attached form a non-aromatic heterocyclic ring optionally substituted by with one or more substituents selected from halogen, (C$_1$-C$_6$)alkyl, (C$_6$-C$_{12}$)aryl, (C$_2$-C$_9$)heteroaryl, (C$_1$-C$_6$)alkyl(C$_6$-C$_{12}$)aryl, halo(C$_6$-C$_{12}$)aryl, and halo (C$_2$-C$_9$)heteroaryl;
$R^4$ and $R^5$ are independently selected from H, (C$_1$-C$_6$) alkyl, or taken together with the carbon to which they are attached to form a spiro (C$_3$-C$_{10}$)cycloalkyl ring or spiro (C$_3$-C$_{10}$)cycloalkoxy ring;
$R^6$ is —H, halogen, —CN, (C$_6$-C$_{12}$)aryl, (C$_6$-C$_{12}$)aryloxy, (C$_1$-C$_6$)alkyloxy; (C$_1$-C$_6$)alkyl optionally substituted by one to four halo or (C$_1$-C$_6$)alkyl;
$A^1$ is (C$_2$-C$_6$)alkynyl; (C$_6$-C$_{12}$)aryl, (C$_2$-C$_9$)heteroaryl, (C$_2$-C$_9$)heterocycloalkyl or benzo(C$_2$-C$_9$)heterocycloalkyl optionally substituted with one or more substituents selected from the group consisting of halo, (C$_1$-C$_6$)alkyl optionally substituted by one to three halo; (C$_1$-C$_6$)alkenyl, amino, (C$_1$-C$_6$)alkylamino, (C$_1$-C$_6$) dialkylamino, (C$_1$-C$_6$)alkoxy, nitro, CN, —OH, (C$_1$-C$_6$)alkyloxy optionally substituted by one to three halo; (C$_1$-C$_6$)alkoxycarbonyl, and (C$_1$-C$_6$) alkylcarbonyl;
$A^2$ is H, (C$_6$-C$_{12}$)aryl, (C$_2$-C$_9$)heteroaryl, (C$_2$-C$_9$)heterocycloalkyl or benzo(C$_2$-C$_9$)heterocycloalkyl optionally substituted with one or more substituents selected from the group consisting of halo, (C$_1$-C$_6$)alkyl optionally substituted by one to three halo; (C$_1$-C$_6$)alkylenyl, amino, (C$_1$-C$_6$) alkylamino, (C$_1$-C$_6$)dialkylamino, (C$_1$-C$_6$)alkoxy, O(C$_3$-C$_6$ cycloalkyl), (C$_3$-C$_6$) cycloalkoxy, nitro, CN, OH, (C$_1$-C$_6$)alkyloxy optionally substituted by one to three halo; (C$_3$-C$_6$) cycloalkyl, (C$_1$-C$_6$) alkoxycarbonyl, (C$_1$-C$_6$) alkylcarbonyl, (C$_1$-C$_6$) haloalkyl;
with the proviso that the sum of n+t+y+z is not greater than 6;
with the proviso that when p is 0; $X^2$ is NH—SO$_2$ and $X^3$ is NH;
with the proviso that when n is 1; t is 0; y is 1; z is 1; $X^2$ is NH; E is O; $X^3$ is NH; $A^2$ is H and $X^5$ is a direct bond; $A^1$ is not unsubstituted phenyl, halophenyl or isopropenyl phenyl;
with the proviso that when n is 1; t is 0; y is 1; z is 1; $X^2$ is O; E is O; $X^3$ is NH; A is (C$_6$-C$_{12}$)aryl and $X^5$ is a direct bond; $A^2$ is H and $R^4$ is H then $R^5$ is not cyclohexyl; and with the proviso that when n is 1; t is 0; y is 1; z is 1; X is NH; E is O; X is CH$_2$; $R^4$ and $R^5$ are both hydrogen; $A^2$ is H and $X^5$ is a direct bond; then $A^1$ is not unsubstituted phenyl.

In particular, the inhibitor of ganglioside metabolism is described in the patent application WO2012129084 incorporated herein by reference and is selected from compounds having the following formulas:

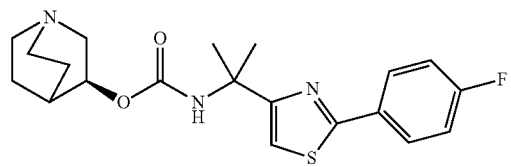

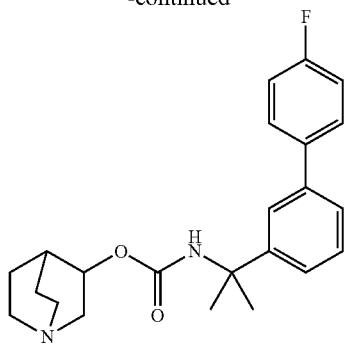

In one embodiment, the inhibitor of ganglioside metabolism is described in the patent application WO2014043068 incorporated herein by reference and is selected from the group comprising 1-azabicyclo[2.2.2]oct-3-yl [2-(2,4'-difluorobiphenyl-4-yl)propan-2-yl]carbamate; 1-azabicyclo[2.2.2]oct-3-yl {2-[4-(1,3-benzothiazol-6-yl)phenyl]propan-2-yl}carbamate; 1-azabicyclo[3.2.2]non-4-yl {1-[5-(4-fluorophenyl)pyridin-2-yl]cyclopropyl}carbamate; 1-azabicyclo[2.2.2]oct-3-yl {1-[3-(4-fluorophenoxy)phenyl]cyclopropyl}carbamate; 1-azabicyclo[2.2.2]oct-3-yl{1-[4-(1,3-benzothiazol-5-yl)phenyl]cyclopropyl}carbamate; 1-azabicyclo[2.2.2]oct-3-yl [1-(4'-fluoro-3'-methoxybiphenyl-4yl)cyclopropyl]carbamate; 1-azabicyclo[2.2.2]oct-3-yl [3-(4'-fluorobiphenyl-4-yl)oxetan-3-yl]carbamate; 1-azabicyclo[2.2.2]oct-3-yl {1-[6-(4-fluorophenoxy)pyridin-2-yl]cyclopropyl}carbamate; 1-azabicyclo[2.2.2]oct-3-yl [3-(4'-fluorobiphenyl-4-yl)pentan-3-yl]carbamate; 1-azabicyclo[2.2.2]oct-3-yl {2-[2-(4-fluorophenyl)-2H-indazol-6-yl]propan-2-yl}carbamate; 1-azabicyclo[2.2.2]oct-3-yl {2-[2-(1H-pyrrol-1-yl)pyridin-4-yl]propan-2-yl}carbamate; 1-(3-ethyl-1-azabicyclo[2.2.2]oct-3-yl)-3-[1-(4'-fluorobiphenyl-4-yl)cyclopropyl]urea; N-(1-azabicyclo[2.2.2]oct-3-yl)-N'-[1-(4'-fluorobiphenyl-4yl)cyclopropyl]ethanediamide; 1-azabicyclo[2.2.2]oct-3-yl (1-{4[(4,4difluorocyclohexyl)oxy]phenyl}cyclopropyl) carbamate; 1-(4-methyl-1-azabicyclo[3.2.2]non-4-yl)-3-[1-(5-phenylpyridin-2-yl)cyclopropyl]urea; 1-[1-(4'-fluorobiphenyl-4-yl)cyclopropyl]-1-methyl-3-(3-methyl-1-azabicyclo[2.2.2]oct-3-yl)urea; 1-[1-(4'-fluorobiphenyl-4-yl)cyclopropyl]-1-methyl-3-(3-methyl-1-azabicyclo[2.2.2]oct-3-yl)urea; 1-{2-[4'-(2-methoxyethoxy)biphenyl-4-yl]propan-2-yl}-3-(3-methyl-1-azabicyclo[2.2.2]oct-3-yl)urea; 2-(1-azabicyclo[3.2.2]non-4-yl)-N-[1-(5-phenylpyridin-2-yl)cyclopropyl]acetamide; 3-(4'-fluorobiphenyl-4-yl)-3-methyl-N-(4-methyl-1-azabicyclo[3.2.2]non-4-yl)butanamide; N-[2-(biphenyl-4-yl)propan-2-yl]-N'-(3-methyl-1-azabicyclo[2.2.2]oct-3-yl)sulfuric diamide; N-[2-(4'-fluorobiphenyl-4-yl)propan-2-yl]-N'-(3-methyl-1-azabicyclo[2.2.2]oct-3-yl)sulfuric diamide; 1-(3-butyl-1-azabicyclo[2.2.2]oct-3-yl)-3-{2-[1-(4-fluorophenyl)-1H-pyrazol-4-yl]propan-2-yl}urea; 1-azabicyclo[2.2.2]oct-3-yl [4-(4-fluorophenyl)-2-methylbut-3-yn-2-yl]carbamate; 1-(3-butyl-1-azabicyclo[2.2.2]oct-3-yl)-3-[4-(4-fluorophenyl)-2-methylbut-3-yn-2-yl]urea; N-[1-(4'-fluorobiphenyl-4-yl)cyclopropyl]-1,4-diazabicyclo[3.2.2]nonane-4-carboxamide; 1-(2-(4'-fluoro-[1,1'-biphenyl]-4-yl)propan-2-yl)-3-(3-methyl-1-azabicyclo[3.2.2]nonan-3-yl)urea; 1-(2-(4'-fluoro-[1,-biphenyl]-4-yl)propan-2-yl)-3-(4-methyl-1-azabicyclo[4.2.2]decan-4-yl)urea; 1-(2-(4'-fluoro-[1,1'-biphenyl]-4-yl)propan-2-yl)-3-(3-methyl-1-azabicyclo[4.2.2]decan-3-yl)urea; and 1-(2-(4'-fluoro-[1,1'-biphenyl]-4-yl)propan-2-yl)-3-(5-methyl-1-azabicyclo[4.2.2]decan-5-yl)urea.

In one embodiment, the inhibitor of gangliosides metabolism is described in the patent application WO2014043068 incorporated herein by reference and comprises the following formula:

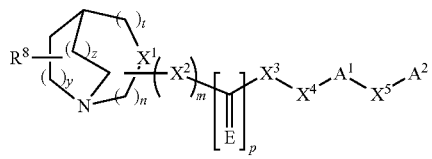

I wherein:
n is 1, 2 or 3;
m is 0 or 1;
p is 0 or 1;
t is 0, 1 or 2;
y is 1 or 2;
z is 0, 1 or 2;
E is S, O, NH, NOH, $NNO_2$, NCN, NR, NOR or $NSO_2R$;
$X^1$ is $CR^1$ when m is 1 or N when m is 0;
$X^2$ is O, —NH, —$CH_2$—, $SO_2$, NH—$SO_2$; $CH(C_1-C_6)$ alkyl or —$NR^2$;
$X^3$ is O, —NH, —$CH_2$—, CO, —$CH(C_1-C_6)$ alkyl, $SO_2NH$, —CO—NH— or —$NR^3$;
$X^4$ is $CR^4R^5$, $CH_2CR^4R^5$ or $CH_2$—$(C_1-C_6)$alkyl-$CR^4R^5$;
$X^5$ is a direct bond, O, S, $SO_2$, $CR^4R^5$; $(C_1-C_6)$alkyl, $(C_1-C_6)$alkyloxy, $(C_1-C_6)$alkenyl, $(C_1-C_6)$alkenyloxy;
R is $(C_6-C_{12})$aryl, $(C_2-C_9)$heteroaryl, $(C_1-C_6)$alkyl, $(C_2-C_9)$heteroaryl$(C_1-C_6)$alkyl;
$R^1$ is H, CN, $(C_1-C_6)$alkylcarbonyl, or $(C_1-C_6)$alkyl;
$R^2$ and $R^3$ are each independently —H, $(C_1-C_6)$alkyl optionally substituted by one or more substituents selected from the group consisting of halogen, $(C_1-C_6)$alkyl, $(C_6-C_{12})$aryl, $(C_2-C_9)$heteroaryl, $(C_1-C_6)$alkyl$(C_6-C_{12})$aryl, halo$(C_6-C_{12})$aryl, and halo$(C_2-C_9)$heteroaryl, or optionally when $X^2$ is —$NR^2$ and $X^3$ is —$NR^3$, $R^2$ and $R^3$ may be taken together with the nitrogen atoms to which they are attached form a non-aromatic heterocyclic ring optionally substituted by with one or more substituents selected from halogen, $(C_1-C_6)$alkyl, $(C_6-C_{12})$aryl, $(C_2-C_9)$heteroaryl, $(C_1-C_6)$alkyl$(C_6-C_{12})$aryl, halo$(C_6-C_{12})$aryl, and halo $(C_2-C_9)$heteroaryl;
$R^4$ and $R^5$ are independently selected from H, $(C_1-C_6)$ alkyl, or taken together with the carbon to which they are attached to form a spiro $(C_3-C_{10})$cycloalkyl ring or spiro $(C_3-C_{10})$cycloalkoxy ring;
$R^6$ is —H, halogen, —CN, $(C_6-C_{12})$aryl, $(C_6-C_{12})$aryloxy, $(C_1-C_6)$alkyloxy; $(C_1-C_6)$alkyl optionally substituted by one to four halo or $(C_1-C_6)$alkyl;
$A^1$ is $(C_2-C_6)$alkynyl; $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, $(C_1-C_6)$alkyl optionally substituted by one to three halo; $(C_1-C_6)$alkenyl, amino, $(C_1-C_6)$alkylamino, $(C_1-C_6)$ dialkylamino, $(C_1-C_6)$alkoxy, nitro, CN, —OH, $(C_1-C_6)$alkyloxy optionally substituted by one to three halo; $(C_1-C_6)$alkoxycarbonyl, and $(C_1-C_6)$ alkylcarbonyl;
$A^2$ is H, $(C_6-C_{12})$aryl, $(C_2-C_9)$heteroaryl, $(C_2-C_9)$heterocycloalkyl or benzo$(C_2-C_9)$heterocycloalkyl optionally substituted with one or more substituents selected from the group consisting of halo, (C₁-C₆)alkyl optionally substituted by one to three halo; (C₁-C₆)alkylenyl, amino, (C₁-C₆) alkylamino, (C₁-C₆)dialkylamino, (C₁-C₆)alkoxy, O(C₃-C₆ cycloalkyl), (C₃-C₆) cycloalkoxy, nitro, CN, OH, (C₁-C₆)alkyloxy optionally substituted by one to three halo; (C₃-C₆) cycloalkyl, (C₁-C₆) alkoxycarbonyl, (C₁-C₆) alkylcarbonyl, (C₁-C₆) haloalkyl;

with the proviso that the sum of n+t+y+z is not greater than 6;

with the proviso that when p is 0; X² is NH—SO₂ and X³ is NH;

with the proviso that when n is 1; t is 0; y is 1; z is 1; X² is NH; E is O; X³ is NH; A² is H and X⁵ is a direct bond; A¹ is not unsubstituted phenyl, halophenyl or isopropenyl phenyl;

with the proviso that when n is 1; t is 0; y is 1; z is 1; X² is O; E is O; X³ is NH; A is (C₆-C₁₂)aryl and X⁵ is a direct bond; A² is H and R⁴ is H then R⁵ is not cyclohexyl; and with the proviso that when n is 1; t is 0; y is 1; z is 1; X is NH; E is O; X is CH₂; R⁴ and R⁵ are both hydrogen; A² is H and X⁵ is a direct bond; then A¹ is not unsubstituted phenyl.

In particular, the inhibitor of gangliosides metabolism is described in the patent application WO2014043068 incorporated herein by reference and is selected from compounds having the following formulas:

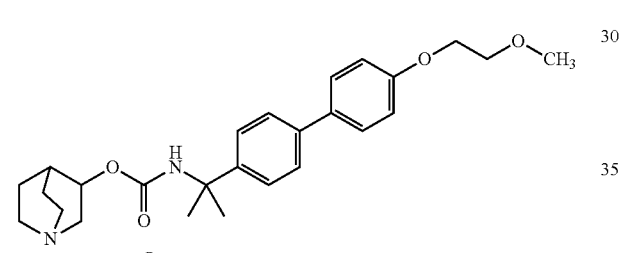

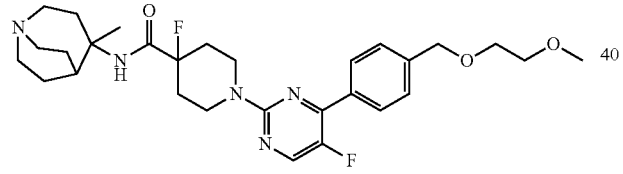

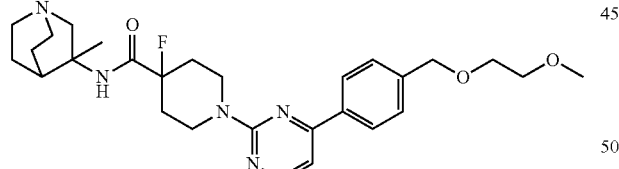

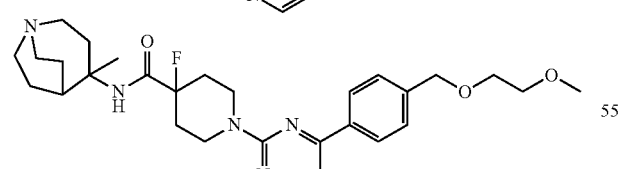

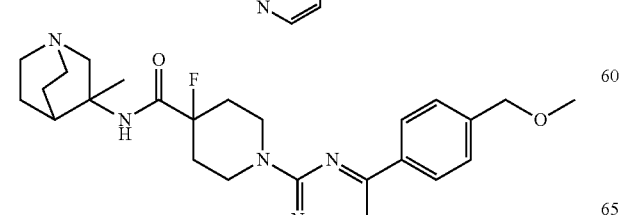

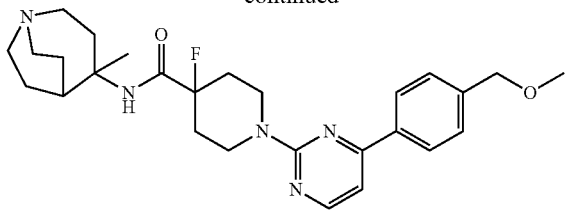

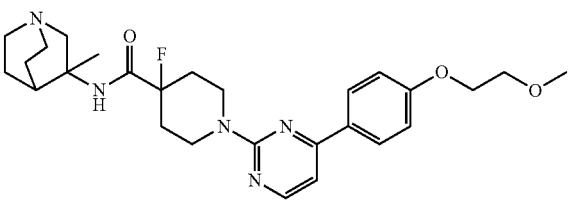

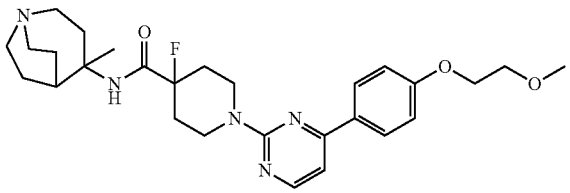

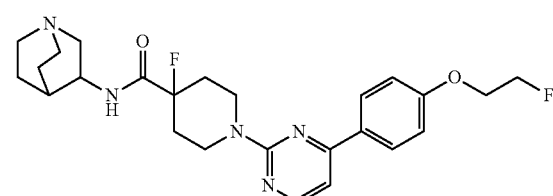

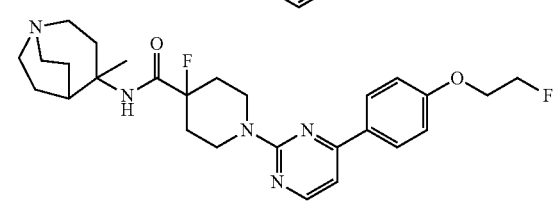

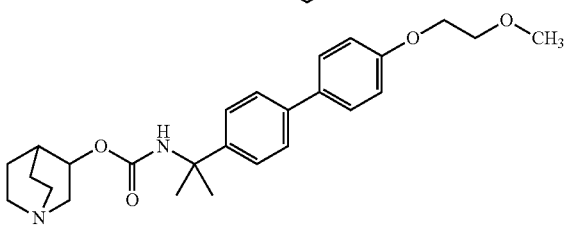

In one embodiment, the inhibitor of gangliosides metabolism is described in the patent application WO2014043068 and is selected from the group comprising (S)-quinuclidin-3-yl (2-(2-(4-fluorophenyl)thiazol-4-yl)propan-2-yl)carbamate (S)-2-hydroxysuccinate (GZ 452), quinuclidin-3-yl (2-(4'-fluoro-[1, -biphenyl]-3-yl)propan-2-yl)carbamate (GZ 161) and (1R,2R)-octanoic acid[2-(2',3'-dihydro-benzo[1,4]dioxin-6'-yl)-2-hydroxy-1-pyrrolidin-1-ylmethyl-ethyl]-amide-L-tartaric acid (GZ 638).

In one embodiment, the inhibitor scaffold of the gangliosides metabolism is described in Richards S et al. (J Med Chem. 2012 May 10; 55(9):4322-35) incorporated herein by reference and has the following formula:

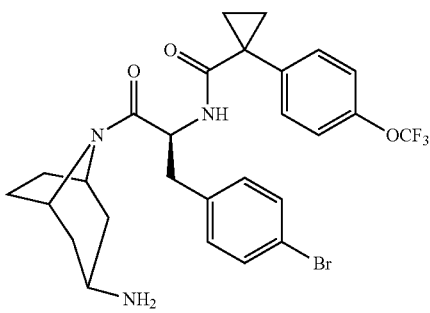 [SMILES: NC1CC2CCC(C1)N2C(=O)[C@H](Cc1ccc(Br)cc1)NC(=O)C1(c2ccc(OC(F)(F)F)cc2)CC1]

EXEL-0346 (having an $IC_{50}$ as low as 2 nM).

In one embodiment, the inhibitor of the invention is a peptide inhibiting the gangliosides metabolism. A non-limiting example of such a peptide is described in Koltun E et al. Bioorg Med Chem Lett. 2011 Nov. 15; 21(22):6773-7 incorporated herein by reference and having the following formula:

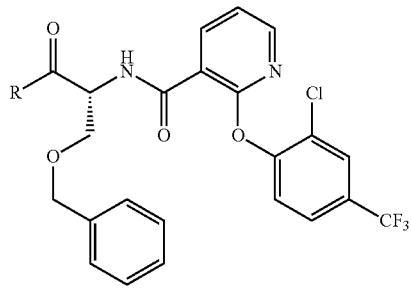

wherein R is:

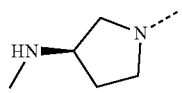

In one embodiment, the inhibitor is a chemical chaperone inhibitor chaperone. Examples of chemical chaperons include, but are not limited to, isofagomine, miglastat, trans-4-(2-Amino-3,5-dibrombenzylamino)-cyclohexanol also named ambroxol, and 5-(4-chlorophenyl)-6-ethyl-2,4-pyrimidinediamine also named pyrimethamine or Daraprim.

In one embodiment, the inhibitor of gangliosides metabolism is a chemical chaperone as described in the U.S. Pat. No. 7,501,439 and is (3R,4R,5R)-5-(hydroxymethyl)-3,4-piperidinediol also named isofagomine D-tartrate (Afegostat), having the following formula:

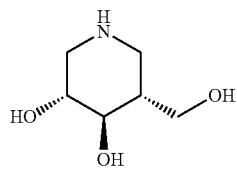

In one embodiment, the inhibitor of gangliosides metabolism is a chemical chaperone as described in the European patent EP0240907 and is ambroxol having the following formula:

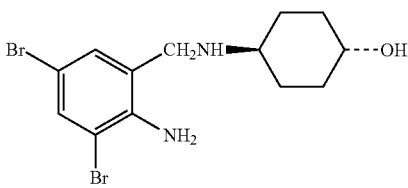

Other examples of chemical chaperone include without limitation, 1-deoxygalactonojirimycin (DGJ), α-homogalactonojirimycin, α-homoallonojirimycin, β-1-C-butyl-DGJ, NB-DGJ, and N-nonyl-DNJ.

In one embodiment, the inhibitor of ganglioside metabolism is described in the U.S. Pat. Nos. 5,236,838; 5,549,892; and 6,451,600 incorporated herein by reference and is imiglucerase also named Cerezyme.

In one embodiment, the inhibitor of gangliosides metabolism inhibits GM3 synthase.

In one embodiment, the inhibitor of GM3 synthase is a miRNA.

Examples of GM3 synthase inhibitors include without limitation ATGTACAGGAGCCAGACTCCAGTTTTGGC-CACTGACTGGAGTCTCTCC TGTACAT (SEQ ID NO: 3) and/or ATAACAGAGCCATAGCCGTCTGTTTTGGC-CACTGACTGACAGACGGCTGGC TCTGTTAT (SEQ ID NO: 4).

In one embodiment of the invention, the GM3 synthase inhibitor is a miRNA having a sequence of at least 20, 30, 40, 50 or 55 nucleotides (preferably contiguous nucleotides) of SEQ ID NO: 3.

In one embodiment of the invention, the GM3 synthase inhibitor is a miRNA having a sequence comprising or consisting of at least 20 contiguous nucleotides of SEQ ID NO: 3, such as 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58 or 59 contiguous nucleotides of SEQ ID NO: 3.

In one embodiment of the invention, the GM3 synthase inhibitor is a miRNA having a sequence comprising, or consisting of at least 20 contiguous nucleotides of SEQ ID NO: 3, such as 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58 or 59 contiguous nucleotides of SEQ ID NO: 3 and 1, 2, 3, 4, or 5 additional nucleotides in 3' and/or in 5'.

In one embodiment, the GM3 synthase inhibitor is a function conservative sequence of SEQ ID NO: 3, wherein said function conservative sequence comprises, or consists of from 9 to 70, 12 to 60, or 15 to 50 nucleotides that has at least about 75%, 80%, 85%, 90%, 95% or more than about 95%, 96%, 97%, 98%, 99% of identity with SEQ ID NO: 3 and that conserves the capacity of inhibiting GM3 synthase expression as SEQ ID NO: 3.

In one embodiment, the function conservative sequence of SEQ ID NO: 3 comprises or consists of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 nucleotides.

The term "identity" or "identical", when used in a relationship between two or more nucleotide sequences, refers to the degree of sequence relatedness between nucleotide sequences, as determined by the number of matches between strings of two or more bases. "Identity" measures the percent of identical matches between the smaller of two or more sequences with gap alignments (if any) addressed by a particular mathematical model or computer program (i.e., "algorithms"). Identity of related nucleotide sequences can be readily calculated by known methods. Such methods include, but are not limited to, those described in Arthur M. Lesk, Computational Molecular Biology: Sources and Methods for Sequence Analysis (New-York: Oxford University Press, 1988); Douglas W. Smith, Biocomputing: Informatics and Genome Projects (New-York: Academic Press, 1993); Hugh G. Griffin and Annette M. Griffin, Computer Analysis of Sequence Data, Part 1 (New Jersey: Humana Press, 1994); Gunnar von Heinje, Sequence Analysis in Molecular Biology: Treasure Trove or Trivial Pursuit (Academic Press, 1987); Michael Gribskov and John Devereux, Sequence Analysis Primer (New York: M. Stockton Press, 1991); and Carillo et al., 1988. SIAM J. Appl. Math. 48(5):1073-1082. Preferred methods for determining identity are designed to give the largest match between the sequences tested. Methods of determining identity are described in publicly available computer programs. Preferred computer program methods for determining identity between two sequences include the GCG program package, including GAP (Devereux et al., 1984. Nucl. Acid. Res. 12(1 Pt 1):387-395; Genetics Computer Group, University of Wisconsin Biotechnology Center, Madison, Wis.), BLASTP, BLASTN, TBLASTN and FASTA (Altschul et al., 1990. J. Mol. Biol. 215(3):403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990. J. Mol. Biol. 215(3):403-410). The well-known Smith Waterman algorithm may also be used to determine identity.

In one embodiment of the invention, said function conservative sequence of SEQ ID NO: 3 may be a sequence comprising SEQ ID NO: 3 between other nucleic acids in C-terminal and N-terminal. Said function conservative sequence may also be a fragment of SEQ ID NO: 3.

In one embodiment of the invention, the GM3 synthase inhibitor is a miRNA having a sequence of at least 20, 30, 40, 50 or 55 nucleotides (preferably contiguous nucleotides) of SEQ ID NO: 4.

In one embodiment of the invention, the GM3 synthase inhibitor is a miRNA having a sequence comprising or consisting of at least 20 contiguous nucleotides of SEQ ID NO: 4, such as 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58 or 59 contiguous nucleotides of SEQ ID NO: 4.

In one embodiment of the invention, the GM3 synthase inhibitor is a miRNA having a sequence comprising, or consisting of at least 20 contiguous nucleotides of SEQ ID NO: 4, such as 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58 or 59 contiguous nucleotides of SEQ ID NO: 4 and 1, 2, 3, 4, or 5 additional nucleotides in 3' and/or in 5'.

In one embodiment, the GM3 synthase inhibitor is a function conservative sequence of SEQ ID NO: 4, wherein said function conservative sequence comprises, or consists of from 9 to 70, 12 to 60, or 15 to 50 nucleotides that has at least about 75%, 80%, 85%, 90%, 95% or more than about 95%, 96%, 97%, 98%, 99% of identity with SEQ ID NO: 4 and that conserves the capacity of inhibiting GM3 synthase expression as SEQ ID NO: 4.

In one embodiment, the function conservative sequence of SEQ ID NO: 4 comprises or consists of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 nucleotides.

In one embodiment of the invention, said function conservative sequence of SEQ ID NO: 4 may be a sequence comprising SEQ ID NO: 4 between other nucleic acids in C-terminal and N-terminal. Said function conservative sequence may also be a fragment of SEQ ID NO: 4.

Other examples of GM3 synthase inhibitors include without limitation a carbon-linked analog of cytidine monophospho-N-acetylneuraminic acid (CMP-NANA), as described in Hatanaka et al., Heterocycles 43:531-534 (1996) incorporated herein by reference.

Other inhibitors of the expression or activity of the GM3 synthase or methods to produce such inhibitors are described in the patent application US20090082303, WO2005108600, WO2011133918 or U.S. Pat. No. 6,280,989 all incorporated herein by reference, including without limitation, interfering RNAs blocking GM3 synthase transcription and having the following sequences: GGGUUAUUCUGAACAUGUUTT (SEQ ID NO: 7), GAAGACCCAGCTTGT-TAATGTGTGCTGT CCAT-TAACAAGCTGGGTCTTCTTTTT (SEQ ID NO: 8), GCCAATGATTTGTTCGTTAGTGT GCTGTCCTAACGAACAAATCATTGGCTTTTT (SEQ ID NO: 9), ATCACTTCTCAGTTTCACAT (SEQ ID NO: 10), GCTTTGAGCTCGGGTGTACC (SEQ ID NO: 11), GGCCTTCTCATCTTGCTTTG (SEQ ID NO: 12), TCTTT-TAATAACAAGCTGGG (SEQ ID NO: 13), GGATGTCTTTTAATAACAAG (SEQ ID NO: 14), AACACAAGCAATGTACATTT (SEQ ID NO: 15), TCCACACTCCAAACACAAGC (SEQ ID NO: 16), TTA-CATGGTCAGGGTCCACA (SEQ ID NO: 17), TCT-GAGCTCTCTTTACATGG (SEQ ID NO: 18), AAGACTTGCTGAGCATATTT (SEQ ID NO: 19), ACAT-TCCTTCTGCAAGACTT (SEQ ID NO: 20), GGCAAACTTGGGACGACATT (SEQ ID NO: 21), TCTGCACAAAAGGGAGTAAG (SEQ ID NO: 22), TTACTGGAGAACTTCCGGAA (SEQ ID NO: 23), GGACTTTACTGGAGAACTTC (SEQ ID NO: 24), AGT-ATTCCTCCGCTTCCAAT (SEQ ID NO: 25), AATCCGTGCAGTATTCCTCC (SEQ ID NO: 26), ACTGTTTAACCTTATCACAA (SEQ ID NO: 27), TATCCCTCAACTGGTGCACT (SEQ ID NO: 28), GTAGTTTTATTTCCAACATG (SEQ ID NO: 29), AGT-CATCCTTATAGTAGTTT (SEQ ID NO: 30), TGAAAT-CAACACTCTTAAAT (SEQ ID NO: 31), TTGAAGCCAGTTGAAATCAA (SEQ ID NO: 32), TTTACCATTGCTTGAAGCCA (SEQ ID NO: 33), CCCAGAATGGCAGGGTTTCC (SEQ ID NO: 34), ACCTGCTTCCAAAAGAAGAG (SEQ ID NO: 35), CTGCCACCTGCTTCCAAAAG (SEQ ID NO: 36), TTTTTCTGCCACCTGCTTCC (SEQ ID NO: 37), TTTGGCTGCAGTGGGATTTT (SEQ ID NO: 38), TGGATTCAAAATCCTGAAAT (SEQ ID NO: 39), TCT-GAGTACTGAAGGATGTC (SEQ ID NO: 40), GAGGCTCTGAGTACTGAAGG (SEQ ID NO: 41), TGACTGAGGCTCTGAGTACT (SEQ ID NO: 42), ATCTCGGCCCCAGAACCTTG (SEQ ID NO: 43), TGCATGGTCTGAAAGTTCAT (SEQ ID NO: 44), ACCAGCTTTAAGAGGAACTT (SEQ ID NO: 45), TTT-CACCACTCCCTCTTTGA (SEQ ID NO: 46), TTTCTGTGTTCAAAATTCAC (SEQ ID NO: 47), AGAGTTGCATTTTCAACTGA (SEQ ID NO: 48), CTGT-CAAAAACAGCTCTCAG (SEQ ID NO: 49), TATCTGCAGGATGGAGAAAT (SEQ ID NO: 50), ACAT-GAGCTGCACTTCAAAG (SEQ ID NO: 51), CCAATT- CAATTCTTAAGTTT (SEQ ID NO: 52), GTTACATA-CAATTCTCTTTG (SEQ ID NO: 53), GCAGAAGTTTTACAAATTAA (SEQ ID NO: 54), CAAAAGAGTGACCTCCCCTC (SEQ ID NO: 55), CAC-CATCAAAAGAGTGACCT (SEQ ID NO: 56), AAT-GAGGTTCAGGGCCACCA (SEQ ID NO: 57), TCACAC-CAAGCAGCGCAGCA (SEQ ID NO: 58), GGATCCTCCGTGGGTCACAC (SEQ ID NO: 59), ATCCTGGGAGTGGATCCTCC (SEQ ID NO: 60), GCTACGGAGCACGTCATCCT (SEQ ID NO: 61), GCA-GACCCAGTATCAGCAGC (SEQ ID NO: 62), GCCGCTGCATCGCAGACCCA (SEQ ID NO: 63), CCCTGGTTGGTTCTCGAGTC (SEQ ID NO: 64), CCTCCAGGACAGCTTCCCTG (SEQ ID NO: 65), TATGTCCCTCTCCGACCAGG (SEQ ID NO: 66), TCACCTCAGACAGACACTGG (SEQ ID NO: 67), AGGGTGTACTCTCCCATGAC (SEQ ID NO: 68), GTGTTTCCCAAAACATTATT (SEQ ID NO: 69), TTTATAATACTGGGAAGATT (SEQ ID NO: 70), GGTATACACCGCCAGGTAGG (SEQ ID NO: 71), ATC-CATATAACAGGCACATG (SEQ ID NO: 72), CTTCC-TATCTCACCTGTTTC (SEQ ID NO: 73), ACAGCAG-GAAATTTGTTGGT (SEQ ID NO: 74), GGTAGATGACTGAATCATGG (SEQ ID NO: 75), GTGACATGGTAGATGGACAC (SEQ ID NO: 76), GCTGCAGTAATGAAGGCGGG (SEQ ID NO: 77), CGGTGTAGGTCTGCAGAGTC (SEQ ID NO: 78), CAGTAGTCACCTTCTGACTG (SEQ ID NO: 79), GCACTGAGTTCTAGAGGAGA (SEQ ID NO: 80), ACCAAGAGCAGTGCACTGAG (SEQ ID NO: 81), TGC-CACTTACTGTAGCCAGC (SEQ ID NO: 82), ACTGTT-TAACCTATTTAAAT (SEQ ID NO: 83), CACTTGGCAT-TGCTGTTTCT (SEQ ID NO: 84), CCTTCAGGAGCTCTAAGATA (SEQ ID NO: 85), AGCTCTCTTCTGACTGTGAC (SEQ ID NO: 86), GCACTGAGTTCTTATCACAA (SEQ ID NO: 87).

Another object of the invention is a pharmaceutical composition for treating (or for use in treating) a motor neuron disease comprising or consisting of or consisting essentially of at least one inhibitor of gangliosides metabolism as described herein above and at least one pharmaceutically acceptable excipient.

Another object of the invention is a medicament for treating (or for use in treating) a motor neuron disease comprising or consisting of or consisting essentially of at least one inhibitor of gangliosides metabolism described here above.

As used herein, the term "consisting essentially of", with reference to a composition, pharmaceutical composition or medicament, means that the at least one inhibitor of gangliosides metabolism of the invention is the only one therapeutic agent or agent with a biologic activity within said composition, pharmaceutical composition or medicament. Examples of pharmaceutically acceptable excipients include, but are not limited to, water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In addition, pharmaceutically acceptable excipients may comprise some excipients, such as, for example, surfactants (e.g. hydroxypropylcellulose); suitable carriers, such as, for example, solvents and dispersion media containing, for example, water, ethanol, polyol (e.g., glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextrose, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; and the like.

Another object of the present invention is a method for treating a motor neuron disease, wherein the method comprises (or consists of or consists essentially of) administering to a subject in need thereof at least one inhibitor of gangliosides metabolism as described herein above, or the pharmaceutical composition or the medicament of the invention. In one embodiment, a therapeutically effective amount of at least one inhibitor of gangliosides metabolism is administered to the subject.

Another object of the present invention is a method for decreasing gangliosides aggregates or gangliosides accumulation in a subject in need thereof, wherein said method comprises, consists of or consists essentially of administering to the subject a therapeutically effective amount of at least one inhibitor of gangliosides metabolism as described herein above, or the pharmaceutical composition or the medicament of the invention.

Another object of the present invention is a method for decreasing gangliosides synthesis in a subject, wherein said method comprises, consists of or consists essentially of administering to a subject in need thereof at least one inhibitor of gangliosides metabolism as described herein above, or the pharmaceutical composition or the medicament of the invention.

Another object of the present invention is a method for decreasing neuronal death in a subject, wherein said method comprises, consists of or consists essentially of administering to a subject in need thereof at least one inhibitor of gangliosides metabolism as described herein above, or the pharmaceutical composition or the medicament of the invention.

Another object of the present invention is a method for decreasing autolysosomes accumulation in a subject, wherein said method comprises, consists of or consists essentially of administering to a subject in need thereof at least one inhibitor of gangliosides metabolism as described herein above, or the pharmaceutical composition or the medicament of the invention.

Examples of motor neuron diseases include without limitation, hereditary spastic paraplegia (HSP), hereditary spastic paraparesis, familial spastic paraplegias, French settlement disease, or Strumpell-Lorrain disease, infantile-onset ascending hereditary spastic paralysis, MASA syndrome, also called CRASH syndrome and Gareis-Mason syndrome, cataracts with motor neuronopathy, short stature and skeletal abnormalities, MAST syndrome, Allan-Hemdon-Dudley syndrome, Troyer syndrome, Lison syndrome, spastic ataxia 2, SPOAN syndrome, peripheral neuropathies, Kjellin's syndrome.

In one embodiment, the motor neuron disease is selected from hereditary spastic paraplegia (HSP), hereditary spastic paraparesis, familial spastic paraplegias, French settlement disease, or Strumpell-Lorrain disease, infantile-onset ascending hereditary spastic paralysis, MASA syndrome, also called CRASH syndrome and Gareis-Mason syndrome, cataracts with motor neuronopathy, short stature and skeletal abnormalities, MAST syndrome, Allan-Hemdon-Dudley syndrome, Troyer syndrome, Lison syndrome, spastic ataxias (in particular hereditary spastic ataxia, such as, for example, spastic ataxia 2), SPOAN syndrome, hereditary motor and sensory neuropathies (HMSN), peripheral neuropathies (in particular HSP presenting peripheral neuropathies) and Kjellin's syndrome.

In one embodiment, the motor neuron disease is caused by a mutation in a SPG (for "spastic paraplegia") gene. In one embodiment, the motor neuron disease is caused by a mutation in the SPG11, SPG4, SPG7, SPG15, SPG48, SPG8 and/or SPG31 gene. In one embodiment, the motor neuron disease is caused by a mutation in the SPG11 and/or SPG4 and/or SPG7 gene. In one embodiment, the motor neuron disease is caused by a mutation in the SPG11 gene. In one embodiment, the motor neuron disease is caused by a mutation in the SPG4 gene. In one embodiment, the motor neuron disease is caused by a mutation in the SPG7 gene. In one embodiment, the motor neuron disease does not result from a mutation in the SPG26 and/or SPG46 gene. In one embodiment, the motor neuron disease does not result from a mutation in the SPG26 gene. In one embodiment, the motor neuron disease does not result from a mutation in the SPG46 gene.

In one embodiment, the motor neuron disease is a HSP. In one embodiment, the motor neuron disease in not SPG26 and/or SPG46. In one embodiment, the motor neuron disease is a HSP selected from SPG11, SPG4, SPG7, SPG15, SPG48, SPG8 and SPG31. In one embodiment, the motor neuron disease is SPG11, SPG15, SPG48, SPG4 or SPG7. In one embodiment, the motor neuron disease is SPG11, SPG15 or SPG48; preferably SPG11. In one embodiment, the motor neuron disease is SPG4. In one embodiment, the motor neuron disease is SPG7.

In one embodiment, the method of the invention is for curing the motor neuron disease. In another embodiment, the method of the invention is for alleviating at least one symptom of the motor neuron disease, such as, for example, at least one motor or cognitive symptom of the motor neuron disease.

In one embodiment, the method of the invention is for alleviating at least one symptom of SPG11. Examples of symptoms of SPG11 include, but are not limited to abnormality of the periventricular white matter and/or agenesis of corpus callosum at brain imaging; decreased number of peripheral myelinated nerve fibers; degeneration of the lateral corticospinal tracts; ventriculomegaly; macular degeneration; strabismus; visual evoked potentials with increased latencies and decreased amplitudes; Babinski sign; knee clonus; ankle clonus; obesity; aplasia/hypoplasia of the corpus callosum; cerebral cortical atrophy; retinal degeneration (Kjelling syndrome); extrapyramidal signs such as parkinsonism; seizures; axonal, motor, or sensorimotor peripheral neuropathy; involuntary movements of the eyes (nystagmus); saccadic smooth pursuit; gait disturbance; dysarthria; ataxia; saccadic smooth pursuit; motor polyneuropathy; thenar muscle atrophy; tip-toe gait; spasticity (progressive muscle stiffness); paraplegia (eventual paralysis of the lower limbs); numbness, tingling, or pain in the arms and legs; disturbance in the nerves used for muscle movement; exaggerated reflexes of the lower limbs; reduced bladder control; muscle wasting; involuntary movements of the eyes; abnormal curvature of the spine (scoliosis); high-arched feet (pes cavus); difficulty swallowing (dysphagia); speech difficulties (dysarthria); mental deterioration; intellectual disability; memory, communication, or learning disability.

In one embodiment, the method of the invention is for alleviating at least one cognitive symptom of SPG11. Examples of cognitive symptoms of SPG11 include, but are not limited to mental deterioration; intellectual disability; memory, communication, or learning disability.

In one embodiment, the method of the invention is for alleviating at least one motor symptom of SPG11. Examples of motor symptoms of SPG11 include, but are not limited to saccadic smooth pursuit; motor polyneuropathy; thenar muscle atrophy; tip-toe gait; axonal, motor, or sensorimotor peripheral neuropathy; involuntary movements of the eyes (nystagmus); saccadic smooth pursuit; gait disturbance; dysarthria; ataxia (lack of muscle control); spasticity (progressive muscle stiffness); paraplegia(eventual paralysis of the lower limbs); numbness, tingling, or pain in the arms and legs; disturbance in the nerves used for muscle movement; exaggerated reflexes of the lower limbs; muscle wasting; involuntary movements of the eyes; abnormal curvature of the spine (scoliosis); difficulty swallowing (dysphagia); and speech difficulties (dysarthria).

In one embodiment, the method of the invention is for alleviating at least one symptom of SPG4. Examples of symptoms of SPG4 include, but are not limited to genetic anticipation; low back pain; seizures; degeneration of the lateral corticospinal tracts; mild vermis atrophy and/or thin corpus callosum; Babinski sign; decreased ability to sense vibrations in the ankles; exaggerated reflexes (hyperreflexia); high arches in the feet (pes cavus); ankle spasms; ataxia (lack of muscle control); lower limb muscle weakness; spasticity (progressive muscle stiffness); involuntary movements of the eyes (nystagmus); urinary bladder sphincter dysfunction; paraplegia; aggressive behavior; agitation; apathy; dementia; depression; disinhibition; intellectual disability; memory, communication, or learning disability; and excessive daytime sleepiness.

In one embodiment, the method of the invention is for alleviating at least one cognitive symptom of SPG4.

Examples of cognitive symptoms of SPG4 include, but are not limited to aggressive behavior; agitation; apathy; dementia; depression; disinhibition; intellectual disability; memory, communication, or learning disability; and excessive daytime sleepiness.

In one embodiment, the method of the invention is for alleviating at least one motor symptom of SPG4. Examples of motor symptoms of SPG4 include, but are not limited to ankle spasms; ataxia (lack of muscle control); lower limb muscle weakness; spasticity (progressive muscle stiffness); involuntary movements of the eyes (nystagmus); urinary bladder sphincter dysfunction; and paraplegia.

In one embodiment, the method of the invention is for alleviating at least one symptom of SPG7. Examples of symptoms of SPG7 include, but are not limited to degeneration of the lateral corticospinal tracts; cerebral cortical atrophy; cerebellar atrophy; Babinski sign; hyperreflexia; impaired vibration sensation in the lower limbs; optic atrophy; high arches in the feet (pes cavus); abnormal curvature of the spine (scoliosis); dysarthria; dysphagia; gait ataxia; lower limb muscle weakness; lower limb spasticity; nystagmus; spastic gait; spastic paraplegia; urinary bladder sphincter dysfunction; deficits in attention; memory impairment; and verbal learning.

In one embodiment, the method of the invention is for alleviating at least one cognitive symptom of SPG7. Examples of cognitive symptoms of SPG7 include, but are not limited to deficits in attention; memory impairment; and verbal learning.

In one embodiment, the method of the invention is for alleviating at least one motor symptom of SPG7. Examples of motor symptoms of SPG7 include, but are not limited to dysarthria; dysphagia; gait ataxia; lower limb muscle weakness; lower limb spasticity; nystagmus; spastic gait; spastic paraplegia; and urinary bladder sphincter dysfunction.

In one embodiment, the subject is affected, preferably is diagnosed with, a motor neuron disease. In another embodiment, the subject of the invention is at risk of developing a motor neuron disease, preferably a HSP.

Examples of risk factors include, but are not limited to, genetic factors, spastic paraplegia genes L1 cell adhesion molecule (L1CAM)/NCAM (chromosome Xq28), PLP1/MPLP, ATL1/ATLASTIN-1, SPAST/SPASTIN, CYP7B1/OAH1, NIPA1/NIPA1, PGN/PARAPLEGIN, KIAA0196/STRUMPELLIN, KIF5A/KINESIN HC5A, KIAA1840/SPATACSIN, RTN2/RETICULON 2, HSPD1/HSP60, ZFYVE26/SPASTIZIN, BSCL2/SEIPIN, ERLIN2/SPFH2, SPG20/SPARTIN, ACP33/MASPARDIN, SLC16A2/MCT8, B4GALNT1/B4GALNT1, DDHD1/PAPLA1; KIF1A/KINESIN3, REEP1/REEP1, ZFYVE27/PROTRUDIN, FA2H/FA2H, NTE/PNPLA6, SLC33A1/ACoA CARRIER, C19orf12/C19ORF12, GJC2/CONNEXIN 47, GBA2/GBA2, AP4B1/AP4B1, KIAA0415/AP5Z1, TECPR2/KIAA0329, AP4M1/AP4M1, AP4E1/AP4E1, AP4S1/AP4S1, VPS37A/VPS37A, DDHD2/DDHD2, C12orf65/C120RF65, CYP2U1/CYP2U1, TFG/TFG, KIF1C/KINESIN FAMILY MEMBER 1C, USP8/UBIQUITIN-SPECIFIC PROTEASE 8, WDR48/WD REPAET DOMAIN 48, ARL6IP1/ADP-RIBOSYLATION FACTOR-LIKE 6 INTERACTING PROTEIN 1, ERLIN1/ER LIPID RAFT ASSOCIATED 1, AMPD2/ADENOSINE MONOPHOSPHATE DEAMINASE2, ENTPD1/ECTONUCLEOSIDE TRIPHOSPHATE DIPHOSPHOHYDROLASE, NT5C2/5'-NUCLEOTIDASE, CYTOSOLIC II, ARSI/ARYLSULFATASE FAMILY, MEMBER I, PGAP1/POST-GPI ATTACHMENT TO PROTEINS 1, FLRT1/FIBRONECTIN LEUCINE RICH TRANSMEMBRANE PROTEIN 1, RAB3GAP2/RAB3 GTPASE ACTIVATING PROTEIN SUBUNIT 2 (NON-CATALYTIC), MARS/METHIONYL-TRNA SYNTHETASE, ZFR/ZINC FINGER RNA-BINDING PROTEIN, REEP2/RECEPTOR EXPRESSION-ENHANCING PROTEIN 2, GAD1/GLUTAMATE DECARBOXYLASE 1, CCT5/c SUBUNIT OF THE CYTOSOLIC CHAPERONIN CONTAINING T-COMPLEX PEPTIDE-1, OPA3/OPTIC ATROPHY 3 PROTEIN, BICD2/BICAUDAL D HOMOLOG 2, MAG/MYELIN ASSOCIATED GLYCOPROTEIN, LYST/LYSOSOMAL TRAFFICKING REGULATOR, MT-ATP6/ATP SYNTHASE 6, AP5B1/DKFZp761E198, AP5M1/C14orf108, AP5S1/C20orf29, mutations on chromosomes 15q; 10q23.3-24.2, 14q24.1, 8, 7p22.1; 16q; 2q33.2; 3q27-q28; Xq11.2; 9q; 1q24-q32; 13q14; 6q23-q24.1; 10q22.1-q24.1; 1p31.1-p21.1; 14q12-q21; Xq24-q25; 12q23-q24; 8p21.1-q13.3; 4p16-p15; 11p14.1-p11.2; 10q24.3-q25.1; 11q13; Xq22.

In one embodiment, the risk factor is selected from, spastic paraplegia genes L1 cell adhesion molecule (L1CAM)/NCAM (chromosome Xq28), PLP1/MPLP, ATL1/ATLASTIN-1, SPAST/SPASTIN, CYP7B1/OAH1, NIPA1/NIPA1, PGN/PARAPLEGIN, KIAA0196/STRUMPELLIN, KIF5A/KINESIN HC5A, KIAA1840/SPATACSIN, RTN2/RETICULON 2, HSPD1/HSP60, ZFYVE26/SPASTIZIN, BSCL2/SEIPIN, ERLIN2/SPFH2, SPG20/SPARTIN, ACP33/MASPARDIN, SLC16A2/MCT8, DDHD1/PAPLA1; KIF1A/KINESIN3, REEP1/REEP1, ZFYVE27/PROTRUDIN, FA2H/FA2H, NTE/PNPLA6, SLC33A1/ACoA CARRIER, C19orf12/C19ORF12, GJC2/CONNEXIN 47, AP4B1/AP4B1, KIAA0415/AP5Z1, TECPR2/KIAA0329, AP4M1/AP4M1, AP4E1/AP4E1, AP4S1/AP4S1, VPS37A/VPS37A, DDHD2/DDHD2, C12orf65/C120RF65, CYP2U1/CYP2U1, TFG/TFG, KIF1C/KINESIN FAMILY MEMBER 1C, USP8/UBIQUITIN-SPECIFIC PROTEASE 8, WDR48/WD REPAET DOMAIN 48, ARL6IP1/ADP-RIBOSYLATION FACTOR-LIKE 6 INTERACTING PROTEIN 1, ERLIN1/ER LIPID RAFT ASSOCIATED 1, AMPD2/ADENOSINE MONOPHOSPHATE DEAMINASE2, ENTPD1/ECTONUCLEOSIDE TRIPHOSPHATE DIPHOSPHOHYDROLASE, NT5C2/5'-NUCLEOTIDASE, CYTOSOLIC II, ARSI/ARYLSULFATASE FAMILY, MEMBER I, PGAP1/POST-GPI ATTACHMENT TO PROTEINS 1, FLRT1/FIBRONECTIN LEUCINE RICH TRANSMEMBRANE PROTEIN 1, RAB3GAP2/RAB3 GTPASE ACTIVATING PROTEIN SUBUNIT 2 (NON-CATALYTIC), MARS/METHIONYL-TRNA SYNTHETASE, ZFR/ZINC FINGER RNA-BINDING PROTEIN, REEP2/RECEPTOR EXPRESSION-ENHANCING PROTEIN 2, GAD1/GLUTAMATE DECARBOXYLASE 1, CCT5/c SUBUNIT OF THE CYTOSOLIC CHAPERONIN CONTAINING T-COMPLEX PEPTIDE-1, OPA3/OPTIC ATROPHY 3 PROTEIN, BICD2/BICAUDAL D HOMOLOG 2, MAG/MYELIN ASSOCIATED GLYCOPROTEIN, LYST/LYSOSOMAL TRAFFICKING REGULATOR, MT-ATP6/ATP SYNTHASE 6, AP5B1/DKFZp761E198, AP5M1/C14orf108, AP5S1/C20orf29, mutations on chromosomes 15q; 10q23.3-24.2, 14q24.1, 8, 7p22.1; 16q; 2q33.2; 3q27-q28; Xq11.2; 9q; 1q24-q32; 13q14; 6q23-q24.1; 10q22.1-q24.1; 1p31.1-p21.1; 14q12-q21; Xq24-q25; 12q23-q24; 8p21.1-q13.3; 4p16-p15; 11p14.1-p11.2; 10q24.3-q25.1; 11q13; Xq22.

In one embodiment, the motor neuron disease is SPG11. Examples of SPG11 pathologic allelic variants include without limitation c.118C>T; c.267G>A; c.268G>T; c.349G>T; c.359delT; c.398delG; c.408_428del21; c.442+1G>C;

c.529_533delATATT; c.642delT; c.654_655delinsG; c.704_705delAT; c.733_734delAT; c.869+1G>A; c.1203delA; c.1235C>G; c.1282A>T; c.1457-2A>G; c.1471_1472delCT; c.1549_1550delCT; c.1550_1551delTT; c.1668delT; c.1679C>G; c.1697_1712del16insTACTCCCAT; c.1735+3+6delAAGT; c.1837_18388insA; c.1845_1846delGT; c.1951C>T; c.2146C>T; c.2163_2164insT; c.2198T>G; c.2316+1G>A; c.2355_2356del2; c.2444G>T; c.2444+1G>C; c.2472insT; c.2608A>G; c.2697G>A; c.2716delC; c.2833A>G; c.2834+1G>T; c.2842_2843insG; c.2849_2850insT; c.3075_3076insA; c.3145_3146insCA; c.3291+1G>T; c.3602_3603delAT; c.3664_3665insT; c.3719_3720delTA; c.3741_3742insA; c.4046T>A; c.4307_4308delAA; c.4461_4462delGT; c.4668T>A; c.4846C>T; c.5255delT; c.5399_5407delAGATinsTGGAGGAG; c.5410_5411delTG; c.5470C>T; c.5532_5533delCA; c.5623C>T; c.5703delT; c.5769delT; c.5798delC; c.5867-3237_6478-451 del8323; c.5870C>G; c.5898+5493_6509-491del; c.5970C>G; c.5974C>T; c.5977C>T; c.5986_5987insT; c.5985delCTGT; c.5987_5990dupCTCT; c.5989_5992delCTGT; c.5992insT; c.6091C>T; c.6100C>T; c.6157G>A; c.6206-1G>C; c.6451delG; c.6477+4 A>G; c.6737_6740delTTGA; c.6739_6742delGAGT; c.6754+4insTG; g.96677_99386del2710; r.6755_7151del397; c.6790_6791insC; c.6832_6833delAG; c.6856C>T; c.6898_6899delCT; c.7000-3-2insGGA; c.7023C>A; c.7029_7030insT; c.7088_7089insATTA; c.7101_7102insT; c.7151+4 7151+7delAGTA; c.7152-1G>C; c.7156_7157insAAAC.

In one embodiment, the motor neuron disease is SPG4. Examples of SPG4 pathologic allelic variants include without limitation c.334G>A, c.1157A>G, 1340-1344del, 1447A>G, 1617-1618+2del, 1853+1G>T, 1210C>G; 1233G>A; 1267T>G; 1283T>G; 1288A>G; 1401C>G; 1468G>A; 1504G>T; 1620C>T; 1788G>A; 1792C>T; 702C>T; 873A>T; 907C>A; 932C>G; 1416C>T; 1416C>T; 1809C>T; 578-579insA; 852del11; 882-883insA; 906delT; 1299delG; 1340del5; 1340del5; 1340del5; 1520delT; 1574delGG; 1634del22; 1684-1685insTT; 1685del4; 808-2a>g; 1129+2t>g; 1223+1g>t; 1299+1g>a; 1538+5g>a; 1538+3del4; 1661+1g>t; 1662-2a>t; 1812+1g>a; 1813-2a>g; 1813-2a>g; 1813-2a>g; 1853+1g>a.

In one embodiment, the motor neuron disease is SPG7. Examples of SPG7 pathologic allelic variants include without limitation 1A>T; 28G>A; 233T>A; 244-246delACA; 698T>C; 784del2; 850_-851 delTTinsC; 1045G>A; 1047insC; 1057_-1085del29; 1447-1778 del 331; 1450-1458del 9; 1519 C>T; 155211 G>T; 1616delC; 1636G>A; 1749G>C; 1715C>T; 1729G>A; 1742-1744del3; 1904C>T; 1948G>C; 2026T>C; 2075G>C; 2191G>A; 2216dupA; 2228 Ins A.

In one embodiment, the subjected to be treated is older than 10, 20, 30, 40, 50, 60, 70, 80, 90 years old.

In one embodiment, the at least one inhibitor of gangliosides metabolism described here above or the pharmaceutical composition or the medicament of the invention is to be administered at a dose determined by the skilled artisan and personally adapted to each subject.

In one embodiment of the invention, the at least one inhibitor of gangliosides metabolism described here above, the pharmaceutical composition, the medicament of the invention is to be administered at a therapeutically effective amount.

It will be understood that the total daily usage of the compound of the invention, composition, pharmaceutical composition and medicament of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific composition employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from about 1 to about 10000 mg per adult per day, preferably 2 to about 2000, more preferably from about 5 to about 500 mg per adult per day. Preferably, the compositions contain 1, 10, 20, 30, 40, 50, 60, 70, 80, 90, 100, 250, 500, 1000 and 2,000 mg of the active ingredient for the symptomatic adjustment of the dosage to the patient to be treated. A medicament may typically contain from about 1 to about 10000 mg of the active principle, preferably about 2 to about 2000, more preferably from about 5 to about 500 mg of the active ingredient. An effective amount of the drug may ordinarily be supplied at a dosage level from about 0.01 mg/kg to about 100 mg/kg of body weight per day, preferably from about 0.02 mg/kg to 20 mg/kg of body weight per day, more preferably from about 0.05 mg/kg to 5 mg/kg of body weight per day.

In one embodiment, the at least one inhibitor of gangliosides metabolism described here above, the pharmaceutical composition or the medicament of the invention is to be administered systemically or locally.

In one embodiment, the at least one inhibitor of gangliosides metabolism described here above, the pharmaceutical composition or the medicament of the invention is to be administered orally, by injection, topically, nasally, by inhalation, buccally, rectally, intratracheally, by endoscopy, transmucosally, by percutaneous administration or by perispinal administration.

In one embodiment, the at least one inhibitor of gangliosides metabolism described here above, the pharmaceutical composition, the medicament of the invention is to be administered by injection, preferably is to be systemically injected. Examples of formulations adapted to systemic injections include, but are not limited to: liquid solutions or suspensions, solid forms suitable for solution in, or suspension in, liquid prior to injection. Examples of systemic injections include, but are not limited to, intravenous, subcutaneous, intramuscular, intradermal, and intraperitoneal injection, or perfusion. In another embodiment, when injected, the composition, the pharmaceutical composition or the medicament of the invention is sterile. Methods for obtaining a sterile pharmaceutical composition include, but are not limited to, GMP synthesis (GMP stands for "Good manufacturing practice").

In one embodiment, the at least one inhibitor of gangliosides metabolism described here above, the pharmaceutical composition, the medicament of the invention is to be orally administered. Examples of formulations adapted to oral administration include, but are not limited to: solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing/or disintegrating tablet, powder, solid forms suitable for solution in, or suspension in, liquid prior to oral administration and effervescent tablet. Examples of liquid forms adapted to oral administration include, but are not limited to, solutions, suspensions, drinkable solutions, elixirs, sealed phial, potion, drench, syrup and liquor.

In another embodiment, the at least one inhibitor of gangliosides metabolism described here above, the pharmaceutical composition, the medicament of the invention is to be topically administered. Examples of formulations adapted to topical administration include, but are not limited to, sticks, waxes, creams, lotions, ointments, balms, gels, masks, leave-on washes and/or the like.

In one embodiment, the at least one inhibitor of gangliosides metabolism described here above, the pharmaceutical composition or the medicament of the invention is to be administered in a sustained-release form. In another embodiment, the composition, the pharmaceutical composition or the medicament of the invention comprises a delivery system that controls the release of the agent.

In one embodiment, the at least one inhibitor of gangliosides metabolism described here above, the pharmaceutical composition or the medicament of the invention is to be administered perispinally or intra-nasally in improved delivery, either by local diffusion; by improved transport into the cerebrospinal fluid (CSF); or by direct transport into the CNS.

In one embodiment, a therapeutically effective amount of the at least one inhibitor of gangliosides metabolism described here above, the pharmaceutical composition or the medicament of the invention is administered at least once a day, twice a day, at least three times a day or at least four times a day.

In another embodiment, a therapeutically effective amount of the at least one inhibitor of gangliosides metabolism described here above, the pharmaceutical composition, medicament of the invention is administered every two, three, four, five, or six days.

In another embodiment, a therapeutically effective amount of the at least one inhibitor of gangliosides metabolism described here above, the pharmaceutical composition, medicament of the invention is administered twice a week, every week, every two weeks, or once a month.

In another embodiment, a therapeutically effective amount of the at least one inhibitor of gangliosides metabolism described here above or the pharmaceutical composition of the invention, the medicament of the invention is administered every month for a period at least 2; 3; 4; 5; 6 months or for the rest of the life of the subject.

In another embodiment, a therapeutically effective amount of the at least one inhibitor of gangliosides metabolism described here above or the pharmaceutical composition or the medicament of the invention of the invention ranges from about 1 µg to 100 g, 1 mg to 1 g, 10 mg to 500 mg.

In another embodiment, a therapeutically effective amount of the at least one inhibitor of gangliosides metabolism described here above or the pharmaceutical composition or the medicament of the invention of the invention ranges from about 10 to 100 mg, preferably 60 mg.

In another embodiment, a therapeutically effective amount of the at least one inhibitor of gangliosides metabolism described here above, the pharmaceutical composition or the medicament of the invention ranges from about 0.1 µg/kg to 1 g/kg of body weight, 0.1 mg/kg of body weight to 500 mg/kg, 10 mg/kg to 100 mg/kg of body weight.

BRIEF DESCRIPTION OF THE DRAWINGS

FIG. 1A Genomic structure of the Spg11 gene (top), the targeting vector (middle) and the targeted locus upon excision of the neomycin resistance cassette and action of the Cre-recombinase (bottom). The mutations introduced were c.6052C>T (p.Arg2018*), corresponding to c.6091C>T (p.Arg2031*) in humans, and c.6061C>T (p.Gln2021*), corresponding to c.6100 C>T (p.Arg2034*) in humans. FIG. 1B Western blot of brain protein extracts showing the absence of spatacsin in Spg11$^{-/-}$ samples and much lower levels of spastizin, encoded by Spg15. Representative image from three independent experiments. *: nonspecific band. FIG. 1C, FIG. 1D A Spg11$^{+/+}$ (C) and an Spg11−/− (D) mouse at 16 months of age. Knockout mice had an abnormal posture and kyphosis of the spine. FIG. 1E, FIG. 1F Single video frames of Spg11$^{+/+}$ (E) and Spg11$^{-/-}$ (F) mice walking freely in a straight corridor. The foot/base angle (FBA) at toe-off position is indicated by white lines. FIG. 1G FBA values recorded during a free walk. From the age of four months onwards, FBA decreased in Spg11$^{-/-}$ mice (n≥12 animals/genotype/age; Kruskal-Wallis test; * p≤0.05 and ***: p≤0.001). FIG. 1H, FIG. 1I. Gait angle sketch (H) and values recorded (I) during a forced walk on a treadmill. From the age of four months onwards, gait angle decreased in Spg11$^{-/-}$ mice (n≥12 animals/genotype/age; Kruskal-Wallis test; *: p≤0.05 and *: p≤0.001). FIG. 1J From the age of six weeks, Spg11$^{-/-}$ mice were able to stay on accelerated rotarod for a significantly shorter period of time than heterozygous and control mice (n≥12 animals/genotype/age; Kruskal-Wallis test; : p≤0.01 and *: p≤0.001). FIG. 1K, FIG. 1L NeuN and GFAP immunostaining in the primary motor cortex of Spg11$^{+/+}$ (K) and Spg11$^{-/-}$ (L) mice at 16 months of age. Scale bars: 200 µm. FIG. 1O, FIG. 1P Quantification of total GFAP-positive cells in the primary motor cortex layers I+II+III (O) and V+VI (P). Neuron loss was accompanied by marked astrogliosis (n≥10 slices/animal and n≥5 animals/genotype/age; Kruskal-Wallis test; *:p≤0.001).

FIGS. 2A-2C are a set of images showing an accumulation of autofluorescent particles colocalizing with Lamp1 in the cortical motor neurons of Spg11$^{-/-}$ mice. FIG. 2A Autofluorescent material (excitation 488 nm, emission 515-530 nm) in Spg11$^{+/+}$ and Spg11$^{-/-}$ cortical motor neurons at 6 weeks, 4 months, 8 months and 16 months of age. Knockout mice had autofluorescent deposits in their cortical motor neurons from the age of six weeks onwards. At 16 months of age, these autofluorescent materials were also present in control mice, but in smaller amounts than in knockout mice. Scale bars: 10 µm. FIG. 2B Autofluorescent materials, indicated by arrowheads in Spg11$^{-/-}$ cortical motor neurons at 8 months of age, upon excitation at 405 nm, 473 nm, 543 nm and 635 nm. Scale bars: 20 µm. FIG. 2C Lamp-1 (lysosome marker) immunostaining and autofluorescent material in Spg11$^{+/+}$ and in Spg11$^{-/-}$ cortical motor neurons from six-week-old and eight-month-old animals. Confocal microscopy images show autofluorescent particles surrounded by Lamp-1-positive staining in Spg11$^{-/-}$ neurons. Scale bars: 10 µm.

FIGS. 3A-3C are a set of graphs and images showing early changes in lysosomal function and late accumulation of p62 particles in the cortical motor neurons of Spg11$^{-/-}$ mice. FIG. 3A p62 immunostaining and autofluorescence in Spg11$^{+/+}$ and in Spg11$^{-/-}$ cortical motor neurons at 6 weeks, 8 months and 16 months of age. Confocal microscopy images show autofluorescent particles colocalizing with p62-positive staining only in the cortical motor neurons of 16-month-old Spg11$^{-/-}$ mice. Scale bars: 10 µm. FIG. 3B Western blot showing levels of LC3I, LC3-II and tubulin levels in extracts from Spg11$^{+/+}$ and Spg11$^{-/-}$ mouse cortices taken from animals of different ages. Quantification of LC3-II band intensities with normalization with respect to tubulin. The graph shows mean±SEM values. n=3 independent samples. FIG. 3C Western blot showing levels of the precursor of cathepsin D (CstDp), and the mature form of the protease (CstDm) and tubulin in extracts from Spg11$^{+/+}$ and Spg11$^{-/-}$ mouse cortices taken from animals of different ages. Quantification of mature cathepsin D band intensities normalized with respect to tubulin. The graph shows mean±SEM values. n=3 independent samples loaded twice. Kruskal-Wallis test, *:p≤0.05.

FIGS. 4A-4L are a set of graphs and images showing that spatacsin loss promotes the accumulation of undigested material in lysosomes. FIGS. 4A-4F Electron micrographs of cortical neurons from two-month-old Spg11$^{+/+}$ (A and B) or Spg11$^{-/-}$ (C-F) mice. FIG. 4B Higher magnification of the zone marked in A. FIG. 4D and FIG. 4E: Higher magnification of lipofuscin particles from the marked zone in C. The insets in D and E show the membranous and granular structures present in lipofuscin-like structures, indicated by arrowheads. FIG. 4F Electron micrographs showing the clustering of lysosomes containing undigested material around lipofuscin-like structures. Asterisks indicate structures with a low density consistent with lipid droplets. The inset in FIG. 4F shows the membrane surrounding a lipofuscin-like particle. Scale bars: 5 µm (A and C); 500 nm (B, D-F). FIG. 4G Cathepsin D immunoelectron microscopy revealed with diaminobenzidine (DAB) showing the presence of DAB precipitates in lipofuscin-like structures (arrowheads). Note the presence of DAB precipitates in a lysosome (arrow). Scale bar: 500 nm. FIG. 4H Electron microscopy images of cortical neurons in the brain of an SPG11 patient (duration of disease: 10 years; age at death: 32 years), showing the accumulation of lipofuscin (arrowheads). The patient has the typical clinical features of SPG11 and carries, in trans, the heterozygous mutations c.2358_2359delinsTT (p.Glu786_Gly787delinsAspfs*) in exon 13 and c.4868delT (p.Leu1623Tyrfs*17) in exon 28. Scale bar: 2 µm. FIGS. 4I-4L Quantification of various lysosome parameters on electron micrographs of cortical neurons from two-month-old Spg11$^{+/+}$ or Spg11$^{-/-}$ mice. Graphs show the means±SEM. n>40 cells analyzed in two independent animals for each genotype. t-test; *:p=0.041 and ***:p≤0.0001.

FIGS. 5A-5F are a set of graphs and images showing that spatacsin loss promotes the accumulation of GM2 and GM3 in cortical neurons. FIG. 5A GM2 immunostaining and autofluorescent material in Spg11$^{+/+}$ and Spg11$^{-/-}$ cortical motor neurons from six-week-old and eight-month-old animals. Confocal microscopy images showing the colocalization of autofluorescent particles with GM2-positive staining in six-week-old and eight-month-old animals. Scale bars: 10 µm. FIG. 5B Quantification of the mean (left panel) and variance (right panel) of the GM2 immunostaining intensity per neuron. The graph shows mean±SEM values. n>10 neurons quantified in 5 independent cortex slices. Kruskal-Wallis test; *: p≤0.0001. FIG. 5C GM3 immunostaining and autofluorescent material in Spg11$^{+/+}$ and Spg11$^{-/-}$ cortical motor neurons from six-week-old and eight-month-old animals. Confocal microscopy images showing the colocalization of autofluorescent particles with GM3 staining only at the age of eight months and in Spg11$^{-/-}$ neurons. Scale bars: 10 µm. FIG. 5D Quantification of the mean (left panel) and variance (right panel) of the GM3 immunostaining intensity per neuron. FIGS. 5E-5F Quantification of the mean (left panel) and variance (right panel) of the GD2 (E) and GD3 (F) immunostaining intensity per neuron. The graph shows mean±SEM values. n>10 neurons quantified in 5 independent cortex slices. Kruskal-Wallis test; :p≤0.01; ***:p≤0.0001.

FIGS. 6A-6F are a set of graphs and images showing that accumulation of GM2 and GM3 in cortical neurons contributes to neuronal death. FIG. 6A GM2 and neuronal marker 3III-tubulin immunostaining in primary cultures of Spg11$^{+/+}$ and Spg11$^{-/-}$ cortical neurons. FIG. 6B Quantification of the intensity of fluorescence of GM2 (left panel) and GM3 (right panel) immunostainings in primary cultures of Spg11$^{+/+}$ and Spg11$^{-/-}$ cortical neurons. The graph shows mean±SEM values. n>11 independent measurements with at least 200 neurons quantified in each experiment. T-test; *: p=0.03 (GM2) and p=0.0099 (GM3). C GM2 or GM3 immunostaining in cells transfected with vector expressing GFP and miRNA (arrowhead) to downregulate GM3 synthase. FIG. 6D Quantification of the intensity of fluorescence of GM2 (left panel) or GM3 (right panel) in neurons transfected with vectors expressing control miRNA or two different miRNA against GM3 synthase. n>50 neurons in two independent experiments. One way ANOVA; *: p=0.041; p=0.0028 and *: p≤0.001. FIG. 6E Quantification of neuronal death 30 hours after incubation of neurons with glutamate (200 µM) in primary cultures of Spg11$^{+/+}$ and Spg11$^{-/-}$ cortical neurons transfected with vectors expressing control miRNA or two different miRNA against GM3 synthase. n>5 experiments with at least 100 neurons quantified in each experiment. Kruskal Wallis test; **:p=0.0058; *:p=0.0123. FIG. 6F Quantification of neuronal death 30 hours after incubation of neurons with glutamate (200 µM) in primary cultures of Spg11$^{+/+}$ or Spg11$^{-/-}$ cortical neurons treated with Miglustat. n>8 experiments with at least 100 neurons quantified in each experiment. Kruskal Wallis test; *:p=0.0188; ***:p=0.0002.

FIG. 7A Immunostaining of iPS cells with pluripotency markers. FIG. 7B Immunostaining of neuronal cultures derived from iPS cell lines with antibodies against the neuronal marker 3-III tubulin and the glutamatergic marker v-Glut1. Scale bar: 10 µm. FIG. 7C GM2 and Lamp1 immunostaining of neurons derived from iPS cells. Scale bar: 5 µm. FIG. 7D Quantification of the relative amount of GM2 and GM3 in lysosomes of neurons derived from iPS cells. n>30 neurons, in three independent experiments. T-test; : p=0.0042 (GM2); * p=0.0002 (GM3). FIG. 7E Quantification of the proportion of GM2 (left panel) or GM3 (right panel) immunostaining colocalized with Lamp1 staining. n>30 neurons, in three independent experiments. t-test, ***:p≤0.0001.

FIGS. 8A-8C are a set of graphs and images showing that spg11l knockout causes neuronal death in the cerebellum.

FIG. 8A, FIG. 8B Cerebellar sections immunostained for GFAP (astrocyte marker), Calbindin (Purkinje cell marker), and Hoechst-33258 (blue, nucleus marker) revealed a severe loss of Purkinje cells in knockout mice (B) compared to the control mice (B). Scale bars: 100 µm. PCL: Purkinje Cell Layer. FIG. 8C The number of Purkinje cells was reduced from eight months of age in knockout mice (n≥5 slices per animal and n≥5 animals/genotype/age; Kruskal-Wallis test; ***:p<0.001).

FIGS. 9A-9C are a set of images showing an accumulation of autofluorescent particles colocalizing with Lamp1 in cerebellar Purkinje cells of Spg11 knockout mice. FIG. 9A Autofluorescent material (excitation 488 nm, emission 515-530 nm) in Spg11$^{+/+}$ and in Spg11$^{-/-}$ Purkinje cells from six-week-old, four-month-old, eight-month-old and sixteen-month old animals. Knockout mice already displayed autofluorescent deposits in Purkinje cells from the age of six weeks onwards. Scale bars: 10 min FIG. 9B. Lamp-1 (Lysosome marker) immunostaining compared to autofluorescent material in Spg11$^{+/+}$ and in Spg11$^{-/-}$ Purkinje cells from six-week-old and eight-month-old animals. Confocal microscopy images showed autofluorescent particles surrounded by Lamp-1-positive staining in knockout animals. Scale bars: 10 µm. FIG. 9C. p62 immunostaining and autofluorescence in Spg11$^{+/+}$ and in Spg11$^{-/-}$ Purkinje cells at 6 weeks and 8 months of age. Confocal microscopy images show autofluorescent particles colocalizing with p62-positive staining only in the Purkinje cells of 8-month-old Spg11$^{-/-}$ mice. Scale bars: 10 µm.

FIGS. 10A-10D are a set of graphs and images showing that spatacsin loss promotes the accumulation of GM2 and GM3 in cerebellar Purkinje cells. FIG. 10A GM2 immunostaining and autofluorescent material in Spg11$^{+/+}$ and Spg11$^{-/-}$ Purkinje cells from six-week-old and eight-month-old animals. Confocal microscopy images showing the colocalization of autofluorescent particles with GM2-positive staining in eight-month-old animals. Scale bars: 10 µm. FIG. 10B Quantification of the mean (left panel) and variance (right panel) of the GM2 immunostaining intensity per Purkinje cell. The graph shows mean±SEM values. n>10 Purkinje cells quantified in 5 independent cerebellar slices. Kruskal-Wallis test; *:p≤0.05; :p≤0.01; *:p≤0.0001. FIG. 10C GM3 immunostaining and autofluorescent material in Spg11$^{+/+}$ and Spg11$^{-/-}$ Purkinje cells from six-week-old and eight-month-old animals. Confocal microscopy images showing the colocalization of autofluorescent particles with GM3 staining only at the age of eight months and in Spg11$^{-/-}$ neurons. Scale bars: 10 µm. FIG. 10D Quantification of the mean (left panel) and variance (right panel) of the GM3 immunostaining intensity per Purkinje cell. The graph shows mean±SEM values. n>10 Purkinje cells quantified in 5 independent cerebellar slices. Kruskal-Wallis test; ***:p≤0.0001.

FIGS. 11A-11F are a set of graphs and images showing that Spatacsin loss promotes lysosomal accumulation of gangliosides in neurons derived from SPG11 patients. FIG. 11A Immunostaining of brain organoids differentiated for 90 days in vitro with antibody against the progenitor marker Pax6 and the neuron-specific marker βIII-tubulin. Note that neuronal cells are concentrated at the periphery of the organoids. Scale bar: 50 µm FIG. 11B GM2 and Lamp1 immunostaining in the neuronal layer of organoids derived from healthy subjects or SPG11 patients. βIII-tubulin shows the neuronal identity of the cells that were analyzed. Confocal microscopy images showing the accumulation of GM2-positive staining in lysosomes labelled by Lamp1 staining of organoids derived from SPG11 patients (arrowheads). Scale bar: 10 µm FIGS. 11C-11F Quantification of the mean (left panel) and variance (right panel) of the GM2 (C), GM3 (D), GD2 (E), and GD3 (F) immunostaining intensity per neuron. The graph shows mean±SEM values. N>10 neurons quantified in five independent cortex slices. One-way ANOVA; ***p≤0.001.

FIGS. 12A-E are a set of graphs and images showing that Spatacsin loss induces lysosomal accumulation of gangliosides in primary cultures of cortical neurons. FIG. 12A GM2 and Lamp1 immunostaining of Spg11$^{+/+}$ and Spg11$^{-/-}$ neurons cultured for six days in vitro. Confocal microscopy images showing the accumulation of GM2-positive staining of lysosomes labeled by Lamp1 staining. Scale bar: 10 µm FIGS. 12B-12E Quantification of the proportion of GM2 (B), GM3 (C), GD2 (D), and GD3 (E) staining that is localized in lysosomes. The graphs show the mean±SEM values. N>50 neurons quantified in three independent neuron preparations. T-test; p≤0.01, * p≤0.001.

FIGS. 13A-13I is a set of graphs and images showing that GM2 accumulation in lysosomes promotes the formation of autolysosomes. FIG. 13A Proportion of lysosomes stained with Lamp1 that were also positive for p62 in Spg11$^{+/+}$ and Spg11$^{-/-}$ neurons after three and six days in vitro. N>50 neurons quantified in at least four independent neuron preparations. Two-way ANOVA; *p=0.04; *p<0.001. FIG. 13B Immunostaining of Spg11$^{-/-}$ neurons with GM2 antibody, lysosomal marker Lamp1, and the autophagy marker p62. Arrowheads indicate autolysosomes, which were positive for GM2 staining. Scale bar: 10 µm. FIG. 13C Proportion of lysosomes stained with Lamp1 that were also positive for both p62 and GM2 in Spg11$^{+/+}$ and Spg11$^{-/-}$ neurons after three and six days in vitro. N>50 neurons quantified in at least four independent neuron preparations. Two-way ANOVA; *p<0.001. FIG. 13D Quantification of the fluorescence intensity of GM2 immunostaining of primary cultures of Spg11$^{+/+}$ and Spg11$^{-/-}$ cortical neurons cultured for six days in vitro with various concentrations of miglustat. N>3 measurements with at least 200 neurons quantified in each experiment. FIG. 13E Effect of miglustat treatment (100 µM) on the proportion of lysosomes stained with Lamp1 that were also positive for p62 in Spg11$^{+/+}$ and Spg11$^{-/-}$ neurons after six days in vitro. N>50 neurons quantified in at least four independent neuron preparations. Two-way ANOVA; *p<0.001. FIG. 13F Effect of the downregulation of GM3 synthase with two independent miRNAs (GM3S-1 and GM3S-2) on the proportion of lysosomes stained with Lamp1 that were also positive for p62 in control neurons after six days in vitro. N>20 neurons quantified in at least three independent neuron preparations. Two-way ANOVA; *p<0.001. FIG. 13G Effect of Neu1 downregulation on staining with antibodies directed against GM2 and Lamp1. Note the increase in the number of lysosomes labeled with GM2 after downregulation of Neu1. Scale Bar: 10 µm. FIG. 13H Quantification of the proportion of GM2 staining that is localized to lysosomes in neurons transfected with vectors expressing two independent miRNAs directed against Neu1. N>20 neurons quantified in three independent neuron preparations. One-way ANOVA; *p=0.02; p=0.0017. FIG. 13I Effect of Neu1 downregulation with two independent miRNAs (Neu1-1 and Neu1-2) on the proportion of lysosomes stained with Lamp1 that were also positive for p62 in control neurons after six days in vitro. N>20 neurons quantified in three independent neuron preparations. One-way ANOVA; *p<0.001. In all, the graph shows the mean±SEM values.

FIGS. 14A-14B are a set of graphs and images showing that treatments modulating GM2 levels modulate neuronal death triggered by glutamate. FIG. 14A Quantification of neuronal death 30 hours after incubation of neurons with glutamate (200 µM) in primary cultures of control neurons transfected with vectors that downregulate Neu1 with two independent miRNAs (Neu1-1 and Neu1-2). N>3 independent experiments. One-way ANOVA; *p=0.016; p=0.003. FIG. 14B Western blot analysis of p62 levels in Spg11$^{+/+}$ and Spg11$^{-/-}$ cortical neurons treated or not with miglustat (100 µM). Neurons were incubated with glutamate (200 µM) for 24 hours. Graph showing the quantification of the relative amount of p62 normalized to tubulin in Spg11$^{+/+}$ and Spg11$^{-/-}$ cortical neurons treated with miglustat or glutamate. N>5 independent experiments. One-way ANOVA; p<0.01. in all, the graph shows the mean: SEM values.

FIGS. 15A-15B are a set of images showing the purification of lysosome-enriched fractions from Spg11$^{+/+}$ and Spg11$^{-/-}$ mouse brain. FIG. 15A Scheme showing the procedure used to purify fractions enriched in lysosomes. FIG. 15B Western blot analysis of whole brain lysate, fractions S20, P20, and the lysosome-enriched fraction obtained from Spg11$^{+/+}$ and Spg11$^{-/-}$ mouse brain.

FIGS. 17A-17C are a set of graphs and images showing that downregulation of GM3 synthase decreases ganglioside levels in cultured neurons. FIG. 17A qRT-PCR showing the decrease in GM3 synthase mRNA in mouse NIH-3T3 cells transfected with the vectors expressing two different miRNAs targeting the GM3 synthase or a control vector. N=3. Kruskal-Wallis test, *p=0.048; **p=0.003. FIG. 17B GM2 immunostaining of cells transfected with vector expressing GFP and miRNA to downregulate GM3 synthase. The arrow indicates a cell transfected with miRNA against GM3 synthase, showing weak GM2 staining. Arrowheads indicate non-transfected cells. Scale bar: 10 µm. FIG. 17C Quantification of the fluorescence intensity of GM2 in neurons transfected with vectors expressing control miRNA or two different miRNAs against GM3 synthase. N>50 neurons in two independent experiments. One-way ANOVA, *p=0.03, **p=0.001.

FIGS. 19A-19D are a set of graphs and images showing that Spg11 knockout mice develop a cognitive and memory deficit. FIGS. 19A-19B The Y-maze principle (A) and spontaneous alternation values (B). Knockout mice did not show a preference between the visited and the unknown arm of the maze from four months of age (n=12 animals/genotype/age; Kruskal-Wallis test; *p≤0.001). This altered cognitive behavior underlines a spatial learning or a memory deficit FIGS. 19C-19D Fear conditioning. Percentage of time spent in a frozen posture on day 1 before and after electrical shocks (C). There was no obvious learning deficit during the conditioning of the mice at any age. Percentage of time spent in a frozen posture on day 2, without any electrical shocks, after conditioning (D). Although the task was learned, knockout mice spent less time in a frozen position from eight months of age, indicating a cognitive and memory deficit (n≥10 animals/genotype/age; Kruskal-Wallis test; p≤0.01 and ***p≤0.001).

FIGS. 20A-20E are a set of graphs and images showing that miglustat treatment prevents motor dysfunction in zebrafish zspg11 model. FIG. 20A. Phenotype of morphants that were non-injected or injected with 1.2 pmol zspg11spl or 1.2 pmol mismatch (mm) morpholino. 48 hours post fertilization, morphants were classified as normal phenotype, slowly swimming, paralyzed or curly morphants. Injection of zspg11spl morpholino leads a large proportion of paralyzed or slowly swimming phenotypes. Treatment with miglustat decreased the proportion of paralyzed morphants. N>100 morphants analyzed in each groups. Chi Square test * p<0.0001. FIG. 20B-20C. Tracking (B) and quantification of distance travelled (C) by larvae following a touch-evoked escape response. Injection of zspg11spl morpholino impaired the swimming of morphants, which was corrected when treated by miglustat. N=12 morphants analyzed in each condition. One-way ANOVA * p<0.001. FIGS. 20D-20E. Immunostaining (D) and quantification (E) of GM2 immunostaining in the telencephalon of morphants injected with 1.2 pmol zspg11spl or 1.2 pmol mismatch (mm) morpholino. Injection of zspg11spl morpholino increased the mean and variance of GM2 immunostaining intensity. This phenotype was corrected when morphants were treated with miglustat. N>6 morphants analyzed in each condition. One-way ANOVA *** p<0.001

EXAMPLES

The present invention is further illustrated by the following examples.

Example 1: Spg11-Knockout Mice Develop an Early-Onset Motor Deficit, Before the Occurrence of Neurodegeneration A Spg11-knockout mouse model was generated, in which we analyzed behavior, neuronal death and cellular changes during aging. The Spg11-knockout mice presented motor dysfunction from the age of six weeks, and neuronal death was first detected in the cerebral cortex and cerebellum at the age of eight months, recapitulating the main features of the human pathology. Neuronal death was preceded by the early and progressive accumulation of lipids, including the GM2 and GM3 gangliosides, in lysosomes. Accumulation of lipids in lysosomes was also observed in cortical neurons in the brain of SPG11 patients. GM2 and GM3 also accumulated in lysosomes in neurons derived from hiPSC obtained from skin biopsies of a SPG11 patient, confirming that these lipids contribute to the pathology. Using cultured neurons, we decreased gangliosides levels either by downregulating a key enzyme in their biosynthesis, or by treating them with Miglustat, a drug preventing gangliosides biosynthesis and approved for treatment of Gaucher Type I and Niemann Pick type C disease. Decreasing gangliosides levels prevented neuronal death induced by glutamate.

Figure 1A:
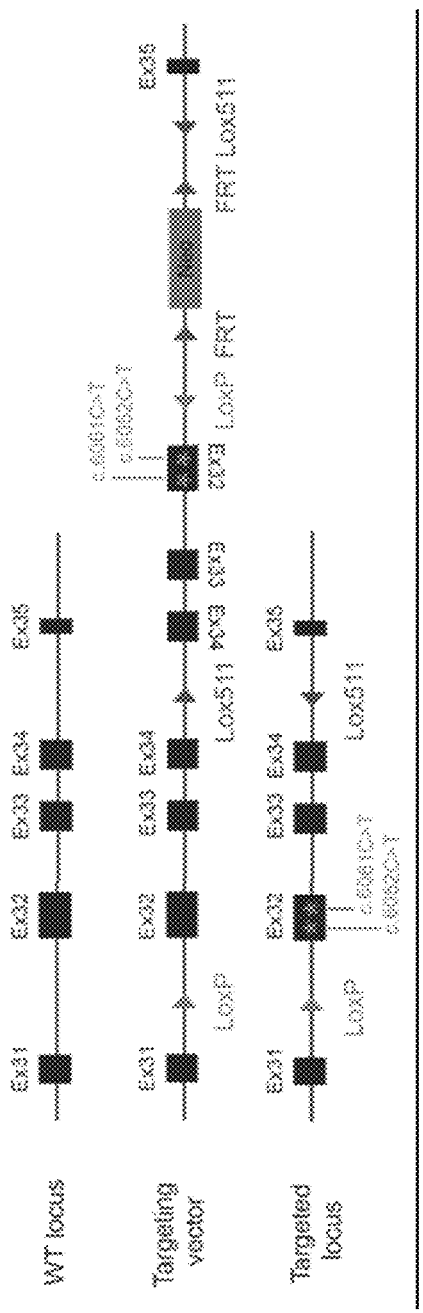
FIGS. 1A-1P are a set of graphs and images showing that spg11 knockout cause an early motor deficit in mice, before neuron loss.

We investigated the physiopathological role of spatacsin in neurodegeneration, by invalidating Spg11 expression in mice. We inserted two successive stop codons into exon 32 of the gene (FIG. 1A), mimicking the most frequent mutation of this exon that is observed in SPG11 patients. We used western blotting to check that the disruption of the Spg11 gene resulted in spatacsin depletion (FIG. 1B). When heterozygous mice (Spg11$^{+/-}$) were mated, knockout mice were generated in the expected Mendelian ratio and were viable. They developed normally, were fertile and had survival rates similar to those of their wild-type and heterozygous littermates. Spg11$^{-/-}$ mice had no dysmorphic features or abnormalities up to the age of eight months compared to control littermates. However, at 16 months, the age at which we stopped the study for ethical reasons, most of the knockout mice had an abnormal posture with spread hind limbs, lower pelvic elevation and pronounced kyphosis of the thoracic spine (FIGS. 1C and D).

We first evaluated the consequences of spatacsin invalidation for motor function and the time course of neuronal death, focusing on motor functions controlled by neurons in the cortex and cerebellum. From the age of four months onwards, Spg11$^{-/-}$ mice displayed a progressive gait disorder, which was quantified by measuring the foot-base angle (FBA) of the hind paws in the toe-off position (FIGS. 1E, F and G). Similarly, recording the walking of mice on a treadmill at moderate speed (10 cm·s$^{-1}$) showed that gait angle, the position of the hind paws relative to the axis of the body, was significantly larger in knockout mice than in control mice, from the age of four months onwards (FIGS. 1H and I). With age, Spg11$^{-/-}$ mice displayed a spreading of the hind limbs and began to drag their feet slightly during a forced walk. The motor deficit was even more marked in the rotarod test, a forced run paradigm. Spg11$^{-/-}$ mice displayed the first signs of motor impairment and ataxic gait as early as six weeks of age in this test. The knockout mice remained on an accelerating rotarod for significantly less time than heterozygous and control mice (FIG. 1J), and this motor deficit worsened with time. Motor performance decreased with age in controls and heterozygous mice, but was systematically better in these mice than in knockout mice.

Figure 1M:
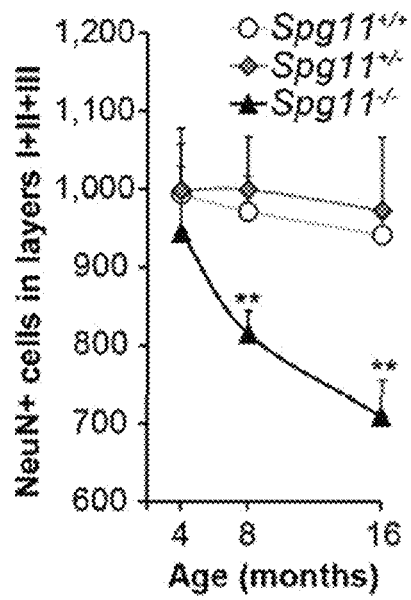
FIG. 1M, FIG. 1N Quantification of total NeuN-positive cells in the primary motor cortex layers I+II+III (M) and V+VI (N). The immunostaining revealed a significant decrease in the numbers of neurons from layers I-VI of the motor cortex in knockout mice, from eight months of age onwards (n≥10 slices/animal and n≥5 animals/genotype/age; Kruskal-Wallis test; : p≤0.01 and *: p≤0.001).
Figure 1N:
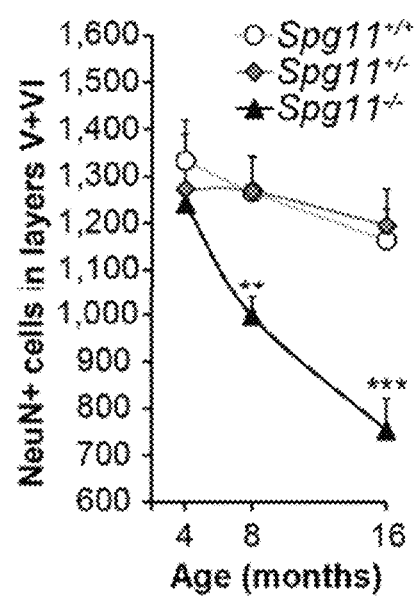
Figure 1O:
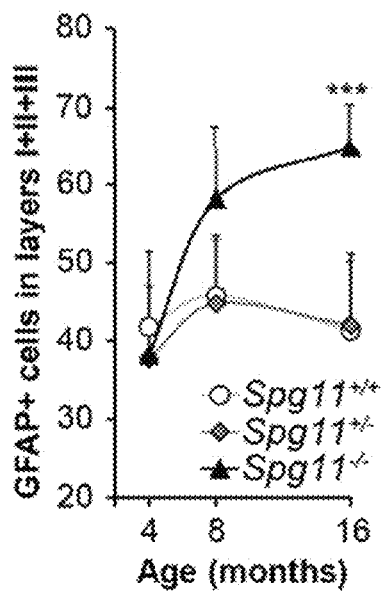
Figure 1P:
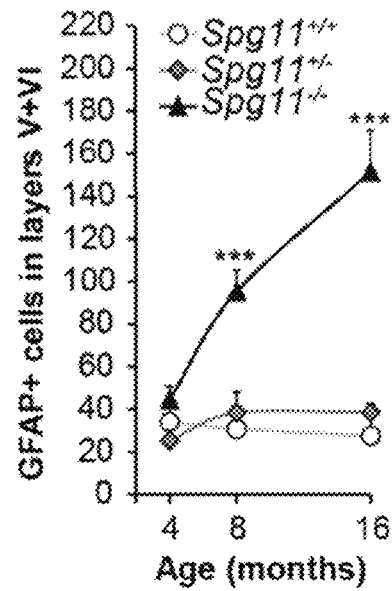
Figure 8C:
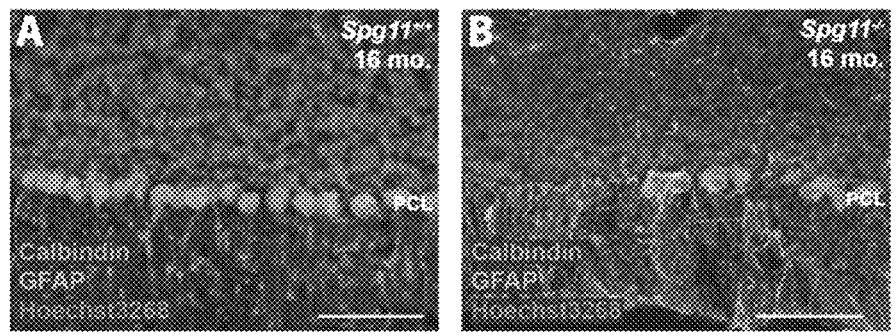
Figure 8C:
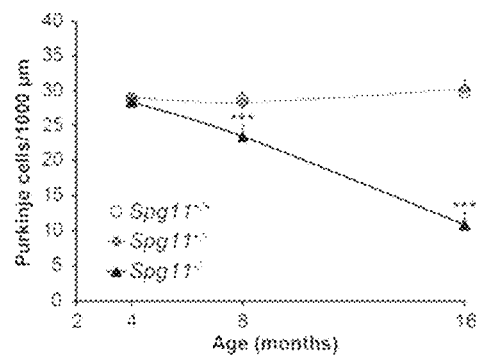

We investigated whether the behavioral phenotypes resulted from neurodegeneration, by analyzing the cortex and cerebellum in Spg11$^{-/-}$ mice. At various ages, we determined the total number of cortical neurons in the primary motor cortex by immunostaining for NeuN (FIGS. 1K and L). On coronal sections of the brain, the number of neurons in the cortical layers was unaffected in four-month-old knockout mice, but were significantly smaller than those in Spg11$^{+/+}$ mice from the age of eight months onwards (FIGS. 1M and N). Neuronal degeneration worsened with time and was accompanied by astrogliosis, as shown by the increase in GFAP-positive cells (FIGS. 1L, O and P). In the cerebellum, the number of Purkinje cells, labeled by Calbindin-immunostaining, was greatly reduced in the cerebellum of knockout mice compared to control mice from the age of eight months (FIG. 8C). Furthermore, the degeneration of Purkinje cells was accompanied by marked astrogliosis, revealed by GFAP-immunostaining, as in the primary motor cortex (FIG. 8A-B). Thus, motor function was impaired before the occurrence of overt neuronal death, suggesting the presence of early neuronal dysfunction.

Example 2: Spatacsin Loss Leads to Early Lysosomal Dysfunction in Neurons

Figure 2A:
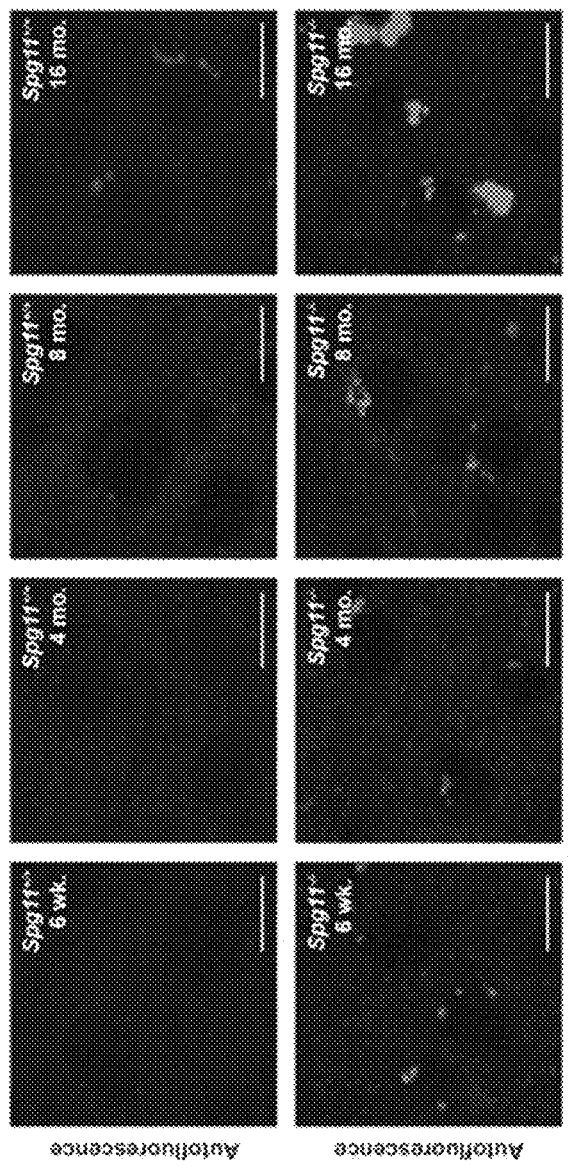
Figure 3A:
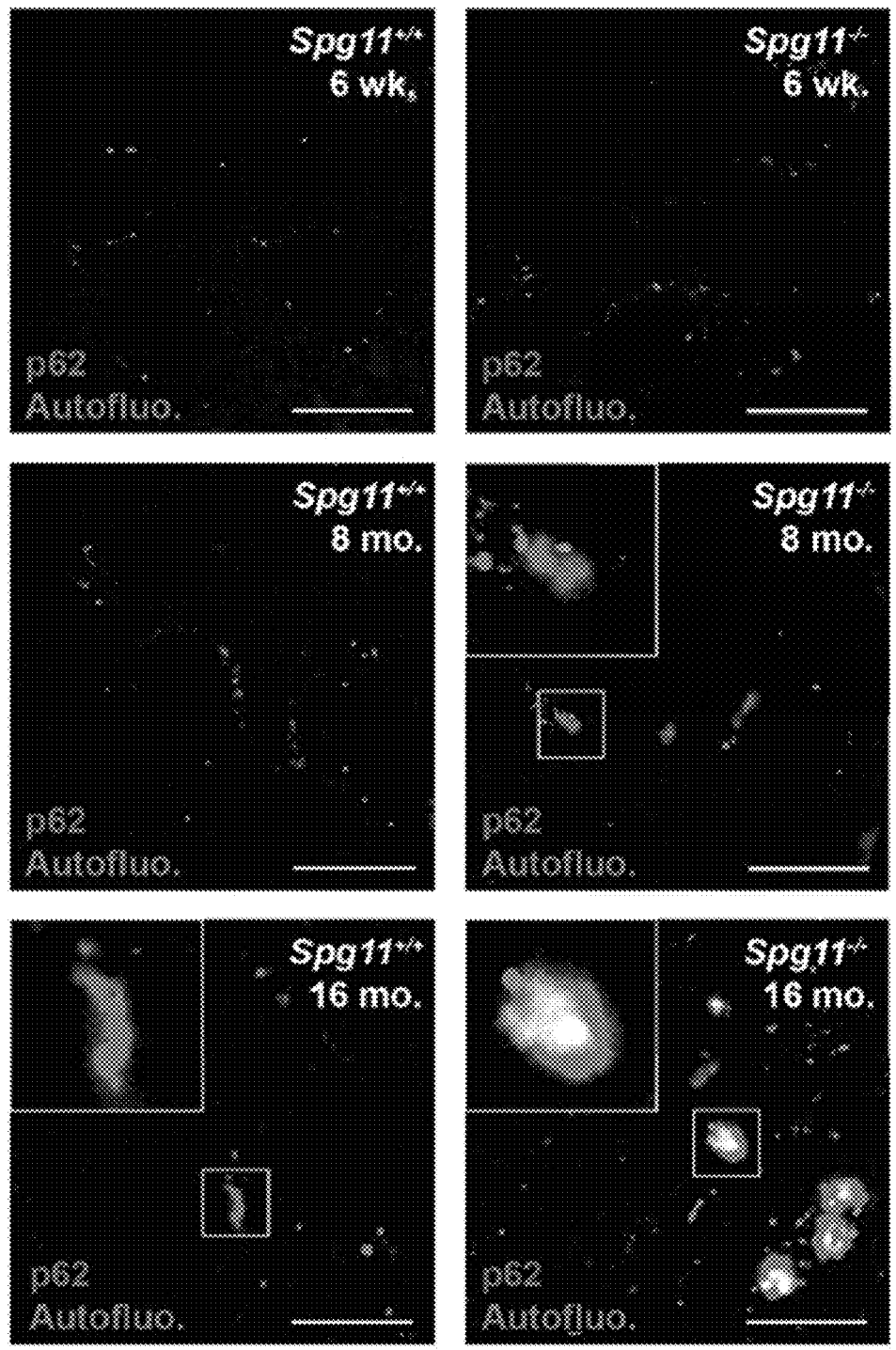
Figure 9A:
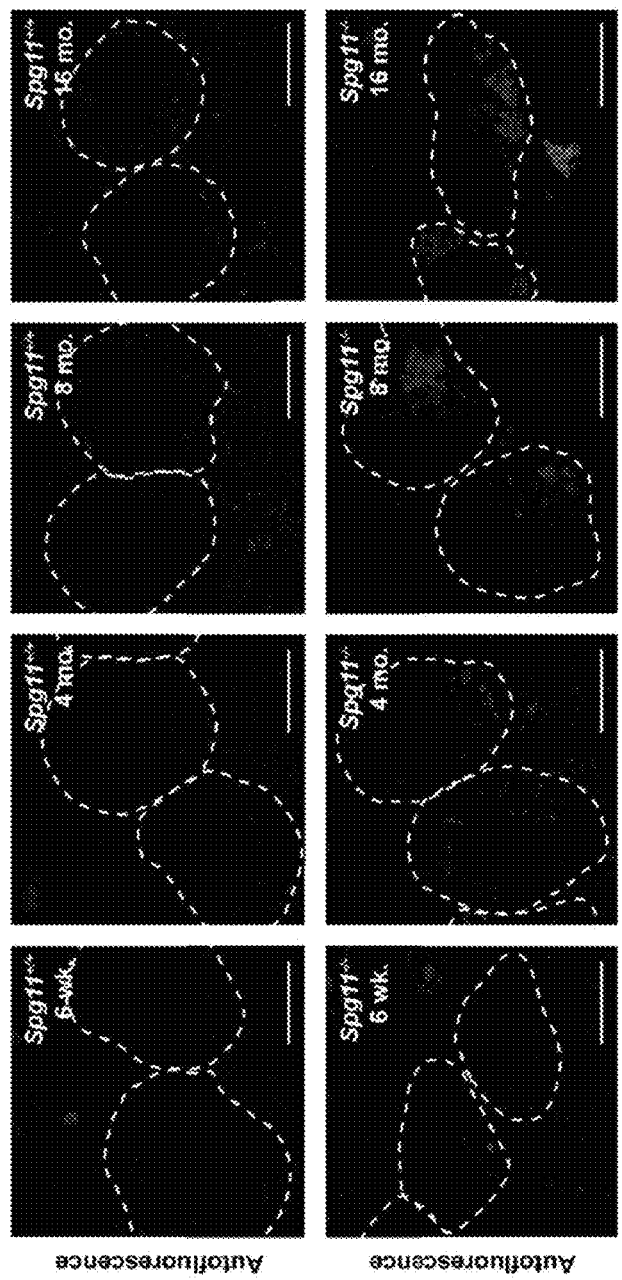
Figure 12C:
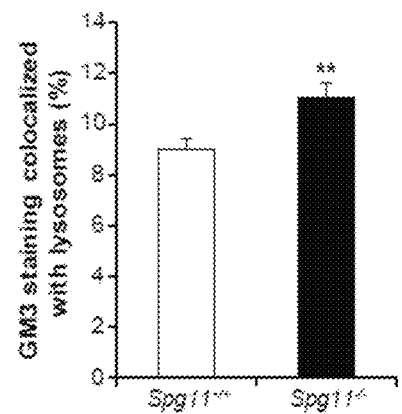
Figure 12D:
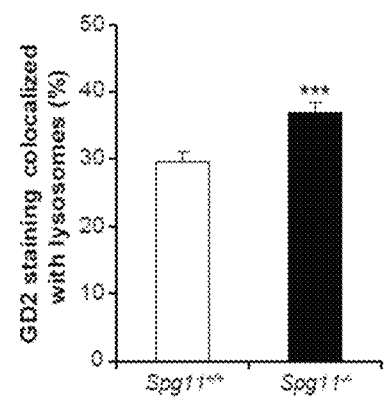
Figure 12E:
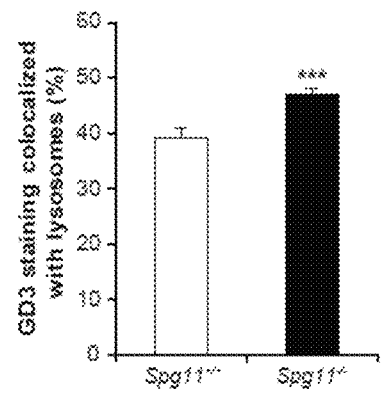

Autofluorescent intracellular material accumulated in the neurons of the cerebral cortex in Spg11$^{-/-}$ mice. This accumulation began at the age of six weeks in knockout mice, whereas large autofluorescent particles were not detected until the age of 16 months in control mice. At this stage, deposits were more frequent and larger in the motor neurons of knockout mice (FIG. 2A). Autofluorescence was not detected upon excitation at 635 nm (FIG. 2B), so it was possible to analyze its colocalization with various markers. Lamp1 immunoreactivity surrounded the autofluorescent aggregates (FIG. 2C), suggesting that the loss of spatacsin altered lysosomal function. Lysosomes play a key role in autophagosome degradation, and lysosomal dysfunction is thought to lead to the accumulation of autophagolysosomes. We therefore investigated whether the autofluorescent aggregates colocalized with p62, a marker of autophagy substrates. The colocalization of p62 with autofluorescent aggregates was observed only in Spg11$^{-/-}$ mice at 16 months of age (FIG. 3A). In six week- and eight-month-old Spg11$^{-/-}$ animals and in 16-month-old Spg11$^{+/+}$ mice, p62 was not associated with autofluorescent aggregates. Similar autofluorescent aggregates surrounded by Lamp1 immunostaining were observed in Purkinje cells in the cerebellum of Spg11$^{-/-}$ mice (FIGS. 9A and B). The autophagy marker p62 also colocalized with the autofluorescent aggregates in Purkinje cells of Spg11$^{-/-}$ mice from the age of 8 months (FIG. 9C). These data suggest that autophagic substrates accumulate in lysosomal structures in the cerebral and cerebellar cortex at late stages of the disease in Spg11$^{-/-}$ mice.

We further investigated changes in autophagy or lysosomal dysfunction, by carrying out western blotting to determine the levels of LC3-II, the lipidated form of LC3 recruited to autophagosomes, and cathepsin D, a lysosomal protease. LC3-II levels were similar in control and knockout mice, at all ages (FIG. 3B). By contrast, the levels of mature cathepsin D, the active form of the lysosomal protease, were significantly higher in the cortex of young, 6-week- and 4-month-old Spg11$^{-/-}$ mice than in controls. Mature cathepsin D levels increased with age, so the difference between genotypes was no longer evident at the ages of eight and 16 months (FIG. 3C). Thus, spatacsin loss led to an early change in lysosomal function before the accumulation of the p62 autophagic marker that was only detected at a late stage of the disease.

Figure 4I:
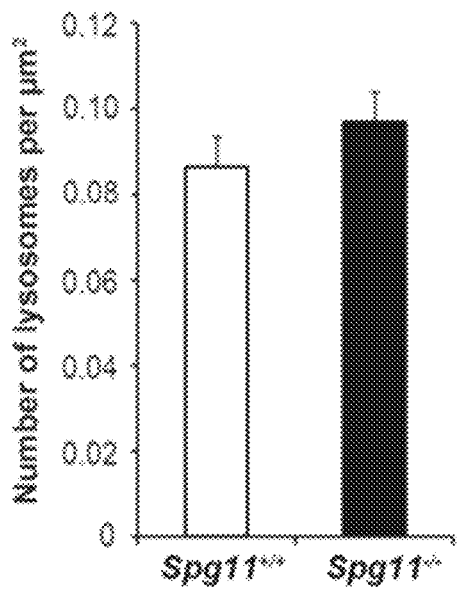
Figure 4J:
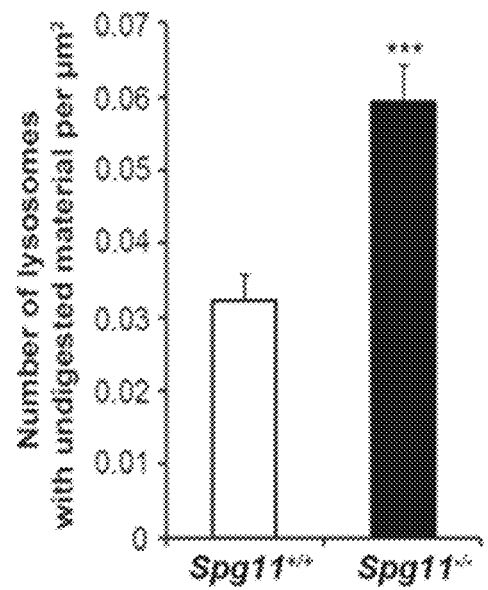
Figure 4K:
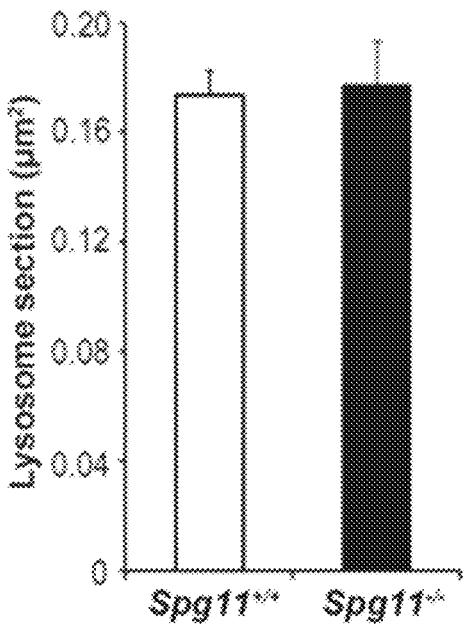
Figure 4L:
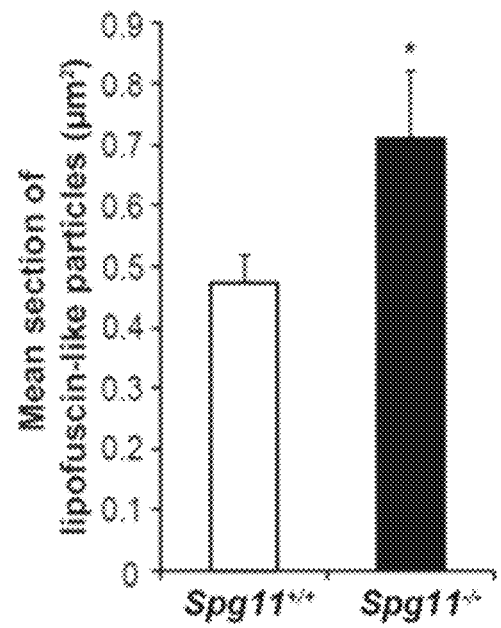

Example 3: Spatacsin Loss Promotes Lipid Accumulation in Lysosomes in Mouse and Human Brain We evaluated the consequences of spatacsin invalidation for lysosome dysfunction at early stages, by using electron microscopy to analyze cortical neurons at the age of two months (FIG. 4). The mean density and surface area of lysosomes did not differ between genotypes (FIGS. 4I and K). However, the number of organelles containing undigested material was significantly higher in Spg11$^{-/-}$ (FIGS. 4C-F and J) than in control neurons (FIG. 4A-B). Some of these lysosome particles also contained granular and membranous material in addition to lipid droplets and were reminiscent of lipofuscin-like structures (FIGS. 4D, E and F). We also observed a clustering of lysosomes containing undigested material, together with larger lipofuscin-like structures containing lipid droplets, in the neuronal soma (FIG. 4F). These structures were positive for cathepsin D, suggesting a lysosomal origin (FIG. 4G). The lipofuscin-like structures were already significantly larger in Spg11$^{-/-}$ cortical neurons than in control neurons, at the age of two months (FIG. 4L). Similar structures were observed in a large number in cortical neurons in the brain of an SPG11 patient (Denora et al, Brain. 2016 June; 139(Pt 6):1723-34) carrying two truncating heterozygous mutations in trans (FIG. 4H), suggesting that they contribute to the neuropathological process. These data suggest that an absence of spatacsin results in lysosomal dysfunction in mouse cortical neurons in animals as young as two months old, long before the occurrence of neuronal death. The significant increase in lipid- and membrane-containing structures in Spg11$^{-/-}$ neurons suggests that lipid clearance by lysosomes may be impaired.

Example 4: Spatacsin Loss Promotes the Progressive Accumulation of GM2, GM3, GD2 and GD3 Gangliosides We investigated the nature of the lipids accumulating in the cerebral cortex of Spg11$^{-/-}$ mice by performing a lipidomic analysis at an early stage of the disease. Lipids were extracted from the cortex of six-week-old mice and analyzed by liquid chromatography-high-resolution mass spectrometry. Amongst the various classes of lipids, the levels of only two species, GM2 and GM3 gangliosides, were significantly higher in the Spg11$^{-/-}$ mouse cortex than in control mouse cortex (Table 1; p-value of 0.08 for both lipids, n=3).

The identity of these lipids was verified by tandem mass spectrometry experiments. We therefore assessed the accumulation of these compounds in the cortical neurons of Spg11$^{-/-}$ brains using specific antibodies directed against the lipid species. Immunostaining showed that GM2 colocalized with autofluorescent lysosomes in knockout mice, from the age of six weeks, whereas it had a punctate distribution in neurons of control mice. Quantification of the fluorescence intensity showed that GM2 levels were higher in Spg11$^{-/-}$ than in control neurons in cortex at all ages (FIG. 5B). Interestingly, quantification of the variance of the fluorescence intensity, which is an indication of non-homogenous distribution of the staining, strongly increased with age in knockout tissues (FIG. 5B). Accordingly, GM2 accumulated in all autofluorescent aggregates in knockout mice. This accumulation increased with age, as did the size of the autofluorescent lysosomes (FIG. 5A). GM3 staining was punctate and cytoplasmic in control and Spg11$^{-/-}$ cortical neurons from six-week-old animals, but was stronger in Spg11$^{-/-}$ animals (FIGS. 5C and D). Quantification of the variance of the fluorescence intensity also indicated a non-homogenous staining of GM3 in knockout animals (FIG. 5D). Indeed, GM3 accumulated in the autofluorescent lysosomes in the cortex of Spg11$^{-/-}$ mice, from the age of six

TABLE 1

Relative amounts of different classes of lipids in cortex of 6-week old Spg11$^{+/+}$ and Spg11$^{-/-}$ mice. Arbitrary units.

|  | Spg11$^{+/+}$ | Spg11$^{-/-}$ | Fold change |
|---|---|---|---|
| Fatty Acyls |  |  |  |
| Free fatty acids (FA) | 4.77 ± 0.08 | 4.18 ± 0.56 | 0.88 |
| Glycerolipids |  |  |  |
| Monocylglycerols (MG) | 4.05 ± 0.06 | 4.18 ± 0.20 | 1.03 |
| Diacylglycerols (DG) | 103.99 ± 2.33 | 100.13 ± 2.66 | 0.96 |
| Triacylglycerols (TG) | 258.08 ± 13.70 | 267.64 ± 12.17 | 1.04 |
| Cardiolipines (CL) | 14.08 ± 0.76 | 13.36 ± 0.35 | 0.95 |
| Glycerophospholipids |  |  |  |
| Lyso-Glycerophosphocholines (LPC) | 115.45 ± 4.39 | 121.68 ± 14.62 | 1.05 |
| Lyso-Glycerophosphoethanolamines (LPE) | 11.19 ± 0.88 | 11.31 ± 0.62 | 1.01 |
| Lyso-Glycerophoshoinositols (LPI) | 5.03 ± 0.20 | 5.40 ± 0.35 | 1.07 |
| Lyso-Glycerophosphoserines (LPS) | 4.72 ± 0.51 | 4.71 ± 0.77 | 1.00 |
| Glycerophosphocholines (PC) | 16032.99 ± 248.62 | 14787.83 ± 437.22 | 0.92 |
| Glycerophosphoethanolamines (PE) | 1414.49 ± 39.95 | 1372.83 ± 102.54 | 0.97 |
| Glycerophosphoglycerols (PG) | 26.04 ± 1.06 | 26.18 ± 1.86 | 1.01 |
| Glycerophoshoinositols (PI) | 206.66 ± 7.79 | 209.01 ± 14.42 | 1.01 |
| Glycerophosphoserines (PS) | 184.55 ± 3.91 | 175.11 ± 19.02 | 0.95 |
| Sphingolipids |  |  |  |
| Ceramides | 93.92 ± 9.17 | 94.04 ± 11.81 | 1.00 |
| Hexosylceramides | 132.73 ± 21.34 | 96.99 ± 15.27 | 0.73 |
| Gangliosides GM1 | 11.70 ± 0.29 | 11.15 ± 1.13 | 0.95 |
| Gangliosides GM2 | 0.17 ± 0.05 | 0.39 ± 0.02* | 2.26 |
| Gangliosides GM3 | 0.55 ± 0.03 | 0.82 ± 0.05* | 1.49 |
| Gangliosides GD1 | 76.79 ± 7.47 | 80.06 ± 3.40 | 1.04 |
| Sphingomyelins | 424.73 ± 14.74 | 432.38 ± 37.48 | 1.02 |
| Sulfoglycosphingolipids | 90.72 ± 14.57 | 75.89 ± 17.92 | 0.84 |
| Sterol Lipids |  |  |  |
| Steryl esters | 1.64 ± 0.12 | 1.62 ± 0.07 | 0.99 |
| Cholesterol | 32.47 ± 0.48 | 31.10 ± 0.67 | 0.96 |

*p = 0.08, Mann-Whitney's test (n = 3).

weeks onwards. (FIG. 5C). Similar patterns of GM2 and GM3 accumulation were observed in the Purkinje cells of Spg11$^{-/-}$ mice (FIG. 10A-D).

Our lipidomic analysis was performed on the whole cortex. It is thus possible that other lipids may accumulate in lysosomes despite the absence of a global change in their levels. It is also possible that some lipids were not detected because of (i) their low level in total lipid extracts and/or (ii) ion suppression effects due to the presence of several lipid classes, including highly intense phospholipids. Therefore, we purified fractions enriched in lysosomes from the brains of Spg11$^{+/+}$ and Spg11$^{-/-}$ mice (FIGS. 15A-B), and extracted lipids using the Folsch procedure (Folch et al., J Biol Chem 1957, 226, 497). Briefly, brain tissue was homogenized with a 2:1 chloroform-methanol mixture and washed by addition of 0.2 volumes of water. The resulting mixture separates into two phases. Lipidomic analysis was performed on the Folsch upper phase, which contains gangliosides. The levels of gangliosides GM2, GM3, GD2, and GD3 were markedly higher in lysosomal fractions obtained from Spg11$^{-/-}$ mouse brains than those of control brains (Table 2). We confirmed the enrichment of these gangliosides in lysosomes by immunostaining with specific antibodies. The lipids GM3, GD2, and GD3 were colocalized with lysosomes, as GM2 was. Quantification of fluorescence intensity showed that the levels of the four lipids species increased with age and were higher in Spg11$^{-/-}$ mouse brains than control brains (FIGS. 5B, D, E and F). Quantification of the variance of the fluorescence intensity increased with age in knockout tissues, consistent with their accumulation in large lysosomes. The levels of complex gangliosides (GM1, GD1, and GT1) were slightly, but not significantly higher in the lysosome-enriched fractions (Table 2). Accordingly, there was no difference in the localization of GM1 between Spg11$^{+/+}$ and Spg11$^{-/-}$ mouse brain as assessed by immunostaining (data not shown).

TABLE 2

Relative amounts of various classes of gangliosides in lysosome-enriched fractions obtained from the brains of eight-month-old Spg11$^{+/+}$ and Spg11$^{-/-}$ mice. Arbitrary units.

| | Spg11$^{+/+}$ | Spg11$^{-/-}$ | Fold change |
|---|---|---|---|
| GM3 | | | |
| GM3 (d18:1/18:1) | 14.2 ± 3.1 | 42.3 ± 5.3 * | 2.98 |
| GM3 (d18:1/18:0) | 518.2 ± 89.5 | 1316.6 ± 194.1 * | 2.54 |
| GM3 (d18:1/20:0) | 51.1 ± 8.7 | 170.3 ± 24.5 * | 3.34 |
| GM2 | | | |
| GM2 (d18:1/18:0) | 286.5 ± 46.3 | 957.6 ± 119.5 * | 3.34 |
| GM2 (d18:1/20:0) | 68.9 ± 12.3 | 296.9 ± 40.9 * | 4.31 |
| GD3 | | | |
| GD3 (d18:1/18:0) | 155.8 ± 23.9 | 321.0 ± 45.2 * | 2.06 |
| GD3 (d18:1/18:0) | 139.8 ± 26.7 | 307.7 ± 41.0 * | 2.20 |
| GD3 (d18:1/20:0) | 39.9 ± 8.5 | 87.1 ± 12.3 * | 2.18 |
| GD2 | | | |
| GD2 (d18:1/18:0) | 53.1 ± 8.4 | 145.3 ± 22.7 * | 2.73 |
| GD2 (d18:1/20:0) | 54.7 ± 10.9 | 159.9 ± 24.2 * | 2.93 |
| GM1 | | | |
| GM1 (d18:1/18:1) | 52.8 ± 11.7 | 84.9 ± 10.7 | 1.61 |
| GM1 (d18:1/18:0) | 478.8 ± 87.2 | 778.7 ± 91.5 | 1.63 |
| GM1 (d18:1/20:0) | 198.6 ± 40.5 | 322.3 ± 42.7 | 1.62 |
| GD1 | | | |
| GD1 (d18:1/18:1) | 280.2 ± 65.6 | 338.4 ± 40.1 | 1.21 |
| GD1 (d18:1/18:0) | 4025.6 ± 1221.1 | 4648.3 ± 615.8 | 1.15 |
| OAc-GD1 (d18:1/18:0) | 174.3 ± 39.3 | 222.2 ± 19.0 | 1.27 |
| GD1 (d18:1/20:0) | 1653.3 ± 404.0 | 1781.7 ± 225.9 | 1.08 |
| GT1 | | | |
| GT1 (d18:1/18:0) | 493.4 ± 174.0 | 535.5 ± 74.3 | 1.09 |
| OAc-GT1 (d18:1/18:0) | 192.9 ± 60.9 | 243.4 ± 34.1 | 1.26 |
| GT1 (d18:1/20:0) | 220.6 ± 74.7 | 230.1 ± 32.5 | 1.04 |
| OAc-GT1 (d18:1/20:0) | 140.8 ± 37.8 | 163.7 ± 23.7 | 1.16 |

* $p < 0.05$, T-test with Benjamini-Hochberg procedure (n > 7).

These data confirm that a loss of spatacsin function leads to the early and progressive accumulation of gangliosides in the lysosomes of neurons in the cerebral and cerebellar cortex before neurodegeneration occurs.

Example 5: Ganglioside Accumulation Contributes to Neurodegeneration in Cultured Neurons We then evaluated the consequences of GM2 and GM3 accumulation in neurodegeneration, using primary cultures of cortical neurons. Immunostaining with GM2 and GM3 antibodies showed that both species of gangliosides accumulated significantly in cultured neurons derived from knockout embryos (FIGS. 6A and B). Expression of miRNA targeting the GM3 synthase, a key enzyme in the biosynthetic pathway of gangliosides, significantly decreased the levels of GM2 and GM3 (FIGS. 6C and D). We could thus test the implication of ganglioside accumulation in neuronal death. As a model, we evaluated neuronal death triggered by glutamate, which has been implicated in many models of neurodegenerative diseases. Neuronal death was higher in cells obtained from Spg11$^{-/-}$ embryos compared to control neurons (FIG. 6E). Importantly, when levels of GM2 and GM3 were decreased after downregulation of GM3 synthase, the neuronal death due to glutamate was strongly decreased in Spg11$^{-/-}$ neurons (FIG. 6E). Next, we assessed the effect of Miglustat, a substrate reduction therapy (SRT), on neuronal death induced by glutamate. Miglustat is an inhibitor of glucosylceramide synthase that has been used to decrease brain levels of GM2 in a mouse model of Tay Sachs disease (Platt et al, Science. 1997 Apr. 18; 276(5311):428-31). In Spg11$^{-/-}$ neurons, Miglustat decreased the neuronal death induced by glutamate in a dose-dependent manner (FIG. 6F). These data suggest that accumulation of GM2 and GM3 contributes to neuronal death.

Example 6: Spatacsin Loss Promotes Simple Ganglioside Accumulation in Autolysosomes in Primary Cultures of Cortical Neurons Since GM2 and GM3 accumulated in primary cultures of cortical neurons derived from Spg11−/− mouse embryos, we further analyzed whether gangliosides also accumulated in their lysosomes, as gangliosides accumulated in brain organoids, which are embryonic-like structures. GM2, GM3, GD2, and GD3 significantly accumulated in lysosomes in cultured neurons derived from Spg11−/− embryos (FIGS. 12A-E). Primary cultures of cortical neurons are thus a good model to investigate the consequences of ganglioside accumulation on cellular function. GM2 was the ganglioside that accumulated the most in lysosomes and we therefore used it as a marker for ganglioside accumulation in subsequent experiments.

We then investigated the consequences of ganglioside accumulation on lysosomal function of Spg11 knockout neurons. Loss of spatacsin impairs autophagic clearance and results in accumulation of autolysosomes. Accordingly, the proportion of lysosomes that were autolysosomes, defined by positive staining for the lysosomal marker Lamp1 and the autophagic marker p62, was higher in Spg11$^{-/-}$ neurons than in control neurons and this proportion increased over time in cultured Spg11−/− neurons (FIG. 13A). We then investigated whether GM2 contributed to increase the proportion of autolysosomes. Close examination of GM2 staining in neurons showed that it mainly accumulated in a subset of lysosomes that were also stained with p62 (FIG. 13B). The proportion of lysosomes stained with p62 and GM2 antibodies was higher in Spg11$^{-/-}$ neurons than in control neurons and increased over time (FIG. 13C), suggesting that GM2 could contribute to the accumulation of autolysosomes.

Example 7: GM2 Contributes to the Accumulation of Autolysosomes

Figure 17C:
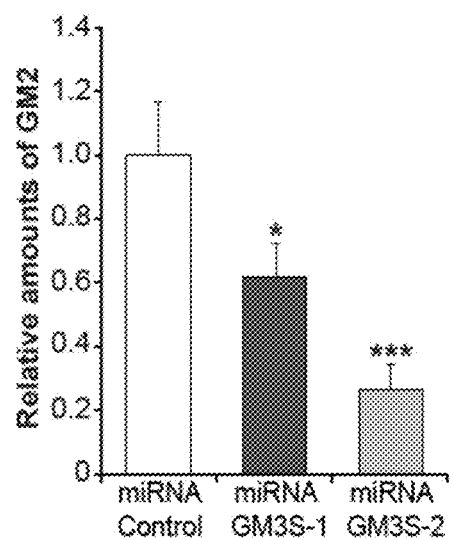

We evaluated the role of GM2 in the accumulation of autolysosomes using miglustat, a substrate reduction therapy (SRT) that inhibits glucosylceramide synthase, an early step in glycosphingolipid synthesis. In our in vitro model, miglustat significantly decreased the levels of GM2 in a dose-dependent manner in control and Spg11$^{-/-}$ neurons (FIG. 13D). Miglustat (100 µM) also strongly decreased the proportion of lysosomes positive for the p62 marker in Spg11$^{-/-}$ neurons (FIG. 13E). We more directly tested the role of ganglioside accumulation in the formation of autolysosomes using two independent miRNAs that target GM3 synthase, the enzyme producing the first ganglioside in the biosynthetic pathway, and from which all other sialylated gangliosides are generated. Expression of these miRNAs significantly decreased the expression of GM3 synthase mRNA and GM2 levels (FIG. 17A-C). When levels of GM2 were decreased after downregulation of GM3 synthase, the proportion of lysosomes containing p62 was significantly decreased in Spg11$^{-/-}$ neurons (FIG. 13F). Overall, our data suggest that the accumulation of GM2 in autolysosomes prevents the degradation of their content and their recycling.

Figure 13G:
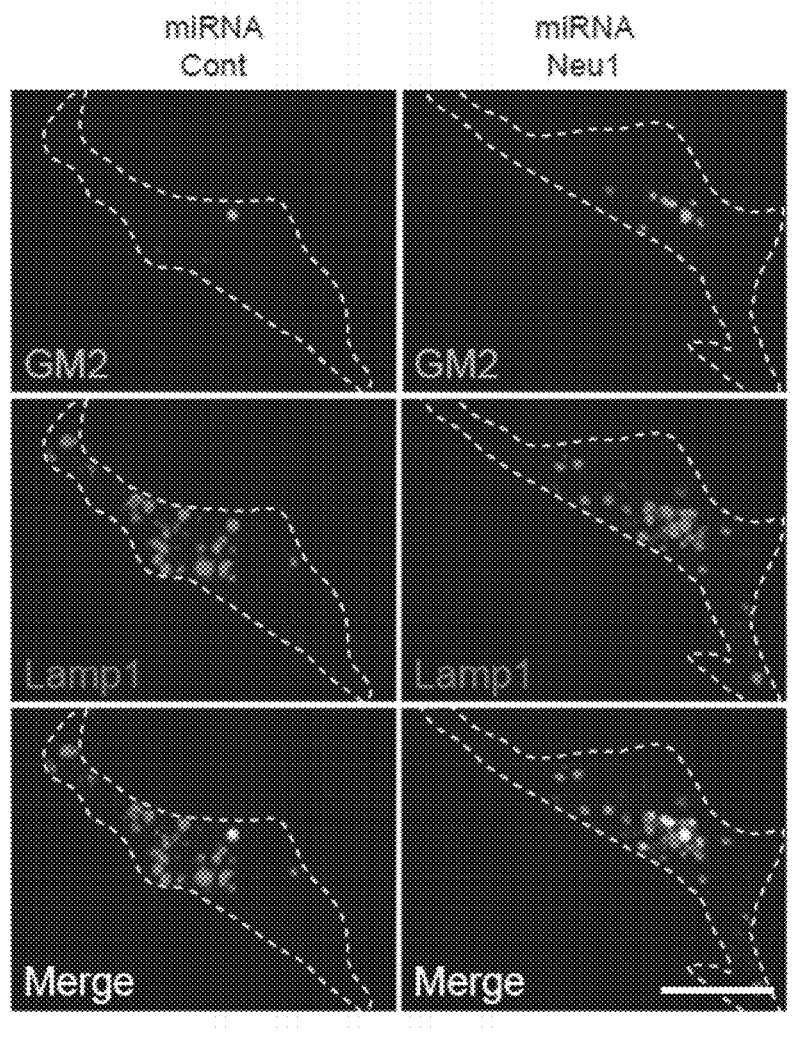
Figure 18:
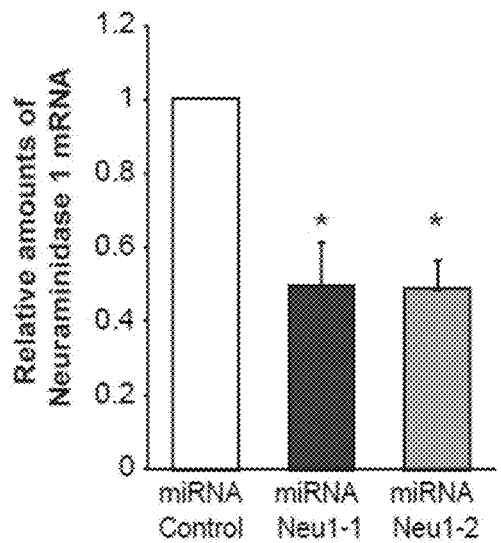
FIG. 18 Downregulation of Neu1 by transfection of vectors expressing specific miRNAs. qRT-PCR showing the decrease in Neu1 mRNA in mouse NIH-3T3 cells transfected with the vectors expressing two different miRNAs targeting Neu1 or a control vector. N=4. Kruskal-Wallis test, *p<0.05.

We directly tested this hypothesis by downregulating the expression of neuraminidase 1 (Neu1), an enzyme involved in the degradation of gangliosides in lysosomes, in control cells. We used two independent miRNA sequences that efficiently downregulated Neu1 expression (FIG. 18). Downregulation of Neu1 promoted significant accumulation of GM2 in lysosomes in transfected cells (FIGS. 13G and H). Increased GM2 levels in lysosomes, after downregulation of Neu1, resulted in a significant increase in the proportion of lysosomes positive for the autophagic marker p62 (FIG. 13I). This suggests that GM2 accumulation in lysosomes leads to the accumulation of autolysosomes.

Example 8: GM2 Contributes to Neurodegeneration in Cultured Neurons

We then investigated whether accumulation of GM2 and autolysosomes contribute to neurodegeneration using primary cultures of mouse cortical neurons. We evaluated neuronal death triggered by glutamate, which occurs in many models of neurodegenerative diseases. Glutamate treatment has been shown to increase ganglioside levels in cultured neurons (Park D. H. et al., Anal Chem, 2016). Accordingly, we observed a moderate, but significant, increase in overall GM2 levels, both in control (+20.0±4.6%, p=0.02, t-test, n>9) and Spg11$^{-/-}$ neurons (+15.7±3.9% p=0.007, t-test, n>10).

Neuronal death triggered by glutamate was significantly higher in neurons obtained from Spg11$^{-/-}$ embryos than control neurons (FIG. 6F). Miglustat treatment of Spg11$^{-/-}$ neurons decreased glutamate-induced neuronal death in a dose-dependent manner (FIG. 6F). Similar data were obtained when GM2 levels were decreased after downregulation of GM3 synthase (FIG. 6E). These data suggest that GM2 accumulation contributes to neuronal death. We confirmed this hypothesis by inducing the accumulation of gangliosides in lysosomes, after downregulating Neu1, and monitoring neuronal death triggered by glutamate. Increasing ganglioside levels sensitized the neurons to glutamate-triggered cell death (FIG. 14A).

We monitored p62 levels in control and Spg11$^{-/-}$ neurons treated with glutamate for 24 hours to determine whether ganglioside-mediated autolysosome accumulation contributed to glutamate-induced neuronal death. We observed no difference in p62 levels in control neurons. In contrast, glutamate treatment significantly increased p62 levels in Spg11$^{-/-}$ neurons, which was inhibited when GM2 levels were decreased by miglustat treatment (FIG. 14B). These data suggest that GM2 contributes to neuronal death by promoting the accumulation of autolysosomes.

Example 9: Spatacsin Loss Promotes the Lysosomal Accumulation of GM2 and GM3 Gangliosides in Human Neurons To test whether the accumulation of gangliosides is also relevant for human pathology, we used patient-derived induced pluripotent stem (iPS) cells. Firstly, we used fibroblasts from a first SPG11 patient with a homozygous stop mutation in exon 32 (c.6100 C>T, p.R2034X), a mutation similar to the one introduced in the Spg11$^{-/-}$ mouse model (FIG. 1A). The patient had typical SPG11 pathology with onset of the disease at 6 years of age, spastic gait with distal wasting at age 19. Cerebral imaging showed thin corpus callosum as well as cortical atrophy (Stevanin et al, Nat Genet. 2007 March; 39(3):366-72). Fibroblasts of this patient, as well as those of a sex- and age-matched control, were derived into iPS cells.

Figure 7A:
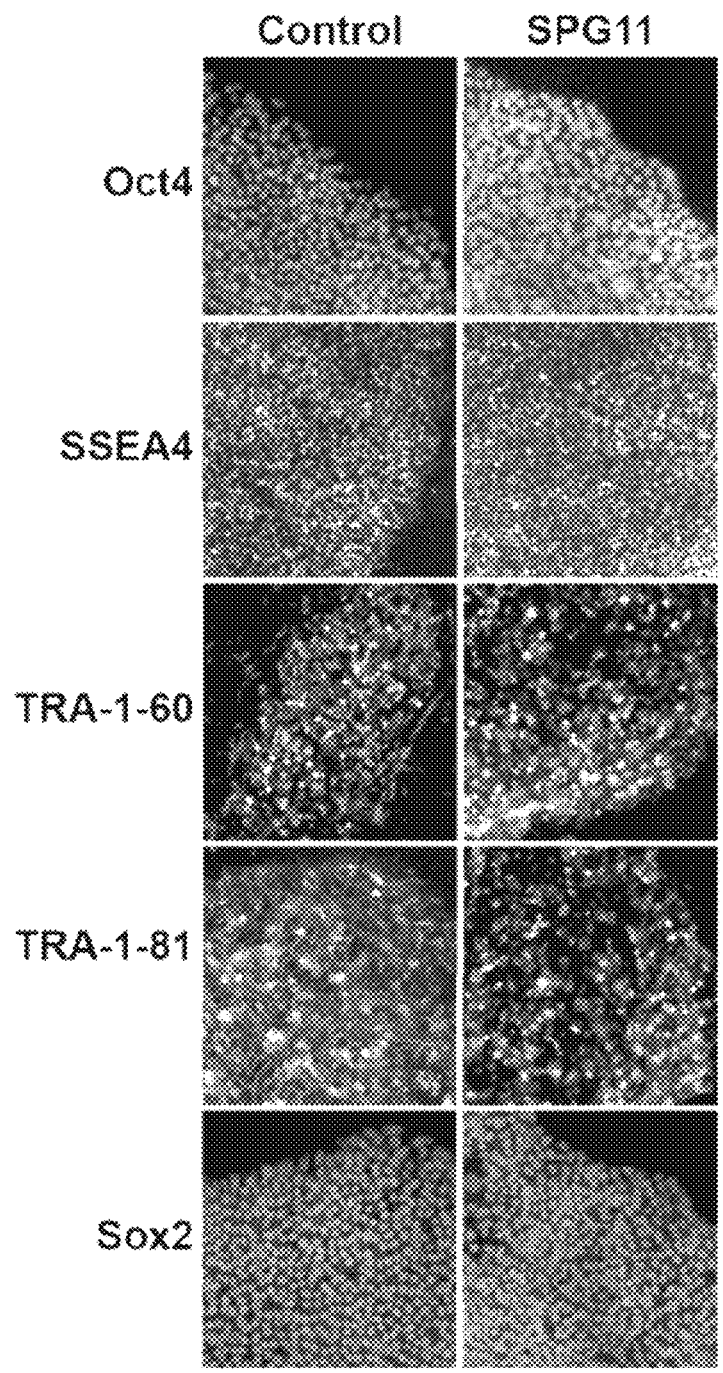
FIGS. 7A-7E are a set of graphs and images showing the accumulation of GM2 and GM3 in lysosomes of neurons derived from SPG11 patient iPS cells.
Figure 7B:
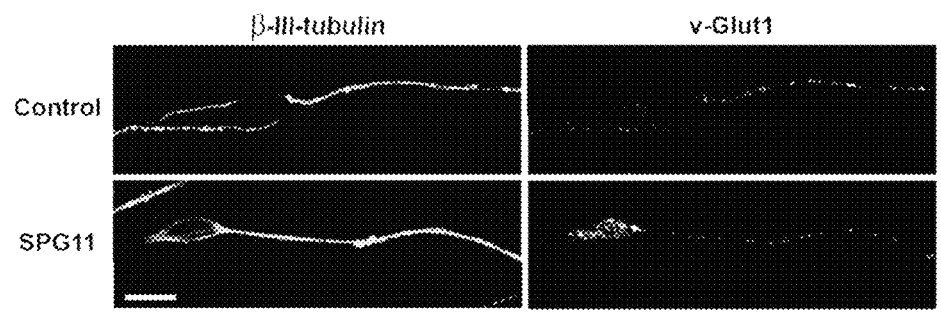
Figure 7C:
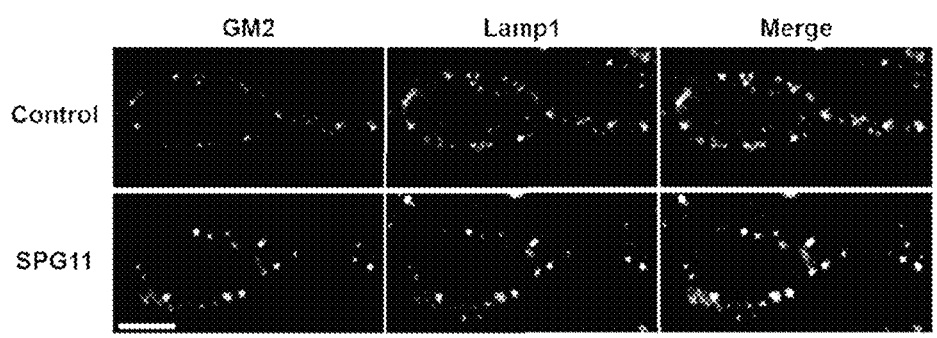
Figure 7D:
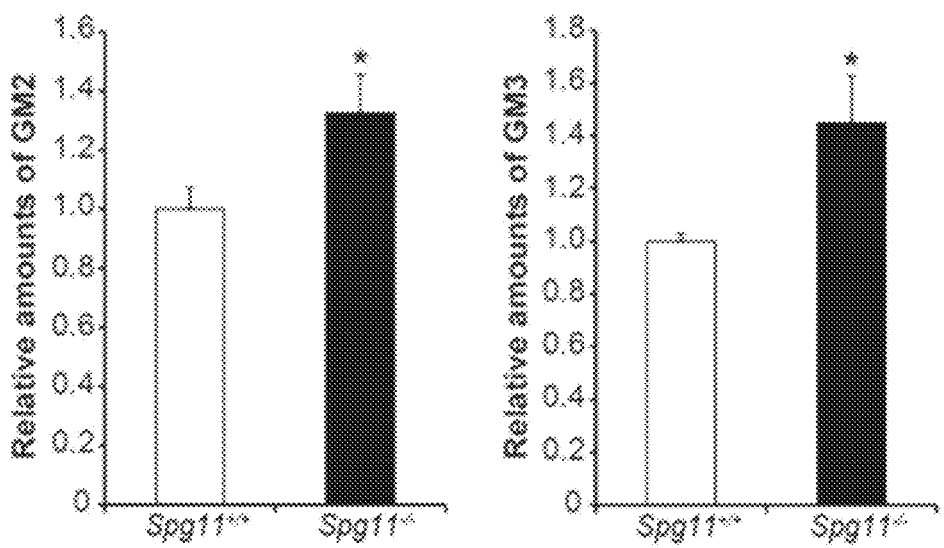
Figure 7E:
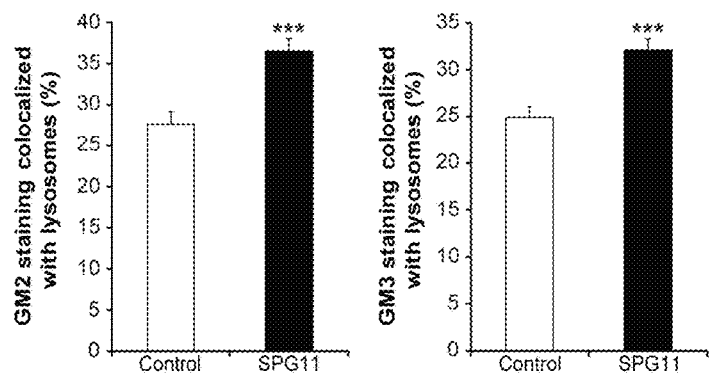

The iPS cell lines were examined for markers of pluripotency (FIG. 7A). They were then differentiated into neural progenitor and then into glutamatergic neurons for 49 days in vitro, as shown by the positive staining for neuron specific marker 3III-tubulin and v-Glut1 (FIG. 7B). To analyze the accumulation of gangliosides in absence of spatacsin, the neurons were immunostained with antibodies against GM2 or GM3 (FIG. 7C). The levels of GM2 and GM3 were up-regulated in neurons derived from the first SPG11 patient compared to control (FIG. 7D). This difference was not observed in neural progenitor suggesting that the accumulation of gangliosides occurred with differentiation or aging of neurons. Finally, we performed double immunostaining of gangliosides and lysosomes to examine whether GM2 and GM3 accumulated in lysosomes (FIG. 7C). As observed in the brain of Spg11$^{-/-}$ mouse, the proportion of GM2 and GM3 co-localized with lysosomes was significantly higher in neurons derived from the first SPG11 patient than in control neurons (FIG. 7E). These results indicate that the pathological pathway identified in mouse is shared with human neurons.

Figure 16:
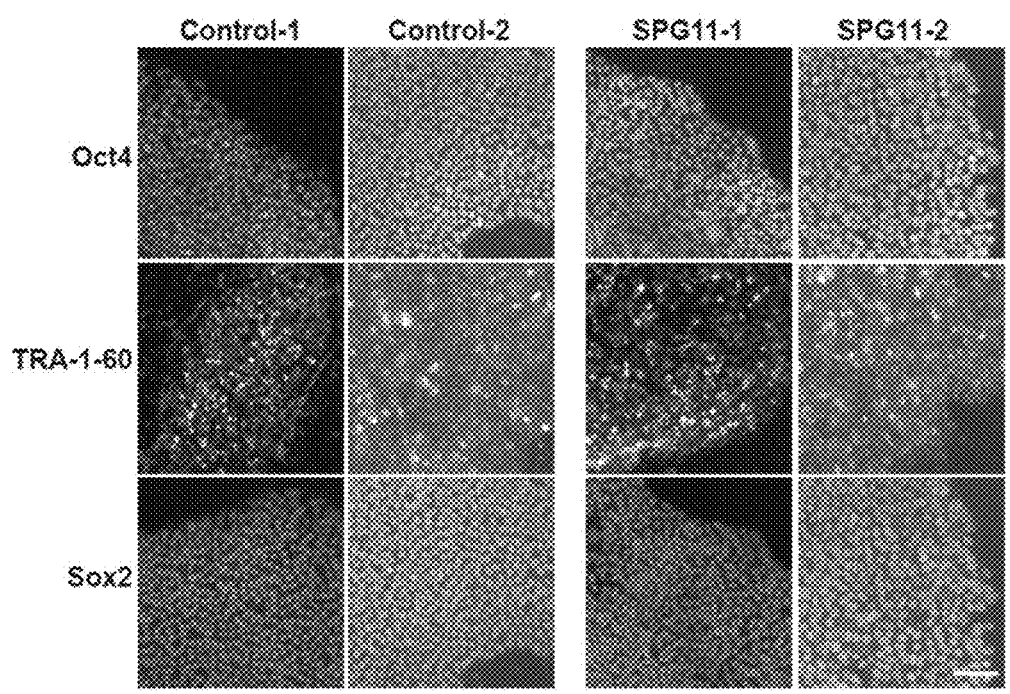
FIG. 16. Characterization of iPS cells derived from fibroblasts of healthy subjects or SPG11 patients. Immunostaining of iPS cells with pluripotency markers. Scale bar: 20 µm.

Thereafter, we differentiated iPS cells derived from fibroblasts of two other independent SPG11 patients into brain organoids. Brain organoids are laminated cerebral cortex-like structures comprising transcriptionally and electrophysiologically mature neurons, synaptically connected and surrounded by a network of nonreactive glial cells. The second patient SPG11 carried two heterozygous truncating mutations in trans (c.2431 C>T, pGln811X; deletion of exon 29). This patient had normal intellectual development, and experienced gait difficulties by age 14, gradually worsened and became stick-dependent at age 20. Examination at age 23 showed that she could still walk with sticks. Spasticity and weakness was present in the lower limbs while tone and strength was normal in the upper limbs. She had increased reflexes with ankle clonus and bilateral extensor plantar reflex as well as Hoffman sign in the upper limbs. Deep sensation was normal. She had postural tremor in the arms, normal eye gaze and no cognitive impairment. There was no evident cerebellar sign. The third patient SPG11 carried two heterozygous truncating mutations in trans (c.1951 C>T, pArg651X; c.5623 C>T, pGln1875X). This woman had onset of spastic gait at age 17. At age 27, she presented with moderate spastic gait, needing walking aids since age 26, and more recently a wheelchair. She had increased reflexes in lower limbs, including bilateral extensor plantar reflexes and Hoffman signs were present in the upper limbs. She had moderate weakness in the legs and decreased deep sensation at the ankles. Bradykinesia was evident and the finger-nose test was performed with mild tremor. Cognition was clinically normal and she exhibited no abnormal eye movements. Cerebral imaging showed a thin corpus callosum. Fibroblasts of two sex- and age-matched controls were also used to derive iPS cells. We validated the iPS cell lines with markers of pluripotency (FIG. 16).

iPS cells of SPG11 patients (second and third) and healthy subjects were differentiated into brain organoids with predominant cortical identity in vitro using a free floating tridimensional culture method (Pasca A. M. et al., Nat. Methods, 2015). Briefly, iPS cells aggregation and differentiation is promoted to form a neuroectoderm-like epithelium, in turn generating cortical neurons that ultimately self-organize in a manner reminiscent of early corticogenesis. After 90 days of differentiation, the organoids were organized in layers of radial glial cells labeled by Pax6 and Nestin, and peripheral layers of neurons that expressed 3III-tubulin and NeuN (FIG. 11A and data not shown). We examined whether gangliosides accumulated in lysosomes in the peripheral layer of neurons using antibodies directed against these lipid species (FIG. 11B-F). GM2, GM3, and GD3 had a punctuate localization in the neurons of the peripheral layer of control and SPG11 brain organoids, and they largely colocalized with lysosomes in the neurons of the SPG11 brain organoids (FIG. 11B, and data not shown). Quantification of fluorescence intensity showed GM2 and GM3 levels to be higher in SPG11 cortical organoids than control organoids (FIG. 11C-F). Furthermore, the variance of the fluorescence intensity of GM2, GM3, and GD3 staining was also higher in organoids derived from SPG11 patients than those derived from healthy controls, consistent with their accumulation in lysosomes. There was no difference in GD2 staining between organoids derived from SPG11 patients and healthy controls, in agreement with the lack of a difference in GD2 staining in the cortices of Spg11$^{+/+}$ and Spg11$^{-/-}$ mice at early stages (FIG. 5E). Overall, these data show that simple gangliosides accumulated in lysosomes of the human neurons, starting at early stages of development represented by the cortical organoid model.

Example 10: Spatacsin Loss Causes a Cognitive Deficit in Mice

Symptoms of SPG11 patients generally include cognitive impairment and mental retardation. Thus, in order to investigate whether Spg11 knock out mouse recapitulate the cognitive deficits observed in humans, we subjected mice to the Y-maze spontaneous-alternation test to evaluate any cognitive deficits. This test relies on the tendency of mice to explore new environments and is used to monitor spatial memory (Hughes, R. N., Neurosci Biobehav Rev, 2004) (FIG. 19A). During the first phase, mice were allowed to freely explore the only open arm of the maze and were confined there for one minute by closing a door behind them. During the second phase, they were placed at the entrance of the maze with both arms open. As expected, Spg11$^{+/+}$ and Spg11$^{+/-}$ mice naturally chose to explore the unknown arm of the maze, a new environment, in ~75% of the trials, rather than the part of the maze that had already been explored. In contrast, Spg11$^{-/-}$ mice showed a lower tendency to enter the unknown arm than the Spg11$^{+/+}$ mice at six weeks of age, and from four months on, the Spg11$^{-/-}$ mice showed no preference between the visited and unknown arms (FIG. 19B), suggesting an alteration in short-term spatial working memory in the knockout mice. We performed a fear conditioning experiment, in which a neutral context was associated with two aversive electric shocks, to determine whether different types of memory were affected. Freezing normally reflects the stress behavior in response to an aversive stimulus. The freezing baseline slightly increased with age, but we observed no significant differences between knockout mice and wild-type or heterozygous littermates. The two electric shocks triggered a marked increase of freezing in all groups (FIG. 19C). The next day, the percentage of time that wild-type and heterozygous mice spent in a frozen posture without an electric shock was high, showing that the task was learned. In contrast, Spg11$^{-/-}$ mice spent less time in a frozen posture from eight months on (FIG. 19D), suggesting that the knockout mice had a long-term emotional memory deficit.

Figure 20E:
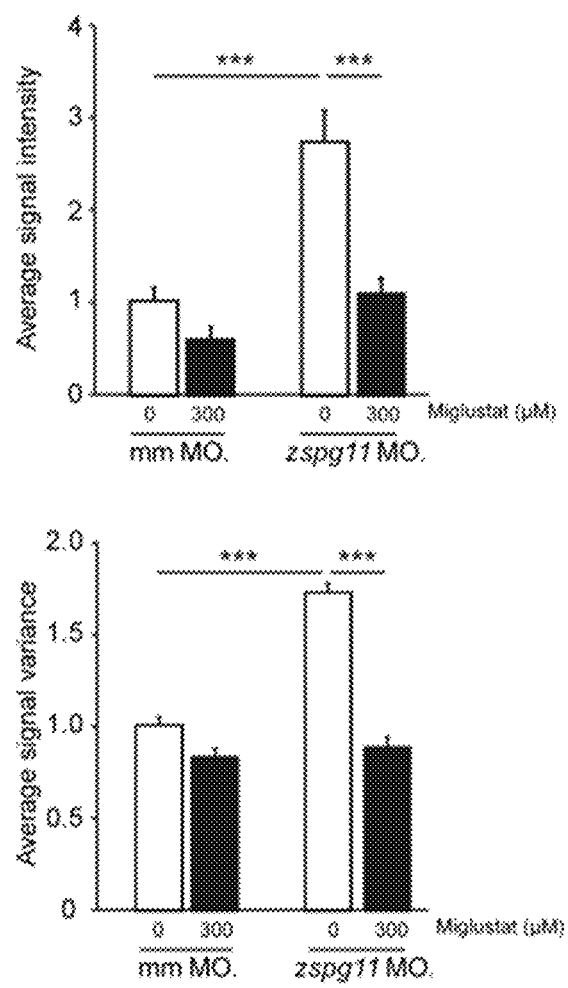

Example 11: Inhibition of Ganglioside Synthesis Rescues Spg11 Pathology in a Zebrafish Model We tested whether inhibition of ganglioside synthesis could be a therapeutic strategy. Since gangliosides accumulate in lysosomes at embryonic stages, we used as a model zebrafish larvae that were injected with morpholinos to decrease expression of spatacsin. Larvae injected with zspg11 morpholinos presented with a motor phenotype that was characterized by either a loss of motility or a paralysis (FIG. 20A) that was rarely or never observed in larvae injected with a mismatch morpholino or in unjected larvae, respectively. When larvae were treated with miglustat, the proportion of paralyzed larvae was significantly reduced in a dose-dependent manner compared to controls. To confirm these data, we monitored the distance travelled by larvae following a touch-evoked escape response. Morphants injected with zspg11 morpholinos showed significantly shorter touch-induced escapes than larvae injected with control morpholinos. This phenotype was significantly corrected when larvae were treated with miglustat (FIG. 20B, C) while miglustat had no effect on morphants injected with mistmach morpholino. Finally, to test whether this action of miglustat relied on its effect on gangliosides synthesis, we monitored the GM2 gangliosides by immunofluorescence in larvae. Zebrafish injected with zspg11 morpholinos had a stronger GM2 staining in the telencephalon than larvae injected with mismatch morpholinos. The stronger staining with GM2 antibody was corrected in larvae treated by miglustat (FIG. 20D, E). Together, these data show that inhibiting the synthesis of gangliosides improves the motor phenotype of a zebrafish model of the SPG11 pathology.

Example 12: Accumulation of GM2 Gangliosides in Brain of SPG4, SPG7 and SPG11 Patient We checked whether gangliosides are implicated in the physiopathology of other forms of HSP. We examined the brain cortex of two patients carrying mutations in the SPG4 gene or the SPG7 gene, and compared them to the brain cortex of a patient affected by SPG11 pathology (Denora et al, 2016) and to a patient with no neurological disease dead at age 61 from acute pancreatitis. Patient FSP-SAL-PIR-625 carries the heterozygous c.1215_1219del (p.Asn405LysfsX36) mutation in the SPG4 gene. This man died from a vesical cancer at 59 years old. The first symptoms were detected at the age 25, he needed walking aid at 37 and required wheelchair at 48 years. Clinical examination revealed strong spasticity of the lower limbs with progressive motor deficit. Upper limbs weren't affected but there was a tetrapyramidal syndrome with bilateral Hoffmann and Babinski signs. Spastic paraplegia Rating Scale was 43/52 at 55 years and increased to 49/52 at 58 years of age. Deep sensation was decreased and finally abolished at 43 years old. No extrapyramidal or cerebellar sign were detected. Brain and medullar MRI were unremarkable at 38 and 55 years old, electromyography at 59 years was normal except signs of left carpian compression. Patient AAR-247 had two compound heterozygote mutations in SPG7: c.1749G>C (p.Trp583Cys) in exon 13 and c.2181+2dup in exon 16. This woman died from pancreatic cancer at the age of 56. The first symptoms were detected at about 30 years of age with instability, and then with stiff legs. She needed walking aid at 45 and required wheelchair at 50 years. She was dysarthric without swallowing difficulties. Clinical evaluation at the age of 55 showed spasticity of lower limbs, tetrapyramidal syndrome with bilateral Babinski sign and proximal mild motor deficit of the lower limbs. Deep sensation was impaired. She had a cerebellar syndrome as shown by the 16.5/40 SARA score. Oculomotor examination showed asymmetric ptosis, saccadic pursuit and limitation of the vertical gaze. Brain MRI performed when the patient was 40 and 55 years old revealed cerebellar atrophy predominantly affecting the vermis. Electromyography was normal twice, at 43 and 55 years of age. Neuropsychological assessment was performed at 55 years old showing normal cognitive capacities but apathy and depressive signs.

Figure 21:
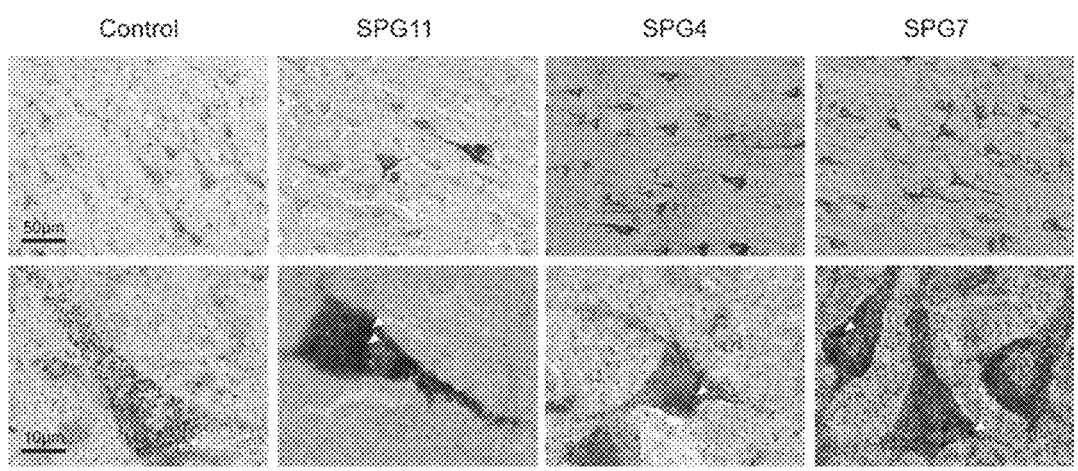
FIG. 21 is a set of images showing the neuronal accumulation of GM2 in the brain cortex of SPG11, SPG4 and SPG7 patients. Immunostaining with GM2 antibody of brain slices of frontal cortex of SPG11, SPG4 and SPG7 patients, compared to brain slices of a control without neurological symptoms. Note the presence of neurons with higher GM2 immunostaining in SPG11, SPG4 and SPG7 patient slices. At higher magnification, white arrowheads indicate vesicular accumulation of GM2 in neurons of SPG11, SPG4 and SPG7 patients.

40 μm-thick slices of the motor cortices of the four individuals were stained with the anti-GM2 antibody. Consistent with data obtained in the cortex of Spg11 knockout mice, we observed that some neurons of the SPG11 patients were strongly stained with GM2 antibody. Higher magnification images showed the presence of GM2 in large vesicles (FIG. 21). In the cortex of SPG4 and SPG7 patients, we observed that the intensity of GM2 staining was slightly increased in some neurons. At higher magnification, we also observed that GM2 staining was concentrated in large vesicles. Altogether, these data suggest that the GM2 ganglioside accumulates in neurons of SPG4 and SPG7 patients, although at a lower level compared to SPG11 patient. This may explain the difference in severity of symptoms between these patients.

Impact

Our data demonstrate that early alteration of lysosomal function, including accumulation of GM2 and GM3 gangliosides in lysosomes, contributes to the early stages of SPG11 physiopathology, including in human-derived models. We identify gangliosides as putative targets to prevent or slow down the progression of the SPG11 pathology. Accumulation of gangliosides is not restricted to SPG11 patients but is also found in brain of SPG4 and SPG7 patients, suggesting that gangliosides are a therapeutic target in various forms of HSP caused by mutations in gene affecting various cellular pathways.

Materials and Methods

Generation and Breeding of Spg11-Knockout Mice

Spg11-knockout mice were generated as previously described (Schnutgen et al., Nat Biotechnol. 2003 May; 21(5):562-5). The gene targeting vector was constructed by inserting a fragment corresponding to mouse exon 32 to exon 34 (sv129 genetic background) into intron 34 in an inverse orientation, with c.6052C>T and c.6061C>T substitutions in exon 32 (FIG. 1A). MCI-129Sv/Pas ES cell lines were transfected with the resulting construct and screened by Southern blotting and by PCR. Homologous recombinant clones were injected into blastocysts. Chimeric mice were mated with C57BL/6 females to obtain germline transmission. The Neo selection cassette was removed by crossing with a flp-expressing mouse. The ubiquitous insertion of exon 32-bearing stop mutations was achieved by crossing the mice with a line expressing Cre recombinase under the control of the CMV promoter. Heterozygous mice were then backcrossed with C57BL/6N mice for 10 generations.

Genotyping was performed by PCR with the 5'-GC-CAAGGTATGCACCAGACGGGG-3' (SEQ ID NO: 1) and 5'-TCCTGCCCTTCACCACGTCAGG-3' (SEQ ID NO: 2) primers. PCR products of 493 and 434 bp were obtained for the invalidated and wild-type alleles, respectively. Mice were housed in same-sex groups and maintained on a 12-hour light/12-hour dark cycle with unrestricted access to food and water.

Behavioral Evaluation

All behavioral procedures were performed between 8:00 a.m. and 1:00 p.m. Bias was minimized by testing mice in experimental cohorts randomly, regardless of their genotype. To measure foot/base angle (FBA), mice were trained to walk on a horizontal corridor leading to a dark box and ordinary food. They were filmed individually with a Panasonic Full HD Camera HC-V720 during four walks. The FBA at the toe-off positions of the hind paws was measured with ImageJ, using single video frames from recordings. The treadmill test was performed with an apparatus consisting of a plastic chamber containing a 4×16 cm treadmill (CleverSys). The mice were tested individually at a controlled speed of 10 cm·s$^{-1}$. After a one-minute habituation phase, the gait of the mice was recorded for 20 s (80 frames per s, BCam). Gait was analyzed with GaitScan software (CleverSys). Motor coordination and equilibrium were evaluated with a Rotarod apparatus (accelerating model LE8200, Bioseb). Mice were placed on the accelerating rod at a starting speed of 4 rpm. The final speed of 40 rpm was reached within five minutes. Mice were tested on two consecutive days, in five trials per day, with an interval of 15 minutes between trials. The duration of time for which they were able to remain on the rod was recorded. Cognitive function was monitored using the Y-maze and fear conditioning tests. The Y-maze consists of three transparent arms of equal length separated by the same distance (40 cm long, 20 cm high, 10 cm wide, 120°). Visual cues are placed in the room. One arm of the maze (arm B) was blocked by a removable opaque partition and the mice were placed individually in the starting arm (arm A) of the apparatus facing the center of the maze. The mouse was allowed to walk freely into the maze. When it arrived at the end of the open arm (arm C), the partition was put in place retaining the mouse. After 1 min, the mouse was immediately placed in the starting arm again (arm A), and the partition was removed to offer two choices. Alternation was defined as spontaneous entry into the unvisited arm (arm B). On the contrary, re-entry into the already explored arm (arm C) was considered to be an error. Contextual fear conditioning was performed in a Plexiglas chamber (17× 17×25 cm) placed in a sound-attenuating box (Fear Conditioning Systems Series 46000, Ugo Basile SRL Comerio Italy). The walls of the chamber are covered by a removable checkerboard context. The bottom of the chamber is composed of a stainless steel grid floor (rods were 2 mm in diameter and spaced 1 cm apart) connected to a scrambled shock generator. Training was initiated by placing the mice in the training context and the freezing baseline was scored during the first 120 s. Then, two electric shocks (2 sec, 0.62 mA spaced by 60 sec) were delivered under the control of AnyMaze software. The end of the training session consisted of a 120 sec period during which freezing was recorded. Contextual fear conditioning was tested 24 h after training by returning mice to the training chamber and scoring freezing for 180 sec without electrical shocks.

Antibodies

Antibodies used in the study were: rabbit anti-spatacsin (Protein Tech); rabbit anti-spastizin (Murmu et al, 2011 Mol Cell Neurosci. 2011 July; 47(3):191-202); mouse anti-α-tubulin (Abcam); mouse anti-NeuN (Millipore); rabbit anti-GFAP (DAKO); monoclonal mouse anti-Calbindin, 1:300, (Swant); rat anti-Lamp1 (Clone 1D4B), mouse anti-Lamp1 (clone H5G11; Santa Cruz Biotechnologies), mouse-anti-clathrin (clone X-22, Abcam; clone 23, BD Biosciences), rabbit anti-Pax-6 (Covance), rabbit anti-sox2 (Millipore), mouse anti-oct4 (Santa Cruz biotechnology), mouse anti-Tra1-60 (Millipore), rabbit anti-PIP5K1B (Proteintech), rabbit anti-dynamin1 (Abcam), mouse anti-GRP78 (BD Biosciences), mouse anti-p62 (Abcam); rabbit anti-cathepsin D (Abcam); rabbit anti-LC3 (Novus Biologicals); rabbit anti-v-Glut1 (Synaptic Systems), mouse anti-β-III tubulin (clone TUJ1, Covance), mouse anti-GM2 (Dobrenis et al, 1992; Natoli et al, 1986) (kindly provided by Dr. Dobrenis) and mouse anti-GM3 (Cosmo Bio), mouse anti-GD2 (Millipore), and mouse anti-GD3 (Invitrogen). For immunoblotting, the secondary antibodies were conjugated to horseradish peroxidase (Jackson Laboratories) or fluorochromes (IR-dye 800 or IR-dye 680; LI-COR). Secondary antibodies used for immunofluorescence were from Life Technologies.

Immunohistochemical Analyses

Mice were anesthetized by the intraperitoneal injection of 1/6 2% xylazine (Rompun), 1/3 ketamine (10 mg·ml$^{-1}$, Imalgen 1000) in phosphate-buffered saline (PBS) and were subjected to the intracardiac perfusion of 4% paraformaldehyde in PBS. Brains were dissected and post-fixed by incubation for 24 h in 4% paraformaldehyde. Brain slices (20 μm) were cut on a freezing microtome (Microm HM450, Thermo Scientific) and maintained in 0.02% sodium azide in PBS at 4° C. After 90 minutes incubation in blocking solution, sections were incubated with primary antibodies in 2% BSA/0.25% Triton X-100 in PBS overnight at 4° C. After washing, the sections were incubated with the secondary antibodies for 90 minutes at room temperature, and mounted in Fluoromount-G mounting medium (Southern Biotechnology). Staining specificity was determined by incubation in the absence of primary antibodies. Images were obtained with a NanoZoomer 2.0-RS (Hamamatsu) equipped with a 20× objective. The number of neurons and astrocytes in each primary motor cortex layer was determined with ImageJ software. Identical brightness, contrast and color balance adjustments were applied to all groups. Confocal images were acquired with an Olympus FV-1000 confocal laser scanning microscope, with a 60× objective. Autofluorescence was triggered by excitation with a 488 nm laser.

Lipidomic Analysis

The cerebral cortices of six-week-old Spg11$^{-/-}$ mice and Spg11$^{+/+}$ mice were processed and analyzed as described previously (Seyer et al, Metabolomics. 2016; 12:91). After liquid chromatography-high-resolution mass spectrometry analysis, samples were re-injected for higher energy collisional dissociation (HCD) tandem mass spectrometry experiments (MS/MS) in negative ion mode, with the instrument set in targeted mode, using inclusion lists. The isolation width was set at m/z 0.4, the normalized collision energy was 26% and mass resolution was set at 17,500 FWHM at m/z 200. HCD mass spectra were inspected manually to confirm the identity of the ganglioside species.

Lysosome Fractions

Lysosome-enriched fractions were purified from whole brains of eight-month old animals following the self-generated Percoll gradient protocol described previously (Graham J. M., Curr Protoc Cell Biol, 2001) (FIG. 15A). At the end of the protocol, the lysosome-enriched fractions were washed once in PBS and the protein quantified by the BCA kit (Pierce). Western blots were performed as described previously (Esteves T. et al., The American J of Human Genetics, 2014). Lysosome-enriched fractions were extracted according to the Folch procedure (Folch J. et al., J Biol Chem, 1957). The desalted Folch upper phases (aqueous phases), containing gangliosides, were analyzed by liquid chromatography coupled with high resolution mass spectrometry (LC-HRMS) in the negative ionization mode to detect deprotonated singly [M-H]− and doubly charged ions [M−$_2$H]$^{2−}$. Data was treated and analyzed as described previously (Seyer A. et al., Metabolomics, 2016). The relative amount of each lipid was quantified as the area of its chromatographic peak, and it was normalized to the concentration of proteins in each lysosome-enriched fraction. The lysosome fractions were further separated using self-generated Percoll gradients. Lysosome fractions were mixed with Percoll to get a solution of 50% Percoll (v:v) and centrifuged at 20,000 g for 90 min. Eight fractions of equal volume were collected from the top, and were analyzed by western blot.

Primary Culture of Neurons

Mouse primary cultures of cortical neurons were treated with Miglustat (Tocris) from the second day in culture. Medium was changed every three days. Immunostaining were performed after six days of culture in vitro, as previously described (Murmu et al., 2011). To downregulate GM3 synthase expression, vectors expressing miRNA were produced using the Block-it kit (Life Technologies). The miRNA sequences were: ATGTACAGGAGCCA-GACTCCAGTTTTGGCCACTGACTGGAGTCTCTCC TGTACAT (miRNA GM3S-1) (SEQ ID NO: 3), ATAACAGAGCCATAGCCGTCTGTTTTGGC-CACTGACTGACAGACGGCTGGC TCTGTTAT (miRNA GM3S-2) (SEQ ID NO: 4), TCTACAGAGCC-GATCTGCTTCGTTTTGGC-CACTGACTGACGAAGCAGAGGCT CTGTAGA (miRNA Neu1-1) (SEQ ID NO: 5) and CTACGAT-GAAGGCTGTAGAGGGTTTTGGC-CACTGACTGACCCTCTACACTTC ATCGTAG (miRNA Neu1-2) (SEQ ID NO: 6). Neurons were transfected with vectors expressing the miRNA and GFP using the Neon transfection system (Life Technologies). The efficiency of the miRNA sequences was validated by transfecting NIH-3T3 cells and performing quantitative RT-PCR using a LightCycler 480 apparatus (Roche) following the manufacturer's instructions. Immunostaining was performed after six days of culture in vitro, as previously described (Murmu R. P. et al., Mol Cell Neurosci, 2011), and images acquired using an Apotome2 microscope (Zeiss) with an objective Plan-Apochromat 63x (N.A. 1.4), or an with Olympus FV-1000 confocal microscope. Quantification of gangliosides levels was performed either with an automated Array-Scan XTI apparatus (Thermo-Fisher) using the General Intensity Measurement protocol, or with ImageJ on image acquired on a Nikon Eclipse Ti-U microscope. Neuronal death was induced by addition of 200 µM glutamate (Sigma-Aldrich) in culture medium. Colocalization of ganglioside staining with lysosomes was quantified using ImageJ. A mask was made from the Lamp1 staining channel and the corresponding ganglioside fluorescence was quantified as the percentage of total ganglioside fluorescence in every cell. Neuronal death was induced by the addition of 200 µM glutamate (Sigma-Aldrich) in culture medium. To quantify neuronal death, 30 hours after glutamate treatment all neurons were labeled with 100 nM Cell tracker Deep Red (Life Technologies) and dead cells were labeled by propidium iodide (5 µM). Alternatively, thirty hours after glutamate treatment, neurons were fixed in 4% paraformaldehyde and immunostained with Tuj-1 antibody. The number of Tuj-1-positive cells per well was quantified with an automated ArrayScan XTI apparatus (Thermo-Fisher) using the compartmental analysis protocol. Neuronal death was quantified by comparing glutamate-treated and non-treated neurons.

Cellular Reprogramming, Characterization and Differentiation of iPS

Skin biopsies were collected from three healthy female subjects and three SPG11 female patients. Fibroblasts were reprogrammed into iPS cells by transient expression of OCT3/4, L-MYC, SOX2, KLF4 and LYN28 using episomal vectors. iPS cells were cultured on Geltrex matrix in complete E8 medium (Life technologies). To assess pluripotency of iPS cells, they were differentiated into embryoid bodies (EBs). iPSc clones were collected by collagenase treatment and resuspended in E8 medium without FGF2. Two weeks later, EBs were plated on polyornithine (20 µg/ml) and laminin (10 µg/ml)-coated cover slips and incubated for 7 additional days. EBs were assessed for markers of the three germ layers: ectoderm (Nestin, Millipore), mesoderm (α-smooth muscle actin, Abcam) and endoderm (α-fetoprotein, Cell Signalling). iPS cells and EBS also analyzed by real-time qPCR assays (TaqMan hPSC Scorecard Panel; Life Technologies) to confirm expression of pluripotency markers. iPS cells were differentiated into forebrain neural progenitors and then into an enriched population of cortical neurons. Neurons were grown for 7 weeks and were fixed and processed for immunostaining. Images were acquired with a Zeiss apotome system (AxoVision LE Rel 4.5). ImageJ was used to quantify the colocalization of GM2 or GM3 staining with lysosomes. Alternatively, iPS cells were differentiated into brain organoids following the protocol previously described (Pasca A. M. et al., Nat. Methods 2015). After 90 days in vitro, organoids were fixed in 4% paraformaldehyde for 24 h, cryoconserved, and stored at −80° C. Organoid slices (12 µm) were cut on a cryostat (LEICA_CM3050S) and processed for immunostaining as described for the mouse brain slices. Images were obtained using a Leica SP-8 confocal microscope with a 60× objective (NA 1.4). Quantification of ganglioside accumulation was performed as for the mouse brain sections.

Electron Microscopy

For standard electron microscopy analysis, a formalin-fixed sample of frontal cortex obtained from a SPG11 patient (Denora et al, Brain. 2016 June; 139(Pt 6):1723-34) was deparaffinized and fixed by incubation for an additional 24 h in 2% glutaraldehyde in 0.1 M phosphate buffer, pH 7.4. Samples of the mouse motor cortex were fixed by incubation in 1% glutaraldehyde. Samples were then post-fixed in 2% osmium tetroxide, dehydrated and embedded in Araldite. Pre-embedding immunohistochemistry was ALSO performed. Ultrathin sections were cut and stained with uranyl acetate and lead citrate, and examined in a Hitachi transmission electron microscope. Images were analyzed with ImageJ to quantify the surface of cytoplasm and lysosomes as well as the number of lysosomes in each section.

Western Blot Analysis

Cells or tissues were lysed by incubation in 100 mM NaCl, 10 mM Tris HCl pH 7.4, 1 mM EGTA, 2 mM MgCl$_2$, 1% SDS and Halt™ Protease Inhibitor Cocktail (Thermo Scientific) for 5 minutes at room temperature. Western blots were performed and signals were visualized with a chemiluminescence substrate (SuperSignal West Dura), or acquired with an Odyssey ClX (Li-COR). Signal intensities were quantified with ImageJ software.

Zebrafish Modeling

Modeling of Spg11 pathology in zebrafish was performed as described previously (Martin, 2012). The knock-down of zspg11 was performed using a morpholino targeting a splice donor site, zspg11spl (5'-ACCAATCAT- AGCGTCTCGTACCCTC-3'—SEQ ID NO: 88). The control morpholino mmzspg11sp1 (5'-ACgAATgA-TAGCcTCTCGTAgCgTC-3'—SEQ ID NO: 89) containing five mismatch nucleotides was used to distinguish specific phenotypic effects resulting from the knock-down of zspg11 from non-specific effects due to injection or morpholino toxicity. One nl of 1.2 mM solution of zspg11sp1 or mmzspg11sp1 were injected into the yolk of one- to two-cell stage embryos. After injection, embryos were maintained at 28° C. in E3 medium, containing miglustat (Tocris Bioscience) at 100 or 300 uM or DMSO for control groups. At 24 hpf they were manually dechorionated using fine forceps. The embryo morphology was observed at 48 hpf. To quantify motor activity, we monitored the touch-evoked escape response at 48 hours post-fertilization in fishes with no obvious developmental abnormalities as previously described (Martin, 2012). Images were acquired at 500 images per sec. Tracking of the touch evoked escape response was performed using the Image J manual tracking plugin. Assessment of GM2 ganglioside levels was performed by whole-mount in vivo immunohistochemistry using 48 hpf embryos fixed in 4% paraformaldehyde in PBS for 2 h at room temperature. Embryos were washed 3 times (5 min each) in PBS-0.1% Triton X-100 (PBST). Embryos were blocked for 1 h in 5% normal goat serum in PBS containing 1% DMSO and 1% Triton X-100 (PBDT), then incubated overnight at 4° C. in blocking solution containing the GM2 primary antibody. After 4 washes in PBST at room temperature, embryos were incubated with an anti IgM antibody coupled to Alexa-488 (Thermo Fishser), overnight at room temperature in PBDT. Before observation, embryos were washed 3 times in PSBT and mounted in a drop of Fluoromount™ Aqueous Mounting Medium (Sigma Aldrich). Whole-mount embryos were imaged on a confocal microscope (Leica SP8, 40X, NA 0.8). Larvae were oriented in the same position for image capture to minimize potential biases in quantification. Image stacks were collected with a step-size of 0.35 µm. Using ImageJ software, the maximum intensity projections of z-stacks were used for quantification of fluorescence in the telencephalon. Mean and variance of the fluorescence intensity were quantified for each morphant in a square of 100 pixels per 100 pixels.

Immunocytochemistry of Patient Brains

Frontal cortex from three affected patients (SPG4, SPG7 and SPG11) and from one non-neurological patient were fixed in formalin. Tissue sections were cut on a vibratome (40 µm) and collected in phosphate buffered saline solution (PBS). Endogenous peroxidases were quenched by incubation for 20 min at room temperature in PBS containing 0.1% Triton™ X-100 (Sigma), 10% methanol and 0.003% $H_2O_2$. Brain sections were washed three times in PBS and incubated in the blocking solution (PBS, 0.4% Triton X-100, 4% normal goat serum, 2% bovine serum albumin) for 1 h at room temperature. Sections were incubated for 24 h at 4° C. with anti-GM2 IgM diluted at 1/150 in the same blocking solution. Sections were washed three times in PBS and incubated for 2 h at room temperature with anti-IgM biotinylated secondary antibody (1:200) diluted in blocking solution. Bound antibodies were visualized using the ABC amplification system (Vectastain ABC kit, Vector Laboratories) with 3,3'-diaminobenzidine tetrahydrochloride (DAB Metal Concentrate; Biogenex) as substrate. The sections were dehydrated twice in ethanol and xylene solutions and mounted with Eukitt.

Statistics

A Kolmogorov-Smirnov analysis was first carried out to determine whether the data were normally distributed. Data sets were compared using the Kruskal-Wallis test for non-parametric data and two-tailed Student's t-test or one-way ANOVA for parametric data. A P value of 0.05 or less was considered to be statistically significant. Lipidomic data were analyzed with standard nonparametric tests in R software, after log 10-transformation. Differences between genotypes were assessed with the Mann-Whitney's test. A P value of 0.1 or less was considered statistically significant.

Ethical Approval

The care and treatment of animals followed European legislation (No. 2010/63/UE) and national (Ministère de l'Agriculture, France) guidelines for the detention, use and ethical treatment of laboratory animals. All experiments on animals were approved by the local ethics committee (Ce5/2012/045 approval number) and were conducted by authorized personnel. Patient-derived materials were obtained through procedures approved by the ethics committee with the written, informed consent of the family (approval SST04/11/04052011 for Human cortex samples; approval RBM-1-029 for skin biopsies).

The invention claimed is:

1. A method for reducing ganglioside metabolism in a subject suffering from a motor neuron disease, comprising administering to the subject an inhibitor of glucosylceramide synthase (GCS), and wherein said motor neuron disease is a hereditary spastic paraplegia (HSP) selected from the group consisting of SPG11, SPG4, and SPG7, wherein said inhibitor of GCS is selected from the group consisting of an imino sugar, a ceramide analog, a carboxamide, a carbamate, a glycoside hydrolase chaperone, imiglucerase and a nucleic acid inhibitor of gene expression.

2. The method according to claim 1, wherein said nucleic acid inhibitor of gene expression is selected from the group consisting of ribozyme, ribonucleic acid interference (RNAi), an antisense oligonucleotide, a small interfering RNA (siRNA), a short hairpin RNA (shRNA), a microRNA (miRNA), a DNAzyme, a peptide nucleic acid (PNA), a modified or synthetic DNA or RNA degradation-resistant polynucleoside amide, a locked nucleic acid (LNA), an antisense RNA (asRNA), or a morpholino.

3. The method according to claim 1, wherein said inhibitor of GCS is an imino sugar selected from the group consisting of
N-butyldeoxynojirimycin (NB-DNJ),
quinuclidin-3-yl (2-(4'-fluoro-[1,-biphenyl]-3-yl)propan-2-yl)carbamate (GZ161);
N-[(1R,2R)-1-(2,3-dihydro-1,4-benzodioxin-6-yl)-1-hydroxy-3-(1-pyrrolidinyl)-2-propanyl]octanamide;
N-(5-adamantane-1-yl-methoxypentyl) deoxynojirimycin (AMP-DNJ or Miglustat);
N-butyl-1-deoxy-nojirimycin (KTB-DNJ);
N-ethyl-1-dexynojirimycin (NE-DNJ);
N-butyldeoxymannojixamycin;
N-5-carboxyl-1-deoxynojiramycin;
N-docecyl-1-deoxynojirimycin;
nojirimycin bisulfate;
nojiximycin-1-sulfonic acid;
N-(n-nonyl)-1-deoxynojirimycin;
N-(7-oxadecyl)-1-deoxynojirimycin;
N-(7-oxa-9,9,9,-trifluorononyl)-1-deoxynojirimycin;
(2R,3S,4R,5S)-2-(Hydroxymethyl)-3,4,5-piperidinetriol;
N-butyldeoxygalactonojirimycin (NB-DGJ);
N-(n-nonyl)deoxynojirimycin;
(3S,4S)-3-(hydroxymethyl)pyrrolidine-3,4-diol (isoLAB);
1,4-dideoxy-1,4-imino-D-arabinitol;
(2S,3R,4S,5R)-3,4,5-trihydroxy-6-oxopiperidine-2-carboxylic acids;
D-glucaro-delta-lactam, 1,4-dideoxy-2-hydroxymethyl-1,4-imino-D-threitol;
(2S,3S,4R)-2,4-bis(hydroxymethyl)pyrrolidine-3,4-diol; isoDGDP;
D-threo-1-phenyl-2-decanoylamino-3-morpholino-propanol (PDMP);
L-threo-1-phenyl-2-decanoylamino-3-morpholino-propanol;
DL-erythro-1-phenyl-2-amino-1,3-propanediol;
D-threo (R,R)-1-phenyl-2-amino-1,3-propanediol;
1-phenyl-2-palmitoylamino-3-morpholino-1-propanol;
1-phenyl-2-palmitoylamino-3-pyrrolidino-1-propanol (P4);
D-threo-1-ethylenedioxyphenyl-2-palmitoyl-3-pyrrolidino-propanol (EtDO-P4);
DL-threo-1-phenyl-2-palmitoylamino-3-pyrrolidino-1-propanol (DL-threo-P4);
2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)acetamide;
N-((1R,2R)-1-(2,3-dihydrobenzo[b][1,4]dioxin-6-yl)-1-hydroxy-3-(pyrrolidin-1-yl)propan-2-yl)nonanamide;
BML-119;
IV-231B;
(S)-quinuclidin-3-yl (2-(2-(4-fluorophenyl)thiazol-4-yl) propan-2-yl)carbamate (S)-2-hydroxysuccinate (GZ 452);
quinuclidin-3-yl (2-(4'-fluoro-[1, -biphenyl]-3-yl)propan-2-yl)carbamate;
(1R,2R)-octanoic acid[2-(2',3'-dihydro-benzo [1,4] dioxin-6'-yl)-2-hydroxy-1-pyrrolidin-1-ylmethyl-ethyl]-amide-L-tartaric acid;
EXEL-0346;
isofagomine;
trans-4-(2-amino-3,5-dibrombenzylamino)-cyclohexanol;
5-(4-chlorophenyl)-6-ethyl-2,4-pyrimidinediamine;
(3R,4R,5R)-5-(hydroxymethyl)-3,4-piperidinediol;
ambroxol;
α-homogalactonojirimycin;
α-homoallonojirimycin;
β-1-C-butyl-DGJ; and
N-nonyl-DNJ.

4. The method according to claim 1, wherein the inhibitor is administered by oral, topical, transdermal, intramuscular, subcutaneous, intravenous, parenteral, intranasal or perispinal administration.

5. The method according to claim 1, wherein said inhibitor of GCS is an imino sugar.

6. The method according to claim 1, wherein the subject with HSP presents with peripheral neuropathy.

7. The method according to claim 1, wherein the subject with HSP presents with ataxia.

8. The method according to claim 1, wherein the inhibitor of GCS is Miglustat.

9. The method according to claim 1, wherein said inhibitor of GCS is an analog of D-threo-1-phenyl-2-decanoylamino-3-morpholino-propanol (PDMP).

10. The method according to claim 1, wherein said inhibitor of GCS is a ceramide analog.

11. The method according to claim 1, wherein said inhibitor of GCS is a carboxamide.

12. The method according to claim 1, wherein said inhibitor of GCS is a carbamate.

13. The method according to claim 1, wherein said inhibitor of GCS is a glycoside hydrolase chaperone.

14. The method according to claim 1, wherein the inhibitor of GCS is imiglucerase.

* * * * *

SEQUENCE LISTING

```
<160> NUMBER OF SEQ ID NOS: 89

<210> SEQ ID NO 1
<211> LENGTH: 23
<212> TYPE: DNA
<213> ORGANISM: Artificial Sequence
<220> FEATURE:
<223> OTHER INFORMATION: Genotyping primer forward

<400> SEQUENCE: 1
gccaaggtat gcaccagacg ggg                                          23

<210> SEQ ID NO 2
<211> LENGTH: 22
<212> TYPE: DNA
<213> ORGANISM: Artificial Sequence
<220> FEATURE:
<223> OTHER INFORMATION: Genotyping primer reverse

<400> SEQUENCE: 2
```
tcctgccctt caccacgtca gg                                      22

<210> SEQ ID NO 3
<211> LENGTH: 59
<212> TYPE: DNA
<213> ORGANISM: Artificial Sequence
<220> FEATURE:
<223> OTHER INFORMATION: miRNA GM3S-1

<400> SEQUENCE: 3
atgtacagga gccagactcc agttttggcc actgactgac tggagtctct cctgtacat    59

<210> SEQ ID NO 4
<211> LENGTH: 59
<212> TYPE: DNA
<213> ORGANISM: Artificial Sequence
<220> FEATURE:
<223> OTHER INFORMATION: miRNA GM3S-2

<400> SEQUENCE: 4
ataacagagc catagccgtc tgttttggcc actgactgac agacggctgg ctctgttat    59

<210> SEQ ID NO 5
<211> LENGTH: 59
<212> TYPE: DNA
<213> ORGANISM: Artificial Sequence
<220> FEATURE:
<223> OTHER INFORMATION: miRNA Neu1-1

<400> SEQUENCE: 5
tctacagagc cgatctgctt cgttttggcc actgactgac gaagcagagg ctctgtaga    59

<210> SEQ ID NO 6
<211> LENGTH: 59
<212> TYPE: DNA
<213> ORGANISM: Artificial Sequence
<220> FEATURE:
<223> OTHER INFORMATION: miRNA Neu1-2

<400> SEQUENCE: 6
ctacgatgaa ggctgtagag ggttttggcc actgactgac cctctacact tcatcgtag    59

<210> SEQ ID NO 7
<211> LENGTH: 21
<212> TYPE: RNA
<213> ORGANISM: Artificial Sequence
<220> FEATURE:
<223> OTHER INFORMATION: iRNA GM3 synthase

<400> SEQUENCE: 7
ggguuauucu gaacauguut t                                       21

<210> SEQ ID NO 8
<211> LENGTH: 54
<212> TYPE: RNA
<213> ORGANISM: Artificial Sequence
<220> FEATURE:
<223> OTHER INFORMATION: iRNA GM3 synthase

<400> SEQUENCE: 8
gaagacccag cttgttaatg tgtgctgtcc attaacaagc tgggtcttct tttt          54

<210> SEQ ID NO 9
<211> LENGTH: 54
<212> TYPE: RNA
<213> ORGANISM: Artificial Sequence
<220> FEATURE:
<223> OTHER INFORMATION: iRNA GM3 synthase

<400> SEQUENCE: 9
gccaatgatt tgttcgttag tgtgctgtcc taacgaacaa atcattggct tttt    54

<210> SEQ ID NO 10
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 10
atcacttctc agtttcacat    20

<210> SEQ ID NO 11
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 11
gctttgagct cgggtgtacc    20

<210> SEQ ID NO 12
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 12
ggccttctca tcttgctttg    20

<210> SEQ ID NO 13
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 13
tcttttaata acaagctggg    20

<210> SEQ ID NO 14
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 14
ggatgtcttt taataacaag    20

<210> SEQ ID NO 15
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 15
aacacaagca atgtacattt    20

```
<210> SEQ ID NO 16
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 16
tccacactcc aaacacaagc                                               20

<210> SEQ ID NO 17
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 17
ttacatggtc agggtccaca                                               20

<210> SEQ ID NO 18
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 18
tctgagctct ctttacatgg                                               20

<210> SEQ ID NO 19
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 19
aagacttgct gagcatattt                                               20

<210> SEQ ID NO 20
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 20
acattccttc tgcaagactt                                               20

<210> SEQ ID NO 21
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 21
ggcaaacttg ggacgacatt                                               20

<210> SEQ ID NO 22
<211> LENGTH: 20
<212> TYPE: RNA
<213> ORGANISM: Artificial Sequence
<220> FEATURE:
<223> OTHER INFORMATION: iRNA GM3 synthase
```

-continued

```
<400> SEQUENCE: 22
tctgcacaaa agggagtaag                                                 20

<210> SEQ ID NO 23
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 23
ttactggaga acttccggaa                                                 20

<210> SEQ ID NO 24
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 24
ggactttact ggagaacttc                                                 20

<210> SEQ ID NO 25
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 25
agtattcctc cgcttccaat                                                 20

<210> SEQ ID NO 26
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 26
aatccgtgca gtattcctcc                                                 20

<210> SEQ ID NO 27
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 27
actgtttaac cttatcacaa                                                 20

<210> SEQ ID NO 28
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 28
tatccctcaa ctggtgcact                                                 20

<210> SEQ ID NO 29
```

```
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 29
gtagttttat ttccaacatg                                                 20

<210> SEQ ID NO 30
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 30
agtcatcctt atagtagttt                                                 20

<210> SEQ ID NO 31
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 31
tgaaatcaac actcttaaat                                                 20

<210> SEQ ID NO 32
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 32
ttgaagccag ttgaaatcaa                                                 20

<210> SEQ ID NO 33
<211> LENGTH: 20
<212> TYPE: RNA
<213> ORGANISM: Artificial Sequence
<220> FEATURE:
<223> OTHER INFORMATION: GM3 synthase

<400> SEQUENCE: 33
tttaccattg cttgaagcca                                                 20

<210> SEQ ID NO 34
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 34
cccagaatgg cagggtttcc                                                 20

<210> SEQ ID NO 35
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 35
```
acctgcttcc aaaagaagag                                           20

<210> SEQ ID NO 36
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 36
ctgccacctg cttccaaaag                                           20

<210> SEQ ID NO 37
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 37
tttttctgcc acctgcttcc                                           20

<210> SEQ ID NO 38
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 38
tttggctgca gtgggatttt                                           20

<210> SEQ ID NO 39
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 39
tggattcaaa atcctgaaat                                           20

<210> SEQ ID NO 40
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 40
tctgagtact gaaggatgtc                                           20

<210> SEQ ID NO 41
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 41
gaggctctga gtactgaagg                                           20

<210> SEQ ID NO 42
<211> LENGTH: 20
<212> TYPE: RNA

```
<213> ORGANISM: Artificial Sequence
<220> FEATURE:
<223> OTHER INFORMATION: iRNA GM3 synthase

<400> SEQUENCE: 42
tgactgaggc tctgagtact                                          20

<210> SEQ ID NO 43
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 43
atctcggccc cagaaccttg                                          20

<210> SEQ ID NO 44
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 44
tgcatggtct gaaagttcat                                          20

<210> SEQ ID NO 45
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 45
accagcttta agaggaactt                                          20

<210> SEQ ID NO 46
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 46
tttcaccact ccctctttga                                          20

<210> SEQ ID NO 47
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 47
tttctgtgtt caaaattcac                                          20

<210> SEQ ID NO 48
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 48
agagttgcat tttcaactga                                          20
```

<210> SEQ ID NO 49
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 49
ctgtcaaaaa cagctctcag                                                  20

<210> SEQ ID NO 50
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 50
tatctgcagg atggagaaat                                                  20

<210> SEQ ID NO 51
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 51
acatgagctg cacttcaaag                                                  20

<210> SEQ ID NO 52
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 52
ccaattcaat tcttaagttt                                                  20

<210> SEQ ID NO 53
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 53
gttacataca attctctttg                                                  20

<210> SEQ ID NO 54
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 54
gcagaagttt tacaaattaa                                                  20

<210> SEQ ID NO 55
<211> LENGTH: 20
<212> TYPE: RNA
<213> ORGANISM: Artificial Sequence
<220> FEATURE:

<223> OTHER INFORMATION: iRNA GM3 synthase

<400> SEQUENCE: 55
caaaagagtg acctcccctc                                               20

<210> SEQ ID NO 56
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 56
caccatcaaa agagtgacct                                               20

<210> SEQ ID NO 57
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 57
aatgaggttc agggccacca                                               20

<210> SEQ ID NO 58
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 58
tcacaccaag cagcgcagca                                               20

<210> SEQ ID NO 59
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 59
ggatcctccg tgggtcacac                                               20

<210> SEQ ID NO 60
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 60
atcctgggag tggatcctcc                                               20

<210> SEQ ID NO 61
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 61
gctacggagc acgtcatcct                                               20

-continued

```
<210> SEQ ID NO 62
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 62
gcagacccag tatcagcagc                                              20

<210> SEQ ID NO 63
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 63
gccgctgcat cgcagaccca                                              20

<210> SEQ ID NO 64
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 64
ccctggttgg ttctcgagtc                                              20

<210> SEQ ID NO 65
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 65
cctccaggac agcttccctg                                              20

<210> SEQ ID NO 66
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 66
tatgtccctc tccgaccagg                                              20

<210> SEQ ID NO 67
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 67
tcacctcaga cagacactgg                                              20

<210> SEQ ID NO 68
<211> LENGTH: 20
<212> TYPE: RNA
<213> ORGANISM: Artificial Sequence
<220> FEATURE:
<223> OTHER INFORMATION: iRNA GM3 synthase
```

```
<400> SEQUENCE: 68
agggtgtact ctcccatgac                                               20

<210> SEQ ID NO 69
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 69
gtgtttccca aaacattatt                                               20

<210> SEQ ID NO 70
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 70
tttataatac tgggaagatt                                               20

<210> SEQ ID NO 71
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 71
ggtatacacc gccaggtagg                                               20

<210> SEQ ID NO 72
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 72
atccatataa caggcacatg                                               20

<210> SEQ ID NO 73
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 73
cttcctatct cacctgtttc                                               20

<210> SEQ ID NO 74
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 74
acagcaggaa atttgttggt                                               20

<210> SEQ ID NO 75
<211> LENGTH: 20
```

```
<212> TYPE: RNA
<213> ORGANISM: Artificial Sequence
<220> FEATURE:
<223> OTHER INFORMATION: iRNA GM3 synthase

<400> SEQUENCE: 75
ggtagatgac tgaatcatgg                                              20

<210> SEQ ID NO 76
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 76
gtgacatggt agatggacac                                              20

<210> SEQ ID NO 77
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 77
gctgcagtaa tgaaggcggg                                              20

<210> SEQ ID NO 78
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 78
cggtgtaggt ctgcagagtc                                              20

<210> SEQ ID NO 79
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 79
cagtagtcac cttctgactg                                              20

<210> SEQ ID NO 80
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 80
gcactgagtt ctagaggaga                                              20

<210> SEQ ID NO 81
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 81
```
accaagagca gtgcactgag                                              20

<210> SEQ ID NO 82
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 82
tgccacttac tgtagccagc                                              20

<210> SEQ ID NO 83
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 83
actgtttaac ctatttaaat                                              20

<210> SEQ ID NO 84
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 84
cacttggcat tgctgtttct                                              20

<210> SEQ ID NO 85
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 85
ccttcaggag ctctaagata                                              20

<210> SEQ ID NO 86
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 86
agctctcttc tgactgtgac                                              20

<210> SEQ ID NO 87
<211> LENGTH: 20
<212> TYPE: RNA
<213> ORGANISM: Artificial Sequence
<220> FEATURE:
<223> OTHER INFORMATION: iRNA GM3 synthase

<400> SEQUENCE: 87
gcactgagtt cttatcacaa                                              20

<210> SEQ ID NO 88
<211> LENGTH: 25
<212> TYPE: DNA
<213> ORGANISM: Artificial Sequence

```
<220> FEATURE:
<223> OTHER INFORMATION: zspg11sp1 primer

<400> SEQUENCE: 88
accaatcata gcgtctcgta ccctc                                           25

<210> SEQ ID NO 89
<211> LENGTH: 25
<212> TYPE: DNA
<213> ORGANISM: Artificial Sequence
<220> FEATURE:
<223> OTHER INFORMATION: mmzspg11sp1 primer

<400> SEQUENCE: 89
acgaatgata gcctctcgta gcgtc                                           25
```